US008309516B2

(12) United States Patent
Hart et al.

(10) Patent No.: US 8,309,516 B2
(45) Date of Patent: Nov. 13, 2012

(54) INSECTICIDAL PROTEINS

(75) Inventors: Hope Hart, Research Triangle Park, NC (US); Jeng S. Chen, Research Triangle Park, NC (US); Cheryl Stacy, Research Triangle Park, NC (US); Frederick Walters, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 286 days.

(21) Appl. No.: 12/529,246

(22) PCT Filed: Mar. 26, 2008

(86) PCT No.: PCT/US2008/058182
§ 371 (c)(1),
(2), (4) Date: Sep. 25, 2009

(87) PCT Pub. No.: WO2008/121633
PCT Pub. Date: Oct. 9, 2008

(65) Prior Publication Data
US 2010/0017914 A1    Jan. 21, 2010

Related U.S. Application Data

(60) Provisional application No. 60/920,493, filed on Mar. 28, 2007.

(51) Int. Cl.
*C07K 14/325*    (2006.01)
(52) U.S. Cl. ........................................................ 514/4.5
(58) Field of Classification Search .................. None
See application file for complete search history.

(56) References Cited

U.S. PATENT DOCUMENTS

| | | | |
|---|---|---|---|
| 5,424,409 | A | 6/1995 | Ely et al. |
| 5,659,123 | A | 8/1997 | Van Rie et al. |
| 5,763,241 | A | 6/1998 | Fischhoff et al. |
| 6,015,891 | A | 1/2000 | Adang et al. |
| 6,063,597 | A | 5/2000 | English et al. |
| 6,204,246 | B1 | 3/2001 | Bosch et al. |
| 6,489,155 | B1 | 12/2002 | Takayama et al. |
| 6,500,617 | B1 | 12/2002 | Stemmer et al. |
| 7,030,295 | B2 | 4/2006 | Chen et al. |
| 7,230,167 | B2 | 6/2007 | Chen et al. |
| 2003/0046726 | A1* | 3/2003 | Koziel et al. ............ 800/278 |
| 2003/0120054 | A1* | 6/2003 | Chen et al. ............ 536/23.2 |
| 2005/0216970 | A1 | 9/2005 | Steiner et al. |
| 2005/0283857 | A1 | 12/2005 | Adang et al. |

FOREIGN PATENT DOCUMENTS

| | | |
|---|---|---|
| EP | 0213818 | 3/1987 |
| WO | WO9117254 | 11/1991 |
| WO | WO 98/22595 | * 5/1998 |
| WO | WO9900407 | 1/1999 |
| WO | WO9911797 | 3/1999 |
| WO | WO9931248 | 6/1999 |
| WO | WO03018810 | 3/2003 |

OTHER PUBLICATIONS

Shadenkov et al 1993, Molecular Biology 27(4): 586-591.*
Adang et al, The reconstruction and expression of a *Bacillus thuringiensis* cryIIIA gene in protoplasts and potato plants Plant Molecular Biology, vol. 21 (1993), pp. 1131-1145.
Carroll et al, Proteolytic processing of a coleopteran-specific δ-endotoxin produced by *Bacillus thuringiensis* var. *tenebrionis* Biochemical Journal, vol. 26 (1989), pp. 99-105.
Carroll et al, Intramolecular Proteolytic Cleavage of *Bacillus thuringiensis* Cry3A δ-Endotoxin May Facilitate Its Coleopteran Toxicity Journal of Invertebrate Pathology, vol. 70 (1997) pp. 41-49.
Chen et al., Site-directed mutations in a highly conserved region of *Bacillus thuringiensis* δ-endotoxin affect inhibition of short circuit current across *Bombyx mori* midguts Proc. Natl Acad. Sci., vol. 90, pp. 9041-9045 (1993).
Gazit et al, The structure and organization within the membrane of the helices composing the pore-forming domain of *Bacillus thuringiensis* δ-endotoxin are consistent with an "umbrella-like" structure of the pore Proceedings of the National Academy of Sciences, USA, vol. 95 (Oct. 1998), pp. 12289-12294.
Gazit et al., The Assembly and Organization of the α5 and α7 Helices from the Pore-forming Domain of *Bacillus thuringiensis* δ-endotoxin The Journal of Biological Chemistry, vol. 270, No. 6 (Feb. 10, 1995), pp. 2571-2578.
Gazit, E. & Shai, Y., Structural and Functional Characterization of the α5 Segment of *Bacillus thuringiensis* δ-Endotoxin Biochemistry 1993, 32, 3429-3436.
Ge et al., Functional Domains of *Bacillus thuringiensis* Insecticidal Crystal Proteins The Journal of Biological Chemistry, vol. 266, No. 27, pp. 17954-17958 (1991).
Ge et al., Location of the *Bombyx mori* specificity domain on a *Bacillus thuringiensis* δ-endotoxin protein Proc. Natl. Acad. Sci., vol. 86, pp. 4037-4041 (1989).
Gillikin et al, Partial Characterization of Digestive Tract Proteinases from Western Corn Rootworm Larvae, *Diabrotica virgifera* Archives of Insect Biochemistry and Physiology, vol. 19 (1992), pp. 285-298.

(Continued)

*Primary Examiner* — David H Kruse
(74) *Attorney, Agent, or Firm* — Gregory W. Warren; Syngenta Participations AG

(57) ABSTRACT

Compositions and methods for controlling plant pests are disclosed. In particular, novel engineered hybrid insecticidal proteins (eHIPs) having toxicity to at least corn rootworm are provided. By fusing unique combinations of complete or partial variable regions and conserved blocks of at least two different *Bacillus thuringiensis* (Bt) Cry proteins or a modified Cry proteins an eHIP having activity against corn rootworm is designed. Nucleic acid molecules encoding the novel eHIPs are also provided. Methods of making the eHIPs and methods of using the eHIPs and nucleic acids encoding the eHIPs of the invention, for example in transgenic plants to confer protection from insect damage are also disclosed.

24 Claims, 16 Drawing Sheets

OTHER PUBLICATIONS

Li et al, Crystal structure of insecticidal δ-endotoxin from *Bacillus thuringiensis* at 2.5 Å resolution Nature, vol. 353 (Oct. 31, 1991), pp. 815-821.

Martinez-Ramirez, A.C. and Real M.D., Proteolytic Processing of *Bacillus thuringiensis* CryIIIA Toxin and Specific Binding to Brush-Border Membrane Vesicles of *Leptinotarsa decemlineata* (Colorado Potato Beetle) Pesticide Biochemistry and Physiology, vol. 54 (1996), pp. 115-122, Article No. 0015.

McPherson et al, Characterization of the Cleopteran-Specific Protein Gene of *Bacillus Thuringiensis* Var. *tenebrionis* Bio/Technology, vol. 6 (1988), pp. 61-66.

Oppert B., Protease Interactions With *Bacillus thuringiensis* Insecticidal Toxins Archives of Insect Biochemistry and Physiology, vol. 42 (1999), pp. 1-12.

Sekar et al., Molecular cloning and characterization of the insecticidal crystal protein gene of *Bacillus thuringiensis* var. *tenebrionis* Proceedings of the National Academy of Sciences, USA, vol. 84 (Oct. 1987), pp. 7036-7040.

Slaney et al, Mode of Action of *Bacillus thuringiensis* Toxin CryIIIA: An Analysis of Toxicity in *Leptinotarsa decemlineata* (Say) and *Diabrotica undecimpunctata* Howardi Barber Insect Biochemistry Molecular Biology, vol. 22, No. 1 (1992), pp. 9-18.

Sutton et al, Synthetic cryIIIA gene from *Bacillus thuringiensis* improved for high expression in plants Transgenic Research, vol. 1 (1992), pp. 228-236.

Wu S.J., Dean, D.H., Functional Significance of Loops in The Receptor Binding Domain of *Bacillus thuringiensis* CryIIIA δ-Endotoxin Journal of Molecular Biology, vol. 255 (1996), pp. 628-640.

Wu et al, Enhanced toxicity of *Bacillus thuringiensis* Cry3A δ-Endotoxin in coleopterans by mutagenesis in a receptor binding loop Federation of European Biochemical Societies Letters, vol. 473 (2000), pp. 227-232.

Haider et al, Specificity of *Bacillus thuringiensis* Var. *colmeri* Insecticidal Delta-Endotoxin in Determined by Differential Proteolytic Processing of the Protoxin by Larval Gut Proteases European Journal of Biochemistry, vol. 156, No. 3 (May 1, 1986), pp. 531-540.

Smedley et al, Mutagenesis of three surface-exposed loops of a *Bacillus thuringiensis* insecticidal toxin reveals residues important for toxicity, receptor recognition and possibly membrane insertion Society for General Microbiology, vol. 142, No. Part 7 (Jul. 1996), vol. 1617-1624.

Grochulski et al., *Bacillus thuringiensis* CryA(a) Insecticidal Toxin: Crystal Structure and Channel Formation Journal Mol. Biol., (1995) 254:447-464.

Shadenkov et al., Construction of a Hybrid Gene from CryIIIA and CryIA(a) δ-Endotoxin Genes of *Bacillus thuringiensis* and Expression of Its Derivatives in *Escherichia coli* Cells Molecular Biology, vol. 27, No. 4, Part 2, pp. 586-591 (1993).

Garczynski, et. al., Identification of Putative Insect Brush Border Membrane-Binding Molecules Specific to *Bacillus thuringiensis* δ-Endotoxin by Protein Blot Analysis Applied and Environmental Microbiology, vol. 57, No. 10, Oct. 1991, p. 2816-2820.

Naimov, S., et al., Carboxy-Terminal Extension Effects on Crystal Formation and Insecticidal Properties of Colorado Potato Beetle-Active *Bacillus thuringiensis* δ-Endotoxin Molecular Biotechnology, vol. 32, 2006, pp. 185-196.

Naimov, S., et al., *Bacillus thuringiensis* Delta-Endotoxin Cry1 Hybrid Proteins with Increased Activity against the Colorado Potato Beetle Applied and Environmental Microbiology, vol. 67, No. 11, Nov. 2001, pp. 5328-5330.

Syngenta Participations AG., "International Application No. PCT/US08/58182" International Search Report, Aug. 1, 2008.

\* cited by examiner

Fig. 1A

Alignment:    Global Protein alignment against reference molecule
Parameters:   Scoring matrix: BLOSUM 62

Reference molecule: Cry3A055, Region 1-598
Number of sequences to align: 19

| Pos | Name | Sequence | Start | End | Length | Matches | %Identity |
|---|---|---|---|---|---|---|---|
| Ref 1 | Cry3A055 | (SEQ ID NO: 70) | | 598 | 598 aa | | |
| 2 | moCry3A | (SEQ ID NO: 68) | 1 | 597 | 597 aa | 594 | 99 |
| 3 | Native Cry3A | (SEQ ID NO: 131) | 1 | 644 | 644 aa | 594 | 92 |
| 4 | 8AF | (SEQ ID NO: 64) | 1 | 640 | 640 aa | 524 | 81 |
| 5 | T7-8AF | (SEQ ID NO: 133) | 1 | 654 | 654 aa | 524 | 80 |
| 6 | 2OL-8A | (SEQ ID NO: 2) | 1 | 668 | 668 aa | 517 | 77 |
| 7 | FR8a | (SEQ ID NO: 4) | 1 | 653 | 653 aa | 518 | 79 |
| 8 | FRCG | (SEQ ID NO: 6) | 1 | 652 | 652 aa | 514 | 78 |
| 9 | FRD3 | (SEQ ID NO: 16) | 1 | 615 | 615 aa | 518 | 84 |
| 10 | FR-cg-dm3 | (SEQ ID NO: 18) | 1 | 614 | 614 aa | 514 | 83 |
| 11 | FR8a-12aa | (SEQ ID NO: 12) | 1 | 641 | 641 aa | 515 | 80 |
| 12 | WR-9mut | (SEQ ID NO: 14) | 1 | 599 | 599 aa | 589 | 98 |
| 13 | DM23A | (SEQ ID NO: 62) | 1 | 653 | 653 aa | 510 | 78 |
| 14 | FR8a-9F | (SEQ ID NO: 8) | 1 | 653 | 653 aa | 524 | 80 |
| 15 | FR-9F-cg-del6 | (SEQ ID NO: 20) | 1 | 646 | 646 aa | 520 | 80 |
| 16 | FR-9F-catg | (SEQ ID NO: 10) | 1 | 652 | 652 aa | 520 | 79 |
| 17 | V4F | (SEQ ID NO: 32) | 1 | 598 | 598 aa | 571 | 95 |
| 18 | 5*V4F | (SEQ ID NO: 34) | 1 | 611 | 611 aa | 565 | 92 |
| 19 | Cry1Ab | (SEQ ID NO: 72) | 1 | 648 | 648 aa | 213 | 31 |

Fig. 1B

```
Cry3A055       1                                                                                     MTADNNTEALDSSTTKDV
moCry3A        1                                                                                     MTADNNTEALDSSTTKDV
Cry3A          1                                        MNPNNRSEHDTIKTTENNEVPTNHVQYPLAETPNPTLEDLNYKEFLRMTADNNTEALDSSTTKDV
8AF            1                                                                                     MTADNNTEALDSSTTKDV
T7-8AF         1                                                               MASMTGGQQMGRGSMTADNNTEALDSSTTKDV
2OL-8A         1                                                               MASMTGGQQMGRGSMTADNNTEALDSSTTKDV
FR8a           1                                                               MASMTGGQQMGRGSGSTSNGRQCAGIRPYDGRQQHRGLDSSTTKDV
FRCG           1                                                                           MTSNGRQCAGIRPYDGRQQHRGLDSSTTKDV
FRD3           1                                                                           MTSNGRQCAGIRPYDGRQQHRGLDSSTTKDV
FR-cg-dm3      1                                                                           MTSNGRQCAGIRPYDGRQQHRGLDSSTTKDV
FR8a-12aa      1                                                                           MTSNGRQCAGIRPYDGRQQHRGLDSSTTKDV
WR-9mut        1                                                                                     MYDGRQQHRGLDSSTTKDV
DM23A          1                                                                                     MYDGRQQHRGLDSSTTKDV
FR-9F          1                                                                           MTSNGRQCAGIRPMTADNNTEALDSSTTKDV
FR-9F-cg-del6  1                                                                           MTSNGRQCAGIRPMTADNNTEALDSSTTKDV
FR-9F-catg     1                                                                                MCAGIRPMTADNNTEALDSSTTKDV
V4F            1                                                                                     MTADNNTEALDSSTTKDV
5*V4F          1                                                                           MTSNGRQCAGIRPYDGRQQHRGLDSSTTKDV
Cry1Ab         1                                                                           MDNNPNINECIPYNCLSNPEVEV Cry3A055      19 ------IQKGISVVGDLLGVVGFPFGGAL--VSFYTNFLNTIWPSEDP--WKAFMEQVEALMDQKIADYAKNKALAELQGLQNNVEDYVSALSSWQKNPAAPFRNPHSQGR
moCry3A       19 ------IQKGISVVGDLLGVVGFPFGGAL--VSFYTNFLNTIWPSEDP--WKAFMEQVEALMDQKIADYAKNKALAELQGLQNNVEDYVSALSSWQKNPVSS-RNPHSQGR
Cry3A         66 ------IQKGISVVGDLLGVVGFPFGGAL--VSFYTNFLNTIWPSEDP--WKAFMEQVEALMDQKIADYAKNKALAELQGLQNNVEDYVSALSSWQKNPVSS-RNPHSQGR
8AF           19 ------IQKGISVVGDLLGVVGFPFGGAL--VSFYTNFLNTIWPSEDP--WKAFMEQVEALMDQKIADYAKNKALAELQGLQNNVEDYVSALSSWQKNPAAPFRNPHSQGR
T7-8AF        33 ------IQKGISVVGDLLGVVGFPFGGAL--VSFYTNFLNTIWPSEDP--WKAFMEQVEALMDQKIADYAKNKALAELQGLQNNVEDYVSALSSWQKNPAAPFRNPHSQGR
2OL-8A        47 ------IQKGISVVGDLLGVVGFPFGGAL--VSFYTNFLNTIWPSEDP--WKAFMEQVEALMDQKIADYAKNKALAELQGLQNNVEDYVSALSSWQKNPAAPFRNPHSQGR
FR8a          32 ------IQKGISVVGDLLGVVGFPFGGAL--VSFYTNFLNTIWPSEDP--WKAFMEQVEALMDQKIADYAKNKALAELQGLQNNVEDYVSALSSWQKNPAAPFRNPHSQGR
FRCG          32 ------IQKGISVVGDLLGVVGFPFGGAL--VSFYTNFLNTIWPSEDP--WKAFMEQVEALMDQKIADYAKNKALAELQGLQNNVEDYVSALSSWQKNPVSS-RNPHSQGR
FRD3          32 ------IQKGISVVGDLLGVVGFPFGGAL--VSFYTNFLNTIWPSEDP--WKAFMEQVEALMDQKIADYAKNKALAELQGLQNNVEDYVSALSSWQKNPVSS-RNPHSQGR
FR-cg-dm3 pr  32 ------IQKGISVVGDLLGVVGFPFGGAL--VSFYTNFLNTIWPSEDP--WKAFMEQVEALMDQKIADYAKNKALAELQGLQNNVEDYVSALSSWQKNPAAPFRNPHSQGR
FR8a-12aa     20 ------IQKGISVVGDLLGVVGFPFGGAL--VSFYTNFLNTIWPSEDP--WKAFMEQVEALMDQKIADYAKNKALAELQGLQNNVEDYVSALSSWQKNPAAPFRNPHSQGR
WR-9mut       20 ------IQKGISVVGDLLGVVGFPFGGAL--VSFYTNFLNTIWPSEDP--WKAFMEQVEALMDQKIADYAKNKALAELQGLQNNVEDYVSALSSWQKNPAAPFRNPHSQGR
DM23A         32 ------IQKGISVVGDLLGVVGFPFGGAL--VSFYTNFLNTIWPSEDP--WKAFMEQVEALMDQKIADYAKNKALAELQGLQNNVEDYVSALSSWQKNPAAPFRNPHSQGR
FR-9F         32 ------IQKGISVVGDLLGVVGFPFGGAL--VSFYTNFLNTIWPSEDP--WKAFMEQVEALMDQKIADYAKNKALAELQGLQNNVEDYVSALSSWQKNPAAPFRNPHSQGR
FR-9F-cg-del6 26 ------IQKGISVVGDLLGVVGFPFGGAL--VSFYTNFLNTIWPSEDP--WKAFMEQVEALMDQKIADYAKNKALAELQGLQNNVEDYVSALSSWQKNPAAPFRNPHSQGR
FR-9F-catg    32 ------IQKGISVVGDLLGVVGFPFGGAL--VSFYTNFLNTIWPSEDP--WKAFMEQVEALMDQKIADYAKNKALAELQGLQNNVEDYVSALSSWQKNPVSS-RNPHSQGR
V4F           19 ------IQKGISVVGDLLGVVGFPFGGAL--VSFYTNFLNTIWPSEDP--WKAFMEQVEALMDQKIADYAKNKALAELQGLQNNVEDYVSALSSWQKNPAAPFRNPHSQGR
5*V4F         32 ------IQKGISVVGDLLGVVGFPFGGAL--VSFYTNFLNTIWPSEDP--WKAFMEQVEALMDQKIADYAKNKALAELQGLQNNVEDYVSALSSWQKNPAAPFRNPHSQGR
Cry1Ab        24 LGGERIETGYTPIDISLSLTQFLLSEFVPGAGFVLGLVDIIWGIFGPSQWDAFLVQIEQLINQRIEEFARNQAISRLEGLSNLYQIYAESFREWEADPT---NPALREE
```

Fig. 1C

```
                                                   CB1                                                          CB2
Cry3A055        120 IRELFSQAESHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTLT
moCry3A         119 IRELFSQAESHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTLT
Cry3A           166 IRELFSQAESHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTLT
8AF             120 IRELFSQAESHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTLT
T7-8AF pro      134 IRELFSQAESHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTLT
2OL-8A          148 IRELFSQAESHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTLT
FR8a            133 IRELFSQAESHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTLT
FRCG            132 IRELFSQAESHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTLT
FRD3            133 IRELFSQAESHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTLT
FR-cg-dm3       132 IRELFSQAESHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTLT
FR8a-12aa       121 IRELFSQAESHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTLT
WR-9mut         121 IRELFSQAESHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTLT
DM23A           133 IRELFSQAESHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTLT
FR8a-9F         133 IRELFSQAESHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTLT
FR-9F-cg-del6   126 IRELFSQAESHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTLT
FR-9F-catg      132 IRELFSQAESHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTLT
V4F             120 IRELFSQAESHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTLT
5*V4F           133 IRELFSQAESHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTLT
Cry1Ab          130 MRIQFNDMNSALTTAIPLFAVQN YQVPLLSVYVQAANLHLSVLRDVSVFGQRW GFDAATINSRYNDLTRLIGN YTDHAVRWYNTGLERVWGPDSRDWIRYNQFRRELTLT <---- Domain I | Domain II ---->
Cry3A055        230 VLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSNDIITSPFYGNK
moCry3A         229 VLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSNDIITSPFYGNK
Cry3A           276 VLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSNDIITSPFYGNK
8AF             230 VLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSNDIITSPFYGNK
T7-8AF          244 VLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSNDIITSPFYGNK
2OL-8A          258 VLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSNDIITSPFYGNK
FR8a            243 VLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSNDIITSPFYGNK
FRCG            242 VLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSNDIITSPFYGNK
FRD3            243 VLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSNDIITSPFYGNK
FR-cg-dm3       242 VLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSNDIITSPFYGNK
FR8a-12aa       231 VLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSNDIITSPFYGNK
WR-9mut         231 VLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSNDIITSPFYGNK
DM23A           243 VLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSNDIITSPFYGNK
FR8a-9F         243 VLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSNDIITSPFYGNK
FR-9F-cg-del6   236 VLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSNDIITSPFYGNK
FR-9F-catg      242 VLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSNDIITSPFYGNK
V4F             230 VLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSNDIITSPFYGNK
5*V4F           243 VLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSNDIITSPFYGNK
Cry1Ab          240 VLDIVSLFPNYDSRTYPIRTVSQLTREIYT NPV--LENFDGSFRGSAQGIEGSIRSPHLMDILNSITIYTDAHRGEY------YWSGHQIMASPVGFSGPEFTFPLYGTM
```

Fig. 1D

```
                         Domain II          Domain III                                                                                CB3
Cry3A055   339 -SSEPVQNLEFN-GEKVYRAVANTNLAVWPSAVYSGVTKVEESQYNDQTDEASTQTYDSKRNVGAVSW------DSIDQLPPETTDEPLEKGYSHQLNYVMCFLMQGSRG  441 TI------PV LTWTHKSVDEFNMIDSKKITQLPLVKAYKLQSGASVVAGPRFTGGDIL
moCry3A    338 -SSEPVQNLEFN-GEKVYRAVANTNLAVWPSAVYSGVTKVEESQYNDQTDEASTQTYDSKRNVGAVSW------DSIDQLPPETTDEPLEKGYSHQLNYVMCFLMQGSRG  440 TI------PV LTWTHKSVDEFNMIDSKKITQLPLVKAYKLQSGASVVAGPRFTGGDIL
Cry3A      385 -SSEPVQNLEFN-GEKVYRAVANTNLAVWPSAVYSGVTKVEESQYNDQTDEASTQTYDSKRNVGAVSW------DSIDQLPPETTDEPLEKGYSHQLNYVMCFLMQGSRG  487 TI------PV LTWTHKSVDEFNMIDSKKITQLPLVKAYKLQSGASVVAGPRFTGGDIL
8AF        339 -SSEPVQNLEFN-GEKVYRAVANTNLAVWPSAVYSGVTKVEESQYNDQTDEASTQTYDSKRNVGAVSW------DSIDQLPPETTDEPLEKGYSHQLNYVMCFLMQGSRG  441 TI------PV LTWTHKSVDEFNMIDSKKITQLPLVKAYKLQSGASVVAGPRFTGGDIL
T7-8AF     353 -SSEPVQNLEFN-GEKVYRAVANTNLAVWPSAVYSGVTKVEESQYNDQTDEASTQTYDSKRNVGAVSW------DSIDQLPPETTDEPLEKGYSHQLNYVMCFLMQGSRG  455 TI------PV LTWTHKSVDEFNMIDSKKITQLPLTKSTNLGSGTSVVKGPGFTGGDIL
2OL-8A     367 -SSEPVQNLEFN-GEKVYRAVANTNLAVWPSAVYSGVTKVEESQYNDQTDEASTQTYDSKRNVGAVSW------DSIDQLPPETTDEPLEKGYSHQLNYVMCFLMQGSRG  469 TI------PV LTWTHKSVDEFNMIDSKKITQLPLTKSTNLGSGTSVVKGPGFTGGDIL
FR8a       352 -SSEPVQNLEFN-GEKVYRAVANTNLAVWPSAVYSGVTKVEESQYNDQTDEASTQTYDSKRNVGAVSW------DSIDQLPPETTDEPLEKGYSHQLNYVMCFLMQGSRG  454 TI------PV LTWTHKSVDEFNMIDSKKITQLPLTKSTNLGSGTSVVKGPGFTGGDIL
FRCG       351 -SSEPVQNLEFN-GEKVYRAVANTNLAVWPSAVYSGVTKVEESQYNDQTDEASTQTYDSKRNVGAVSW------DSIDQLPPETTDEPLEKGYSHQLNYVMCFLMQGSRG  453 TI------PV LTWTHKSVDEFNMIDSKKITQLPLTKSTNLGSGTSVVKGPGFTGGDIL
FRD3       352 -SSEPVQNLEFN-GEKVYRAVANTNLAVWPSAVYSGVTKVEESQYNDQTDEASTQTYDSKRNVGAVSW------DSIDQLPPETTDEPLEKGYSHQLNYVMCFLMQGSRG  454 TI------PV LTWTHKSVDEFNMIDSKKITQLPLTKSTNLGSGTSVVKGPGFTGGDIL
FR-Cg-dm3  351 -SSEPVQNLEFN-GEKVYRAVANTNLAVWPSAVYSGVTKVEESQYNDQTDEASTQTYDSKRNVGAVSW------DSIDQLPPETTDEPLEKGYSHQLNYVMCFLMQGSRG  453 TI------PV LTWTHKSVDEFNMIDSKKITQLPLTKSTNLGSGTSVVKGPGFTGGDIL
FR8a-12aa  340 -SSEPVQNLEFN-GEKVYRAVANTNLAVWPSAVYSGVTKVEESQYNDQTDEASTQTYDSKRNVGAVSW------DSIDQLPPETTDEPLEKGYSHQLNYVMCFLMQGSRG  442 TI------PV LTWTHKSVDEFNMIDSKKITQLPLTKSTNLGSGTSVVKGPGFTGGDIL
WR-9mut    340 -SSEPVQNLEFN-GEKVYRAVANTNLAVWPSAVYSGVTKVEESQYNDQTDEASTQTYDSKRNVGAVSW------DSIDQLPPETTDEPLEKGYSHQLNYVMCFLMQGSRG  442 TI------PV LTWTHKSVDEFNMIDSKKITQLPLVKAYKLQS

Fig. 1E

```
                         CB5
Cry3A055  546 TINKGDTLTYNSFNLASFSTPFELSGNNLQIGVTG--LSAGDK VYIDKIEFIPVN
moCry3A   545 TINKGDTLTYNSFNLASFSTPFELSGNNLQIGVTG--LSAGDK VYIDKIEFIPVN
Cry3A     592 TINKGDTLTYNSFNLASFSTPFELSGNNLQIGVTG--LSAGDK VYIDKIEFIPVN VTFEAEYDLERAQKAVNELFTSSNQIGLKTDVTDYHIDQV
8AF       546 TMSSGSNLQSGSFRTVGFTTPFNFSNGSSVFTLSAHVFNSGNE VYIDRIEFVPAE VTFEAEYDLERAQKAVNELFTSSNQIGLKTDVTDYHIDQV
T7-8AF    560 TMSSGSNLQSGSFRTVGFTTPFNFSNGSSVFTLSAHVFNSGNE VYIDRIEFVPAE VTFEAEYDLERAQKAVNELFTSSNQIGLKTDVTDYHIDQV
2OL-8A    574 TMSSGSNLQSGSFRTVGFTTPFNFSNGSSVFTLSAHVFNSGNE VYIDRIEFVPAE VTFEAEYDLERAQKAVNELFTSSNQIGLKTDVTDYHIDQV
FR8a      559 TMSSGSNLQSGSFRTVGFTTPFNFSNGSSVFTLSAHVFNSGNE VYIDRIEFVPAE VTFEAEYDLERAQKAVNELFTSSNQIGLKTDVTDYHIDQV
FRCG      558 TMSSGSNLQSGSFRTVGFTTPFNFSNGSSVFTLSAHVFNSGNE VYIDRIEFVPAE VTFEAEYDLERAQKAVNELFTSSNQIGLKTDVTDYHIDQV
FRD3      559 TMSSGSNLQSGSFRTVGFTTPFNFSNGSSVFTLSAHVFNSGNE VYIDRIEFVPAE VT
FR-cg-dm3 558 TMSSGSNLQSGSFRTVGFTTPFNFSNGSSVFTLSAHVFNSGNE VYIDRIEFVPAE VT
FR8a-12aa.547 TINKGDTLTYNSFNLASFSTPFELSGNNLQIGVTG--LSAGDK VYIDRIEFVPAE VTFEAEYDLERAQKAVNELFTSSNQIGLKTDVTDYHIDQV
WR-9mut   559 TMSSGSNLQSGSFRTVGFTTPFNFSNGSSVFTLSAHVFNSGNE VYIDRIEFVPAE VTFEAEYDLERAQKAVNELFTSSNQIGLKTDVTDYHIDQV
DM23A     559 TMSSGSNLQSGSFRTVGFTTPFNFSNGSSVFTLSAHVFNSGNE VYIDRIEFVPAE VTFEAEYDLERAQKAVNELFTSSNQIGLKTDVTDYHIDQV
FR8a-9F   552 TMSSGSNLQSGSFRTVGFTTPFNFSNGSSVFTLSAHVFNSGNE VYIDRIEFVPAE VTFEAEYDLERAQKAVNELFTSSNQIGLKTDVTDYHIDQV
FR-9F-cg-del6 558 TMSSGSNLQSGSFRTVGFTTPFNFSNGSSVFTLSAHVFNSGNE VYIDRIEFVPAE VTFEAEYDLERAQKAVNELFTSSNQIGLKTDVTDYHIDQV
FR-9F-catg 546 TINKGDTLTYNSFNLASFSTPFELSGNNLQIGVTG--LSAGDK VYIDKIEFIPVN
V4F       559 TINKGDTLTYNSFNLASFSTPFELSGNNLQIGVTG--LSAGDK VYIDKIEFIPVN
5*V4F     
Cry1Ab    554 TMSSGSNLQSGSFRTVGFTTPFNFSNGSSVFTLSAHVFNSGNE VYIDRIEFVPAE VTFEAEYDLERAQKAVNELFTSSNQIGLKTDVTDYHIDQV
```

Fig. 2A

Alignment: Global Protein alignment against reference molecule
Parameters: Scoring matrix: BLOSUM 62

Reference molecule: 8AF Protein, Amino acids 1-640
Number of sequences to align: 18

| Pos | Name | Sequence ID | Start | End | Length | Matches | %Identity |
|---|---|---|---|---|---|---|---|
| Ref 1 | 8AF | SEQ ID NO: 64 | 1 | 640 | 640 aa | 634 | 99 |
| 2 | 8AFdm3T | SEQ ID NO: 155 | 1 | 640 | 640 aa | 636 | 99 |
| 3 | -CatG8AF | SEQ ID NO: 147 | 1 | 639 | 639 aa | 640 | 98 |
| 4 | FR8a-9F | SEQ ID NO: 8 | 1 | 653 | 653 aa | 631 | 98 |
| 5 | FR8a-12 AA | SEQ ID NO: 12 | 1 | 641 | 641 aa | 634 | 97 |
| 6 | FR8a | SEQ ID NO: 4 | 1 | 653 | 653 aa | 636 | 97 |
| 7 | FR-9F-catg | SEQ ID NO: 10 | 1 | 653 | 653 aa | 628 | 96 |
| 8 | cap8AFdm3T | SEQ ID NO: 159 | 1 | 653 | 653 aa | 630 | 96 |
| 9 | FRCG | SEQ ID NO: 16 | 1 | 652 | 652 aa | 626 | 95 |
| 10 | DM23A | SEQ ID NO: 62 | 1 | 653 | 653 aa | 633 | 94 |
| 11 | 2OL-8A | SEQ ID NO: 2 | 1 | 668 | 668 aa | 596 | 93 |
| 12 | 8AFdm3 | SEQ ID NO: 149 | 1 | 602 | 602 aa | 634 | 92 |
| 13 | FR8a +34 | SEQ ID NO: 160 | 1 | 687 | 687 aa | 589 | 91 |
| 14 | FR-12-cg-dm3 | SEQ ID NO: 18 | 1 | 603 | 603 aa | 598 | 91 |
| 15 | 9F-cg-dm3 | SEQ ID NO: 24 | 1 | 614 | 614 aa | 590 | 91 |
| 16 | Cap8AFdm3 | SEQ ID NO: 153 | 1 | 615 | 615 aa | 545 | 90 |
| 17 | 5*V4F | SEQ ID NO: 34 | 1 | 611 | 611 aa | 368 | 83 |
| 18 | V3A | SEQ ID NO: 30 | 1 | 596 | 596 aa | | 56 |

Fig. 2B

| | | |
|---|---|---|
| 8AF | 1 | MTADNNTEALDSSTTKDVIQKGISVVGD |
| 8AFdm3T | 1 | MTADNNTEALDSSTTKDVIQKGISVVGD |
| -CatG8AF | 1 | MTADNNTEALDSSTTKDVIQKGISVVGD |
| FR8a-9F | 1 | MTADNNTEALDSSTTKDVIQKGISVVGD |
| FR8a-12 AA | 1 | MYDGRQQHRGLDSSTTKDVIQKGISVVGD |
| FR8a | 1 | MTSNGRQCAGIRPYDGRQQHRGLDSSTTKDVIQKGISVVGD |
| FR-9F-catg | 1 | MTSNGRQCAGIRPMTADNNTEALDSSTTKDVIQKGISVVGD |
| cap8AFdm3T | 1 | MTSNGRQCAGIRPYDGRQQHRGLDSSTTKDVIQKGISVVGD |
| FRCG | 1 | MTSNGRQCAGIRPYDGRQQHRGLDSSTTKDVIQKGISVVGD |
| DM23A | 1 | MTSNGRQCAGIRPYDGRQQHRGLDSSTTKDVIQKGISVVGD |
| 2OL-8A | 1 | MTSNGRQCAGIRPYDGRQQHRGLDSSTTKDVIQKGISVVGD |
| 8AFdm3 | 1 | MTADNNTEALDSSTTKDVIQKGISVVGD |
| FR8a +34 | 1 | MASMTGGQQMGRGSGSTSNGRQCAGIRPYDGRQQHRGLDSSTTKDVIQKGISVVGD |
| FR-12-cg-dm3 | 1 | MKETAAAKFERQHMDSPDLGTLVPRGSMADIGSTMTSNGRQCAGIRPYDGRQQHRGLDSSTTKDVIQKGISVVGD |
| 9F-cg-dm3 | 1 | MYDGRQQHRGLDSSTTKDVIQKGISVVGD |
| Cap8AFdm3 | 1 | MTSNGRQCAGIRPMTADNNTEALDSSTTKDVIQKGISVVGD |
| 5*V4F | 1 | MTSNGRQCAGIRPYDGRQQHRGLDSSTTKDVIQKGISVVGD |
| V3A | 1 | MTADNNTEALDSSTTKDVIQKGISVVGD |

| | | |
|---|---|---|
| 8AF | 29 | LLGVVGFPFGGALVSFYTNFLNTIWPSEDPWKAFMEQVEALMDQKIADYAKNKALAELQGIQNNVEDYVSALSSWQKNPAAPFRNPHSQGRIRELFSQAE |
| 8AFdm3T | 29 | LLGVVGFPFGGALVSFYTNFLNTIWPSEDPWKAFMEQVEALMDQKIADYAKNKALAELQGLQNNVEDYVSALSSWQKNPAAPFRNPHSQGRIRELFSQAE |
| -CatG8AF | 29 | LLGVVGFPFGGALVSFYTNFLNTIWPSEDPWKAFMEQVEALMDQKIADYAKNKALAELQGLQNNVEDYVSALSSWQKNPVSS-RNPHSQGRIRELFSQAE |
| FR8a-9F | 42 | LLGVVGFPFGGALVSFYTNFLNTIWPSEDPWKAFMEQVEALMDQKIADYAKNKALAELQGLQNNVEDYVSALSSWQKNPAAPFRNPHSQGRIRELFSQAE |
| FR8a-12 AA | 30 | LLGVVGFPFGGALVSFYTNFLNTIWPSEDPWKAFMEQVEALMDQKIADYAKNKALAELQGLQNNVEDYVSALSSWQKNPAAPFRNPHSQGRIRELFSQAE |
| FR8a | 42 | LLGVVGFPFGGALVSFYTNFLNTIWPSEDPWKAFMEQVEALMDQKIADYAKNKALAELQGLQNNVEDYVSALSSWQKNPAAPFRNPHSQGRIRELFSQAE |
| FR-9F-catg | 42 | LLGVVGFPFGGALVSFYTNFLNTIWPSEDPWKAFMEQVEALMDQKIADYAKNKALAELQGLQNNVEDYVSALSSWQKNPAAPFRNPHSQGRIRELFSQAE |
| cap8AFdm3T | 42 | LLGVVGFPFGGALVSFYTNFLNTIWPSEDPWKAFMEQVEALMDQKIADYAKNKALAELQGLQNNVEDYVSALSSWQKNPAAPFRNPHSQGRIRELFSQAE |
| FRCG | 42 | LLGVVGFPFGGALVSFYTNFLNTIWPSEDPWKAFMEQVEALMDQKIADYAKNKALAELQGLQNNVEDYVSALSSWQKNPAAPFRNPHSQGRIRELFSQAE |
| DM23A | 42 | LLGVVGFPFGGALVSFYTNFLNTIWPSEDPWKAFMEQVEALMDQKIADYAKNKALAELQGLQNNVEDYVSALSSWQKNPAAPFRNPHSQGRIRELFSQAE |
| 2OL-8A | 42 | LLGVVGFPFGGALVSFYTNFLNTIWPSEDPWKAFMEQVEALMDQKIADYAKNKALAELQGLQNNVEDYVSALSSWQKNPVSS-RNPHSQGRIRELFSQAE |
| 8AFdm3 | 29 | LLGVVGFPFGGALVSFYTNFLNTIWPSEDPWKAFMEQVEALMDQKIADYAKNKALAELQGLQNNVEDYVSALSSWQKNPAAPFRNPHSQGRIRELFSQAE |
| FR8a +34 | 57 | LLGVVGFPFGGALVSFYTNFLNTIWPSEDPWKAFMEQVEALMDQKIADYAKNKALAELQGLQNNVEDYVSALSSWQKNPAAPFRNPHSQGRIRELFSQAE |
| FR-12-cg-dm3 | 76 | LLGVVGFPFGGALVSFYTNFLNTIWPSEDPWKAFMEQVEALMDQKIADYAKNKALAELQGLQNNVEDYVSALSSWQKNPVSS-RNPHSQGRIRELFSQAE |
| 9F-cg-dm3 | 30 | LLGVVGFPFGGALVSFYTNFLNTIWPSEDPWKAFMEQVEALMDQKIADYAKNKALAELQGLQNNVEDYVSALSSWQKNPAAPFRNPHSQGRIRELFSQAE |
| Cap8AFdm3 | 42 | LLGVVGFPFGGALVSFYTNFLNTIWPSEDPWKAFMEQVEALMDQKIADYAKNKALAELQGLQNNVEDYVSALSSWQKNPAAPFRNPHSQGRIRELFSQAE |
| 5*V4F | 42 | LLGVVGFPFGGALVSFYTNFLNTIWPSEDPWKAFMEQVEALMDQKIADYAKNKALAELQGLQNNVEDYVSALSSWQKNPAAPFRNPHSQGRIRELFSQAE |
| V3A | 29 | LLGVVGFPFGGALVSFYTNFLNTIWPSEDPWKAFMEQVEALMDQKIADYAKNKALAELQGLQNNVEDYVSALSSWQKNPAAPFRNPHSQGRIRELFSQAE |

Fig. 2C

```
                                          CB1                                                                CB2
8AF            129 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL
8AFdm3T        129 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL
-CatG8AF       128 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL
FR8a-9F        142 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL
FR8a-12 AA     130 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL
FR8a           142 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL
FR-9F-catg     142 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL
cap8AFdm3T     141 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL
FRCG           142 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL
DM23A          142 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL
2OL-8A         157 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL
8AFdm3         129 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL
FR8a +34       176 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL
FR-12-cg-dm3   129 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL
9F-cg-dm3      141 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL
Cap8AFdm3      142 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL
5*V4F          142 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL
V3A            129 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL <--- Domain I    Domain II --->

8AF            229 TVLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSN
8AFdm3T        229 TVLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSN
-CatG8AF       228 TVLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSN
FR8a-9F        242 TVLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSN
FR8a-12 AA     230 TVLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSN
FR8a           242 TVLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSN
FR-9F-catg     241 TVLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSN
cap8AFdm3T     242 TVLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSN
FRCG           241 TVLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSN
DM23A          242 TVLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSN
2OL-8A         257 TVLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSN
8AFdm3         229 TVLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSN
FR8a +34       276 TVLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSN
FR-12-cg-dm3   229 TVLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSN
9F-cg-dm3      241 TVLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSN
Cap8AFdm3      242 TVLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSN
5*V4F          242 TVLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSN
V3A            229 TVLDIVSLFPNYDSRTYPIRTVSQLTREIYT NPVL--ENFDGSFRGSAQGIEGSIRSPHLMDILNSITIYTDAHRGEY-----YWSGHQIMASPVGFSG
```

Fig. 2D

```
8AF          328 DIITSPFYGNK-SSEPVQNLEFN-GEKVYRAVANTNLAVWPSAVYSGVTKVEFSQYNDQTDEASTQTYDSKRNVGAVSW------DSIDQLPPETTDEPL
8AFdm3T      328 DIITSPFYGNK-SSEPVQNLEFN-GEKVYRAVANTNLAVWPSAVYSGVTKVEFSQYNDQTDEASTQTYDSKRNVGAVSW------DSIDQLPPETTDEPL
-CatG8AF     327 DIITSPFYGNK-SSEPVQNLEFN-GEKVYRAVANTNLAVWPSAVYSGVTKVEFSQYNDQTDEASTQTYDSKRNVGAVSW------DSIDQLPPETTDEPL
FR8a-9F      341 DIITSPFYGNK-SSEPVQNLEFN-GEKVYRAVANTNLAVWPSAVYSGVTKVEFSQYNDQTDEASTQTYDSKRNVGAVSW------DSIDQLPPETTDEPL
FR8a-12 AA   329 DIITSPFYGNK-SSEPVQNLEFN-GEKVYRAVANTNLAVWPSAVYSGVTKVEFSQYNDQTDEASTQTYDSKRNVGAVSW------DSIDQLPPETTDEPL
FR8a         341 DIITSPFYGNK-SSEPVQNLEFN-GEKVYRAVANTNLAVWPSAVYSGVTKVEFSQYNDQTDEASTQTYDSKRNVGAVSW------DSIDQLPPETTDEPL
FR-9F-catg   340 DIITSPFYGNK-SSEPVQNLEFN-GEKVYRAVANTNLAVWPSAVYSGVTKVEFSQYNDQTDEASTQTYDSKRNVGAVSW------DSIDQLPPETTDEPL
cap8AFdm3T   341 DIITSPFYGNK-SSEPVQNLEFN-GEKVYRAVANTNLAVWPSAVYSGVTKVEFSQYNDQTDEASTQTYDSKRNVGAVSW------DSIDQLPPETTDEPL
FRCG         340 DIITSPFYGNK-SSEPVQNLEFN-GEKVYRAVANTNLAVWPSAVYSGVTKVEFSQYNDQTDEASTQTYDSKRNVGAVSW------DSIDQLPPETTDEPL
DM23A        341 DIITSPFYGNK-SSEPVQNLEFN-GEKVYRAVANTNLAVWPSAVYSGVTKVEFSQYNDQTDEASTQTYDSKRNVGAVSW------DSIDQLPPETTDEPL
2OL-8A       356 DIITSPFYGNK-SSEPVQNLEFN-GEKVYRAVANTNLAVWPSAVYSGVTKVEFSQYNDQTDEASTQTYDSKRNVGAVSW------DSIDQLPPETTDEPL
8AFdm3       328 DIITSPFYGNK-SSEPVQNLEFN-GEKVYRAVANTNLAVWPSAVYSGVTKVEFSQYNDQTDEASTQTYDSKRNVGAVSW------DSIDQLPPETTDEPL
FR8a +34     375 DIITSPFYGNK-SSEPVQNLEFN-GEKVYRAVANTNLAVWPSAVYSGVTKVEFSQYNDQTDEASTQTYDSKRNVGAVSW------DSIDQLPPETTDEPL
FR-12-cg-dm3 328 DIITSPFYGNK-SSEPVQNLEFN-GEKVYRAVANTNLAVWPSAVYSGVTKVEFSQYNDQTDEASTQTYDSKRNVGAVSW------DSIDQLPPETTDEPL
9F-cg-dm3    340 DIITSPFYGNK-SSEPVQNLEFN-GEKVYRAVANTNLAVWPSAVYSGVTKVEFSQYNDQTDEASTQTYDSKRNVGAVSW------DSIDQLPPETTDEPL
Cap8AFdm3    341 DIITSPFYGNK-SSEPVQNLEFN-GEKVYRAVANTNLAVWPSAVYSGVTKVEFSQYNDQTDEASTQTYDSKRNVGAVSW------DSIDQLPPETTDEPL
5+V4F        341 DIITSPFYGNK-SSEPVQNLEFN-GEKVYRAVANTNLAVWPSAVYSGVTKVEFSQYNDQTDEASTQTYDSKRNVGAVSW------DSIDQLPPETTDEPL
V3A          321 PEFTEPLYGTMGNAAPQQRIVAQLGQGVYRTLSST---LYREFFNIGINNQQLSVL-DGTEFA----YGTSSNLPSAVYRKSGTVDSLDEIPPQNNNVPP
                                                        Domain II          Domain III 8AF          420 EKGYSHQLNYVMCFLMQGSRGTI------PV LTWTHKSVDFFNMIDSKKITQLPLTKSTNLGSGTSVVKGPGFTGGDII RRTSPGQISTLRVNITAPLSQ
8AFdm3T      420 EKGYSHQLNYVMCFLMQGSRGTI------PV LTWTHKSVDFFNMIDSKKITQLPLTKSTNLGSGTSVVKGPGFTGGDII RRTSPGQISTLRVNITAPLSQ
-CatG8AF     419 EKGYSHQLNYVMCFLMQGSRGTI------PV LTWTHKSVDFFNMIDSKKITQLPLTKSTNLGSGTSVVKGPGFTGGDII RRTSPGQISTLRVNITAPLSQ
FR8a-9F      433 EKGYSHQLNYVMCFLMQGSRGTI------PV LTWTHKSVDFFNMIDSKKITQLPLTKSTNLGSGTSVVKGPGFTGGDII RRTSPGQISTLRVNITAPLSQ
FR8a-12 AA   421 EKGYSHQLNYVMCFLMQGSRGTI------PV LTWTHKSVDFFNMIDSKKITQLPLTKSTNLGSGTSVVKGPGFTGGDII RRTSPGQISTLRVNITAPLSQ
FR8a         433 EKGYSHQLNYVMCFLMQGSRGTI------PV LTWTHKSVDFFNMIDSKKITQLPLTKSTNLGSGTSVVKGPGFTGGDII RRTSPGQISTLRVNITAPLSQ
FR-9F-catg   432 EKGYSHQLNYVMCFLMQGSRGTI------PV LTWTHKSVDFFNMIDSKKITQLPLTKSTNLGSGTSVVKGPGFTGGDII RRTSPGQISTLRVNITAPLSQ
cap8AFdm3T   433 EKGYSHQLNYVMCFLMQGSRGTI------PV LTWTHKSVDFFNMIDSKKITQLPLTKSTNLGSGTSVVKGPGFTGGDII RRTSPGQISTLRVNITAPLSQ
FRCG         432 EKGYSHQLNYVMCFLMQGSRGTI------PV LTWTHKSVDFFNMIDSKKIIPSSQITQIPLTKSTNLGSGTSVVKGPGFTGGDII RRTSPGQISTLRVNITAPLSQ
DM23A        433 EKGYSHQLNYVMCFLMQGSRGTI------PV LTWTHKSVDFFNMIDSKKIIPSSQITQIPLTKSTNLGSGTSVVKGPGFTGGDII RRTSPGQISTLRVNITAPLSQ
2OL-8A       448 EKGYSHQLNYVMCFLMQGSRGTI------PV LTWTHKSAEFNNIIPSSQITQIPLTKSTNLGSGTSVVKGPGFTGGDII RRTSPGQISTLRVNITAPLSQ
8AFdm3       420 EKGYSHQLNYVMCFLMQGSRGTI------PV LTWTHKSVDFFNMIDSKKITQLPLTKSTNLGSGTSVVKGPGFTGGDII RRTSPGQISTLRVNITAPLSQ
FR8a +34     467 EKGYSHQLNYVMCFLMQGSRGTI------PV LTWTHKSVDFFNNIIPSSQITQIPLTKSTNLGSGTSVVKGPGFTGGDII RRTSPGQISTLRVNITAPLSQ
FR-12-cg-dm3 420 EKGYSHQLNYVMCFLMQGSRGTI------PV LTWTHKSVDFFNMIDSKKITQLPLTKSTNLGSGTSVVKGPGFTGGDII RRTSPGQISTLRVNITAPLSQ
9F-cg-dm3    432 EKGYSHQLNYVMCFLMQGSRGTI------PV LTWTHKSVDFFNMIDSKKITQLPLTKSTNLGSGTSVVKGPGFTGGDII RRTSPGQISTLRVNITAPLSQ
Cap8AFdm3    433 EKGYSHQLNYVMCFLMQGSRGTI------PV LTWTHKSVDFFNMIDSKKITQLPLTKSTNLGSGTSVVKGPGFTGGDII RRTSPGQISTLRVNITAPLSQ
5+V4F        433 EKGYSHQLNYVMCFLMQGSRGTI------PV LTWTHKSVDFFNNIIPSSQITQIPLTQLALTKSTNLGSGTSVVKGPGFTGGDII RRTSPGQISTLRVNITAPLSQ
V3A          413 RQGFSHRLSHVSMFRSGFSNSSVSIIRAPM ESWIHRSAEFNNIIPSSQITQIPLVKAYKLQSGASVVAGPRETGGDII QCTENGSAATIYVTPDVSYSQ
                                                          CB3
```

Fig. 2E

|  |  | CB4 |  | CB5 |  |
|---|---|---|---|---|---|
| 8AF | 514 | RYRVR IRYAS | TTNLQFHTSIDGRPINQGNFSATMSSGGSNLQSGSFRTVGFTTPFNFSNGSSVFTLSAHVFNSGNE | VYIDRIEFVPAE | VTFEAEYDLERAQK |
| 8AFdm3T | 514 | RYRVR IRYAS | TTNLQFHTSIDGRPINQGNFSATMSSGGSNLQSGSFRTVGFTTPFNFSNGSSVFTLSAHVFNSGNE | VYIDRIEFVPAE | VTFEAEYDLERAQK |
| -CatG8AF | 513 | RYRVR IRYAS | TTNLQFHTSIDGRPINQGNFSATMSSGGSNLQSGSFRTVGFTTPFNFSNGSSVFTLSAHVFNSGNE | VYIDRIEFVPAE | VTFEAEYDLERAQK |
| FR8a-9F | 527 | RYRVR IRYAS | TTNLQFHTSIDGRPINQGNFSATMSSGGSNLQSGSFRTVGFTTPFNFSNGSSVFTLSAHVFNSGNE | VYIDRIEFVPAE | VTFEAEYDLERAQK |
| FR8a-12 AA | 515 | RYRVR IRYAS | TTNLQFHTSIDGRPINQGNFSATMSSGGSNLQSGSFRTVGFTTPFNFSNGSSVFTLSAHVFNSGNE | VYIDRIEFVPAE | VTFEAEYDLERAQK |
| FR8a | 527 | RYRVR IRYAS | TTNLQFHTSIDGRPINQGNFSATMSSGGSNLQSGSFRTVGFTTPFNFSNGSSVFTLSAHVFNSGNE | VYIDRIEFVPAE | VTFEAEYDLERAQK |
| FR-9F-catg | 526 | RYRVR IRYAS | TTNLQFHTSIDGRPINQGNFSATMSSGGSNLQSGSFRTVGFTTPFNFSNGSSVFTLSAHVFNSGNE | VYIDRIEFVPAE | VTFEAEYDLERAQK |
| cap8AFdm3T | 527 | RYRVR IRYAS | TTNLQFHTSIDGRPINQGNFSATMSSGGSNLQSGSFRTVGFTTPFNFSNGSSVFTLSAHVFNSGNE | VYIDRIEFVPAE | VTFEAEYDLERAQK |
| FRCG | 526 | RYRVR IRYAS | TTNLQFHTSIDGRPINQGNFSATMSSGGSNLQSGSFRTVGFTTPFNFSNGSSVFTLSAHVFNSGNE | VYIDRIEFVPAE | VTFEAEYDLERAQK |
| DM23A | 527 | RYRVR IRYAS | TTNLQFHTSIDGRPINQGNFSATMSSGGSNLQSGSFRTVGFTTPFNFSNGSSVFTLSAHVFNSGNE | VYIDRIEFVPAE | VTFEAEYDLERAQK |
| 2OL-8A | 542 | RYRVR IRYAS | TTNLQFHTSIDGRPINQGNFSATMSSGGSNLQSGSFRTVGFTTPFNFSNGSSVFTLSAHVFNSGNE | VYIDRIEFVPAE | VTFEAEYDLERAQK |
| 8AFdm3 | 514 | RYRVR IRYAS | TTNLQFHTSIDGRPINQGNFSATMSSGGSNLQSGSFRTVGFTTPFNFSNGSSVFTLSAHVFNSGNE | VYIDRIEFVPAE | VTFEAEYDLERAQK |
| FR8a +34 | 561 | RYRVR IRYAS | TTNLQFHTSIDGRPINQGNFSATMSSGGSNLQSGSFRTVGFTTPFNFSNGSSVFTLSAHVFNSGNE | VYIDRIEFVPAE | VT----------- |
| FR-12-cg-dm3 | 514 | RYRVR IRYAS | TTNLQFHTSIDGRPINQGNFSATMSSGGSNLQSGSFRTVGFTTPFNFSNGSSVFTLSAHVFNSGNE | VYIDRIEFVPAE | VT----------- |
| 9F-cg-dm3 | 526 | RYRVR IRYAS | TTNLQFHTSIDGRPINQGNFSATMSSGGSNLQSGSFRTVGFTTPFNFSNGSSVFTLSAHVFNSGNE | VYIDRIEFVPAE | VTFEAEYDLERAQK |
| Cap8AFdm3 | 527 | RYRVR IRYAS | TTNLQFHTSIDGRPINQGNFSATMSSGGSNLQSGSFRTVGFTTPFNFSNGSSVFTLSAHVFNSGNE | VYIDRIEFVPAE | VT----------- |
| 5*V4F | 527 | RYRVR IHYAS | TSQITFTLSLDGAPFNQYYFDKTINKGDTLTYNSFNLASFSTPFELSGNN--LQIGVTGLSAGDK | VYIDKIEFIPVN | ------------- |
| V3A | 512 | KYRA3IHYAS | TSQITFTLSLDGAPFNQYYFDKTINKGDTLTYNSFNLASFSTPFELSGNN--LQIGVTGLSAGDK | VYIDKIEFIPVN | ------------- |

| 8AF | 615 | AVNELFTSSNQIGLKTDVTDYHIDQV |
| 8AFdm3T | 615 | AVNELFTSSNQIGLKTDVTDYHIDQV |
| -CatG8AF | 614 | AVNELFTSSNQIGLKTDVTDYHIDQV |
| FR8a-9F | 628 | AVNELFTSSNQIGLKTDVTDYHIDQV |
| FR8a-12 AA | 616 | AVNELFTSSNQIGLKTDVTDYHIDQV |
| FR8a | 628 | AVNELFTSSNQIGLKTDVTDYHIDQV |
| FR-9F-catg | 627 | AVNELFTSSNQIGLKTDVTDYHIDQV |
| cap8AFdm3T | 628 | AVNELFTSSNQIGLKTDVTDYHIDQV |
| FRCG | 627 | AVNELFTSSNQIGLKTDVTDYHIDQV |
| DM23A | 628 | AVNELFTSSNQIGLKTDVTDYHIDQV |
| 2OL-8A | 643 | AVNELFTSSNQIGLKTDVTDYHIDQV |
| 8AFdm3 | 603 | -------------------------- |
| FR-12-cg-dm3 | 662 | AVNELFTSSNQIGLKTDVTDYHIDQV |
| 9F-cg-dm3 | 603 | -------------------------- |
| Cap8AFdm3 | 615 | -------------------------- |
| 5*V4F | 628 | -------------------------- |
| V3A | 610 | -------------------------- |
|  | 595 | -------------------------- |

INSECTICIDAL PROTEINS

This application is a §371 of PCT/US2008/058182, filed Mar. 26, 2008 and published as International Publication No. WO2008/121633 on Oct. 9, 2008, which claims the benefit of U.S. Provisional Application No. 60/920,493, filed Mar. 28, 2007, both of which are incorporated herein by reference in their entirety.

BACKGROUND

The present invention relates to the fields of protein engineering, plant molecular biology and pest control. More particularly the invention relates to novel engineered hybrid proteins having insecticidal activity, nucleic acids whose expression results in the insecticidal proteins, and methods of making and methods of using the insecticidal proteins and corresponding nucleic acids to control insects.

Insect pests are a major cause of crop losses. In the US alone, billions of dollars are lost every year due to infestation by various genera of insects. In addition to losses in field crops, insect pests are also a burden to vegetable and fruit growers, to producers of ornamental flowers, and they are a nuisance to gardeners and homeowners.

Species of corn rootworm are considered to be the most destructive corn pests. In the United States, the three important species are *Diabrotica virgifera virgifera*, the western corn rootworm, *D. longicornis barberi*, the northern corn rootworm and *D. udecimpunctata howardi*, the southern corn rootworm. Only western and northern corn rootworms are considered primary pests of corn in the US Corn Belt. An important corn rootworm pest in the Southern US is the Mexican corn rootworm, *Diabrotica virgifera zeae*. Corn rootworm larvae cause the most substantial plant damage by feeding almost exclusively on corn roots. This injury has been shown to increase plant lodging, to reduce grain yield and vegetative yield as well as alter the nutrient content of the grain. Larval feeding also causes indirect effects on corn by opening avenues through the roots for bacterial and fungal infections which lead to root and stalk rot diseases. Adult corn rootworms are active in cornfields in late summer where they feed on ears, silks and pollen, thus interfering with normal pollination.

Corn rootworms are mainly controlled by intensive applications of chemical pesticides, which are active through inhibition of insect growth, prevention of insect feeding or reproduction, or cause death. Good corn rootworm control can thus be reached, but these chemicals can sometimes also affect other, beneficial organisms. Another problem resulting from the wide use of chemical pesticides is the appearance of resistant insect varieties. Yet another problem is due to the fact that corn rootworm larvae feed underground thus making it difficult to apply rescue treatments of insecticides. Therefore, most insecticide applications are madeprophylactiealiy at the time of planting. This practice results in a large environmental harden. This has been partially alleviated by various farm management practices, but there is an increasing need for alternative pest control mechanisms.

Biological pest control agents, such as *Bacillus thuringiensis* (Bt) strains expressing pesticidal toxins like δ-endotoxins (delta-endotoxins; also called crystal toxins or Cry proteins), have also been applied to crop plants with satisfactory results against primarily lepidopteran insect pests. The δ-endotoxins are proteins held within a crystalline matrix that are known to possess insecticidal activity when ingested by certain insects. The various δ-endotoxins have been classified based upon their spectrum of activity and sequence homology. Prior to 1990, the major classes were defined by their spectrum of activity with the Cry1 proteins active against *Lepidoptera* (moths and butterflies), Cry2 proteins active against both *Lepidoptera* and *Diptera* (flies and mosquitoes), Cry3 proteins active against *Coleoptera* (beetles) and Cry4 proteins active against *Diptera* (Hofte & Whitely, 1989, Microbiol. Rev. 53:242-255). A new nomenclature was developed in 1998 which systematically classifies the Cry proteins based on amino acid sequence homology rather than insect target specificities (Crickmore et al 1998, Microbiol. Molec. Biol. Rev. 62:807-813).

The spectrum of insecticidal activity of an individual δ-endotoxin from Bt is quite narrow, with a given δ-endotoxin being active against only a few species within an Order. For instance, a Cry3A toxin is known to be very toxic to die Colorado potato beetle, *Leptinotarsa decemlineata*, but has very little or no toxicity to related beetles in the genus *Diabrotica* (Johnson et al., 1993, J. Econ. Entomol. 86:330-333). According to Slaney et al (1992, Insect Biochem. Molec. Biol. 22:9-1.8) a Cry3A toxin is at least 2000 times less toxic to southern corn rootworm larvae than to the Colorado potato beetle. It is also known that Cry3A has little or no toxicity to the western corn rootworm or northern corn rootworm.

Specificity of the δ-endotoxins is the result of the efficiency of the various steps involved in producing an active toxic protein and its subsequent interaction with the epithelial cells in an insect mid-gut. To be insecticidal, most known δ-endotoxins must first be ingested by the insect and proteolytically activated to form an active toxin. Activation of the insecticidal crystal (Cry) proteins is a multi-step process. After ingestion, the crystals must first be solubilized in the insect gut. Once solubilized, the δ-endotoxins are activated by specific proteolytic cleavages. The proteases in the insect gut can play a role in specificity by determining where the δ-endotoxin is processed. Once the δ-endotoxin has been solubilized and processed it binds to specific receptors on the surface of the insects' mid-gut epithelium and subsequently integrates into the lipid bilayer of the brush border membrane. Ion channels then form disrupting the normal function of the midgut eventually leading to the death of the insect.

In *Lepidoptera*, which have alkaline pH guts, gut proteases process δ-endotoxins for example, Cry1Aa, Cry 1Ab, Cry1Ac, Cry1B and Cry1F, from 130-140 kDa protoxins to toxic proteins of approximately 60-70 kDa, Processing of the protoxin to toxin has been reported to proceed by removal of both N- and C-terminal amino acids with the exact location of processing being dependent on the specific δ-endotoxin and the specific insect gut fluids involved (Ogiwara et al., 1992, J. Invert. Pathol. 60:121-126). Thus activation requires that the entire C-terminal protoxin tail region be cleaved off. This proteolytic activation of a δ-endotoxin can play a significant role in determining its specificity.

Coleopteran insects have guts that are more neutral to acidic and coleopteran-specific δ-endotoxins are similar to the size of the activated lepidopteran-specific toxins. Therefore, the processing of coleopteran-specific δ-endotoxins was formerly considered unnecessary for toxicity. However, data suggests that coleopteran-active δ-endotoxins are solubilized and proteolyzed to smaller toxic polypeptides. A 73 kDa Cry3A δ-endotoxin protein produced by *B. thuringiensis* var. *tenebrionis* is readily processed in the bacterium at the N-terminus, losing 49-57 residues during or after crystal formation to produce the commonly isolated 67 kDa form (Carroll et al., 1989, Biochem. J. 261:99-1.05). McPherson et al., (1988, Biotechnology 6:61-66) also demonstrated that a native cry3A coding sequence contains two functional translational initiation codons in the same reading frame, one coding for a 73 kDa protein and the other coding for a 67 kDa protein starting at Met-1 and Met-48 respectively, of the deduced amino acid sequence. Both proteins then can be considered naturally occurring full-length Cry3A proteins.

As more knowledge has been gained as to how the δ-endotoxins function, attempts to engineer δ-endotoxins to have new activities have increased. Engineering δ-endotoxins was made more possible by solving the three dimensional structure of Cry3A in 1991 (Li et al., 1991, Nature 353:815-821). Li et al. determined that a Cry3A protein has three structural domains: die N-terminal domain I, from residues 58-290, consists of 7α-helices, domain II, from residues 291-500, contains three β-sheets in a so-called Greek key-conformation, and the C-terminal domain III, from residues 501-644, is a β-sandwich in a so-called jellyroll conformation. The three dimensional structure for the lepidopteran active Cry1Aa toxin has also been solved (Grochulski et al., 1995, J. Mol. Biol. 254:447-464). The Cry1Aa toxin also has three domains: the N-terminal domain I, from residues 33-253, domain II from residues 265-461, and domain III from residues 463-609 with an additional outer strand in one of the β-sheets from by residues 254-264. If the Cry3A and Cry1Aa structures are projected on other Cry1 sequences, domain I runs from about amino acid residue 28 to 260, domain II from about 260 to 460 and domain III from about 460 to 600. See, Nakamura et al., Agric. Biol. Chem. 54(3): 715-724 (1990); Li et al, Nature 353:815-821 (1991); Ge et al, 1. Biol. Chem. 266(27): 17954-17958 (1991); and Honee et al., Mol. Microbiol. 5(11): 2799-2806 (1991); each of which are incorporated herein by reference. Thus, it is now known that based on amino acid sequence homology, known Bt S-endotoxins have a similar three-dimensional structure comprising three domains.

The toxin portions of Bt Cry proteins are also characterized by having five conserved blocks across their amino acid sequence numbered CB1 to CB5 from N-terminus to C-terminus, respectively (Hofte & Whiteley, supra). Conserved block 1 (CB1) comprises approximately 29 amino acids, conserved block 2 (CB2) comprises approximately 67 amino acids, conserved block 3 (CB3) comprises approximately 48 amino acids, conserved block 4 (CB4) comprises approximately 10 amino acids and conserved block 5 (CB5) comprises approximately 12 amino acids. The sequences before and after these five conserved blocks are highly variable and thus are designated the "variable regions," V1-V6. Domain 1 of a Bt δ-endotoxin typically comprises variable region 1, conserved block 1, variable region 2, and the N-terminal 52 amino acids of conserved block 2. Domain II typically comprises approximately the C-terminal 15 amino acids of conserved block 2, variable region 3, and approximately the N-terminal 10 amino acids of conserved block 3, Domain III typically comprises approximately the C-terminal 38 amino acids of conserved block 3, variable region 4, conserved block 4, variable region 5, and conserved block 5. The Cry1 lepidopteran active toxins, among other delta-endotoxins, have a variable region 6 with approximately 1-3 amino acids lying within domain III.

Many Bt strains and δ-endotoxins are active against different insect species and nematodes. However, relatively few of these strains and toxins have activity against coleopteran insects. Further, most of the now known native coleopteran-active δ-endotoxins, for example Cry3A, Cry3B, Cry3C, Cry7A, Cry8A, Cry8B, and Cry8C, have insufficient oral toxicity against corn rootworm to provide adequate field control if delivered, for example, through microbes or transgenic plants. Therefore, other approaches for producing novel toxins active against corn rootworm need to be explored.

Lepidopteran-active δ-endotoxins have been engineered in attempts to improve specific activity or to broaden the spectrum of insecticidal activity. For example, the silk moth (*Bombyx mori*) specificity domain from a Cry1Aa protein was moved to a Cry1Ac protein, thus imparting a new insecticidal activity to the resulting hybrid Bt protein (Ge et al. 1989, PNAS 86:4037-4041). Also, Bosch et al. 1998 (U.S. Pat. No. 5,736,131, incorporated herein by reference) describes *Bacillus thuringiensis* hybrid toxins comprising at their C-terminus domain III of a first Cry protein and at its N-terminus domains I and II of a second Cry protein. Such hybrid toxins were shown to have altered insecticidal specificity against lepidopteran insects. For example, the H04 hybrid toxin, which is also described in De Maagd et al., Appl. Environ. Microbiol. 62(5): 1537-1543 (1996), comprises at its N-terminus domains I and II of a Cry1Ab and at its C-erminus domain III of a Cry1C. H04 is reportedly highly toxic to the lepidopteran insect *Spodoptera exigua* (beet armyworm) compared with the parental Cry1Ab toxin and significantly more toxic than the Cry1C parental toxin, it has also been shown that substitution of domain III of toxins, which are not active against the beet armyworm such as Cry1E and Cry1Ab, by domain III of Cry1C, which is active against beet armyworm, can produce hybrid toxins that are active against this insect. Ail of the hybrids disclosed in Bosch et al, use domains from lepidopteran active Cry proteins to make new toxins with lepidopteran activity. The results do suggest that domain III of Cry1C is an important determinant of specificity for beet armyworm. See also, Bosch et al., *FEMS Microbiology Letters* 118:129-134 (1994); Bosch et al., Bio/Technology 12:915-918 (1994); De Maagd et al, Appl. Environ. Microbiol. 62(8): 2753-2757 (1996); and De Maagd et al., *Mol. Microbiol.* 31(2); 463-471 (1999); each of which is incorporated herein by reference.

Several attempts at engineering the coleopteran-active δ-endotoxins have been reported. Chen and Stacy (U.S. Pat. No. 7,030,295, herein incorporated by reference) successfully created a corn rootworm active toxin by inserting a non-naturally occurring protease recognition site in domain I, domain III, or both domains II and of a Cry3A protein. One of the resulting modified Cry3A proteins, designated Cry3A055, having a protease recognition site inserted in domain I, was active against several species of *Diabrotica* Van Rie et al, 1997, (U.S. Pat. No. 5,659,123) engineered Cry3A by randomly replacing amino acids, thought to be important in solvent accessibility, in domain II with the amino acid alanine. Several of these random replacements confined to domain II were reportedly involved in increased western corn rootworm toxicity. However, others have shown that some alanine replacements in domain II of Cry3A result in disruption of receptor binding or structural instability (Wo and Dean, 1996, J. Mol. Biol. 255; 628-640). English et al., 1999, (Intl. Pat. Appl. Publ. No. WO99/31248) reported amino acid substitutions in Cry3Bb that caused increases in toxicity to southern and western corn rootworm. However, of the 35 reported Cry3Bb mutants, only three, with mutations primarily in domain II and the domain I-domain II interface, were active against western corn rootworm. Further, the variation in toxicity of wild-type Cry3Bb against western corn rootworm in the same assays appear to be greater than any of the differences between the mutated Cry3Bb toxins and the wild-type Cry3Bb. Shadenkov et al. (1993, Mol. Biol. 27:586-591), made a hybrid protein by fusing amino acids 48-565 of a Cry3A protein to amino acids 526-725 of a Cry1Aa protein. Therefore, the cross-over between Cry3A and Cry1Aa sequence was in conserved block 4 located in domain III. Cry3A is very active against the Colorado potato beetle (*Leptinotarsa decemlineata*). However, the hybrid protein disclosed by Shadenkov et al. was not active against Colorado potato beetle even though more than 75% of the hybrid protein was made up of Cry3A sequence. Thus, the addition of only 25% of Cry1Aa sequence destroyed activity against a coleopteran insect that the parent Cry3A was active against. This suggests that hybrid proteins made by fusing portions of a coleopteran-active Cry protein, e.g. Cry3A, and a lepidopteran-active Cry protein, e.g. Cry1A, would not have activity against coleopteran insects, particularly a coleopteran insect that is not naturally susceptible to Cry3A like corn rootworm.

In view of the above discussion, there remains a need to design new and effective pest control agents that provide an economic benefit to farmers and that are environmentally acceptable. Particularly needed are proteins that are toxic to *Diabrotica* species, a major pest of corn, that have a different mode of action than existing insect control products as a way to mitigate the development of resistance. Furthermore, delivery of control agents through products that minimize the burden on the environment, as through transgenic plants, are desirable.

SUMMARY

In view of these needs, it is an object of the present invention to provide novel engineered hybrid insecticidal proteins (eHIPs). Such novel eHIPs are made by fusing unique combinations of variable regions and conserved blocks of at least two different Cry proteins and optionally including a protoxin tail region from a Bt Cry protein at the C-terminus or an N-terminal peptidyl fragment or both. For example, without limitation, by combining complete or partial variable regions and conserved blocks from a first Cry protein that has coleopteran activity with complete or partial variable regions and conserved blocks from a second Cry protein that has lepidopteran activity, and is different from tire first Cry protein, and optionally including a protoxin tail region from a lepidopteran active Bt Cry protein, or an N-terminal peptidyl fragment or both, new engineered hybrid insecticidal proteins are created that have activity against a spectrum of insects different from the first or second parent Cry proteins or both. Such novel eHIPs may comprise complete or partial variable regions, conserved blocks or domains from a modified Cry3A protein and a Cry protein different from the modified Cry3A protein. The peptidyl fragment may confer insecticidal activity upon the eHIP, or may increase the insecticidal activity of the eHIP over an eHIP without the peptidyl fragment, or make the eHIP more stable than an eHIP without the peptidyl fragment. The eHIPs of the invention have surprising and unexpected toxicity to corn rootworm (*Diabrotica* sp.). The invention is further drawn to nucleic acids that encode the eHIPs or which is complementary to one which hybridizes under stringent conditions with the recombinant hybrid nucleic acids according to the invention.

Also included in the invention are vectors containing such recombinant (or complementary thereto) nucleic acids; a plant or micro-organism which includes, and enables expression of such nucleic acids; plants transformed with such nucleic acids, for example transgenic corn plants; the progeny of such plants which contain, the nucleic acids stably incorporated and heritable in a Mendelian manner, and/or the seeds of such plants and such progeny.

The invention also includes compositions and formulations containing the eHIPs, which are capable of inhibiting the ability of insect pests to survive, grow and reproduce, or of limiting insect-related damage or loss to crop plants, for example applying the eHIPs or compositions or formulations to insect-infested areas, or to prophylactically treat insect-susceptible areas or plants to confer protection against the insect pests.

The invention is further drawn to a method of making the eHIPs and to methods of using the nucleic acids, for example in microorganisms to control insects or in transgenic plants to confer protection from insect damage.

The novel eHIPs described herein are highly active against insects. For example, the eHIPs of the present invention can be used to control economically important insect pests such as western corn rootworm (*Diabrotica virgifera virgifera*) northern corn rootworm (*D. longicornis barberi*) and Mexican corn rootworm (*D. virgifera zeae*). Certain eHIPs may also be used to control European corn borer (*Ostrinia nubalalis*) and other lepidopteran insects. The eHIPs can be used singly or in combination with other insect control strategies to confer maximal pest control efficiency with minimal environmental impact.

Other aspects and advantages of the present invention will become apparent to those skilled in the art from a study of the following description of the invention and non-limiting examples.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A-1E shows a sequence alignment of some eHIP embodiments with parental Cry proteins or modified Cry 3A used to construct the eHIPs, including, a Cry3A, Cry1Ab, and Cry3A055, and indicates percent identity. N-terminal peptidyl fragments are underlined. The 5 conserved blocks are labeled CB1-CB5. Location of junctions between domains I, II and III are designated by a vertical dashed line. A cathepsin G protease recognition sequence, AAPF, is in bold.

FIG. 2A-2E shows an alignment of eHiP embodiments that are active against at least western corn rootworm and indicates percent identity compared to the SAP eHiP. N-terminal peptidyl fragments are single underlined. C-terminal protoxin tail regions are double underlined. The 5 conserved blocks are labeled CB1-CB5. Locations of junctions between domains I, II and III axe indicated by "↓" and labeled accordingly. Locations of crossover positions are indicted by a"◆". A cathepsin G protease recognition sequence, AAPF, is in bold.

BRIEF DESCRIPTION OF TEE SEQUENCES IN THE SEQUENCE LISTING

Figure 3:
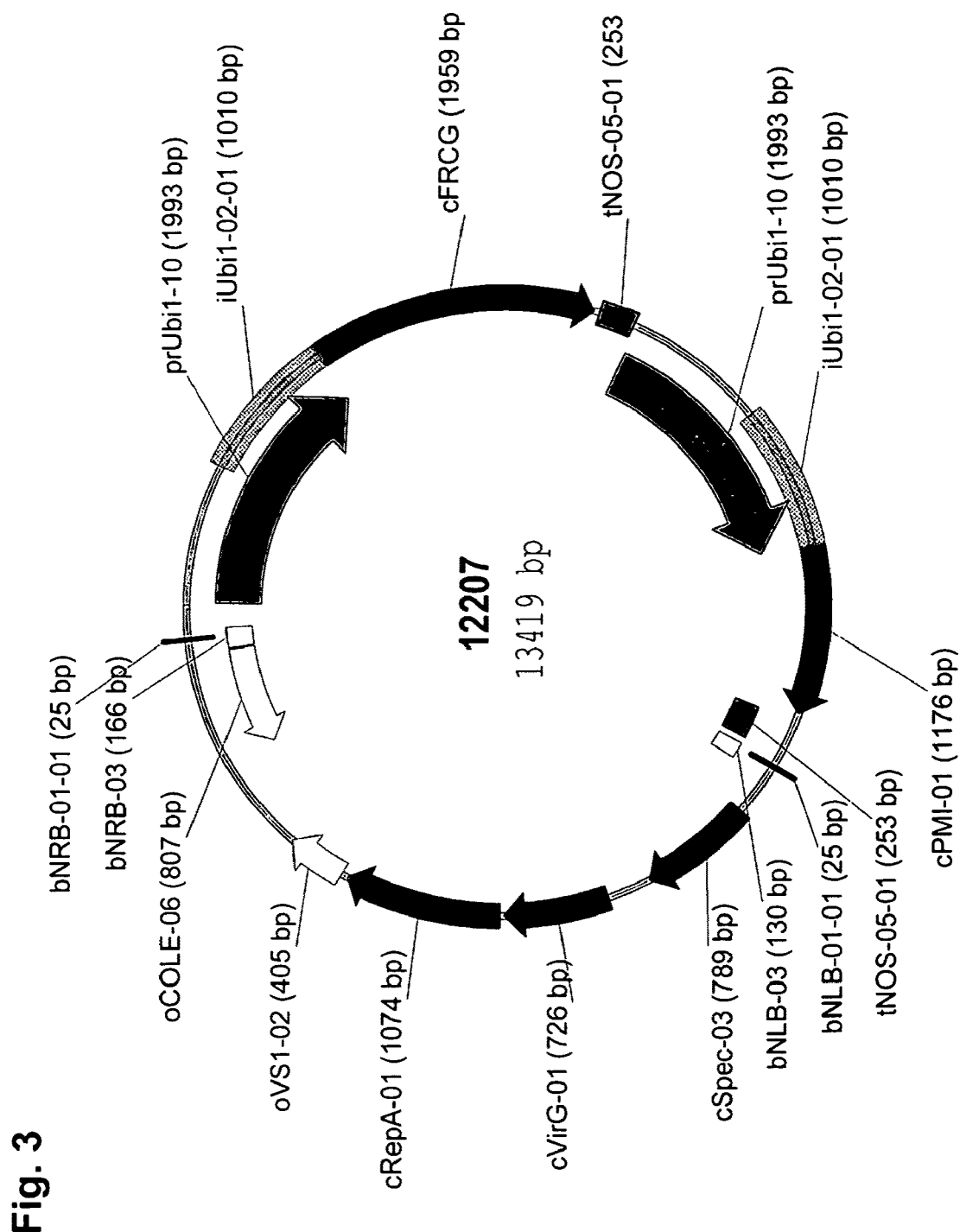
FIG. 3 shows a map of recombinant vector 12207 used to transform corn comprising an expression cassette with a maize ubiquitin promoter operably linked to a FRCG coding sequence operably linked to a NOS terminator.

SEQ ID NO: 1 is the 2OL-8a nucleotide sequence,
SEQ ID NO: 2 is the 2OL-8a encoded by SEQ ID NO: 1.
SEQ ID NO: 3 is the FR8a nucleotide sequence,
SEQ ID NO: 4 is the FR8a encoded by SEQ ID NO: 3.
SEQ ID NO: 5 is the FRCG nucleotide sequence.
SEQ ID NO: 6 is the FRCG encoded by SEQ ID NO: 5,
SEQ ID NO: 7 is the FR8a-9F nucleotide sequence.
SEQ ID NO: 8 is the FR8a-9F encoded by SEQ ID NO: 7.
SEQ ID NO: 9 is the FR-9F-catg nucleotide sequence.
SEQ ID NO: 10 is the FR-9F-catg encoded by SEQ ID NO: 9.
SEQ ID NO: 11 is the FR8a-12AA nucleotide sequence.
SEQ ID NO: 12 is the FR8a-12AA encoded by SEQ ID NO: 11.
SEQ ID NO: 13 is the WR-9mut nucleotide sequence.
SEQ ID NO: 14 is the WR-9mut encoded by SEQ ID NO: 13.
SEQ ID NO: 15 is the FRD3 nucleotide sequence.
SEQ ID NO: 16 is the FRD3 encoded by SEQ ID NO: 15.
SEQ ID NO: 17 is the FR-12-cg-dm3 nucleotide sequence.
SEQ ID NO: 18 is the FR-12-cg-dm3 encoded by SEQ ID NO: 17.
SEQ ID NO: 19 is the 9F-cg-del6 nucleotide sequence.
SEQ ID NO: 20 is the 9F-cg-del6 encoded by SEQ ID NO: 19.
SEQ ID NO: 21 is the FR-cg-dm3 nucleotide sequence.
SEQ ID NO: 22 is the FR-cg-dm3 encoded by SEQ ID NO: 21.
SEQ ID NO: 23 is the 9F-cg-dm3 nucleotide sequence.
SEQ ID NO: 24 is the 9F-cg-dm3 encoded by SEQ ID NO: 23.
SEQ ID NO: 25 is the B8a nucleotide sequence.
SEQ ID NO: 26 is the B8a encoded by SEQ ID NO: 25.
SEQ ID NO: 27 is the 5*B8a nucleotide sequence.
SEQ ID NO: 28 is the 5*B8a encoded by SEQ ID NO: 27.
SEQ ID NO: 29 is the V3A nucleotide sequence.
SEQ ID NO: 30 is the V3A encoded by SEQ ID NO: 29.
SEQ ID NO: 31 is the V4F nucleotide sequence.
SEQ ID NO: 32 is the V4F encoded by SEQ ID NO: 33.
SEQ ID NO: 33 is the 5*V4F nucleotide sequence.
SEQ ID NO: 34 is the 5*V4F encoded by SEQ ID NO: 33.
SEQ ID NO: 35 is the 2OL-7 nucleotide sequence,
SEQ ID NO: 36 is the 2OL-7 encoded by SEQ ID NO: 35.
SEQ ID NO: 37 is the T7-2OL-7 nucleotide sequence.
SEQ ID NO: 38 is the T7-2OL-7 encoded by SEQ ID NO: 37.
SEQ ID NO: 39 is the 5*2OL-7 nucleotide sequence.
SEQ ID NO: 40 is the 5*2OL-7 encoded by SEQ ID NO: 39.
SEQ ID NO: 41 is the 2OL-10 nucleotide sequence.
SEQ ID NO: 42 is the 2OL-10 encoded by SEQ ID NO: 41.
SEQ ID NO: 43 is the 5*2OL-10 nucleotide sequence.
SEQ ID NO: 44 is the 5*2OL-10 encoded by SEQ ID NO: 43.
SEQ ID NO: 45 is the 2OL-12A nucleotide sequence.
SEQ ID NO: 46 is the 2OL-12A encoded by SEQ ID NO: 45.
SEQ ID NO: 47 is the 2OL-13 nucleotide sequence.
SEQ ID NO: 48 is the 2OL-13 encoded by SEQ ID NO: 47.
SEQ ID NO: 49 is the V5 &6 nucleotide sequence.
SEQ ID NO: 50 is the V5&6 encoded by SEQ ID NO: 49.
SEQ ID NO: 51 is the 5*V5&6 nucleotide sequence.
SEQ ID NO: 52 is the 5*V5&6 encoded by SEQ ID NO: 51.
SEQ ID NO: 53 is the 88A-dm3 nucleotide sequence.
SEQ ID NO: 54 is the 88A-dm3 encoded by SEQ ID NO: 53.
SEQ ID NO: 55 is the FR(1Fa) nucleotide sequence.
SEQ ID NO: 56 is the FR(1Fa) encoded by SEQ ID NO: 55.
SEQ ID NO: 57 is the FR(1Ac) nucleotide sequence.
SEQ ID NO: 58 is the FR(1Ac) encoded by SEQ ID NO: 57.
SEQ ID NO: 59 is the FR(1Ia) nucleotide sequence.
SEQ ID NO: 60 is the FR(1Ia) encoded by SEQ ID NO: 59.
SEQ ID NO: 61 is the DM23A nucleotide sequence.
SEQ ID NO: 62 is the DM23A encoded by SEQ ID NO: 61.
SEQ ID NO: 63 is the 8AF nucleotide sequence.
SEQ ID NO: 64 is the 8 AF encoded by SEQ ID NO: 63
SEQ ID NO: 65 is the 5*cry3A055 nucleotide sequence.
SEQ ID NO: 66 is the 5*Cry3A055 encoded by SEQ ID NO: 65.
SEQ ID NO: 67 is a maize optimized cry3Ab nucleotide sequence.
SEQ ID NO: 68 is the Cry3A encoded by SEQ ID NO: 67.
SEQ ID NO: 69 is the cry3A055 nucleotide sequence.
SEQ ID NO: 70 is the Cry3A055 encoded by SEQ ID NO: 69.
SEQ ID NO: 71 is a maize optimized cry1Ab nucleotide sequence.
SEQ ID NO: 72 is the Cry1Ab encoded by SEQ ID NO: 71.
SEQ ID NO: 73 is a maize optimized cry1Ba nucleotide sequence.
SEQ ID NO: 74 is the Cry1Ba encoded by SEQ ID NO: 73.
SEQ ID NO: 75 is a maize optimized cry 1 Fa nucleotide sequence.
SEQ ID NO: 76 is the Cry1 Fa encoded by SEQ ID NO: 75.
SEQ ID NO: 77 is a cry8Aa nucleotide sequence.
SEQ ID NO: 78 is the Cry3Aa encoded by SEQ ID NO: 77.
SEQ ID NO: 79 is a cry1Ac nucleotide sequence,
SEQ ID NO: 80 is the Cry1Ac encoded by SEQ ID NO: 79.
SEQ ID NO: 81 is a cry1Ia nucleotide sequence.
SEQ ID NO: 82 is the Cry1Ia encoded by SEQ ID NO: 81.
SEQ ID NOs 83-125 are primer sequences useful in the present invention.
SEQ ID NOs 126-134 are N-terminal peptidyl fragments.
SEQ ID NO: 135 is a full-length Cry3A protein.
SEQ ID NO: 136-143 are primer sequences useful in the present invention.
SEQ ID NO: 144 is the T7-8AF coding sequence.
SEQ ID NO: 145 is the T7-8AF encoded by A SEQ ID NO: 144.
SEQ ID NO: 146 is the -catG8AF coding sequence.
SEQ ID NO: 147 is the -CatG8AF encoded by SEQ ID NO: 146.
SEQ ID NO: 148 is the 8AFdm3 coding sequence.
SEQ ID NO: 149 is the 8AFdm3 encoded by SEQ ID NO: 148.
SEQ ID NO: 150 is the 8AFlongdm3 coding sequence.
SEQ ID NO: 151 is the 8AFlongdm3 encoded by SEQ ID NO: 150.
SEQ ID NO: 152 is the cap8AFdm3 coding sequence.
SEQ ID NO: 153 is the cap8AFdm3 encoded by SEQ ID NO: 152.
SEQ ID NO: 154 is the 8AFdm3T coding sequence.
SEQ ID NO: 155 is the 8AFdm3T encoded by SEQ ID NO: 154.
SEQ ID NO: 156 is the 8AFlongdm3T coding sequence.
SEQ ID NO: 157 is the 8AFlongdm3T encoded by SEQ ID NO: 156.

SEQ ID NO: 158 is the cap8AFdm3T coding sequence.
SEQ ID NO: 159 is the cap8AFdm3T encoded by SEQ ID NO: 158.
SEQ ID NO: 160 is the FR8a+34 eHIP.

Definitions

For clarity, certain terms used in the specification are defined and presented as follows:

"Activity" of the eHIPs of the invention is meant that the eHIPs function as orally active insect control agents, have a toxic effect, or are able to disrupt or deter insect feeding, which may or may not cause death of the insect. When an eHIP of the invention is delivered to the insect, the result is typically death of the insect, or the insect does not feed upon the source that makes the eHIP available to the insect.

"Associated with/operatively linked" refer to two nucleic acids that are related physically or functionally. For example, a promoter or regulatory DNA sequence is said to be "associated with" a DNA sequence that codes for RNA or a protein if the two sequences are operatively linked, or situated such that the regulatory DNA sequence will affect the expression level of the coding or structural DNA sequence.

In the context of the present invention, a "chimeric insecticidal protein" (CIP) is an insecticidal protein comprising a peptidyl fragment fused to the N-terminus of an eHIP. The peptidyl fragment may confer insecticidal activity upon the eHIP, may increase the insecticidal activity of the eHIP over an eHIP without the peptidyl fragment, or may make the eHIP more stable than an eHIP without the peptidyl fragment, particularly against at least western corn rootworm. The peptidyl fragment is an amino acid sequence that is typically heterologous to (not derived from) a Bt Cry protein but may be derived from a Bt Cry protein. Such peptidyl fragments extend from the N-terminus of the insecticidal protein and do not naturally occur at the N-terminus of Bt Cry proteins. One example of an N-terminal peptidyl fragment has the amino acid sequence MTSNGRQCAGIRP(SEQ ID NO: 129) which is not derived from a Bt Cry protein.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

In the context of the present invention, "connecting" nucleic acids means to join two or more nucleic acids together using any means known in the art. For example, without limitation, the nucleic acids may be ligated together using for example, DNA ligase, or may be annealed using PCR. The nucleic acids may also be joined by chemically synthesizing a nucleic acid using the sequence of two or more separate nucleic acids.

To "control" insects means to inhibit, through a toxic effect, the ability of insect pests to survive, grow, feed, and/or reproduce, or to limit insect-related damage or loss in crop plants. To "control" insects may or may not mean killing the insects, although it preferably means killing the insects.

In the context of the present invention, "corresponding to" means that when the amino acid sequences of certain proteins (for example Bt Cry proteins or modified Cry3A proteins) are aligned with each other, the amino acids that align with certain enumerated positions in for example, but not limited to, a Cry3A toxin (either SEQ ID NO: 68 or SEQ ID NO: 134); a Cry3A055 toxin (SEQ ID NO: 70); or a Cry1Ab toxin (SEQ ID NO: 72), but that are not necessarily in these exact numerical positions relative to the reference amino acid sequence, particularly as it relates to identification of domains I, II and III, and/or the conserved blocks and variable regions, these amino acid positions "correspond to" each other. For example. In delineating Domain I of a hybrid protein, amino acids 11-244 of a Cry3A055 protein (SEQ ID NO: 70) correspond to amino acids 58-290 of a native Cry3A toxin (SEQ ID NO: 135) or to amino acids 11-243 of a native Cry3A toxin (SEQ ID NO: 68) or to amino acids 33-254 of a native Cry1Ab toxin.

In the context of the present invention the words "Cry protein" can be used interchangeably with the words "delta-endotoxin" or "δ-endotoxin"

In the context of the present invention, an "engineered hybrid insecticidal protein" (eHIP) is an insecticidal protein created by fusing unique combinations of variable regions and conserved blocks of at least two different Cry proteins. Such novel eHIPs may comprise complete or partial variable regions, conserved blocks or domains from a modified Cry3A protein and a Cry protein different from the modified Cry3A protein. The eHIPs of the invention may optionally include a protoxin tail region from a Bt Cry protein or an N-terminal peptidyl fragment or both. For example without limitation, an eHIP is created by combining in an N-terminal to C-terminal direction, amino acids 1-468of a Cry3A055 protein (SEQ ID NO: 70), which comprises variable region 1, conserved block 1, variable region 2, conserved block 2, variable region 3, and the N-terminal 24 amino acids of conserved block 3, and amino acids 477-648 of a Cry1Ab protein (SEQ ID NO: 72), which comprises the C-terminal 24 amino acids of conserved block 3, variable region 4, conserved block 4, variable region 5, conserved block 5 and variable region 6, and a 38 amino acid region of a Cry1Ab protoxin tail. An eHIP that comprises an N-terminal peptidyl fragment may also be designated as a "chimeric insecticidal protein (CIP)."

To "deliver" an eHIP means that the eHIP comes in contact with an insect, resulting in a toxic effect and control of the insect. The eHIP may be delivered in many recognized ways, e.g., through a transgenic plant expressing the eHIP, formulated protein compositions), sprayable protein composition(s), a bait matrix, or any other art-recognized toxin delivery system.

"Effective insect-controlling amount" means that concentration of an eHIP that inhibits, through a toxic effect, the ability of insects to survive, grow, feed and/or reproduce, or to limit insect-related damage or loss in crop plants. "Effective insect-controlling amount" may or may not mean killing the insects, although it preferably means killing the insects.

"Expression cassette" as used herein means a nucleic acid sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette comprising the nucleotide sequence of interest may have at least one of its components heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus.

In the case of a multicellular organism, such as a plant, the promoter can also be specific to a particular tissue, or organ, or stage of development.

A "gene" is a defined region that is located within a genome and that, besides the aforementioned coding nucleic acid sequence, comprises other, primarily regulatory, nucleic acids responsible for the control of the expression, that is to say the transcription and translation, of the coding portion. A gene may also comprise other 5' and 3' untranslated sequences and termination sequences. Further elements that may be present are, for example, introns. The regulatory nucleic acid sequence of the gene may not normally be operatively linked to the associated nucleic acid sequence as found in nature and thus would be a chimeric gene.

"Gene of interest" refers to any gene which, when transferred to a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The "gene of interest" may also be one that is transferred to plants for the production of commercially valuable enzymes or metabolites in the plant.

A "heterologous" nucleic acid sequence is a nucleic acid sequence not naturally associated with a host, cell into which it is introduced, including non-naturally occurring multiple copies of a naturally occurring nucleic acid sequence. A heterologous amino acid sequence is one that is not naturally associated with a native amino acid sequence, for example an amino acid sequence of a Cry protein.

A "homologous" nucleic acid sequence is a nucleic acid sequence naturally associated with a host cell into which it is introduced.

"Homologous recombination" is the reciprocal exchange of nucleic acid fragments between homologous nucleic acid molecules.

"Identity" or "percent identity" refers to the degree of similarity between two nucleic acid or protein sequences. For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequencers) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needle-man & Wunsch, *J. Mol. Biol.* 48:443 (1970), by the search for similarity method of Pearson & Lipman, *Proc. Nat'l. Acad. Sci. USA.* 85; 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et ah, infra).

One example of an algorithm that is suitable for determining percent sequence identity and sequence similarity is the BLAST algorithm, which is described in Altschul et al *J. Mol. Biol.* 215:403-410 (1990). Software for performing BLAST analyses is publicly available through the National Center for Biotechnology Information (http://www.ncbi.nlm.nih.gov/). This algorithm Involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990), These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always > 0) and N (penalty score for mismatching residues; always < 0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, 4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Set, USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another widely used and accepted computer program for performing sequence alignments is CLUSTALW v1.6 (Thompson, et al. *Nuc. Acids Res.*, 22: 4673-4680, 1994). The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there were 100 matched amino acids between a 200 and a 400 amino acid proteins, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity.

Another indication that two nucleic acids are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) *Laboratory Techniques in Biochemistry and Molecular Biology-Hybridisation with Nucleic Acid Probes* part I chapter 2 "Overview of principles of hybridization and the strategy of nucleic acid probe assays" Elsevier, New York. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to clone homologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1× SSC, 0.1% SDS at 65° C.

A further indication that two nucleic acids or proteins are substantially identical is that the protein encoded by the first nucleic acid is immunologically cross reactive with, or specifically binds to, the protein encoded by the second nucleic acid. Thus, a protein is typically substantially identical to a second protein, for example, where the two proteins differ only by conservative substitutions.

"Insecticidal" is defined as a toxic biological activity capable of controlling Insects, preferably by killing them.

A nucleic acid sequence is "isocoding with" a reference nucleic acid sequence when the nucleic acid sequence encodes a polypeptide having the same amino acid sequence as the polypeptide encoded by the reference nucleic acid sequence.

An "isolated" nucleic acid molecule or an isolated toxin is a nucleic acid molecule or toxin that, by the hand of man, exists apart from its native environment and is therefore not a product of nature. An isolated nucleic acid molecule or toxin may exist in a purified form or may exist in a non-native environment such as, for example without limitation, a recombinant microbial cell, plant cell, plant tissue, or plant.

A "modified Cry3A toxin" or "Cry3A055" of this invention refers to a Cry3A-derived toxin having at least one additional protease recognition site that is recognized by a gut protease of a target insect, which does not naturally occur in a Cry3A toxin, as described in U.S. Pat. No. 7,030,295, herein incorporated by reference.

A "modified cry3A coding sequence" according to this invention can be derived from a native cry3A coding sequence or from a synthetic cry3A coding sequence and comprises the coding sequence of at least one additional protease recognition site that does not naturally occur in an unmodified cry3A gene.

A "nucleic acid molecule" or "nucleic acid sequence" is a segment of single- or double-stranded DNA or RNA that can be isolated from any source. In the context of the present invention, the nucleic acid molecule is typically a segment of DNA.

A "plant" is any plant at any stage of development, particularly a seed plant.

A "plant cell" is a structural and physiological unit of a plant, comprising a protoplast and a cell wall. The plant cell may be in the form of an isolated single cell or a cultured cell, or as a part of a higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

A "promoter" is an untranslated DNA sequence upstream of the coding region that contains the binding site for RNA polymerase and initiates transcription of the DNA. The promoter region may also include other elements that act as regulators of gene expression.

"Regulatory elements" refer to sequences involved in controlling the expression of a nucleotide sequence. Regulatory elements comprise a promoter operably linked to the nucleotide sequence of interest and termination signals. They also typically encompass sequences required for proper translation of the nucleotide sequence.

"Transformation" is a process for introducing heterologous nucleic acid into a host cell or organism. In particular, "transformation" means the stable integration of a DNA molecule into the genome of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

Nucleotides are indicated by their bases by the following standard abbreviations: adenine (A), cytosine (), thymine (T), and guanine (G). Amino acids are likewise indicated by the following standard abbreviations: alanine (Ala; A), arginine (Arg; R), asparagine (Asn; N) aspartic acid (Asp; D), cysteine (Cys; ), glutamine (Gln; Q), glutamic acid(Glu; E), glycine (Gly; G), histidine (His; H), isoleucine (He; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

DESCRIPTION

This invention relates to novel engineered hybrid insecticidal proteins (eHIPS), created to have activity against at least western corn rootworm, and may further include northern corn rootworm, Mexican corn rootworm, and/or Colorado potato beetle. Some eHIPs have activity against the lepidopteran pest, European corn borer. Such novel eHIPs are made by fusing unique combinations of complete or partial variable regions and conserved blocks of at least two different Cry proteins and optionally include a protoxin tail region from a Bt Cry protein at the C-terminus or an N-terminal peptidyl fragment or both. For example, without limitation, by combining complete or partial variable regions and conserved blocks from a first Cry protein that has coleopteran activity with complete or partial variable regions and conserved blocks from a second Cry protein that has lepidopteran activity and is different from the first Bt Cry protein, and optionally including a protoxin tail region from a Bt Cry protein at the C-terminus or an N-terminal peptidyl fragment or both, new engineered hybrid insecticidal proteins that have activity against a spectrum of insects that is different from the first or second parent Cry protein, or both, is created. Such novel eHIPs may also comprise complete or partial variable regions, conserved blocks or domains from a modified Cry3A protein and a Cry protein different from the modified Cry3A protein. The N-terminal peptidyl fragment or protoxin tail region may confer insecticidal activity upon the eHIP, may increase the insecticidal activity of an eHIP over an eHIP without the peptidyl fragment or protoxin tail region, and/or may make the eHIP more stable than an eHIP without the peptidyl fragment or protoxin tail, region, particularly against at least western corn rootworm. The amino acid sequence of the peptidyl fragment typically is heterologous to (i.e. not derived from) a Bt Cry protein. However, based on the teaching disclosed herein, the skilled person will recognize that an N-terminal peptidyl fragment may be generated using an amino acid sequence derived from a Bt Cry protein. The eHIPs of the invention have surprising and unexpected toxicity to corn rootworm, particularly to western, northern and Mexican corn rootworm. The present invention also relates to nucleic acids whose expression results in eHIPs, and to the making and using of the eHIPs to control insect pests. The expression of the nucleic acids results in eHIPs that can be used to control coleopteran insects such as western, northern or Mexican corn rootworm, or used to control lepidopteran insects such as European corn borer, particularly when expressed in a transgenic plant such as a transgenic corn plant.

In one embodiment, the invention encompasses an engineered hybrid insecticidal protein comprising an amino acid sequence from a first *Bacillus thuringiensis* (Bt) Cry protein comprising complete or partial variable regions and conserved blocks of the first Cry protein fused to an amino acid sequence from a second Bt Cry protein different from the first Bt Cry protein comprising complete or partial variable regions and conserved blocks of the second Cry protein, and optionally comprising; (a) a protoxin tail region of a Bt Cry protein located at the C-terminus; or (b) an N-terminal peptidyl fragment; or both (a) and (b), wherein the eHIP has activity against at least western corn rootworm.

In another embodiment, the present invention encompasses an eHIP comprising an N-terminal region of a first Bt Cry protein fused to a C-terminal region of a second Bt Cry protein different from the first Bt Cry protein, wherein at least one crossover position between the first and the second Bt Cry protein is located in conserved block 2, conserved block 3, variable region 4 or conserved block 4, and optionally comprising: (a) a protoxin tail region of a Bt Cry protein located at the C-terminus; or (b) an N-terminal peptidyl fragment; or both (a) and (b), wherein the eHIP has insecticidal activity against at least western corn rootworm.

In another embodiment, an eHIP according to the invention comprises from N-terminus to C-terminus variable region 1 or a C-terminal portion of variable region 1, conserved block 1, variable region 2, conserved block 2, variable region 3, and an N-terminal portion of conserved block 3 of a first Bt Cry protein fused to a C-terminal portion of conserved block 3, variable region 4, conserved block 4, variable region 5, conserved block 5, and variable region 6 of a second Bt Cry protein.

In another embodiment, an eHIP of the Invention comprises at least two crossover positions between an amino acid sequence from the first Bt Cry protein and an amino acid sequence from the second Bt Cry protein. In one embodiment, a first crossover position is located in conserved block 2 and a second crossover position is located in conserved block 3. In another embodiment, a first crossover junction is located in conserved block 3 and a second crossover position is located in conserved block 4.

In another embodiment, an eHIP of the invention comprises at the C-terminus a protoxin tail region of a Bt. Cry protein. The protoxin tail region may confer insecticidal activity upon the eHIP, meaning that without the protoxin tail region the eHIP would not be active, may increase activity of the eHIP over an eHIP without the protoxin tail region, or may make the eHIP more stable than an eHIP without the protoxin tail region. In one embodiment, the protoxin tail region is from a lepidopteran active Bt Cry protein, in another embodiment, the protoxin tail region is from a Cry1A protein. In yet another embodiment, the protoxin tail region is from a Cry1Aa or a Cry1Ab protein. The protoxin tail region of the invention may comprise an entire protoxin tail of a Bt Cry protein or any fragment thereof. In one aspect of this embodiment, the protoxin tail region of an eHIP comprises at least 38 amino acids from the N-terminus of a protoxin tail of a Cry1Ab protein. In another aspect of this embodiment, the protoxin tail region comprises an amino acid sequence corresponding to amino acids 611-648 of SEQ ID NO: 72. In still another aspect of this embodiment, the protoxin tail region comprises amino acids 611-648 of SEQ ID NO: 72.

In still, another embodiment, an eHIP comprises an N-terminal peptidyl fragment. The N-terminal peptidyl fragment may confer insecticidal activity upon the eHIP, meaning that without the N-terminal peptidyl fragment the protein does not have insecticidal activity, or the N-terminal peptidyl fragment may increase the insecticidal activity of the eHIP over an eHIP without the N-terminal peptidyl fragment, or the N-terminal peptidyl fragment may make the eHIP more stable than an eHIP without an N-terminal peptidyl fragment. In one aspect of this embodiment, the peptidyl fragment comprises an amino acid sequence that is heterologous to (i.e. not derived from) a Bt Cry protein. In another aspect of this embodiment, the N-terminal peptidyl fragment comprises at lest 9 amino acids. In yet another aspect of this embodiment, the peptidyl fragment comprises at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 70, 80, 90 or 100 amino acids. In another aspect of this embodiment, the peptidyl fragment comprises greater than 100 amino acids. In still another aspect of this embodiment, the N-terminal peptidyl fragment comprises the amino acid sequence YDGRQQHRG (SEQ ID NO: 133) or TSNGRQCAGIRP (SEQ ID NO: 134). In yet another aspect of this embodiment, the N-terminal peptidyl fragment comprises an amino acid sequence selected from the group consisting of SEQ ID NO: 126, SEQ ID NO: 127, SEQ ID NO: 1.28, SEQ ID NO: 129, SEQ ID NO: 130, SEQ ID NO: 131, and SEQ ID NO: 132.

In yet another embodiment, the variable regions and conserved blocks of a first Cry protein active against coleopteran insects are used to make the eHIP of the invention in combination with variable regions and conserved blocks of a second Cry protein active against a lepidopteran insect. Coleopteran active Cry proteins include but are not limited to Cry3, Cry7, Cry8, and Cry34/Cry35. The lepidopteran active Cry proteins include but are not limited to Cry1 and Cry9. In one aspect of this embodiment, the first Cry protein is a Cry3A and the second Cry protein is a Cry1A. In another aspect, the Cry3A protein can be replaced with a modified Cry3A, for example without limitation, the Cry3A055 protein disclosed in U.S. Pat. No. 5,659,123, which is herein incorporated by reference. In still another aspect of this embodiment, the Cry3A protein is a Cry3Aa and the Cry1A protein is a Cry1Aa or a Cry1Ab. In another aspect of this embodiment, the Cry3Aa is selected from the following group and has the indicated GenBank Accession Number: Cry3Aa1 (M22472), Cry3Aa2 (J02978), Cry3Aa3 (Y00420), Cry3Aa4 (M30503), Cry3Aa5 (M37207), Cry3Aa6 (U10985), Cry3Aa7 (AJ237900), Cry3Aa8 (AAS79487), Cry3Aa9 (AAW05659), Cry3Aa10 (AAU29411), and Cry3Aa11 (AY882576). In another aspect of this embodiment the Cry1Aa is selected from the following group and has the indicated GenBank Accession Number: Cry1Aa1 (M11250), Cry1Aa2 (M10917), Cry1Aa3 (D00348), Cry1Aa4 (X13535), Cry1Aa5 (D17518), Cry1Aa6 (1143605), Cry1Aa7 (AF081790), Cry 1 Aa8 (I26149), Cry1Aa9 (AB026261), Cry1Aa10 (AF154676), Cry1Aa11 (Y09663), Cry1Aa12 (AF384211), Cry1Aa13 (AF510713), Cry1Aa14 (AY197341), and Cry1Aa15 (DQ062690). In still another aspect of this embodiment, the Cry1Ab is selected from the following group and has the indicated GenBank Accession Number: Cry1Ab1 (M13898), Cry1Ab2 (M12661), Cry1Ab3 (M15271), Cry1Ab4 (D00117), Cry1Ab5 (X04698), Cry1Ab6 (M 37263), Cry1Ab7 (X13233), Cry1Ab8 (M16463), Cry1Ab9 (X54939), Cry1Ab10 (A29125), Cry1Ab11 (112419), Cry1Ab12 (AF059670), Cry1Ab13 (AF254640), Cry1Ab14 (U94191), Cry1Ab15 (AF358861), Cry1Ab16 (AF37560), Cry1Ab17 (AAT46415), Cry1Ab18 (AAQ88259), Cry1Ab19 (AY847289), Cry1Ab20 (DQ241675), Cry1Ab21 (EF683163), and Cry1Ab22 (ABW87320). In yet another aspect of this embodiment, the first Cry protein comprises an amino acid sequence selected from the group consisting of SEQ ID NO: 68, SEQ ID NO: 70, and SEQ ID NO: 135, and the second Cry protein comprises an amino acid sequence set forth in SEQ ID NO: 72.

In one embodiment, the present invention encompasses an eHIP of the invention comprising at least one crossover position between the N-terminal region of the first Cry protein and the C-terminal region of the second Cry protein located in conserved block 3, variable region 4, or conserved block 4. In one aspect of this embodiment, the crossover position in conserved block 3 is located immediately following an amino acid corresponding to Ser451, Phe454, or Leu468 of SEQ ID NO: 70. In another aspect of this embodiment, the crossover position is located in conserved block 3 immediately following Ser451, Phe454, or Leu468 of SEQ ID: 70 or Ser450, Phe453, or Leu467 of SEQ ID NO: 68; or Ser497, Phe100, Leu114 of SEQ ID NO: 135. The crossover positions in certain Cry3A/Cry1Ab eHIP embodiments or modified Cry3A/Cry 1 Ab eHIP embodiments according to die invention are indicated on FIG. 2, which indicates percent identity.

In another embodiment, an eHIP of the invention comprises at least two crossover positions between an amino acid sequence from a first Bt Cry protein and an amino acid sequence from the second Bt Cry protein, hi one aspect of this embodiment, a crossover position between a Cry3A or modified Cry3A and a Cry1Ah or a Cry1Aa is located in conserved block 2 immediately following an amino acid corresponding to Asp232 of SEQ ID NO: 70 and a second crossover position between Cry1Ab and Cry3A or modified Cry3A is located in conserved block 3 immediately following an amino acid corresponding to Leu476 of SEQ ID NO: 72. In another aspect of this embodiment, a crossover position between a Cry3A or modified Cry3A and a Cry1Ab or a Cry1Aa is located in conserved block 2 immediately following Asp232 of SEQ ID NO: 70, or Asp231 of SEQ ID NO: 68, or Asp278 of SEQ ID NO: 135, and a second crossover position between Cry1Ab and Cry3A or modified Cry3A is located in conserved block 3 immediately following Leu476 of SEQ ID NO: 72.

In still another aspect of this embodiment, a first crossover position between a Cry3A or modified Cry3A and a Cry1Ab is located in conserved block 3 immediately following an amino acid corresponding to Leu468 of SEQ ID NO: 70 and a second crossover position between a Cry1Ab and a Cry3A or modified Cry3A is located in conserved block 4 immediately following an amino acid corresponding to Ile527 of SEQ ID NO: 72. In another aspect of this embodiment, the first crossover position between a Cry3A, or modified Cry3Aa and a Cry1Ab is located in conserved block 3 immediately following an Leu468 of SEQ ID NO: 70, or Leu467 of SEQ ID NO: 68, or Leu134 of SEQ ID NO: 135, and the second crossover position between a Cry1Ab and a Cry3A or modified Cry3A is located in conserved block 4 immediately following Ile527 of SEQ ID NO: 72. In yet another aspect of this embodiment, the eHIP comprises the amino acid sequence of SEQ ID NO: 28 or SEQ ID NO: 34.

In one embodiment, the present invention encompasses an eHIP wherein the first Cry protein is a Cry3A or a modified Cry3A and the second Cry protein is a Cry1Aa or Cry1Ab and wherein the eHIP comprises an amino acid sequence that has at least 80% identity to SEQ OD NO: 64. In another embodiment the eHIP comprises an amino acid sequence that has at least 81, 82, 83, 84, 85, 86, 87, 88, 89, 90, 91, 92, 93, 94, 95, 96, 97, 98 or 99% identity to SEQ ID NO: 64. An alignment of certain eHIP embodiments of the invention with SEQ ID NO: 64 is shown in FIG. 2, which indicates percent identity.

In another embodiment, the present invention encompasses an eHIP wherein the first Cry protein is a Cry3A or a modified Cry3A and the second Cry protein is a Cry1Aa or Cry1Ab and wherein the eHIP comprises an amino acid sequence that has at least 75% identity to SEQ OD NO: 70. In another embodiment the eHIP comprises an amino acid sequence that has at least 76, 77, 78, 79, 80, 81, 82, 83, 84, 85, 86, 87, 88, 89, 90, 91, 92, 93, 94, 95, 96, 97, 98 or 99% identity to SEQ ID NO: 70. An alignment of certain eHIP embodiments of the invention with SEQ ID NO: 70 is shown in FIG. 1, which indicates percent identity.

In another embodiment, the present invention encompasses an eHIP having a first crossover position between Cry3A or modified Cry3A and Cry1Aa or Cry1Ab in conserved block; 2 and a second crossover position between Cry1Aa or Cry1Ab and Cry3A or modified Cry3A in conserved block 3 and wherein the eHIP comprises an amino acid sequence that has at least 56% Identity to SEQ OD NO: 64. In one aspect of this embodiment, the eHIP has at least 60, 70 or 80% identity to SEQ ID NO: 64. In another aspect of this embodiment, the eHIP has at least 81, 82, 83, 84, 85, 86, 87, 88, 89, 90, 91, 92, 93, 94, 95, 96, 97, 98 or 99% identity to SEQ ID NO: 64.

In yet another embodiment the present invention encompasses an eHIP comprising an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 16, SEQ ID NO: 18, SEQ ID NO: 22, SEQ ID NO: 24, SEQ ID NO: 30, SEQ ID NO: 34, SEQ ID NO: 62; SEQ ID NO: 64, SEQ ID NO: 147, SEQ ID NO: 153, SEQ ID NO: 155, SEQ ID NO: 159 and SEQ ID NO: 160.

In one embodiment, the eHIPs of the invention have activity against other insect pests including but not limited to northern corn rootworm, Mexican corn rootworm, Colorado potato beetle, and/or European corn borer.

In another embodiment, the present invention encompasses a nucleic acid molecule comprising a nucleotide sequence that encodes an eHIP of the invention. In one aspect of this embodiment, the nucleic acid molecule comprises a nucleotide sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 15, SEQ ID NO: 17, SEQ ID NO: 21, SEQ ID NO: 23, SEQ ID NO: 29, SEQ ID NO: 33, SEQ ID NO: 61; SEQ ID NO: 63, SEQ ID NO: 146, SEQ ID NO: 152, SEQ ID NO: 154 and SEQ ID NO: 158. Specifically exemplified teachings of methods to make nucleic acid molecules that encode eHIPs can be found in Examples 1-41. Those skilled in the art will recognize that modifications can be made to the exemplified methods to make eHIPs encompassed by the present invention.

The present invention further encompasses expression cassettes comprising the nucleic acid molecules, and recombinant vectors and transgenic non-human host cells, such as bacterial cells or plant cells, comprising the expression cassettes of the invention.

The present; invention also encompasses recombinant vectors comprising the nucleic acids of this invention. In such vectors, the nucleic acids are preferably comprised in expression cassettes comprising regulatory elements for expression of the nucleotide sequences in a host cell capable of expressing the nucleotide sequences. Such regulatory elements usually comprise promoter and termination signals and preferably also comprise elements allowing efficient translation of polypeptides encoded by the nucleic acids of the present invention. Vectors comprising the nucleic acids are may be capable of replication in particular host cells, preferably as extrachromosomal molecules, and are therefore used to amplify the nucleic acids of this invention in the host cells. In one embodiment, host cells for such vectors are microorganisms, such as bacteria, in particular *Bacillus thuringiensis* or *E. coli*. In another embodiment, host cells for such recombinant vectors are endophytes or epiphytes. In yet another embodiment, such vectors are viral vectors and are used for replication of the nucleotide sequences in particular host cells, e.g. insect cells or plant cells. Recombinant vectors are also used for transformation of the nucleotide sequences of this invention into host cells, whereby the nucleotide sequences are stably integrated into the DNA of a transgenic host. In one embodiment, the transgenic host is plant such as corn plant.

The eHIPs of the present invention have insect control activity when tested against insect pests in bioassays. In one embodiment, the eHIPs of the Invention are active against coleopteran insects or lepidopteran insects or both. In one aspect of this embodiment, the eHIPs of the invention are active against western corn rootworm, northern corn rootworm, Mexican corn rootworm and/or Colorado potato beetle. In another aspect of this embodiment, the eHIPs of the invention are active against European corn borer. The insect controlling properties of the eHIPs of the invention are further illustrated in Examples 43, 45 and 46.

The present invention also encompasses a composition comprising an effective insect-controlling amount of an eHIP according to the invention.

In another embodiment, the invention encompasses a method of producing a eHIP that is active against insects, comprising: (a) obtaining a host cell comprising a gene, which itself comprises a heterologous promoter sequence operatively linked to a nucleic acid molecule of the invention; and (b) growing the transgenic host cell in such a manner to express an eHIP that is active against insects, In yet another embodiment the invention encompasses a method of producing an insect-resistant transgenic plant, comprising introducing a nucleic acid molecule of the Invention into the transgenic plant, wherein the nucleic acid molecule causes the expression of an eHIP in the transgenic plant in an effective amount to control insects. In one aspect of this embodiment, the insects are coleopteran insects or lepidopteran insects. In another aspect of this embodiment, the coleopteran insects are western corn rootworm, northern corn rootworm, Mexican corn rootworm and/or Colorado potato beetle. In still another aspect of this embodiment, the lepidopteran insects are European corn borer.

In yet a further embodiment, the invention encompasses a method of controlling insects, comprising delivering to the insects an effective amount of an eHIP of the invention. In one aspect of this embodiment the insects are coleopteran Insects or lepidopteran insects. In another aspect of this embodiment, the coleopteran insects are western corn rootworm, northern corn rootworm, Mexican corn rootworm and/or Colorado potato beetle. In still another aspect of this embodiment, the lepidopteran insects are European corn borer. Typically, the eHIP is delivered to the insects orally. In one aspect, the eHIP is delivered orally through a transgenic plant comprising a nucleic acid sequence that expresses an eHIP of the present invention.

The present invention further encompasses a method of controlling insects wherein the transgenic plant further comprises a second nucleic acid molecule or groups of nucleic acid molecules that encode a second pesticidal principle. Examples of such second nucleic acids are those that encode a Bt Cry protein, those that encode a Vegetative Insecticidal Protein, disclosed in U.S. Pat. Nos. 5,849,870 and 5,877,012, incorporated herein by reference, or those that encode a pathway for the production of a non-proteinaceous principle.

The present; invention also encompasses a method of making an engineered hybrid insecticidal protein (eHIP), comprising: (a) obtaining a first Bt Cry protein or modified Bt Cry protein; (b) obtaining a second Bt Cry protein which is different from the first Bt Cry protein or modified Bt Cry protein; (c) combining complete or partial variable regions and conserved blocks of the first Bt Cry protein or modified Bt Cry protein with complete or partial variable regions and conserved blocks of the second Bt Cry protein to make an eHIP that has activity against at least western corn rootworm; and optionally (d) inserting a peptidyl fragment at die N-terminus or a protoxin tail region of a Bt Cry protein at the C-terminus of the eHIP, or both, wherein the N-terminal peptidyl fragment or the C-terminal protoxin region or both confers activity upon the eHIP, or increases the insecticidal activity of the eHIP or makes the eHIP more stable than an eHIP without the peptidyl fragment or protoxin tail region or both.

In another embodiment, the present invention encompasses a method of making an engineered hybrid insecticidal protein (eHIP) comprising: (a) obtaining a first nucleic acid encoding a first Bt Cry protein or modified Bt Cry protein and a second nucleic acid encoding a second Cry protein different from the first Cry protein or modified Bt Cry protein; (b) isolating from the first and second nucleic acids, a nucleotide sequence that encodes complete or partial variable regions and conserved, blocks of the first Bt Cry protein or modified Bt Cry protein and the second Bt Cry protein: (c) connecting together the resulting isolated nucleic acids of step (b) in such a way as to make a new hybrid nucleic acid that encodes a protein, and optionally fusing to a 5' end of said hybrid nucleic acid a nucleic acid that encodes a peptidyl fragment resulting in a 5' extension or fusing to a 3' end of said hybrid nucleic acid a nucleic acid that encodes a protoxin tail region of a Bt Cry protein resulting in a 3' extension, or both; (d) inserting the hybrid nucleic acid with or without one or both of the 5' or 3' extensions into an expression cassette; (e) transforming the expression cassette into a host cell, resulting in said host cell producing an eHIP; and (f) bioassaying the eHIP against at least western corn rootworm, which results in insecticidal activity against western corn rootworm.

In further embodiments of the methods of the invention, the first Bt Cry protein or modified Bt Cry protein is a Cry3A or modified Cry3A and the second Bt Cry protein is A Cry1Aa or Cry1Ab.

In another embodiment of the methods of the invention, the N-terminal peptidyl fragment comprises at 9 amino acids. In one aspect of this embodiment the N-terminal peptidyl fragment comprises the amino acid sequence YDGRQQHRG (SEQ ID NO: 132) or the amino acid sequence TSNGRQCAGIRP (SEQ ID NO: 133). In another aspect of this embodiment the N-terminal peptidyl fragment is selected from the group consisting of SEQ ID NO: 126, SEQ ID NO: 127, SEQ ID NO: 128, SEQ ID NO: 129, SEQ ID NO: 130, SEQ ID NO: 131, and SEQ ID NO: 132.

In still another embodiment of the methods of the invention, the protoxin tail region is from a Cry1Aa or Cry1Ab. In one aspect, of this embodiment, the protoxin tail region comprises at least 38 amino acids. In another aspect of this embodiment, the protoxin tail region comprises an amino acid sequence that corresponds to amino acids 611-648 of SEQ ID NO: 72. In yet another aspect of this embodiment, the protoxin tail region comprises amino acids 611-648 of SEQ ID NO: 72, Specifically exemplified teachings of the methods of making the hybrid nucleic acids and the eHIPs of the invention can be found in Examples 1-41.

In further embodiments, the nucleotide sequences of the invention, particularly a sequence encoding the peptidyl fragment, the protoxin tail, and/or conserved blocks 2, 3 and 4, can be further modified by incorporation of random mutations in a technique known as in vitro recombination or DNA shuffling. This technique is described in Stemmer et al., Nature 370:389-391 (1994) and U.S. Pat. No. 5,605,793, which are incorporated herein by reference. Millions of mutant copies of a nucleotide sequence are produced based on an original nucleotide sequence of this invention and variants with improved properties, such as increased Insecticidal activity, enhanced stability, or different specificity or ranges of target-insect pests are recovered. The method encompasses forming a mutagens zed double-stranded polynucleotide from a template double-stranded polynucleotide comprising a nucleotide sequence of this invention, wherein the template double-stranded polynucleotide has been cleaved into double-stranded-random fragments of a desired size, and comprises the steps of adding to the resultant population of double-stranded random fragments one or more single or double-stranded oligonucleotides, wherein said oligonucleotides comprise an area of identity and an area of heterology to the double-stranded template polynucleotide; denaturing the resultant mixture of double-stranded random fragments and oligonucleotides into single-stranded fragments; incubating the resultant population of single-stranded fragments with a polymerase under conditions which result in the annealing of said single-stranded fragments at said areas of identity to form pairs of annealed, fragments, said areas of identity being sufficient for one member of a pair to prime replication of the other, thereby forming a mutagenized double-stranded polynucleotide; and repeating the second and third steps for at least two further cycles, wherein the resultant mixture in the second step of a further cycle includes the mutagenized double-stranded polynucleotide from the third step of the previous cycle, and the further cycle forms a further mutagenized double-stranded polynucleotide. In a preferred embodiment, the concentration of a single species of double-stranded random fragment in the population of double-stranded random fragments is less than 1% by weight of the total DNA. In a further preferred embodiment, the template double-stranded polynucleotide comprises at least about 100 species of polynucleotides. In another preferred embodiment, the size of the double-stranded random fragments is from about 5 bp to 5 kb. In a further preferred embodiment, the fourth step of the method comprises repeating the second and the third steps for at least 10 cycles.

As biological insect control agents, the eHIPs are produced by expression of the nucleic acids in heterologous host cells capable of expressing the nucleic acids. In one embodiment, *B. thuringiensis* cells comprising modifications of a nucleic acid of this invention are made. Such modifications encompass mutations or deletions of existing regulatory elements, thus leading to altered expression of the nucleic acid, or the incorporation of new regulatory elements controlling the expression of the nucleic acid. In another embodiment, additional copies of one or more of the nucleic acids are added to *Bacillus thuringiensis* cells either by insertion into the chromosome or by introduction of extrachromosomally replicating molecules containing the nucleic acids.

In another embodiment, at least one of the nucleic acids of the invention is inserted into an appropriate expression cassette, comprising a promoter and termination signal. Expression of the nucleic acid is constitutive, or an inducible promoter responding to various types of stimuli to initiate transcription is used. In another embodiment, the cell in which the eHIP is expressed is a microorganism, such as a virus, bacteria, or a fungus. In yet another embodiment, a virus, such as a baculovirus, contains a nucleic acid, of the invention in its genome and expresses large amounts of the corresponding insecticidal protein after infection of appropriate eukaryotic cells that are suitable for virus replication and expression of the nucleic acid. The insecticidal protein thus produced is used as an insecticidal agent. Alternatively, baculoviruses engineered to include the nucleic acid are used to infect insects in vivo and kill them either by expression of the insecticidal toxin or by a combination of viral infection and expression of the insecticidal toxin.

Bacterial cells are also hosts for the expression of the nucleic acids of the invention. In one embodiment, non-pathogenic symbiotic bacteria, which are able to live and replicate within plant tissues, so-called endophytes, or non-pathogenic symbiotic bacteria, which are capable of colonizing the phyllosphere or the rhizosphere, so-called epiphytes, are used. Such bacteria include bacteria of the genera *Agrobacterium, Alcaligenes, Azospirillum, Azotobacter, Bacillus, Clavibacter, Enterobacter, Erwinia, Flavobacter, Klebsiella, Pseudomonas, Rhizobium, Serratia, Streptomyces* and *Xanthomonas*. Symbiotic fungi, such as *Trichoderma* and *Gliocladium* are also possible hosts for expression of the inventive nucleic acids for the same purpose.

Techniques for these genetic manipulations are specific for the different available hosts and are known in the art. For example, the expression vectors pKK223-3 and pKK223-2 can be used to express heterologous genes in *E. coli*, either in transcriptional or translational fusion, behind the tac or trc promoter. For the expression of operons encoding multiple ORFs, the simplest procedure is to insert the operon into a vector such as pKK223-3 in transcriptional fusion, allowing the cognate ribosome binding site of the heterologous genes to be used. Techniques for overexpression in gram-positive species such as *Bacillus* are also known in the art and can be used in the context of this invention (Quax et al. in: Industrial Microorganisms: Basic and Applied Molecular Genetics, Eds. Baltz et al., American Society for Microbiology, Washington (1993)). Alternate systems for overexpression rely for example, on yeast vectors and include the use of *Pichia, Saccharomyces* and Kiuyveromyces (Sreekrishna, In: Industrial microorganisms: basic and applied molecular genetics, Baltz, Hegeman, and Skatrud eds., American Society for Microbiology, Washington (1993); Dequin & Barre, Biotechnology L2:173-1.77 (1.994); van den Berg et al., Biotechnology 8:135-139 (1990)).

In one embodiment, at least one of the eHIPs of the invention is expressed in a higher organism such as a plant. In this ease, transgenic plants expressing effective amounts of the eHIP protect themselves from insect pests. When the insect starts feeding on such a transgenic plant, it also ingests the expressed eHIP. This will deter the insect from further biting into the plant tissue or may even harm or kill the insect. A nucleic acid of the present invention is inserted into an expression cassette, which may then be stably integrated in the genome of the plant. In another embodiment, the nucleic acid is included in a non-pathogenic self-replicating virus. Plants transformed in accordance with the present invention may be monocots or dicots and include, but are not limited to, corn, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugar beet, sunflower, rapeseed, clover, tobacco, carrot, cotton, alfalfa, rice, potato, eggplant, cucumber, *Arabidopsis*, and woody plants such as coniferous and deciduous trees.

Once a desired nucleic acid has been transformed into a particular plant species, it may be propagated in that species or moved into other varieties of the same species, particularly including commercial varieties, using traditional breeding techniques.

A nucleic acid of this invention is preferably expressed in transgenic plants, thus causing the biosynthesis of the corresponding eHIP in the transgenic plants. In this way, transgenic plants with enhanced resistance to insects, particularly corn rootworm, are generated. For their expression in transgenic plants, the nucleic acids of the invention may require other modifications and optimization. Although in many cases genes from microbial organisms can be expressed in plants at high levels without modification, low-expression in transgenic plants may result from microbial nucleic acids having codons that are not preferred in plants. It is known in the art that all organisms have specific preferences for codon usage, and the codons of the nucleic acids described in this invention can be changed to conform with plant preferences, while maintaining the amino acids encoded thereby. Furthermore, high expression in plants is best achieved from coding sequences that, have at least about 35% GC content, preferably more than about 45%, more preferably more than about 50%, and most preferably more than about 60%. Microbial nucleic acids that have low GC contents may express poorly in plants due to the existence of ATTTA motifs that may destabilize messages, and AATAAA motifs that may cause inappropriate polyadenylation. Although preferred gene sequences may be adequately expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17:477-498 (1989)). In addition, the nucleic acids are screened for the existence of illegitimate splice sites that may cause message truncation. All changes required to be made within the nucleic acids such as those described above are made using well known techniques of site directed mutagenesis, PCR, and synthetic gene construction using the methods described, in the published patent applications EP 0 385 962, EP 0 359 472, and WO 93/07278.

In one embodiment of the invention an eHIP coding sequence and/or a parent Bt Cry protein coding sequence is/are made according to the procedure disclosed in U.S. Pat. No. 5,625,136, herein incorporated by reference. In this procedure, maize preferred codons, i.e., the single codon that most frequently encodes that amino acid in maize, are used. The maize preferred codon for a particular amino acid might be derived, for example, from known gene sequences from maize. Maize codon usage for 28 genes from maize plants is found in Murray et al, Nucleic Acids Research 17:477-498 (1989), the disclosure of which is incorporated herein by reference.

In this manner, the nucleotide sequences can be optimized for expression in any plant, it is recognized that all or any part of the gene sequence may be optimized or synthetic. That is, synthetic or partially optimized sequences may also be used.

For efficient initiation of translation, sequences adjacent to the initiating methionine may require modification. For example, they can be modified by the inclusion of sequences known to be effective in plants. Joshi has suggested an appropriate consensus for plants (NAR 15:6643-6653 (1987)) and Clonetech suggests a further consensus translation initiator (1993/1994 catalog, page 210). These consensuses are suitable for use with the nucleic acids of this invention. The sequences are incorporated into constructions comprising the nucleic acids, up to and Including the ATG (whilst leaving the second amino acid unmodified), or alternatively up to and Including the GTC subsequent to the ATG (with the possibility of modifying the second amino acid of the transgene).

Expression of the nucleic acids in transgenic plants is driven by promoters that function in plants. The choice of promoter will vary depending on the temporal and spatial requirements for expression, and also depending on the target species. Thus, expression of the nucleic acids of this invention in leaves, in stalks or stems, in ears, in inflorescences (e.g. spikes, panicles, cobs, etc.), in roots, and/or seedlings is preferred. In many cases, however, protection against more than one type of insect pest is sought, and thus expression in multiple tissues is desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the nucleic acids in the desired cell.

In one embodiment promoters are used that are expressed constitutively including the actin or ubiquitin or cmp promoters or the CaMV 35S and 19S promoters. The nucleic acids of this invention can also be expressed under the regulation of promoters that are chemically regulated. This enables the eHIPs to be synthesized only when the crop plants are treated with the inducing chemicals. Preferred technology for chemical induction of gene expression is detailed in the published application EP 0 332 104 (to Ciba-Geigy) and U.S. Pat. No. 5,614,395, A preferred promoter for chemical induction is the tobacco PR-1a promoter.

In another embodiment a category of promoters which is wound inducible can be used Numerous promoters have been described which are expressed at wound sites and also at the sites of phytopathogen infection. Ideally, such a promoter should only be active locally at the sites of infection, and in this way the eHIPs only accumulate in cells that need to synthesize the eHIPs to kill the invading insect pest. Preferred promoters of this kind include those described by Stanford et al. Mol. Gen. Genet. 215:200-208 (1989), Xu et al. Plant Molec. Biol. 22:573-588 (1993), Logemann et al. Plant Cell 1:151-158 (1989), Rohrmeier & Lehle, Plant Molec. Biol. 22:783-792 (1993), Firek et al. Plant Molec. Biol. 22:129-142 (1993), and Warner et al. Plant J. 3:191-201 (1993).

Tissue-specific or tissue-preferential promoters useful for the expression of genes encoding eHIPs in plants, particularly corn, are those which direct expression in root, pith, leaf or pollen, particularly root. Such promoters, e.g. those isolated faun PEPC or trpA, are disclosed in U.S. Pat. No. 5,625,136, or MTL, disclosed in U.S. Pat. No. 5,466,785. Both U.S. patents are herein incorporated by reference in their entirety.

Further embodiments are transgenic plants expressing the nucleic acids in a wound-inducible or pathogen infection-inducible manner.

In addition to promoters, a variety of transcriptional terminators are also available for use in hybrid nucleic acid construction using tire eHIP genes of the present invention. Transcriptional terminators are responsible for the termination of transcription beyond the transgene and its correct polyadenylation. Appropriate transcriptional terminators and those that are known to function in plants include the CaMV 35S terminator, the tml terminator, the nopaline synthase (NOS) terminator, the pea rbcS E9 terminator and others known in the art. These can be used in both monocotyledons and dicotyledons. Any available terminator known to function in plants can be used in the context of this invention.

Numerous other sequences can be incorporated into expression cassettes described in this invention. These include sequences that have been shown to enhance expression such as intron sequences (e.g. from Adhl and bronzel) and viral leader sequences (e.g. from TMV, MCMV and AMV).

It may be preferable to target expression of the nucleic acids of the present invention to different cellular localizations in the plant. In some cases, localization in the cytosol may be desirable, whereas in other cases, localization in some subcellular organelle may be preferred. Subcellular localization of transgene-encoded enzymes is undertaken using techniques well known in the art. Typically, the DNA encoding the target peptide from a known organelle-targeted gene product is manipulated and fused upstream of the nucleic acid. Many such target sequences are known for the chloroplast and their functioning in heterologous constructions has been shown. The expression of the nucleic acids of the present invention is also targeted to the endoplasmic reticulum or to the vacuoles of the host cells. Techniques to achieve this are well known in the art.

Vectors suitable for plant transformation are described elsewhere in this specification. For *Agrobacterium*-mediated transformation, binary vectors or vectors carrying at least one T-DNA border sequence are suitable, whereas for direct gene transfer any vector is suitable and linear DNA containing only the construction of interest may be preferred. In the case of direct gene transfer, transformation with a single DNA species or co-transformation can be used (Schocher et al. Biotechnology 4:1093-1096 (1986)). For both direct gene transfer and *Agrobacterium*-mediated transfer, transformation is usually (but not necessarily) undertaken with a selectable marker that, may provide resistance to an antibiotic (kanamycin, hygromycin or methotrexate) or a herbicide (basta). Plant transformation vectors comprising the eHIP genes of the present invention may also comprise genes (e.g. phosphomannose isomerase; PMI) which provide for positive selection of the transgenic plants as disclosed in U.S. Pat. Nos. 5,767, 378 and 5,994,629, herein incorporated by reference. The choice of selectable marker is not, however, critical to the invention.

In another embodiment, a nucleic acid of the present invention is directly transformed into the plastid genome. A major advantage of plastid transformation is that, plastids are generally capable of expressing bacterial genes without substantial codon optimization, and plastids are capable of expressing multiple open reading frames under control of a single promoter. Plastid transformation technology is extensively described in U.S. Pat. Nos. 5,451,513, 5,545,817, and 5,545,818, in PCT application no. WO 95/16783, and in McBride et al. (1994) Proc. Nati. Acad. Sci. USA 91, 7301-7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps 12 genes conferring resistance to spectinomycin and/or streptomycin are utilized as selectable markers for transformation (Svab, Z., Hajdukiewicz, P., and Maliga, P. (1990) Proc. Natl. Acad. Sci. USA 87, 8526-8530; Staub, J. M., and Maliga, P. (1992) Plant Cell 4, 39-45). This resulted in stable homoplasmic transformants at a frequency of approximately one per 100 bombardments of target leaves. The presence of cloning sites between these markers allowed creation of a plastid targeting vector for introduction of foreign genes (Staub, J. M., and Maliga, P, (1993) EMBO J. 12, 601-606). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyl transferase (Svab, Z., and Maliga, P. (1993) Proc. Natl. Acad. Sci. USA 90, 913-917). Previously, this marker had been used successfully for high-frequency transformation of the plastid genome of the green alga *Chlamydomonas reinhardtii* (Goldschmidt-Clermont, M. (1991) Nucl. Acids Res. 19:4083-4089). Other selectable markers useful for plastid transformation are known in the art and encompassed within the scope of the invention. Typically, approximately 15-20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleic acid of the present invention is inserted into a plastid-targeting vector and transformed into the plastid genome of a desired plant host. Plants homoplastic for plastid genomes containing a nucleic acid of the present invention are obtained, and are preferentially capable of high expression of the nucleic acid.

The eHIPs of the invention can be used in combination with other pesticidal principles (e.g. Bt Cry proteins) to increase pest target range. Furthermore, the use of the eHIPs of the invention in combination with modified Cry3A toxins, Bt Cry proteins, or other CRW-active principles, such as an RNAi, which have a different mode of action or target a different receptor in the insect gut, has particular utility for the prevention and/or management of corn rootworm resistance. Other insecticidal principles include, but are not limited to, lectins, α-amylase, peroxidase, and cholesterol oxidase. Vip genes, as disclosed in U.S. Pat. No. 5,889,174 and herein incorporated by reference, are also useful in combination with the eHIPs of the present invention.

This co-expression of more than one insecticidal principle in the same transgenic plant can be achieved by making a single recombinant vector comprising coding sequences of more than one insecticidal principle in a so called molecular stack and genetically engineering a plant to contain and express all the insecticidal principles in the transgenic plant. Such molecular stacks may be also be made by using minichromosomes as described, for example in U.S. Pat. No. 7,235,716. Alternatively, a transgenic plant comprising one nucleic acid encoding a first insecticidal principle can be re-transformed with a different nucleic acid encoding a second insecticidal principle and so forth. Alternatively, a plant. Parent 1, can be genetically engineered for the expression of genes of the present invention. A second plant, Parent 2, can be genetically engineered for the expression of a supplemental insect control principle. By crossing Parent 1 with Parent 2, progeny plants are obtained which express all the genes introduced into Parents 1 and 2.

Transgenic seed of the present invention can also be treated with an insecticidal seed coating as described in U.S. Pat. Nos. 5,849,320 and 5,876,739, herein incorporated by reference. Where both the insecticidal seed coating and the transgenic seed of the invention are active against the same target insect, the combination is useful (i) in a method for enhancing activity of a eHIP of the invention against the target Insect and (ii) in a method for preventing development of resistance to a eHIP of the invention by providing a second mechanism of action against the target insect. Thus, the Invention provides a method of enhancing activity against or preventing development of resistance in a target insect, for example corn rootworm, comprising applying an insecticidal seed coating to a transgenic seed comprising one or more eHIPs of the invention.

Even where the insecticidal seed coating is active against a different insect, the insecticidal seed coating is useful to expand the range of insect control, for example by adding an insecticidal seed coating that has activity against lepidopteran insects to the transgenic seed of the invention, which has activity against coleopteran insects, the coated transgenic seed produced controls both lepidopteran and coleopteran insect pests.

EXAMPLES

The invention will be further described by reference to the following detailed examples. These examples are provided for the purposes of illustration only, and are not intended to be limiting unless otherwise specified. Standard recombinant DNA and molecular cloning techniques used here are well known in the art and are described by J. Sambrook, et al. Molecular Cloning; *A. Laboratory Manual*, 3d Ed., Cold Spring Harbor, N.Y.; Cold Spring Harbor Laboratory Press (2001); by T. J. Silhavy, M. L. Berman, and L. W. Enquist, *Experiments with Gem Fusions*, Cold Spring Harbor Laboratory, Cold Spring Harbor, N.Y. (1984) and by Ausubel, F. M. et al., *Current Protocols in Molecular Biology*, New York, John Wiley and Sons Inc., (1988), Reiter, et al. *Methods in Arabidopsis Research*, World Scientific Press (1992), and Schultz et al. *Plant Molecular Biology Manual*, Kluwer Academic Publishers (1998).

Example 1

Parental Coding Sequences

Maize optimized cry3Aa, cry1Ab, cry1Ba, and cry1Fa coding sequences; designated herein mocry3Aa, mocry1Ab, mocry1Ba and mocry1Fa, respectively, were made according to the procedure disclosed in U.S. Pat. No. 5,625,136, herein incorporated by reference in its entirety.

The cry3A055 (SEQ ID NO: 67) coding sequence, which encodes a Cry3A055 protein (SEQ ID NO: 68) was made by modifying the mocry3A coding sequence by inserting a nucleotide sequence that encodes a Cathepsin G protease recognition site into domain I according to U.S. Pat. No. 7,030,295, herein incorporated by reference in its entirety.

The mocry3Aa (SEQ ID NO: 67), which encodes the protein set forth in SEQ ID NO: 68, cry3A055 (SEQ ID NO: 69), which encodes the protein set forth in SEQ ID NO: 70, mocry1Ab (SEQ ID NO: 71), which encodes the protein set forth in SEQ ID NO: 72, mocry1Ba (SEQ ID NO: 73), which encodes the protein set forth in SEQ ID NO: 74, mocry1Fa (SEQ ID NO: 75), which encodes the protein set forth in SEQ ID NO: 76, cry3Aa (SEQ ID NO: 77), which encodes the protein set forth in SEQ ID NO: 78, cry 1Ac (SEQ ID NO: 79), which encodes the protein set forth in SEQ ID NO: 80, and cry1Ia (SEQ ID NO: 81), which encodes the protein set forth in SEQ ID NO: 82, were used in the construction of the hybrid nucleic acids and the proteins which they encode and described in the following Examples.

Example 2

Use of PCR Primers to Construct Hybrid Nucleic Acids

Polymerase Chain Reaction (PCR) is a repetitive, enzymatic, primed synthesis of a nucleic acid sequence. This procedure is well known and commonly used by those skilled in this art (See Mullis, U.S. Pat. Nos. 4,683,195, 4,683,202, and 4,800,159; Saiki, Randall K., Stephen Scharf, Fred Faloona, Kary B. Mullis, Glenn T. Horn, Henry A. Erlich, Norman Amheim [1985] "Enzymatic Amplification of .beta.-Globin Genomic Sequences and Restriction Site Analysis for Diagnosis of Sickle Cell Anemia," Science 230:1350-1354.). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA fragment produced in the previous cycle. This results in the exponential accumulation of the specific target fragment, up to several million-fold in a few hours. By using a thermostable DNA polymerase such as Taq polymerase, which is isolated from the thermophilic bacterium *Thermus aquaticus*, the amplification process can be completely automated.

The chimeric coding sequences described in the following examples were constructed using various combinations of the exemplified primers shown in Table 1. The PCR reaction mixes and PCR thermocycling protocols used in the experiments are listed in Tables 2 and 3, respectively. In each of the examples that follow, the PCR primers are referred to by name and "SEQ ID NO:" and the PCR reaction mixes and PCR thermocycling protocols are referred to by their respective numbers. It will be recognized by the skilled person that other PCR primers and PCR reaction conditions can be used to construct the chimeric coding sequences of the invention and by listing the exemplified primers and PCR conditions that were used in the instant invention is not meant to be limiting in any way.

TABLE 1

Primers used to construct the coding sequences encoding eHIPs.

| Primer Name | Sequence | SEQ ID NO: |
|---|---|---|
| 5'3A-1-bam | 5'-CCGGATCCATGACGGCCGACAACAACACCGAGGC-3' | SEQ ID NO: 83 |
| C3-3A-6 | 5'-CAGGGGGCAGCTGGGTGATCT-3' | SEQ ID NO: 84 |
| C3-1Ab-3 | 5'-AGATCACCCAGATCCCCCTG-3' | SEQ ID NO: 85 |
| 1Ab-6-sac | 5'-CCGAGCTCAGCTCCTACACCTGATCGATGTGGTAGTCGG-3' | SEQ ID NO: 86 |
| 8A-atg-delR1 | 5'-CCGGATCCACCATGACTAGTAACGGCCGCCAGTGTGCTGGTATTCGCCCTTATGAC-3' | SEQ ID NO: 87 |
| C2-3A-4 | 5'-GTCCAGCACGGTCAGGGTCA-3' | SEQ ID NO: 88 |
| reverse | 5'-GCGTGCAGTCAAGTCAGATC-3' | SEQ ID NO: 89 |
| FR8a-OL-1 | 5'-GGTGTTGTTGTCGGCCGTCATAGGGCGAATACCAGCAC-3' | SEQ ID NO: 90 |
| FR8a-OL-2 | 5'-GCCGACAACAACACCGAGGCCCTGGACAGCAGCACCACC-3' | SEQ ID NO: 91 |
| C1-3A-2 | 5'-CAGGTGGGTGTTGGCGGCCTGGGCGTA-3' | SEQ ID NO: 92 |
| 5'FR8a | 5'-GGATCCACCATGACTAGTAAC-3' | SEQ ID NO: 93 |
| 5'FR8a-12aa | 5'-CCGGATCCACCATGTATGACGGCCGACAACAACACC-3' | SEQ ID NO: 94 |
| C2-3A-3 | 5'-TGACCCTGACCGTGCTGGAC-3' | SEQ ID NO: 95 |
| 3'1Ab-dm3 | 5'-GAGCTCCTAGGTCACCTCGGCGGGCAC-3' | SEQ ID NO: 96 |
| 5'FR-del6 | 5'-GGATCCACCATGTGTGCTGGTATTCGCCCTAT-3' | SEQ ID NO: 97 |

TABLE 1-continued

Primers used to construct the coding sequences encoding eHIPs.

| Primer Name | Sequence | SEQ ID NO: |
|---|---|---|
| 5'1Ab-bam | 5'-CCGGATCCATGGACAACAACCCCAACATCAAC-3' | SEQ ID NO: 98 |
| C3-3A-8 | 5'-GATGTCGCCGCCGGTGAAGC-3' | SEQ ID NO: 99 |
| C3-3A-7 | 5'-GCTTCACCGGCGGCGACATC-3' | SEQ ID NO: 100 |
| 1B-5 | 5'-CCGCCGCGACCTGACCCTGGGCGTGCTGGAC-3' | SEQ ID NO: 101 |
| 1B-10 | 5'-CCGAGCTCCTAGAACAGGGCGTTCAC-3' | SEQ ID NO: 102 |
| 3A-22 | 5'-GGCCTTCACCAGGGGCAGCTGGGTGAT-3' | SEQ ID NO: 103 |
| 1B-7 | 5'-ATCACCCAGATCCCCATGGTGAAGGCC-3' | SEQ ID NO: 104 |
| C3-1Ab-2 | 5'-CAGGGGGATCTGGGTGATCT-3' | SEQ ID NO: 105 |
| C3-3A-5 | 5'-AGATCACCCAGCTGCCCCTG-3' | SEQ ID NO: 106 |
| 3A-12-sac | 5'-CCGAGCTCAGCTCAGATCTAGTTCACGGGGATGAACTCGATCTT-3' | SEQ ID NO: 107 |
| C4-3A-10 | 5'-TGGTGCTGGCGTAGTGGATGCGG-3' | SEQ ID NO: 108 |
| C4-3A-9 | 5'-CCGCATCCACTACGCCAGCACCA-3' | SEQ ID NO: 109 |
| C1-1Ab-1 | 5'-TACGTGCAGGCCGCCAACCTGCACCTG-3' | SEQ ID NO: 110 |
| 5'8Aa-dm3 | 5'-AGATCACCCAGCTGCCCCTGGTAAAGGGAGACATGTTATATC-3' | SEQ ID NO: 111 |
| 3'8Aa-dm3 | 5'-GAGCTCCTATGTCTCATCTACTGGGATGAA-3' | SEQ ID NO: 112 |
| tant-OL-2 | 5'-GAGGGTGTGGGCCTTCACCAGGGGCAGCTGGGT-3' | SEQ ID NO: 113 |
| tant-OL-1 | 5'-ACCCAGCTGCCCCTGGTGAAGGCCCACACCCTC-3' | SEQ ID NO: 114 |
| tant-3'sac | 5'-GAGCTCTAGCTTAAGCAGTCCACGAGGTT-3' | SEQ ID NO: 115 |
| 1Ac-OL-2 | 5'-TAAAAAGAAAGTTTCCCTTCACCAGGGGCAGCTGGGT-3' | SEQ ID NO: 116 |
| 1Ac-OL-1 | 5'-ACCCAGCTGCCCCTGGTGAAGGGAAACTTTCTTTTTA-3' | SEQ ID NO: 117 |
| 1Ac-3'sac | 5'-GAGCTCCTATGTTGCAGTAACTGGAATAAA-3' | SEQ ID NO: 118 |
| 1Ia-OL-2 | 5'-AAGACAGATTGAAAGCTTTTACTCAGGGGCAGCTGGGT-3' | SEQ ID NO: 119 |
| 1Ia-OL-1 | 5'-ACCCAGCTGCCCCTGAGTAAAAGCTTTCAATCTGTCTT-3' | SEQ ID NO: 120 |
| 1Ia-3'sac | 5'-GAGCTCCTACATGTTACGCTCAATATGGAGT-3' | SEQ ID NO: 121 |
| FR-1Ab-2 | 5'-GATGTTGTTGAACTCGGCGCTCTTGTGGGTCCA-3' | SEQ ID NO: 122 |
| FR-1Ab-1 | 5'-TGGACCCACAAGAGCGCCGAGTTCAACAACATC-3' | SEQ ID NO: 123 |
| FR-1Ab-4 | 5'-GGCTCGTGGGGATGATGTTGTTGAAGTCGACGCTCTTGTGG-3' | SEQ ID NO: 124 |
| FR-1Ab-3 | 5'-CCACAAGAGCGTCGACTTCAACACATCATCCCCAGCAGCC-3' | SEQ ID NO: 125 |
| CMS94 | 5'-GGCGCGCCACCATGGCTAGCATGACTGGTGG-3' | SEQ ID NO: 136 |
| CMS95 | 5'-GCAGGAACAGGTGGGTGTTG-3' | SEQ ID NO: 137 |
| CMS96 | 5'-CCTGAACACCATCTGGCCCA-3' | SEQ ID NO: 138 |
| CMS97 | 5'-CTGGCTGCTGGGGATGATGTTGTTGAAGTCGACGCTCTT-3' | SEQ ID NO: 139 |
| CMS98 | 5'-GAGCTCTTAGGTCACCTCGGC-3' | SEQ ID NO: 140 |
| CMS99 | 5'-AAGAGCGTCGACTTCAACAACATCATCCCCAGCAGCCAG-3' | SEQ ID NO: 141 |
| CMS100 | 5'-GAAGTACCGCGCCCGCATCCGCTACGCCAGCACCACCAAC-3' | SEQ ID NO: 142 |
| CMS101 | 5'-GTTGGTGGTGCTGGCGTAGCGGATGCGGGCGCGGTACTTC-3' | SEQ ID NO: 143 |

TABLE 2

PCR reaction mixes.

Mix 1

50-100 ng template DNA
0.8 µM primer 1
0.8 µM primer 2
1X Pfu buffer
0.4 mM dNTPs
2% formamide
1.25 units Pfu Polymerase (Stratagene)
2.5 units Taq Polymerase (Qiagen)
water to a total volume of 50 µl Mix 2

50-100 ng template DNA
0.8 µM primer 1
0.8 µM primer 2
1X Taq buffer
0.4 mM dNTPs
2% formamide
2.5 units Taq Polymerase (Qiagen)
water to a total volume of 50 µl Mix 3

50-100 ng template DNA
0.8 µM primer 1
0.8 µM primer 2
1X cDNA Advantage buffer
0.4 mM dNTPs
x units cDNA Advantage
Polymerase (Clontech)
water to a total volame of 50 µl Mix 4

50-100 ng template DNA
0.4 µM primer 1
0.4 µM primer 2
1X PCR buffer (Invitrogen)
0.4 mM dNTPs
2.5 units HotStart Taq Polymerase
water to a total volume of 50 µl Mix 5

50-100 ng template DNA
0.4 µM primer 1
0.4 µM primer 2
1X Pfu buffer (Stratagene)
0.2 mM dNTPs
1.25 units Pfu Turbo Polymerase
water to a total volume of 50 µl

TABLE 3

PCR thermocycling profiles.

Thermocycle Profile 1

94° C. - 5 minutes
20 cycles:

94° C. - 30 seconds
65° C. - 30 seconds
72° C. - 30 seconds
72° C. - 7 minutes
hold at 4° C.

Thermocycle Profile 2

94° C. - 5 minutes
20 cycles:

94° C. - 30 seconds
55° C. - 30 seconds
72° C. - 30 seconds
72° C. - 7 minutes
hold at 4° C.

TABLE 3-continued

PCR thermocycling profiles.

Thermocycle Profile 3

94° C. - 5 minutes
20 cycles:

94° C. - 30 seconds
55° C. - 30 seconds
68° C. - 30 seconds
68° C. - 7 minutes
hold at 4° C.

Thermocycle Profile 4

94° C. - 15 minutes
20 cycles:

94° C. - 30 seconds
50-70° C. - 30 seconds
72° C. - 30 seconds
72° C. - 7 minutes
hold at 4° C.

Thermocycle Profile 5

94° C. - 5 minutes
20 cycles:

94° C. - 30 seconds
55-75° C. - 30 seconds
72° C. - 1 minute
72° C. - 15 minutes
hold at 4° C.

Thermocycle Profile 6

94° C. - 5 minutes
20 cycles:

94° C. - 30 seconds
55-75° C. - 30 seconds
72° C. - 2 minutes
72° C. - 15 minutes
hold at 4° C.

Table 4 shows the relationship between the three domains of Cry3A055, Cry1Ab and Cry3A with their respective variable regions and conserved blocks. The amino acids comprised in the domains, conserved blocks and variable regions are shown for each protein.

TABLE 4

| DOMAIN | REGION | Cry3A055 (SEQ ID NO: 70) | Cry1Ab (SEQ ID NO: 72) | Cry3A (SEQ ID NO: 68) | Cry3A (SEQ ID NO: 131) |
|---|---|---|---|---|---|
| | V1 | 1-10 | 1-32 | 1-10 | 1-57 |
| I | V1 | 11-142 | 33-152 | 11-141 | 58-188 |
| | CB1 | 143-172 | 153-182 | 142-171 | 189-218 |
| | V2 | 173-192 | 183-202 | 172-191 | 219-238 |
| II | CB2 | 193-244 | 203-254 | 192-243 | 239-290 |
| | | 245-259 | 255-269 | 244-258 | 291-305 |
| | V3 | 260-444 | 270-452 | 259-443 | 306-490 |
| III | CB3 | 445-454 | 453-462 | 444-453 | 491-500 |
| | | 455-492 | 463-500 | 454-491 | 501-538 |
| | V4 | 493-513 | 501-520 | 492-512 | 539-559 |
| | CB4 | 514-523 | 521-531 | 513-522 | 560-569 |
| | V5 | 524-586 | 532-596 | 523-585 | 570-632 |
| | CB5 | 587-598 | 597-606 | 586-597 | 633-644 |
| | V6 | | 607-610 | | |
| | Protoxin | | 611-648 | | |

Example 3

Construction of 2OL-8a

A first nucleic acid fragment encoding an N-terminal portion of a Cry3A055 protein (SEQ ID NO: 70) was PCR amplified from a plasmid comprising cry3A055 (SEQ ID NO: 69) using primers 5'3A-1-bam (SEQ ID NO: 83) and C3-3A-6 (SEQ ID NO: 84) and PCR reaction Mix 1 and thermocycle Profile 1. This PCR reaction introduced a point mutation by deleting nucleotide 28 of SEQ ID NO: 69 (cry3A055), which caused a frame shift in the cry3A055 reading frame, and deleted the BamHI site and Kozak sequence (Kozak, ML, 1986. Cell 44:283-92) at the 5' end of the resulting amplicon.

A second nucleic acid fragment encoding a C-terminal portion of a Cry1Ab protein (SEQ ID NO: 72) was PCR amplified from a plasmid comprising mocry1Ab (SEQ ID NO: 71) using primers C3-1Ab-3 (SEQ ID NO: 85) and 1Ab-6-Sac (SEQ ID NO: 86) and PCR reaction Mix 1 and thermocycle Profile 1.

The first and second nucleic acids described above were connected by using them as templates in an overlap PCR reaction (Horton et al., 1989, Gene 77: 61-68) with the primers 5'3A-1-bam (SEQ ID NO: 83) and 1Ab-6-Sac (SEQ ID NO: 86) using PCR reaction Mix 2 and thermocycle Profile 1, except a 45-65° C. gradient was used for the annealing temperature.

The resulting amplicon was ligated as a blunt ended fragment to a pCR2.1-TOPO vector (Invitrogen, Carlsbad, C A) cut with SmaI to form plasmid p2OL8a/CR2.1. A BamHI-SacI fragment, from p2OL8a/CR2.1 was then ligated to pET21a (EMD Biosciences, Inc., San Diego, Calif.), which was cut with Bam HI-SacI and transformed into *E. coli* The BamHI-SacI fragment from p2OL8a/CR2.1 comprised 40 nucleotides derived from the pCR2.1-TOPO vector adjacent to the out of frame amplicon from, the first PCR reaction. L1 gating this BamHI-SacI fragment to pET21a created an open reading frame starting with the start codon (ATG) of a T7 tag and ending with the SacI site of the inserted DNA. This open reading frame was designated 2OL-8a (SEQ ID NO: 1) and encodes the 2OL8a chimeric insecticidal protein (SEQ ID NO: 2). Thus, the 2OL-8a chimeric insecticidal protein comprises, from N-terminus to C-terminus, a peptidyl fragment comprising the amino acid sequence MASMTG-GQQMGRGSTSNGRQCAGIRPYDGRQQHRG (SEQ ID NO: 126), amino acids 10-468 of a Cry3A055 protein (SEQ ID NO: 70), which comprises variable regions 1, conserved block 1, variable region 2, conserved block 2, variable region 3, and the N-terminal 24 amino acids of conserved block 3, and amino acids 477-648 of a Cry1Ab protein (SEQ ID NO: 72), which comprises the C-terminal 24 amino acids of conserved block 3, variable region 4, conserved block 4, variable region 5, conserved block 5, and variable region 6; and 38 amino acids of the Cry1Ab protoxin tail region.

The nucleotides that encode amino acids 1-14 of the peptidyl fragment are derived from the T7-tag and the BamHI cleavage site of the pET21a vector. The nucleotides that encode amino acids 15-26 of the peptidyl fragment are derived from the pCR2.1-TOPO vector. And the nucleotides that encode amino acids 27-35 of the peptidyl fragment are derived from cry3A055 which are out of frame with the remainder of the cry3A055 coding sequence.

Example 4

Construction of FR8a

The FR8a coding sequence was constructed by placing a Kozak sequence (ACC) and a start codon (ATG) just downstream of an N-terminal BamHI site in 2OL-8a (See Example 3). In addition, an EcoRI site in 2OL-8a was disrupted to aid in future vectoring of FR8a. All of these changes were made using one PCR reaction with 2OL-8a as the template and the primers: 8a-aig-delRI (SEQ ID NO: 87) and C2-3A-4 (SEQ ID NO: 88) using PCR reaction Mix 2 and thermocycle Profile 2.

The resulting amplicon was ligated to a pCR2.1-TOPO vector (Invitrogen). A BamHI-PpuMI fragment from the cloned PCR product was then ligated to a PpuMI-NcoI fragment from 2OL8a/pCR2.1 (See Example 3) and a NcoI-BamHI fragment from 2OL8a/pCR2.1 to create FR8a (SEQ ID NO: 3) which encodes the FR8a chimeric insecticidal protein (SEQ ID NO: 4). Thus, the FR8a chimeric insecticidal protein comprises, from N-terminus to C-terminus, a peptidyl fragment comprising the amino acid sequence MTSNGRQ-CAGIRPYDGRQQHRG (SEQ ID NO: 127), amino acids 10-468 of a Cry3A055 protein (SEQ ID NO: 70), which comprises variable regions 1, conserved block 1, variable region 2, conserved block 2, variable region 3, and the N-terminal 24 amino acids of conserved block 3, and amino acids 477-648 of a Cry1Ab protein (SEQ ID NO: 72), which comprises the C-terminal 24 amino acids of conserved block 3, variable region 4, conserved block 4, variable region 5, conserved block 5, and variable region 6; and 38 amino acids of the Cry1Ab protoxin tail region.

The FR8a eHIP was very active against western corn rootworm as shown in Table 5. Therefore, elimination of the T7 amino acid sequence from the N-terminal peptidyl fragment from the 2OL-8a eHIP did not have a negative impact on insecticidal activity.

Adding an additional 34 amino acids to the N-terminus of FR8a created a eHIP, designated FR8a+34 (SEQ ID NO: 160), with an N-terminal peptidyl fragment of 56 amino acids (SEQ ID NO: 131). The 56 amino acid N-terminal peptidyl fragment had no negative effect on activity of FR8a against western corn rootworm (See Table 5).

Example 5

Construction of FRCG

In order to determine if a cathepsin G protease recognition site was necessary for the insecticidal activity of a hybrid protein comprising an N-terminal fragment of Cry3A055, a construct was made which eliminated the cathepsin G site from the FR8a hybrid protein (Example 4). A first MluI-PpuMI nucleic acid fragment from a plasmid comprising FR8a (SEQ ID NO: 3) and a second PpuMI/MluI nucleic acid fragment from a plasmid comprising mocry3Aa (SEQ ID NO: 67) were ligated using standard molecular biology techniques to create FRCG (also designated FR8a-catg) (SEQ ID NO: 5) which encodes the FRCG hybrid protein (SEQ ID NO: 6). Thus, the FRCG chimeric insecticidal protein comprises, from N-terminus to C-terminus, a peptidyl fragment comprising the amino acid sequence MTSNGRQCA-GIRPYDGRQQHRG (SEQ ID NO: 127), amino acids 10-467 of a Cry3A protein (SEQ ID NO: 68), which comprises variable regions 1, conserved block 1, variable region 2, conserved block 2, variable region 3, and the N-terminal 24 amino acids of conserved block 3, and amino acids 477-648 of a Cry1Ab protein (SEQ ID NO: 72), which comprises the C-terminal 24 amino acids of conserved block 3, variable region 4, conserved block 4, variable region 5, conserved block 5, and variable region 6; and 38 amino acids of the Cry1Ab protoxin tail region.

The FRCG protein was as active against western corn rootworm as the FR8a protein (See Table 5) suggesting that a cathepsin G protease site is not required for insecticidal activity of a eHIP.

Example 6

Construction of FR8a-9F

A first approximately 323 bp nucleic acid fragment was PCR amplified from a plasmid comprising FR8a (SEQ ID NO: 3) using primers reverse (SEQ ID NO: 89) and FR8a-OL-1 (SEQ ID NO: 90) and PCR reaction Mix 2 and thermocycle Profile 2. A second approximately 470 bp nucleic acid fragment was PCR amplified from a plasmid comprising FR8a using primers FR8a-OL-2 (SEQ ID NO: 91) and CJ-3A-2 (SEQ ID NO: 92) and PCR reaction Mix 2 and thermocycle Profile 2, The two resulting amplicons were connected by using them as templates in an overlap PCR reaction with primers 5FR8a (SEQ ID NO: 93) and C1-3A-2 (SEQ ID NO: 92) using PCR reaction Mix 2 and thermocycle Profile 2 to amplify the 5' end of FR8a-9F. The overlap PCR product was cloned into a pCR2.1-TOPO vector (Invitrogen) designated 5'FR-9F/pCR2.1. A BamHI/PpuMI fragment of 5'FR-9F/pCR2.1 was then ligated to a PpuMI/BamHI fragment of FR8a to create FR8a-9F (SEQ ID NO: 7) which encodes the FR8a-9F chimeric protein (SEQ ID NO: 8). Thus, the FR8a-9F chimeric insecticidal protein comprises, from N-terminus to C-terminus, a peptidyl fragment comprising the amino acid sequence MTSNGRQCAGIRP (SEQ ID NO: 129), amino acids 1-468 of a Cry3A055 protein (SEQ ID NO: 70), which comprises variable regions 1, conserved block 1, variable region 2, conserved block 2, variable region 3, and the N-terminal 24 amino acids of conserved block 3, and amino acids 477-648 of a Cry1Ab protein (SEQ ID NO: 72), which comprises the C-terminal 24 amino acids of conserved block 3, variable region 4, conserved block 4, variable region 5, conserved block 5, and variable region 6; and 38 amino acids of the Cry1Ab protoxin tail region.

The FR8a-9F eHIP was slightly less active against western corn rootworm than the FR8a eHIP (See Table 5) suggesting that the C-terminal 9 amino acids of the peptidyl fragment of SEQ ID NO: 127 play a role in conferring full insecticidal activity to FR8a.

Example 7

Construction of FR-9F-catg

The FR-9F-catg coding sequence was created to place the out-of-frame cry3A055 derived nucleotides of FR8a back in frame and to eliminate the cathepsin. G protease recognition site. A BamHI/PpuMI fragment of 5'FR-9F/pCR2.1 (See Example 6) was ligated with a PpuMI/BamHI fragment of FRCG (See Example 5) to create the FR-9F-catg coding sequence (SEQ ID NO: 9) which encodes the FR9F-catg chimeric protein (SEQ ID NO: 10). Thus, the FR9F-catg chimeric protein comprises, from N-terminus to C-terminus, a peptidyl fragment comprising the amino acid sequence MTSNGRQCAGIRP (SEQ ID NO: 129), amino acids 1-467 of a Cry3Aa protein (SEQ ID NO: 68), which comprises variable regions 1, conserved block 1, variable region 2, conserved block 2, variable region 3, and the N-terminal 24 amino acids of conserved block 3, and amino acids 477-648 of a Cry1Ab protein (SEQ ID NO: 72), which comprises the C-terminal 24 amino acids of conserved block 3, variable region 4, conserved block 4, variable region 5, conserved block 5, and variable region 6; and 38 amino acids of the Cry1Ab protoxin tail region.

The FR8a-9F-catg eHIP provided the same level of activity as FR8a against western corn rootworm (See Table 5) confirming that an eHIP can be made from either a modified Cry3A or a native Cry 3 sequence.

Example 8

Construction of FR8a-12aa

The nucleotides encoding amino acids 2-13 of the peptidyl fragment comprised in FR8a (SEQ ID NO: 4) were removed using PCR. A fragment was PCR amplified from a plasmid comprising FR8a (SEQ ID NO: 3) using primers 5'FR8a-12aa (SEQ ID NO: 94) and C1-3A-2 (SEQ ID NO: 90) and PCR reaction Mix 1 and thermocycle Profile 1. The resulting amplicon was cloned into pCR2.1-TOPO (Invitrogen), A BamHI-PpuMI fragment from the pCR2.1-TOPO clone was then ligated with a PpuMI-BamHI fragment from a plasmid comprising FR8a to create FR8a-12aa (SEQ ID NO: 11) which encodes the FR8a-12aa chimeric insecticidal protein (SEQ ID NO: 12). Thus, the FR8a-12aa chimeric insecticidal protein comprises, from N-terminus to C-terminus, a peptidyl fragment comprising the amino acid sequence MYDGRQQHRG (SEQ ID NO: 128), amino acids 10-468 of a Cry3A055 protein (SEQ ID NO: 70), which comprises variable regions 1, conserved block 1, variable region 2, conserved block 2, variable region 3, and the N-terminal 24 amino acids of conserved block 3, and amino acids 477-648 of a Cry1Ab protein (SEQ ID NO: 72), which comprises the C-terminal 24 amino acids of conserved block 3, variable region 4, conserved block 4, variable region 5, conserved block 5, and variable region 6; and 38 amino acids of the Cry1Ab protoxin tail region.

The FR8a-12aa eHIP provided the same level of activity as FR8a against western corn rootworm (See Table 5) suggesting that the N-terminal 12 amino acids of the peptidyl fragment of SEQ ID NO: 127 are not necessary for full insecticidal activity of FR8a.

Example 9

Construction of Wr-9mut

A nucleic acid fragment was PCR amplified from FR8a/pCR2.1 (Example 2) using primers 5'FR8a-12aa (SEQ ID NO: 94) and CJ-3A-2 (SEQ ID NO: 92) and PCR reaction Mix 1 and thermocycle Profile 2. The resulting amplicon was cloned into pCR2.1TOPO (Invitrogen). A. BamHI/PpuMI fragment was then ligated to a PpuMI/BamHI fragment of FR8a (SEQ ID NO: 3) to create Wr-9mut (SEQ ID NO: 13) which encodes the WR-9mut protein (SEQ ID NO: 14), which comprises, from N-terminus to C-terminus, a peptidyl fragment comprising the amino acid sequence MYDGRQQHRG (SEQ ID NO: 128), and amino acids 10-598 of a Cry3A055 protein (SEQ ID NO: 70). Thus the WR-9mut protein is Cry3A055 with an N-terminal peptidyl fragment of the invention.

The WR-9mut protein was not active against western corn rootworm. Therefore, the addition of an N-terminal peptidyl fragment to a non-hybrid modified Cry3a protein destroyed insecticidal activity. This suggests that there may be some interaction between the Cry1Ab C-terminal portion of FR8a and the N-terminal peptidyl fragment that confers full insecticidal activity to FR8a.

Example 10

Construction of FRD3

The 3' end of this coding sequence was made by PCR amplifying a fragment from a plasmid comprising FR8a (SEQ ID NO: 3) using primers C2-3A-3 (SEQ ID NO: 95) and 3'1 Ab-dm3 (SEQ ID NO: 96) and PCR reaction Mix 2 and thermocycle Profile 2. The resulting amplicon was cloned into pCR2.1-TOPO (Invitrogen). A 364 bp ApaI/SacI fragment of the cloned amplicon, designated 3'FRD3/pCR2.1, was ligated with a SacI/ApaI fragment of FR8a to create FRD3 (SEQ ID NO: 15) which encodes the FRD3chimeric protein (SEQ ID NO: 16). The FRD3 chimeric protein comprises, from N-terminus to C-terminus, a peptidyl fragment comprising the amino acid sequence MTSNGRQCAGIRPYDGRQQHRG (SEQ ID NO: 127), amino acids 10-468 of a Cry3A055 protein (SEQ ID NO: 70), which comprises complete variable region 1, conserved block; 1, variable region 2, conserved block 2, variable region 3, and the N-terminal 24 amino acids of conserved block 3, and amino acids 477-610 of a Cry1Ab protein (SEQ ID NO: 72), which comprises the C-terminal 24 amino acids of conserved block 3, variable region 4, conserved block 4, variable region 5, conserved block 5, and variable region 6. Thus, the FRD3 chimeric insecticidal protein is a variant of an FR8a chimeric insecticidal protein with the 38 amino acid region of the Cry1Ab protoxin tail deleted.

The FRD3 eHIP provided the same level of activity as FR8a against western corn rootworm (See Table 5) suggesting that the 38 amino acid protoxin tail region of FR8a is not necessary for full insecticidal activity.

Example 11

Construction of FR-12-cg-dm3

A 3082 bp SacI/PpuMI fragment from a plasmid comprising FR8a-12 (See Example 8), a 721 bp PpuMI/MluI fragment of FRCG (See Example 5) and a 923 bp MluI/SacI fragment of FRD3 (See Example 10) were combined to create the FR-12-cg-dm3 coding sequence (SEQ ID NO: 17) which encodes the FR-12-cg-dm3 chimeric protein (SEQ ID NO: 18). The FR-12-cg-dm3 chimeric protein comprises, from N-terminus to C-terminus, a peptidyl fragment comprising the amino acid sequence MYDGRQQHRG (SEQ ID NO: 129), ammo acids 10-467 of a Cry3Aa protein (SEQ ID NO: 70), which comprises complete variable region 1, conserved block 1, variable region 2, conserved block 2, variable region 3, and the N-terminal 24 amino acids of conserved block 3, and amino acids 477-610 of a Cry1.Ab protein (SEQ ID NO: 72), which comprises the C-terminal 24 amino acids of conserved block 3, variable region 4, conserved block 4, variable region 5, conserved block 5, and variable region 6. Thus, the FR-12-cg-dm3 chimeric protein is a variant of FR8a with 12 N-terminal amino acids of the peptidyl fragment, the cathepsin G protease recognition site, and the 38 amino acid region of the Cry1Ab protoxin tail deleted.

The FR-12-cg-dm3 eHIP was not as active against western corn rootworm as FR8a (See Table 5) suggesting that some interaction between the C-terminal portion of FR8a and the N-terminal peptidyl fragment is required for lull insecticidal activity.

Example 12

Construction of 9F-cg-del6

The 5' end of this coding sequence was made by PCR amplifying a fragment from a plasmid comprising FR-9F-catg (See Example 7) using primers 5'FR-del6 (SEQ ID NO: 97) and C1-3A-2 (SEQ ID NO: 92) and PCR reaction Mix 3 and thermocycle Profile 3. The resulting amplicon was cloned into pCR2.1-TOPO. A 215 bp BamHI/PpuMI fragment was then ligated with a 4668 bp PpuMI/BamHI fragment of FR-9F-catg to create FR-9F-cg-del6 (SEQ ID NO: 19) which encodes the FR-9F-cg-del6 chimeric protein (SEQ ID NO: 20). The FR-9F-cg-del6 chimeric protein comprises, from N-terminus to C-terminus, a peptidyl fragment comprising the amino acid sequence MCAGIRP (SEQ ID NO: 130), amino acids 1-467 of a Cry3A protein (SEQ ID NO: 68), which comprises variable regions 1, conserved block 1, variable region 2, conserved block 2, variable region 3, and the N-terminal 24 amino acids of conserved block 3, and amino acids 477-648 of a Cry1Ab protein (SEQ ID NO: 72), which comprises the C-terminal 24 amino acids of conserved block 3, variable region 4, conserved block 4, variable region 5, conserved block 5, and variable region 6; and 38 amino acids of the Cry1Ab protoxin tail region. Thus, the FR-9F-cg-del6 chimeric protein is a variant of FR8a-9F-catg with amino acids 2 to 7 of the peptidyl fragment deleted.

The FR-9F-cg-del6 was not active against western corn rootworm suggesting that the N-terminal peptidyl fragment needs at least 7 amino acids of the C-terminal 9 amino acids of SEQ ID NO: 127 to be active against western corn rootworm.

Example 13

Construction of FR-cg-dm3

A 3839 bp MluI/SacI fragment of FRCG (Example 5) and a 923 bp MluI/SacI fragment of FRD3 (Example 10) were ligated to create FR-cg-dm3 (SEQ ID NO: 21) which encodes the FR-cg-dm protein (SEQ ID NO: 22). The FR-cg-dm3 chimeric insecticidal protein comprises, from N-terminus to C-terminus, a peptidyl fragment comprising the amino acid sequence MTSNGRQCAGIRPYDGRQQHRG (SEQ ID NO: 127), amino acids 10-467 of a Cry3A protein (SEQ ID NO: 68), which comprises variable regions 1, conserved block 1, variable region 2, conserved block 2, variable region 3, and the N-terminal 24 amino acids of conserved block 3, and amino acids 477-6.10 of a Cry1Ab protein (SEQ ID NO: 72), which comprises the C-terminal 24 amino acids of conserved block 3, variable region 4, conserved block 4, variable region 5, conserved block 5, and variable region 6.

The FRD3 eHIP the same level of activity against western corn rootworm as FR8a (See Table 5) confirming that the cathepsin G site and the protoxin tail region of FR8a were not required for full insecticidal activity against western corn rootworm.

Example 14

Construction of 9F-cg-dm3

A MluI/SacI fragment from a plasmid comprising FR-9F-cg (See Example 7) was ligated with a 923 bp MluI/SacI fragment from a plasmid comprising FRD3 (See Example 10) to create 9F-cg-dm3 (SEQ ID NO: 23) which encodes the 9F-cg-dm3 chimeric protein (SEQ ID NO: 24). The 9F-cg-dm3 protein comprises, from N-terminus to C terminus, a peptidyl fragment comprising the amino acid sequence MTSNGRQCAGIRP (SEQ ID NO: 129), amino acids 1-467 of a Cry 3A protein (SEQ ID NO: 68), which comprises variable regions 1, conserved block 1, variable region 2, conserved block 2, variable region 3, and the N-terminal 24 amino acids of conserved block 3, and amino acids 477-610 of a Cry1Ab protein (SEQ ID NO: 72), which comprises the C-terminal 24 amino acids of conserved block 3, variable region 4, conserved block 4, variable region 5, conserved block 5, and variable region 6.

The 9F-cg-dm3 eHIP provided the same level of activity against western corn rootworm (See Table 5) confirming that the C-terminal 9 amino acids of the peptidyl fragment could confer activity when domain I of the eHIP was comprised of either modified Cry3A (Cry3A055) variable regions and conserved blocks or Cry3A variable regions and conserved blocks.

Example 15

Construction of B8a

A nucleic acid fragment encoding an N-terminal portion of a Cry 3A055 protein (SEQ ID NO: 70), was PCR amplified from a plasmid comprising cry3A055 (SEQ ID NO: 69) using primers 5'3A-1-bam (SEQ ID NO: 83) and C3-3A-8 (SEQ ID NO: 99) and PCR reaction Mix 1 and thermocycling Profile 1. A nucleic acid fragment encoding a C-terminal portion of a Cry1Ab protein (SEQ ID NO: 72), comprising variable regions 4-6, was amplified from a plasmid comprising mocry1Ab (SEQ ID NO: 7.1) using primers C3-3A-7 (SEQ ID NO: 100) and 1Ab-6-sac (SEQ ID NO: 86) and PCR reaction Mix 1 and thermocycling Profile 1. The resulting amplicon was designated 2OL8b.

A nucleic acid fragment encoding an N-terminal portion of the Cry3A055 protein (SEQ ID NO: 70), was PCR amplified front a plasmid comprising cry3A055 (SEQ ID NO: 69) using primers 5'3A-1-bam (SEQ ID NO: 83) and C2-3A-4 (SEQ ID NO: 88) and PCR reaction Mix 1 and thermocycling Profile 1.

A nucleic acid fragment encoding a C-terminal portion of a Cry1B a protein (SEQ ID NO: 74) was PCR amplified from a plasmid comprising mocry1Ba (SEQ ID NO: 73) using primers 1B-5 (SEQ ID NO: 101) and 1B-10 (SEQ ID NO: 102) and PCR reaction Mix 1 and thermocycling Profile 1, except a 60° C. annealing temperature was used.

The two above-described PCR products were then used as the templates in an overlap PCR reaction with primers 5'3A-1-bam (SEQ ID NO: 83) and 1B-10 (SEQ ID NO: 102) using PCR reaction Mix 1 and thermocycling Profile 2. The resulting amplicon was designated BIO.

Next, a nucleic acid fragment of cry3A055 (SEQ ID NO: 69) was PCR amplified using 2OL-8b (see above) as the template and primers 5'3A-1-bam (SEQ ID NO: 83) and 3A-22 (SEQ ID NO: 103) with the following PCR conditions: Mix 1, thermocycling profile: 94° C.-45 seconds, 50° C.-70° C. gradient-45 seconds, 72° C.-90 seconds for 30 cycles. Another nucleic acid fragment was PCR amplified using B10 (see above) as the template and primers 1B-7 (SEQ ID NO: 104) and 1B-10 (SEQ ID NO: 102) using PCR reaction Mix 1 and thermocycling Profile 2, except a 60° C. annealing temperature was used. The two resulting PCR products were then used as templates in an overlap PCR reaction with primers 5'3A-1-bam (SEQ ID NO: 83) and 1B-JO (SEQ ID NO: 102) using the following PCR conditions: Mix 2, thermocycling profile: 94° C.-30 seconds, 40° C.-60° C. gradient-30 seconds, 72° C.-60 seconds for 30 cycles.

The resulting PCR product was ligated to a pCR2.1-TOPO vector (Invitrogen) and designated B10/pCR2.1. A BamHi-SacI fragment from B8a/pCR2.1 was then ligated to pET21a (Novagen), which was cut with BamHi/SacL to create the B8a coding sequence (SEQ ID NO: 25), which encodes a B8a hybrid toxin (SEQ ID NO: 26). The B8a hybrid protein comprises, from N-terminus to C-terminus, amino acids 1-468 of a Cry 114055 protein (SEQ ID NO: 70), and amino acids 505-656 of a Cry1Ba protein (SEQ ID NO: 74).

Example 16

Construction of 5*B8a

A BamHI-XbaI fragment from a plasmid comprising 2OL8a (See Example 3) and a XbaI-SacI fragment from a plasmid comprising B8a (See Example 15) were ligated to create 5*B8a (SEQ ID NO: 27), which encodes the 5*B8a chimeric protein (SEQ ID NO: 28). The 5*B8a protein comprises, from N-terminus to C-terminus, a peptidyl fragment comprising the amino acid sequence MTSNGRQCA-GIRPYDGRQQHRG (SEQ ID NO: 127), amino acids 10-467 of a Cry3A055 protein (SEQ ID NO: 70) and amino acids 505-656 of a Cry1Ba protein (SEQ ID NO: 74). Thus, the 5*B8a chimeric protein is the B8a hybrid protein to which an N-terminal peptidyl fragment has been added.

Example 17

Construction of V3A

This gene was PCR amplified using 3 fragments together as templates: the first fragment was amplified from a plasmid comprising cry3A055 (SEQ ID NO: 69) using primers 5'3A-1-bam (SEQ ID NO: 83) and C2-3A-4 (SEQ ID NO: 88) and PCR reaction Mix 1 and thermocycling Profile 1; the second fragment was amplified from a plasmid comprising mocry1Ab (SEQ ID NO: 71) using primers C2-3A-3 (SEQ ID NO: 95) and C3-1Ab-2 (SEQ ID NO: 105) and PCR reaction Mix 1 and thermocycling Profile 1; and the third fragment was amplified from a plasmid comprising cry3A055 (SEQ ID NO: 69) using primers C3-3A-5 (SEQ ID NO: 106) and 3A-12-sac (SEQ ID NO: 107) and PCR reaction Mix 1 and thermocycling Profile 1. These 3 PCR products were then used as templates in an overlap PCR reaction with primers 5'3A-1bam (SEQ ID NO: 83) and 3A 12-sac (SEQ ID NO: 107) using PCR reaction Mix 1 and thermocycling Profile 1, to produce the v3A coding sequence (SEQ ID NO: 29), which encodes the V3A hybrid protein (SEQ ID NO: 30). The V3A hybrid protein comprises, from N-terminus to C-terminus, amino acids 1-226 of a Cry3A055 protein (SEQ ID NO: 70), which comprises variable region 1, conserved block 1, variable region 2, and the N-terminal 34 amino acids of conserved block 2, amino acids 237-474 of a Cry1Ab protein (SEQ ID NO: 72), which comprises the C-terminal 33 amino acids of conserved block 2 variable region 3, and the N-terminal 20 amino acids of conserved block 3, and amino acids 467-598 of a Cry3A055 protein (SEQ ID NO: 70), which comprises the C-terminal 28 amino acids of conserved block 3, variable region 4, conserved block 4, variable region 5, and conserved block 5.

The V3A eHIP comprises two crossover positions. The first crossover between Cry3A055 and Cry1Ab is located in conserved block 2 and the second crossover between Cry1Ab and Cry3A055 is located in conserved block 3. Therefore, V3A is a variant of Cry3A055 in which all of variable region 3 has been replaced with variable region 3 of a Cry1Ab protein. The V3A eHIP was not as active against western corn rootworm as FR8a, suggesting that having Cry1Ab sequence in conserved block 3, variable region 4, conserved block 4, variable region 5 conserved block 5 and/or variable region 6 is important for fall insecticidal activity of FR8a.

The v3A coding sequence was ligated to a pCR2.1-TOPO vector and then subcloned into pET21a using a BamHI/SacI fragment. The V3A protein expressed by the pET21a vector has a T7 tag on the N-terminus. This protein was designated T7-V3A.

Example 18

Construction of V4F

A first nucleic acid fragment, encoding variable regions 1-3 of a Cry3A055 was PCR amplified from a plasmid comprising cry3A055 (SEQ ID NO: 69) using primers 5'3A-1-bam (SEQ ID NO: 83) and C3-3A-6 (SEQ ID NO: 84) and PCR reaction Mix 1 and thermocycling Profile 1.

A second nucleic acid fragment encoding variable region 4 of a Cry1Ab was PCR amplified from a plasmid comprising mocry1Ab (SEQ ID NO: 71) using primers C3-1Ab-3 (SEQ ID NO: 85) and C4-3A-10 (SEQ ID NO: 108) and PCR reaction Mix 1 and thermocycling Profile 1.

A third nucleic acid fragment encoding variable regions 5-6 of Cry3A055 was PCR amplified from a plasmid comprising cry3A055 (SEQ ID NO: 69) using primers C4-3A-9 (SEQ ID NO: 109) and 3A-12sac (SEQ ID NO: 107) and PCR reaction Mix 1 and thermocycling Profile 1.

All three PCR amplicons were combined and used as the template in an overlap PCR reaction with primers 5'3A-1-bam (SEQ ID NO: 83) and 3A-12-sac (SEQ ID NO: 107) using the following PC conditions: Mix 1 and thermocycling profile: 94° C.-30 seconds, 50° C.-70° C. gradient-30 seconds, 72° C.-30 seconds for 20 cycles. The resulting amplicon, designated the v4F coding sequence (SEQ ID NO: 31) which encodes the V4F hybrid toxin (SEQ ID NO: 32), was cloned into a pCR2 i-TOPO vector and designated v4F/pCR2.1. The V4F hybrid protein comprises, from N-terminus to C-terminus, amino acids 1-468 of a Cry3A055 protein (SEQ ID NO: 70), amino acids 477-520, comprising variable region 4, of a Cry1Ab protein (SEQ ID NO: 72), and amino acids 512-598 of a Cry3A055 protein (SEQ ID NO: 70).

The V4F protein has two crossover positions. The first crossover between Cry3A055 and Cry1Ab is in conserved block 3 and the second crossover between Cry1Ab and Cry3A055 is located in conserved, block 4, Therefore, V4F is a variant of Cry3A055 in which all of variable region 4 has been replaced, with variable region 4 of a Cry1Ab protein. The V4F hybrid protein was not active against western corn rootworm suggesting that Cry1Ab sequence at the C-terminal portion of FR8a contributes to the insecticidal activity of FR8a.

A BamHI-SacI fragment of v4F/pCR2.1 was subcloned into pET21. The protein expressed by the resulting plasmid was designated T7-V4F.

Example 19

Construction of 5*V4F

A BamHI-XbaI fragment from a plasmid comprising FR8a (See Example 4) and a XbaI-SacI fragment from V4F/pCR2.1 (See Example 1.8) were ligated to pET21 cut with BamHI-SacI to form 5*V4F/pET21. The 5*V4F coding sequence (SEQ ID NO: 33) encodes the 5*V4F chimeric protein (SEQ ID NO: 34). The 5*V4F chimeric insecticidal protein comprises, from N-terminus to C-terminus, a peptidyl fragment comprising the amino acid sequence MTSNGRQCA-GIRPYDGRQQHRG (SEQ ID NO: 127), amino acids 10-491 of a Cry3A055 protein (SEQ ID NO: 70), amino acids 501-520, comprising variable region 4, of a Cry1Ab protein (SEQ ID NO: 72), and amino acids 512-598 of a Cry3A055 protein (SEQ ID NO: 70).

The 5*V4F eHIP is the V4F hybrid protein with an N-terminal peptidyl fragment (SEQ ID NO: 127) added. The 5*V4F eHIP provided insecticidal activity against western corn rootworm although not at the same level as FR8a. Thus, the N-terminal conferred insecticidal activity to Y4F confirming that there may be some contributory interaction between the C-terminal portion and the N-terminal peptidyl fragment of FR8a.

The protein expressed by the 5*V4F/pET21 plasmid was designated T7-5*V4F and has a T7 tag N-terminal to the 5*V4F peptidyl fragment.

Example 20

Construction of 2OL-7

A nucleic acid fragment encoding variable region 1 of Cry3A055 was PCR amplified from a plasmid comprising cry3A055 (SEQ ID NO: 69) using primers 5'3A-1-bam (SEQ ID NO: 83) and C1-3A-2 (SEQ ID NO: 92) and PCR reaction Mix 1 and thermocycling Profile 1.

A nucleic acid fragment encoding variable regions 2-6 of Cry1Ab was PCR amplified from a plasmid comprising mocry1Ab (SEQ ID NO: 71) using primers C1-1Ab-1 (SEQ ID NO: 110) and 1Ab-6-sac (SEQ ID NO: 86) and PCR reaction Mix 1 and thermocycling Profile 1.

The resulting two amplicons were used as templates in an overlap PCR reaction with primers 5'3A-1-bam (SEQ ID NO: 83) and 1Ab-6sac (SEQ ID NO: 86) using PCR reaction Mix 2 and thermocycling Profile 1, to create the 2OL-7 coding sequence (SEQ ID NO: 35) which encodes the 2OL-7 hybrid protein (SEQ ID NO: 36). The 2OL-7 hybrid protein comprises, from N-terminus to C-terminus, amino acids 1-156 of a Cry3A055 protein (SEQ ID NO: 70), which comprises variable region 1 and the N terminal 14 amino acids of conserved block 1, and amino acids 167-648 of a Cry1Ab protein (SEQ ID NO: 72), which comprises the C-terminal 15 amino acids of conserved block 1, variable region 2, conserved block 2, variable region 3, conserved block 3, variable region 4, conserved block 4, variable region 5, conserved block 5 and variable region 6, and 38 amino acids of the Cry1Ab protoxin tail region. Thus, 2OL-7 is a variant of a Cry1Ab protein with variable region 1 replaced by variable region 1 from a Cry3A055 protein.

The 2OL-7 coding sequence was cloned into pCR2.1-TOPO (invitrogen) and then moved into pET21a using BamHI/SacI which was designated 2OL-7/pET2.1a. The coding sequence in 2OL-7/pET21a was designated T7-2OL-7 (SEQ ID NO: 37). The protein expressed by the 2OL-7/pET21a vector was designated T7-2OL-7 (SEQ ID NO: 38).

Example 21

Construction of 5*2OL-7

A BamHI/XbaI fragment of FR8a (See Example 4), a PpuMI/SacI fragment of 2OL-7 (See Example 20) and a BamHI/SacI fragment of pET21a were ligated to produce 5*2OL-7/pET21a. The 5*2OL-7 coding sequence (SEQ ID NO: 39) encodes the 5*2OL-7 chimeric protein (SEQ ID NO: 40). The 5*2OL7 protein comprises, from N-terminus to C-terminus, a peptidyl fragment comprising the amino acid sequence MTSNGRQCAGIRPYDGRQQHRG (SEQ ID NO: 127), amino acids 10-156 of a Cry3A055 protein (SEQ ID NO: 70), and amino acids 167-643 of a Cry1Ab protein. (SEQ ID NO: 72). Thus, the 5*2OL-7 hybrid protein is the 2OL-7 hybrid protein with a N-terminal peptidyl fragment added.

Example 22

Construction of 2OL-10

A nucleic acid fragment encoding an N-terminal portion of a Cry3A055 protein was PCR amplified from a plasmid comprising cry3A055 (SEQ ID NO: 69) using primers 5'3A-1-bam (SEQ ID NO: 83) and C2-3A-4 (SEQ ID NO: 88) and PCR reaction Mix 1 and thermocycling Profile 1. A nucleic acid fragment encoding a C-terminal portion of a Cry1Ab protein was PCR amplified from a plasmid comprising mocry1Ab (SEQ ID NO: 71) using primers C2-3A-3 (SEQ ID NO: 95) and 1Ab-6-sac (SEQ ID NO: 86) and PCR reaction Mix 1 and thermocycling Profile 1. These 2 PCR products were then used as the templates in an overlap PCR reaction with primers 5'3A-1-bam (SEQ ID NO: 83) and 1Ab-6-sac (SEQ ID NO: 86) using the following PCR conditions: Mix 2, thermocycling profile: 94° C.-30 seconds, 45° C.-65° C. gradient-30 seconds, 72° C.-30 seconds for 20 cycles, resulting in the 2OL-10 coding sequence (SEQ ID NO: 41) which encodes the 2OL-10 hybrid toxin (SEQ ID NO: 42). The 2OL-10 protein comprises, from N-terminus to C-terminus, amino acids 1-232 of a Cry3A055 protein (SEQ ID NO: 70) and amino acids 243-648 of a Cry1Ab protein (SEQ ID NO: 72). Thus, the 2OL-10 hybrid protein is substantially Domain I of a Cry3A055 protein and Domains II and III of a Cry1Ab protein.

The 2OL-10 coding sequence was cloned into pCR2.1-TOPO (Invitrogen) then moved to pET21a using BamHI/SacI. The protein expressed by 2OL-10/pET21a was designated T7-2OL-10.

Example 23

Construction of 5*2OL-10

A BamHI-XbaI fragment from a plasmid comprising FR8a (See Example 4) and a XbaI-SacI fragment from 2OL-10/pCR2.1 (See Example 22) were ligated to pET21 cut with BamHI-SacI to form 5*2OL-10/pET21. The 5*2OL-10 coding sequence (SEQ ID NO: 43) encodes the 5*2OL-10 chimeric protein (SEQ ID NO: 44). The 5*2OL-10 protein comprises, from N-terminus to C-terminus, a peptidyl fragment comprising the amino acid sequence MTSNGRQCA-GIRPYDGRQQHRG (SEQ ID NO: 127), amino acids 10-232 of a Cry3A055 protein (SEQ ID NO: 70) and amino acids 243-648 of a Cry1Ab protein (SEQ ID NO: 72). Thus, the 5*2OL10 chimeric protein is the 2OL-10 hybrid protein with a N-terminal peptidyl fragment added.

Example 24

Construction of 2OL-12A

A first nucleic acid fragment encoding an N-terminal portion of Cry1Ab was PCR amplified from a plasmid comprising mocry1Ab (SEQ ID NO: 71) using primers 5'1Ab bam (SEQ ID NO: 98) and C3-1Ab-2 (SEQ ID NO: 105) and PCR reaction Mix 1 and thermocycling Profile 1.

A second nucleic acid fragment encoding a C-terminal portion of Cry3A055 was PCR amplified from a plasmid comprising cry3A055 (SEQ ID NO: 69) using primers C3-3A-5 (SEQ ID NO: 106) and 3A-12sac (SEQ ID NO: 107) and PCR reaction Mix 1 and thermocycling Profile 1.

The first and second nucleic acid fragment described above were connected by using them as templates in an overlap PCR reaction with primers 5'1Ab-bam (SEQ ID NO: 98) and 3A-12-sac (SEQ ID NO: 107) using Mix 1 and thermocycling Profile 1 to create the 2OL-12A coding sequence (SEQ ID NO: 45) which encodes the 2OL-12A eHIP (SEQ ID NO: 46). The 2OL-12A protein comprises, from N-terminus to C-terminus, amino acids 1-476 of a Cry1Ab protein (SEQ ID NO: 72) and amino acids 469-598 of a Cry3A055 protein (SEQ ID NO: 70).

The 2OL-12A eHIP was not active against western corn rootworm but was active against European corn borer (See Table 6). This demonstrates that eHIP can be constructed using lepidopteran active and coleopteran active Cry proteins without loss of activity against a lepidopteran insect species.

The 2OL-12A coding sequence was cloned into pCR2.1-TOPO (Invitrogen) then moved to pET21a with BamHI/SacI. The protein expressed by the 2OL-12A/pET21a vector was designated T7-2OL-12A. The Example 25

Construction of 2OL-13

Four nucleic acid fragments were generated as follows: fragment 1 was PCR amplified from a plasmid comprising cry3A055 (SEQ ID NO: 69) using primers 5'3A-1-bam (SEQ ID NO: 83) and C1-3A2 (SEQ ID NO: 92) and PCR reaction Mix 1 and thermocycling Profile 1; fragment 2 was PCR amplified from a plasmid comprising mocry1Ab (SEQ ID NO: 71) using primers C2-3A-3 (SEQ ID NO: 95) and C3-1Ab-2 (SEQ ID NO: 105) and PCR reaction Mix 1 and thermocycling Profile 1; fragment 3 was PCR amplified from a plasmid comprising mocry1Ab (SEQ ID NO: 71) using primers C3-1Ab-3 (SEQ ID NO: 85) and C43A-10 (SEQ ID NO: 108) and PCR reaction Mix 1 and thermocycling Profile 1; and fragment 4 was PCR amplified from a plasmid comprising cry3A055 (SEQ ID NO: 69) using primers C4-3A-9 (SEQ ID NO: 109) and 3A-12-sac (SEQ ID NO: 107) and PCR reaction Mix 1 and thermocycling Profile 1.

All four fragments were then used as templates in an overlap PCR reaction using primers 5'3A-bam (SEQ ID NO: 83) and 3A-12-sac (SEQ ID NO: 107) using PCR reaction Mix 1 and thermocycling Profile 1 to create the 2OL-13 coding sequence (SEQ ID NO: 47) which encodes the 2OL-13 hybrid toxin (SEQ ID NO: 48). The 2OL-13protein comprises, from N-terminus to C-terminus, amino acids 1-159 of a Cry3A055 protein (SEQ ID NO: 70), amino acids 170-522 of a Cry1Ab protein (SEQ ID NO: 72), and amino acids 515-598 of a Cry3A055 protein (SEQ ID NO: 70). Thus, the 2OL-13 hybrid toxin is comprised of V1 and the N-terminal portion of CB1 from a Cry3A055 protein; the C-terminal portion of CB1, V2, CB2, V3, CB3, and V4 from a Cry1Ab protein; and CB4, V5, and CB5 from a Cry3A055 protein.

The 2OL-13 coding sequence was cloned into pCR2.1-TOPO (Invitrogen) then moved to pET21a using BamHI/SacI, The protein expressed by the 2OL-13/pET21a vector was designated T7-2OL-13.

Example 26

Construction of 2OL-20

A BamHI/NspI fragment from a plasmid comprising mocry3A (SEQ ID NO: 67), a NspI/HindIII fragment from a plasmid comprising 2OL-8A (SEQ ID NO: 1), and a HindIII/BamHI fragment from pET21a were ligated to make 2OL-20/pET21a.

Example 27

Construction of V5&6

A nucleic acid fragment encoding an N-terminal portion of Cry3A055 was PCR amplified from a plasmid comprising cry3A055 (SEQ ID NO: 69) using primers 5'3A-1-bam (SEQ ID NO: 83) and C4-3A-10 (SEQ ID NO: 108) and PCR reaction Mix 1 and thermocycling Profile 1.

A nucleic acid fragment encoding a C-terminal portion of Cry1Ah was PCR amplified from a plasmid comprising mocry1Ab (SEQ ID NO: 71) using primers C4-3A-9 (SEQ ID NO: 109) and 1Ab-6-sac (SEQ ID NO: 86) and PCR reaction Mix 1 and thermocycling Profile 1.

These two PCR products were then used as the templates in an overlap PCR reaction with primers 5'3A-1-bam (SEQ ID NO: 83) and 1Ab-6-sac (SEQ ID NO: 86) using PCR reaction Mix 1 and thermocycling Profile 2 to create the V5&6 coding sequence (SEQ ID NO: 49), which encodes the V5&6 hybrid toxin (SEQ ID NO: 50). The V5&6 protein comprises, from N-terminus to C-terminus, amino acids 1-524 of a Cry3A055 protein (SEQ ID NO: 70), which comprises V1, CB1, V2, CB2, V3, CB3, V4, and CB4 and amino acids 533-648 of a Cry1Ab protein (SEQ ID NO: 72), which comprises V5, CB5 and V6, and 38 amino acids of a Cry1Ab protoxin tail region.

The V5&6 coding sequence was cloned into pCR2.1-TOPO then moved to pET21 with BamHI/SacI. The protein expressed by V5&6/pET21a was designated T7-V5&6.

Example 28

Construction of 5*V5&6

A BamHI/XbaI fragment of FR8a (See Example 4), a XbaI/SacI fragment of V5&6 (See Example 27) and a BamHI/SacI fragment of pET21a were ligated to form 5*V5&6/pET21, The 5*V5&6 coding sequence (SEQ ID NO: 51) encodes the 5*V5&6 chimeric protein (SEQ ID NO: 52). The 5*V5&6 chimeric insecticidal protein comprises, from N-terminus to C-terminus, a peptidyl fragment comprising the amino acid sequence MTSNGRQCAGIRPYDGRQQHRG (SEQ ID NO: 127), amino acids 10-524 of a Cry3A055 protein (SEQ ID NO: 70), which comprises V1, CB1, V2, CB2, V3, CB3, V4, and CB4, and amino acids 533-648 of a Cry1Ab protein (SEQ ID NO: 72), which comprises V5, CB5 and V6, and 38 amino acids of a Cry1Ab protoxin tail region. Thus, the 5*V5&6 chimeric insecticidal protein is the V5&6 hybrid protein with an N-terminal peptidyl fragment added.

Example 29

Construction of 88A-dm3

A nucleic acid fragment encoding a C-terminal portion of a Cry3Aa protein (SEQ ID NO: 78) was PCR amplified from a plasmid comprising cry3Aa (SEQ ID NO: 77) using primers 5'8Aa-dm3 (SEQ ID NO: 111) and 3'8Aa-dm3 (SEQ ID NO: 112) and PCR reaction Mix 2 and thermocycling Profile 2. The resulting amplicon was cloned into pCR2.1-TOPO (Invitrogen) and designated 88A-dm3/pCR2.1.

A MluI/SacI fragment from 88A-dm3/pCR2.1 and a SacI/MluI fragment from a plasmid comprising FR8a (See Example 4) were ligated to create the 3'8A-dm3 coding sequence (SEQ ID NO: 83) which encodes the 88A-dm3 hybrid protein (SEQ ID NO: 54). The 88A-dm3 protein comprises, from N-terminus to C-terminus, a peptidyl fragment comprising the amino acid sequence MTSNGRQCAGIRPYDGRQQHRG (SEQ ID NO: 127), amino acids 10-468 of a Cry3A055 protein (SEQ ID NO: 70) and amino acids 532-664 of a Cry3Aa protein (SEQ ID NO: 78).

The 88A-dm3 coding sequence was also transformed into pET21a using a BamHI/SacI restriction digest and ligation. The protein expressed by 88A-dm3/pET21a was designated T7-88A-dm3.

Example 30

Construction of FR (1Fa)

A nucleic acid fragment encoding an N-terminal portion of FR8a (See Example 3) was PCR amplified from a plasmid comprising FR8a (SEQ ID NO: 1) using primers C2-3A-3 (SEQ ID NO: 95) and tam-OL-2 (SEQ ID NO: 113) and PCR reaction Mix 3 and thermocycling Profile 3.

A nucleic acid fragment encoding a C-terminal portion of a Cry1 Fa protein (SEQ ID NO: 76) was PCR amplified from a plasmid comprising mocry1Fa (SEQ ID NO: 75) using primers tant-OL-1 (SEQ ID NO: 114) and tant-3'sac (SEQ ID NO: 115) and PCR reaction Mix 3 and thermocycling Profile 3.

These two PCR products were then used as templates in an overlap PCR reaction, with primers C2-3A-3 (SEQ ID NO: 95) and tam-3'sac (SEQ ID NO: 115) using PCR reaction Mix 3 and thermocycling Profile 3. The resulting PCR product was cloned into pCR2.1-TOPO (Invitrogen), A BamHI/MluI fragment from a plasmid comprising FR8a, a MluI/SacI fragment from the overlap PCR product in pCR2.1 and a BamHI/SacI fragment of pET21a were then ligated to create FR (1Fa)/pET21a. The FR (1Fa) coding sequence (SEQ ID NO: 55) encodes the FR (1Fa) chimeric protein (SEQ ID NO: 56). The FR (1 Fa) protein comprises, from N-terminus to C-terminus, a peptidyl fragment comprising the amino acid sequence MTSNGRQCAGIRPYDGRQQHRG (SEQ ID NO: 127), amino acids 10-468 of a Cry3A055 protein (SEQ ID NO: 70) and amino acids 470-649 of a Cry1Fa protein (SEQ ID NO: 76).

Example 31

Construction of FR (1Ac)

Domains I & II of FR8a were PCR amplified from a plasmid comprising FR8a (SEQ ID NO: 1) using primers C2-3A-3 (SEQ ID NO: 95) and 1Ac-OL-2 (SEQ ID NO: 116) and PCR reaction Mix 3 and thermocycling Profile 3. Domain III of Cry1Ac (SEQ ID NO: 80) was PCR amplified from a plasmid comprising cry1Ac (SEQ ID NO: 79) using primers 1Ac-OL-1 (SEQ ID NO: 117) and 1Ac-3'sac (SEQ ID NO: 118) and PCR reaction Mix 3 and thermocycling Profiles.

These 2 PCR products were used as templates in an overlap PCR reaction with primers C2-3A-3 (SEQ ID NO: 95) and 1Ac-3'sac (SEQ ID NO: 118) and the following conditions: Mix 3 and thermocycling profile: 94° C.-30 seconds, 68° C.-30 seconds, 68° C.-30 seconds for 20 cycles. The overlap PCR product was cloned into pCR2.1-TOPO (Invitrogen). A BamHI/MluI fragment from a plasmid comprising FR8a, the MluI/SacI fragment from the overlap PCR product in pCR2.1 and BamHI/SacI fragment of pET21a were ligated to create FR (1 Ac)/pET2.1a. The FR (1Ac) protein comprises, from N-terminus to C-terminus, a peptidyl fragment comprising the amino acid sequence MTSNGRQCA-GIRPYDGRQQHRG (SEQ ID NO: 127), amino acids 10-468 of a Cry3A055 protein (SEQ ID NO: 70) and amino acids 477-608 of a Cry1Ac protein (SEQ ID NO: 80).

Example 32

Construction of FR (1Ia)

A nucleotide fragment encoding Domains I and II of FR8a was PCR amplified from a plasmid comprising FR8a (SEQ ID NO: 3) using primers C2-3A-3 (SEQ ID NO: 95) and 1Ia-OL-2 (SEQ ID NO: 119) and PCR reaction Mix 3 and thermocycling Profile 3. A second nucleotide fragment encoding Domain III of a Cry 1Ia protein (SEQ ID NO: 82) was PCR amplified from a plasmid comprising cry1Ia (SEQ ID NO: 81) using primers 1Ia-OL-1 (SEQ ID NO: 120) and 1Ia-3'sac (SEQ ID NO: 121) and PCR reaction Mix 3 and thermocycling Profile 3. These two PCR products were used as templates in an overlap PCR reaction with primers C2-3A-3 (SEQ ID NO: 95) and 1Ia-3*sac (SEQ ID NO: 121) and PCR reaction Mix 3 and thermocycling profile: 94° C.-30 seconds, 68° C.-45 seconds for 20 cycles. The overlap PCR product was cloned into pCR2.1-TOPO (Invitrogen). The BamHI/MluI fragment from a plasmid comprising FR8a, the MluI/SacI fragment from the overlap PCR product in pCR2.1 and BamHI/SacI fragment of pET21a were ligated to create FR (11a)/pET21a. The FR (11a) protein comprises, from N-terminus to C-terminus, a peptidyl fragment comprising the amino acid sequence MTSNGRQCA-GIRPYDGRQQHRG (SEQ ID NO: 127), amino acids 10-468 of a Cry3A055 protein (SEQ ID NO: 70) and amino acids 513-719 of a Cry1Ia protein (SEQ ID NO: 82).

Example 33

Construction of Dm2-3A

Part of the 5' end of this coding sequence was PCR amplified from a plasmid comprising cry3A055 (SEQ ID NO: 69) using primers C2-3A-3 (SEQ ID NO: 95) and FR-1Ab-2 (SEQ ID NO: 122) and PCR reaction Mix 3 and thermocycling Profile 2. A nucleotide fragment encoding Domain III of Cry1Ab was PCR amplified from a plasmid comprising mocry1Ab (SEQ ID NO: 71) using primers FR1Ab-1 (SEQ ID NO: 123) and 1Ab-6-sac (SEQ ID NO: 86) and PCR reaction Mix 3 and thermocycling Profile 2. These two PCR products were used as the templates in an overlap PCR reaction with primers C2-3A-3 (SEQ ID NO: 95) and 1Ab-6 sac (SEQ ID NO: 86) and PCR reaction Mix 3 and thermocycling Profile 2. The resulting amplicon was cloned into pCR2.1-TOPO (Invitrogen). FR8a BamHI/MluI, and the above PCR product in pCR2.1-TOPO AflIII, FR8a AflIII/SacI were ligated into pET21a BamHI/SacI. The entire coding sequence (BamHI/SacI) was then moved to 1454. The DM2-3A chimeric insecticidal protein comprises, from N-terminus to C-terminus, a peptidyl fragment comprising the amino acid sequence MTSNGRQCAGIRPYDGRQQHRG (SEQ ID NO: 127), amino acids 10-451 of a Cry 3A055 protein (SEQ ID NO: 70), which comprises variable region 1, conserved block 1, variable region 2, conserved block 2, variable region 3, and the N-terminal 7 amino acids of conserved block 3, and amino acids 460-648 of a Cry1Ab protein (SEQ ID NO: 72), which comprises the C-terminal 41 amino acids of conserved block 3, variable region 4, conserved block 4, variable region 5, conserved block 5, and variable region 6. Thus, the DM2-3A eHIP has a cross-over junction between Cry3A055 and Cry1Ab located in conserved block 3 immediately following Ser451 which is upstream of the domain II domain III junction. DM2-3A has insecticidal activity against western corn rootworm but the activity was less than that of the 8AF and FR8a eHIPs as shown in Table 5.

Example 34

Construction of T7-8AF

A nucleic acid fragment encoding an N-terminal portion of a Cry3A055 protein (SEQ ID NO: 70) was PCR amplified from a plasmid comprising cry3A055 (SEQ ID NO: 69) using primers 5> 3A-1-bam (SEQ ID NO: 83) and C3-3A-6 (SEQ ID NO: 84) and PCR reaction Mix 1 and thermocycling Profile 1.

A nucleic acid fragment encoding a C-terminal portion of a Cry1Ab protein (SEQ ID NO: 72) was PCR amplified from a plasmid comprising mocry1Ab (SEQ ID NO: 71) using primers C3-1Ab-3 (SEQ ID NO: 85) and 1Ab-6-Sac (SEQ ID NO: 86) and PCR reaction Mix 1 and thermocycle Profile 1.

The two above-described PCR products were next used as templates in an overlap PCR reaction with the primers 5'3A-1-bam (SEQ ID NO: 83) and 1Ab-6-Sac (SEQ ID NO: 86) using PCR reaction Mix 2 and thermocycling Profile 1.

The resulting amplicon was ligated as a blunt ended fragment to a pCR2.1-TOPO vector (Invitrogen, Carlsbad, Calif.) cut with SmaI to form plasmid p8AF/CR2.1. A BamHI-SacI fragment from p8AF/CR2.1 was then ligated to pET21a (EMD Biosciences, Inc., San Diego, Calif.), which was cut with BamHI-SacI, and transformed into E. coli. The open reading frame was designated T7-8AF (SEQ ID NO: 144) and encodes the T7-8AF hybrid protein (SEQ ID NO: 145). The T7-8AF hybrid protein comprises, from N-terminus to C-terminus, a peptidyl fragment comprising the amino acid sequence MASMTGGQQMGRGS (amino acids 1-14 of SEQ ID NO: 126), amino acids 1-468 of a Cry3A055 protein (SEQ ID NO: 70), which comprises variable region 1, conserved block 1, variable region 2, conserved block 2, variable region 3, and the N-terminal 24 amino acids of conserved block 3, and amino acids 477-648 of a Cry1Ab protein (SEQ ID NO: 72), which comprises the C-terminal 24 amino acids of conserved block 3, variable region 4, conserved block 4, variable region 5, conserved block 5 and variable region 6, and a 38 amino acid region of the Cry1Ab protoxin tail. The T7-8AF hybrid protein had little or no insecticidal activity against western corn rootworm.

Example 35

Construction of 8AF

A BamHI-SacI fragment from plasmid p8AF/CR2.1 (See Example 34) was ligated to a plasmid containing a constitutive Cry1Ac promoter that has been modified from that described by Schnepf et al. (1985. J. Biol. Chem. 260:6264-6272) to correct an internal ATG start codon which exists in the promoter of Schnepf et al. to an ATC codon, which was cut with BamHI-SacI, and transformed into E. coli. The open, reading frame was designated 8AF (SEQ ID NO: 63) and encodes the 8AF eHIP (SEQ ID NO: 64). The 8AF eHIP is similar to the FR8a eHIP but does not contain the optional N-terminal peptidyl fragment. The 8AF eHIP comprises, from N-terminus to C-terminus, amino acids 1-468of a Cry3A055 protein (SEQ ID NO: 70), which comprises variable region 1, conserved block 1, variable region 2, conserved block 2, variable region 3, and the N-terminal 24 amino acids of conserved block 3, and amino acids 477-648 of a Cry1Ab protein (SEQ ID NO: 72), which comprises the C-terminal 24 amino acids of conserved block 3, variable region 4, conserved block 4, variable region 5, conserved block 5 and variable region 6, and a 38 amino acid region of a Cry1Ab protoxin tail. Thus, the 8AF eHIP has a cross-over junction between Cry3A055 and Cry1Ab located in conserved block 3 immediately following Leu468 of SEQ ID NO: 70 which is downstream of the domain II domain III junction. The 8AF eHIP had high activity against western corn rootworm.

Example 36

Construction of -catG8AF

A construct was made without the Cathepsin G (Cat G) site to determine whether the Cat G site in domain I of the 8AF eHIP was necessary for rootworm activity. A 1359 bp BamHI/SalI fragment from a plasmid comprising moCry3A (SEQ ID NO: 67) and a 3483 bp BamHI/SalI fragment from a plasmid comprising 2OL-8a (SEQ ID NO: 1) were ligated to create -catG8AF (SEQ ID NO: 146) which encodes the -catG8AF eHIP (SEQ ID NO: 147).

The -catG8AF eHIP was very active against western corn rootworm demonstrating that the Cathepsin G protease recognition site in the 8AF eHIP is not required for insecticidal activity.

Example 37

Construction of 8AFdm3

The SAP eHIP described in Example 35 has a cross-over point between Cry3A055 and Cry1Ab located in CB3 downstream of the domain II/III junction, resulting in domain III of the 8AF eHIP having a small N-terminal region of domain III of Cry3A055 and the remainder of domain III being Cry1Ab domain III sequence. To determine whether the small N-terminal region of domain III of Cry3A055 was required for insecticidal activity in 8AF, another construct was made having the cross-over between Cry3A055 and Cry1Ab located in CB3 exactly at the domain II-domain III junction.

A nucleic acid fragment encoding part of domain I and domain II of Cry3A055 was PCR amplified from a plasmid comprising FR8a (SEQ ID NO: 3) using primers CMS96 (SEQ ID NO: 138) and CMS97 (SEQ ID NO: 139) and PCR reaction Mix 5 and thermocycle Profile 5.

A nucleic acid fragment encoding domain III of moCry1Ab was PCR amplified from a plasmid comprising mocry1Ab (SEQ ID NO: 71) using primers CMS98 (SEQ ID NO: 140) and CMS99 (SEQ ID NO: 141) and PCR reaction Mix 5 and thermocycle Profile 5.

The resulting two amplicons were used as templates in an overlap PCR reaction with primers CMS96 (SEQ ID NO: 138) and CMS98 (SEQ ID NO: 140) using PCR reaction Mix 5 and thermocycle Profile 6. The resulting amplicon was cloned into pCR4 Blunt (Invitrogen, Carlsbad, Calif.). A 1633 bp StuI/SacI fragment of the cloned amplicon, designated pCR4Blunt-OLWrdm3, and a approximately 3089 bp StuI/SacI fragment of a plasmid comprising cry3A055 (SEQ ID NO: 69) were combined to create 8AFdm3 (SEQ ID NO: 148) which encodes the 8AFdm3 hybrid protein (SEQ ID NO: 149).

The 8AFdm3 hybrid protein comprises, from N-terminus to C-terminus, amino acids 1-454 of a Cry3A055 protein (SEQ ID NO: 70), which comprises domains I and II, which comprise variable region 1, conserved block 1, variable region 2, conserved block 2, variable region 3, and the N-terminal 10 amino acids of conserved block 3, and amino acids 463-610 of a Cry1Ab protein (SEQ ID NO: 72), which comprises all of domain III, comprising the C-terminal 38 amino acids of conserved block 3, variable region 4, conserved block 4, variable region 5, conserved block 5 and variable region 6.

Thus, the 8AFdm3 protein has a cross-over junction between Cry3A055 and Cry1Ab immediately after Phe454 of SEQ ID NO: 70, which is at the domain II-domain III junction. The 8AFdm3 protein had no activity against western corn rootworm. This suggests that the 24 amino acid N-terminal region of CB3 of Cry3A055 or Cry3A, since they have the same sequence in this region, are necessary for activity of an SAP eHIP.

Example 38

Construction of 8AFlongdm3

To determine if the location of the cross-over junction in CB3 between Cry3A or Cry3A005 and Cry1Ab was critical for rootworm activity a construct was made wherein the cross-over junction was placed in CB4 immediately after amino acid 519 of a Cry3A055 protein.

A nucleic acid fragment encoding part of domain I and all of domain II and part of domain III of Cry3A055 was PCR amplified from a plasmid comprising cry3A055 (SEQ ID NO: 69) using primers CMS96 (SEQ ID NO: 138) and CMS101 (SEQ ID NO: 143) and PCR reaction Mix 5 and thermocycle Profile 5.

A nucleic acid fragment encoding part of domain III of Cry1Ab was PCR amplified from a plasmid comprising mocry1Ab (SEQ ID NO: 71) using primers CMS98 (SEQ ID NO: 140) and CMS100 (SEQ ID NO: 142) and PCR reaction Mix 5 and thermocycle Profile 5.

The resulting two amplicons were used as templates in an overlap PCR reaction with primers CMS96 (SEQ ID NO: 138) and CMS98 (SEQ ID NO: 140) using PCR reaction Mix 5 and thermocycle Profile 6. The resulting amplicon was cloned into pCR4 Blunt (Invitrogen, Carlsbad, Calif.). A approximately 460 bp SalI/SacI fragment of the cloned amplicon, designated pCR4Blunt-OL8AFlongdm3, and a approximately 4265 bp SalI/SadI fragment of a plasmid comprising 8AFdm3 (SEQ ID NO: 147) were combined to create 8AFlongdm3 (SEQ ID NO: 150) which encodes the 8AFlongdm3 hybrid protein (SEQ ID NO: 151).

The 8AFlongdm3 hybrid protein comprises, from N-terminus to C-terminus, amino acids 1-519 of a Cry3A055 protein (SEQ ID NO: 70), which comprises domains I and II, which comprise variable region 1, conserved block 1, variable region 2, conserved block 2, variable region 3, conserved block 3, variable region 4, and the N-terminal 6 amino acids of conserved block 4, and amino acids 528-610 of a Cry1Ab protein (SEQ ID NO: 72), which comprises a C-terminal region of domain III, comprising the C-terminal 4 amino acids of conserved block 4, variable region 5, conserved block 5, and variable region 6.

Thus, the 8AFlongdm3 protein has a cross-over junction between Cry3A055 and Cry1Ab in conserved block 4 immediately after Ile519 of SEQ ID NO: 70. The 8AFlongdm3 hybrid Cry protein had no activity against western corn rootworm. This suggests that a critical region for corn rootworm activity of a Cry3A-Cry1A eHIP lies in a region between amino acids corresponding to amino acid 6 of CB3 to amino acid 7 of CB4.

Example 39

Construction of cap8AFdm3

A approximately 1363 bp BamHI/SalI fragment from a plasmid comprising 8AFdm3 (SEQ ID NO: 148) and a approximately 3362 bp BamHI/SalI fragment from a plasmid comprising FR8a (SEQ ID NO: 3) were ligated to create cap8AFdm3 (SEQ ID NO: 152) which encodes the cap8AFdm3 eHIP (SEQ ID NO: 1.53).

The cap8AFdm3 protein had some activity against western corn rootworm as indicated in Table 5. The only difference between the 8AFdm3 hybrid protein, which was not insecticidal, and the cap8AFdm3 eHIP is the presence of an N-terminal peptidyl fragment (SEQ ID NO: 127). Thus, adding a peptidyl fragment to a non-active hybrid Cry protein created a rootworm active engineered hybrid insecticidal protein.

Example 40

Construction of 8AFdm3T

A approximately 4654 bp PmlI/SacI fragment from a plasmid comprising 8AFdm3 (SEQ ID NO: 148) and a approximately J190 bp PmlI/SacI fragment from a plasmid comprising FR8a (SEQ ID NO: 3) were ligated to create 8AFdm3T (SEQ ID NO: 154) which encodes the 8AFdm3T eHIP (SEQ ID NO: 155). The 8AFdm3T eHIP comprises from N-terminus to C-terminus, amino acids 1-454 of a Cry3A055 protein (SEQ ID NO: 70), which comprises domains I and II, which comprise variable region 1, conserved block 1, variable region 2, conserved block 2, variable region 3, and the N-terminal 10 amino acids of conserved block 3, and amino acids 463-610 of a Cry1Ab protein (SEQ ID NO: 72), which comprises all of domain III, comprising the C-terminal 38 amino acids of conserved block; 3, variable region 4, conserved block 4, variable region 5, conserved, block 5, variable region 6, and a 38 amino acid region of a Cry1Ab protoxin tail.

The only difference between the 8AFdm3 hybrid protein and the 8AFdm3T eHIP is the addition of the 38 amino acid Cry1Ab protoxin tail region indicating that addition of a protoxin tail region can change a non-active hybrid Cry protein into an active eHIP.

Example 41

Construction of 8AFlongdm3T

A approximately 4693 bp PmlI/SacI fragment from a plasmid comprising 8AFlongdm3 (SEQ ID NO: 150) and a approximately 190 bp PmlI/SacI fragment from a plasmid comprising FR8a (SEQ ID NO: 3) were ligated to create 8AFlongdm3T (SEQ ID NO: 156) which encodes the 8AFlongdmT hybrid Cry protein (SEQ ID NO: 157).

The only difference between the 8AFlongdm3 hybrid Cry protein and the 8AFlongdm3T hybrid Cry protein, which was not active against western corn rootworm, is the addition of a 38 amino acid Cry1Ab protoxin tail region indicating that the protoxin region was not itself sufficient to confer insecticidal activity to the 8AFlongdm3 hybrid Cry protein. This indicates that a combination of variable regions and conserved blocks in addition to a protoxin tail region and/or an N-terminal peptidyl fragment may be necessary to create some eHIPs.

Example 42

Construction of cap8AFdm3 T

A approximately 4693 bp PmlI/SacI fragment from a plasmid comprising cap8AFdm3 (SEQ ID NO: 152) and a approximately 190 bp PmlI/SacI fragment from a plasmid comprising FR8A (SEQ ID NO: 3) were ligated to create cap8AFdm3T (SEQ ID NO: 158) which encodes the cap8AFdm3T eHIP (SEQ ID NO: 159).

The cap8AFdm3T protein had increased activity against western corn rootworm over the cap8AFdm3 eHIP as indicated in Table 5. The only difference between the cap8AFdm3 eHIP, which had some insecticidal activity against corn rootworm, and the cap8AFdm3T eHIP is the presence of a 38 amino acid protoxin tail region from Cry1Ab. Thus, some hybrid Cry proteins can be made active by adding an N-terminal peptidyl fragment and a protoxin tail region.

Example 43

Testing Hybrid Proteins for Insecticidal Activity

Western Corn Rootworm

Hybrid proteins generated in the above described Examples were tested for insecticidal activity against western corn rootworm in laboratory bioassays. Bioassays were performed using a diet incorporation method. *E. coli* clones that express one of the proteins were grown overnight. 500 μl of an overnight culture was sonicated and the amount of protein to be tested was determined. The protein solution was then mixed with 500 μl of molten artificial diet similar to that described in Marrone et al. (1985, J. of Economic Entomology 78:290-293). After the diet solidified, it was dispensed in a petri-dish and 20 neonate corn rootworm were placed on the diet. The petri-dishes were held at approximately 30° C. Mortality was recorded after 6 days.

Results of the bioassays are shown in Table 5. Column 1 indicates the names of the hybrid Cry proteins, engineered hybrid insecticidal proteins and chimeric insecticidal proteins. Column 2 indicates relative levels of western corn rootworm activity ("−"=<40% mortality; "+"=40-49% mortality; "++"=50-59% mortality; "+++"=60-80% mortality; and "++++"=>80% mortality). Column 3 indicates relative levels of the appropriate protein detected by Western blot. Column 4 indicates presence of a peptidyl fragment ("−"=No peptidyl fragment; #1=SEQ ID NO: 126; #2=SEQ ID NO: 127; #3=SEQ ID NO: 128; #4=SEQ ID NO: 129; #5=SEQ ID NO: 130; #6=SEQ ID NO: 131; #7=SEQ ID NO: 132). Columns 5-7 show the combinations and arrangement of the variable regions (V1-V6), conserved blocks (C1- C5) and associated domains (Domain I-III) from a first Bt Cry protein or modified Cry protein and a second Bt Cry protein different from the first Cry protein or modified Cry protein that make up a core hybrid protein, which are not active against western corn rootworm and eHIPs, which have activity against western corn rootworm. Column 8 indicates the number of amino acids in a protoxin tail region if present and the Cry protein from which the tail region is derived ("1Ab−38"38 amino acids from a Cry1Ab protoxin tail, "1Ba−18"=18 amino acids from a Cry1Ba protoxin tail).

TABLE 5

Results of western corn rootworm bioassays.

| Proteins | CRW | Protein | Peptidyl | Domain I | | | | Domain II | Domain III | | | | | | Protoxin |
|---|---|---|---|---|---|---|---|---|---|---|---|---|---|---|---|
| Tested | Activity | Expressed | Fragment | V1 | C1 | V2 | C2 | V3 | C3 | V4 | C4 | V5 | C5 | V6 | Region |
| 8AF | ++++ | ++ | — | | 3A055 | | | 3A055 | 3A055 | | | 1Ab | | | 1Ab-38 |
| T7-8AF | − | + | #7 | | 3A055 | | | 3A055 | 3A055 | | | 1Ab | | | 1Ab-38 |
| -CatG8AF | ++++ | ++ | — | | 3A | | | 3A | 3A | | | 1Ab | | | 1Ab-38 |
| 8AFdm3 | − | + | — | | 3A055 | | | 3A055 | | | 1Ab | | | | — |
| 8AFdm3T | +++ | ++ | — | | 3A055 | | | 3A055 | | | 1Ab | | | | 1Ab-38 |
| 8AFlongdm3 | − | + | — | | 3A055 | | | 3A055 | | 3A055 | | | 1Ab | | — |
| 8AFlongdm3 | − | + | — | | 3A055 | | | 3A055 | | 3A055 | | | 1Ab | | 1Ab-38 |
| Cap8AFdm3 | + | + | #2 | | 3A055 | | | 3A055 | | | 1Ab | | | | — |
| Cap8AFdm3T | ++ | ++ | #2 | | 3A055 | | | 3A055 | | | 1Ab | | | | 1Ab-38 |
| 2OL-8a | ++++ | ++ | #1 | | 3A055 | | | 3A055 | 3A055 | | | 1Ab | | | 1Ab-38 |
| FR8a +34 | ++++ | ++ | #6 | | 3A055 | | | 3A055 | 3A055 | | | 1Ab | | | 1Ab-38 |
| FR8a | ++++ | ++ | #2 | | 3A055 | | | 3A055 | 3A055 | | | 1Ab | | | 1Ab-38 |
| FRCG | ++++ | ++ | #2 | | 3A | | | 3A | 3A | | | 1Ab | | | 1Ab-38 |
| FR8a-9F | +++ | ++ | #5 | | 3A055 | | | 3A055 | 3A055 | | | 1Ab | | | 1Ab-38 |
| FR8a-9F-catg | ++++ | ++ | #5 | | 3A | | | 3A | 3A | | | 1Ab | | | 1Ab-38 |
| FR8a-12aa | ++++ | ++ | #3 | | 3A055 | | | 3A055 | 3A055 | | | 1Ab | | | 1Ab-38 |
| Cry3A055 | ++++ | ++ | — | | 3A055 | | | 3A055 | | | 3A055 | | | | — |
| 5*Cry3A055 | − | ++ | #2 | | 3A055 | | | 3A055 | | | 3A055 | | | | — |
| Wr-9mut | − | ++ | #3 | | 3A055 | | | 3A055 | | | 3A055 | | | | — |
| FRD3 | ++++ | ++ | #2 | | 3A055 | | | 3A055 | 3A055 | | | 1Ab | | | — |
| FR-12-cg-dm3 | ++ | ++ | #3 | | 3A055 | | | 3A055 | 3A055 | | | 1Ab | | | — |
| 9F-cg-del6 | − | ++ | #5 | | 3A | | | 3A | 3A | | | 1Ab | | | 1Ab-38 |
| FR-cg-dm3 | ++++ | ++ | #2 | | 3A | | | 3A | 3A | | | 1Ab | | | — |
| 9F-cg-dm3 | ++++ | ++ | #5 | | 3A | | | 3A | 3A | | | 1Ab | | | — |
| B8a | − | + | — | | 3A055 | | | 3A055 | 3A055 | | | 1Ba | | | 1Ba-18 |
| 5*B8a | − | + | #2 | | 3A055 | | | 3A055 | 3A055 | | | 1Ba | | | 1Ba-18 |
| V3A | ++ | + | — | | 3A055 | | | 1Ab | | | | 3A055 | | | — |
| V4F | − | ++ | — | | 3A055 | | | 3A055 | | 1Ab | | | 3A055 | | — |
| 5*V4F | ++ | + | #2 | | 3A055 | | | 3A055 | | 1Ab | | | 3A055 | | — |
| 2OL-7 | − | ++ | — | | 3A055 | 1Ab | | 1Ab | | | 1Ab | | | | 1Ab-38 |
| 5*2OL-7 | − | + | #2 | | 3A055 | 1Ab | | 1Ab | | | 1Ab | | | | 1Ab-38 |
| 2OL-10 | − | + | — | | 3A055 | | | 1Ab | | | 1Ab | | | | 1Ab-38 |
| 5*2OL-10 | +/− | +/− | #2 | | 3A055 | | | 1Ab | | | 1Ab | | | | 1Ab-38 |
| 2OL-12A | − | ++ | — | | 1Ab | | | 1Ab | | | 3A | | | | — |
| 2OL-13 | − | − | — | | 3A055 | | | 1Ab | 1Ab | | | 3A055 | | | — |
| 2OL-20 | − | + | — | | 3A | | | 3A | 3A | | | 1Ab | | | 1Ab-38 |
| V5&6 | − | ++ | — | | 3A055 | | | 3A055 | | 3A055 | | | 1Ab | | 1Ab-38 |
| 5*V5&6 | − | ++ | #2 | | 3A055 | | | 3A055 | | 3A055 | | | 1Ab | | 1Ab-38 |
| 88A-dm3 | − | ++ | #2 | | 3A055 | | | 3A055 | 3A055 | | | 8Aa | | | — |
| FR(1Fa) | − | ++ | #2 | | 3A055 | | | 3A055 | 3A055 | | | 1Fa | | | — |
| FR(1Ac) | − | + | #2 | | 3A055 | | | 3A055 | 3A055 | | | 1Ac | | | — |
| FR(1Ia) | − | − | #2 | | 3A055 | | | 3A055 | 3A055 | | | 1Ia | | | — |
| DM23A | + | + | #2 | | 3A055 | | | 3A055 | 3A055 | | | 1Ab | | | 1Ab-38 |

The chimeric insecticidal proteins, 2OL-8a and FR8a, and the 2OL-12A eHIP, were tested against several insect species to determine spectrum of activity. The insects tested included western corn rootworm (WCR), northern corn rootworm (NCR), southern corn rootworm (SCR), Colorado potato beetle (CPB), and European corn borer (ECB). Results of the assays are shown in Table 6. A "+" indicates insecticidal activity. A"−" indicates no activity. The 2OL-8a and FR8a CIPs were active against WCR, NCR and CPB. The 2OL-12 A eHIP was surprisingly active against ECB.

TABLE 6

Activity spectrum of CIPs.

| | Activity Spectrum | | | | |
|---|---|---|---|---|---|
| Protein | WCR | NCR | SCR | CPB | ECB |
| 2OL-8a | + | + | − | + | − |
| FR8a | + | + | − | + | − |
| 2OL-12A | − | nt | nt | nt | + |
| Cry3A055 | + | + | − | + | − |

TABLE 6-continued

Activity spectrum of CIPs.

| | Activity Spectrum | | | | |
|---|---|---|---|---|---|
| Protein | WCR | NCR | SCR | CPB | ECB |
| Cry3A | − | − | − | + | − |
| Cry1Ab | − | − | − | − | + |

Example 44

Insertion of Genes Encoding eHIPS into Plants

Figure 4:
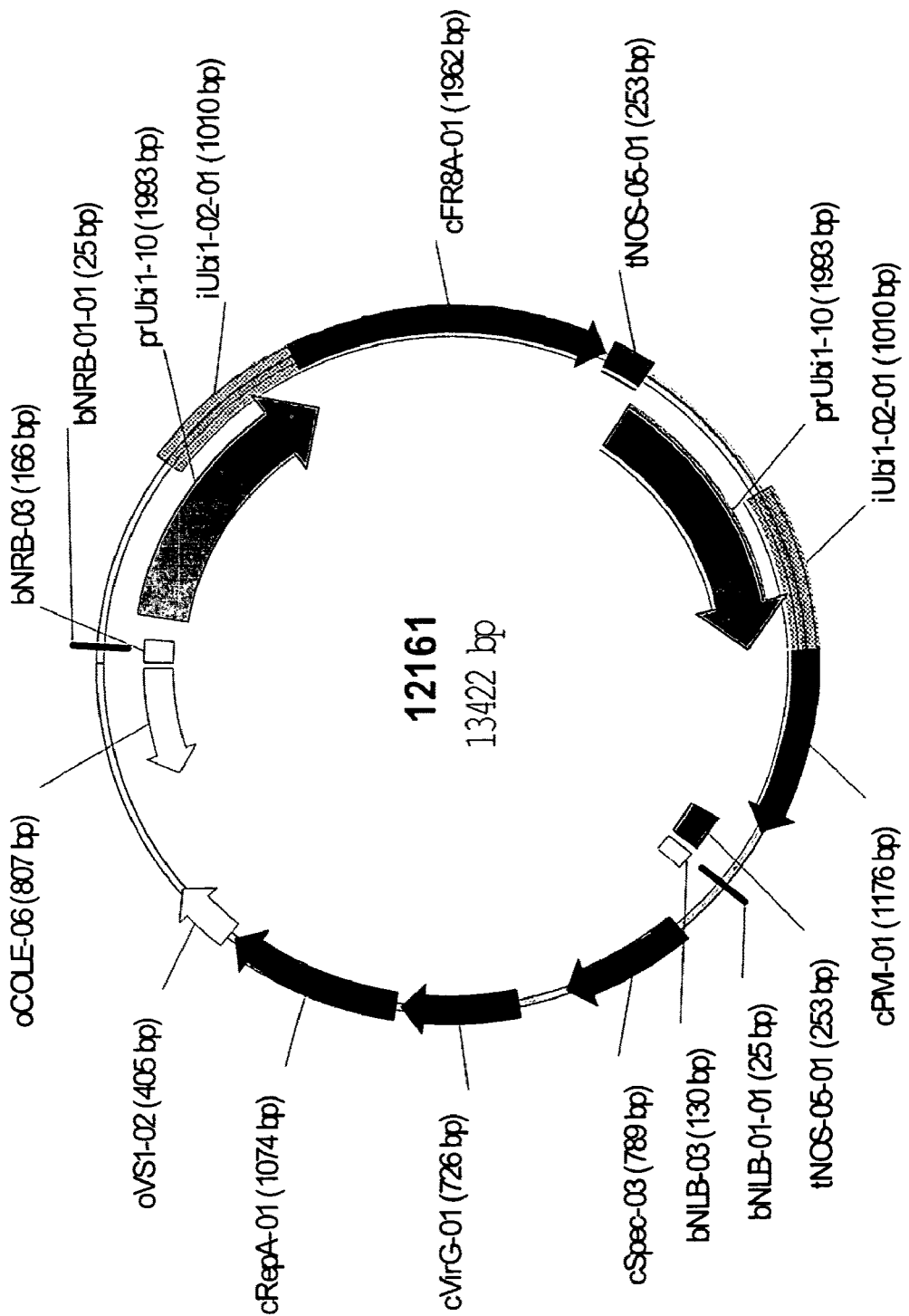
FIG. 4 shows a map of recombinant vector 12161 used to transform corn comprising an expression cassette with a maize ubiquitin promoter operably linked to a FR8a coding sequence operably linked to a NOS terminator.
Figure 5:
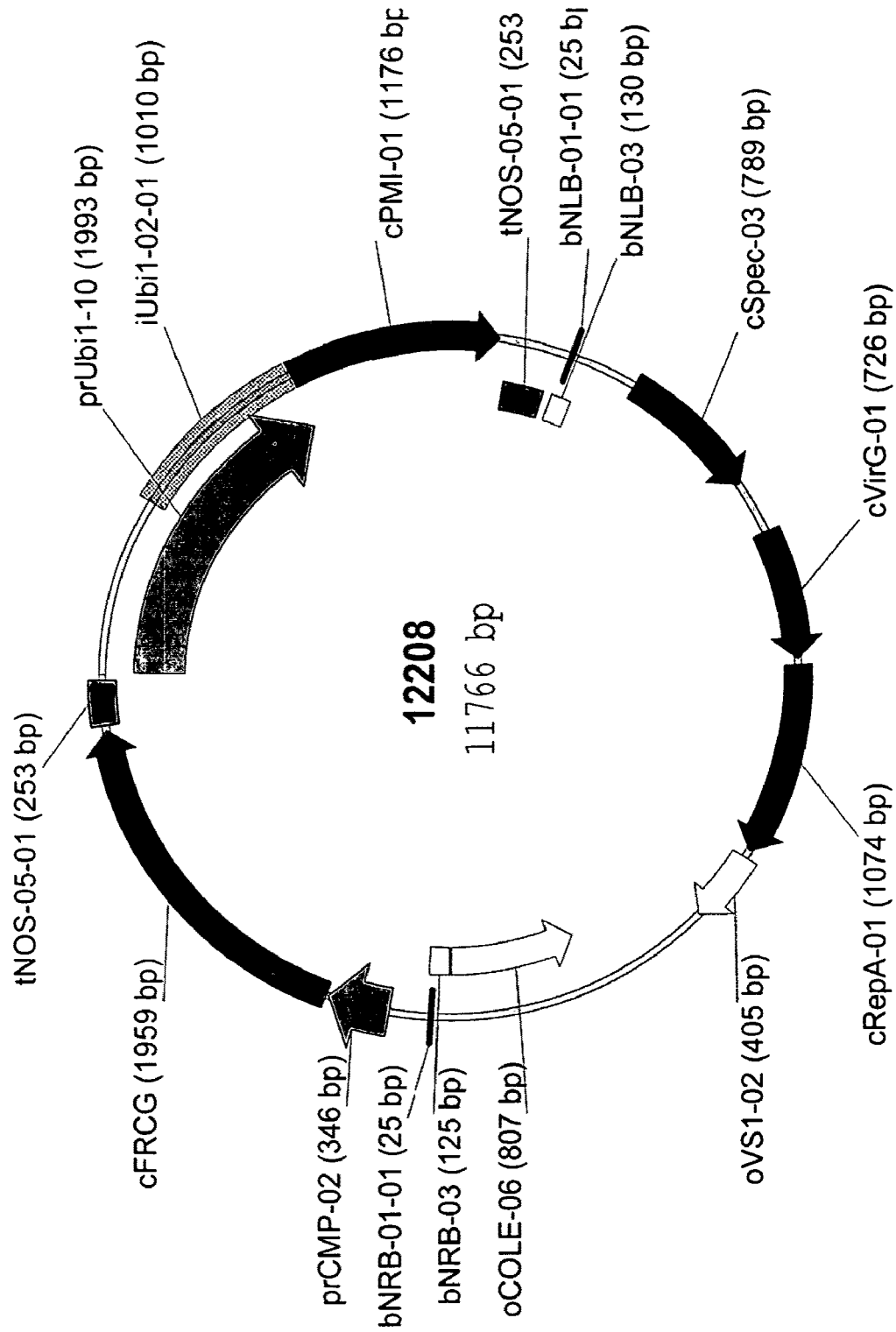
FIG. 5 shows a map of recombinant vector 12208 used to transform corn comprising an expression cassette with a cestrum yellow leaf curling virus promoter (cmp) operably linked to a FRCG coding sequence operably linked to a NOS terminator.
Figure 6:
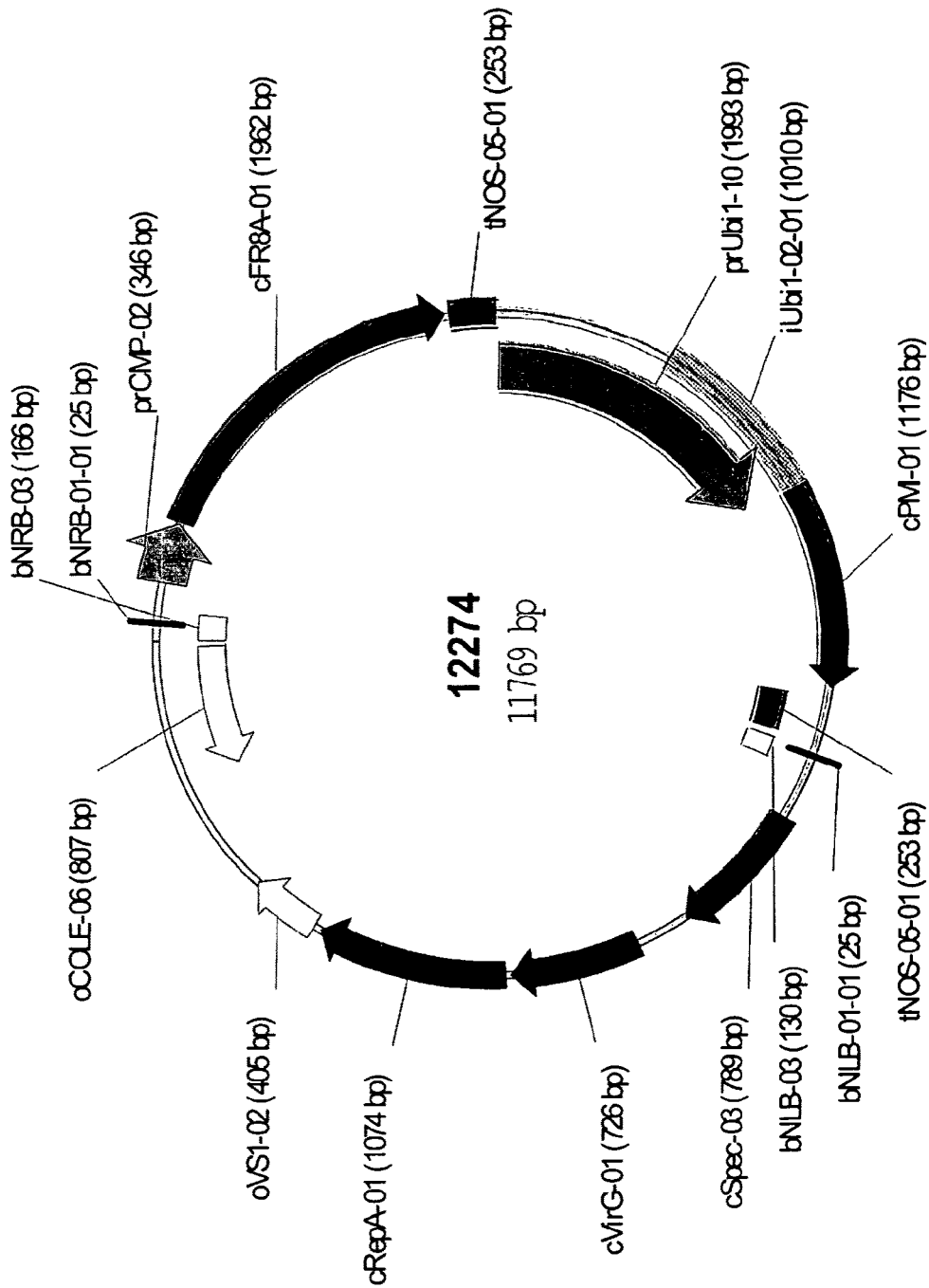
FIG. 6 shows a map of recombinant vector 12274 used to transform corn comprising an expression cassette with a cestrum yellow leaf curling virus promoter (cmp) operably linked to a FR8a coding sequence operably linked to a NOS terminator.
Figure 7:
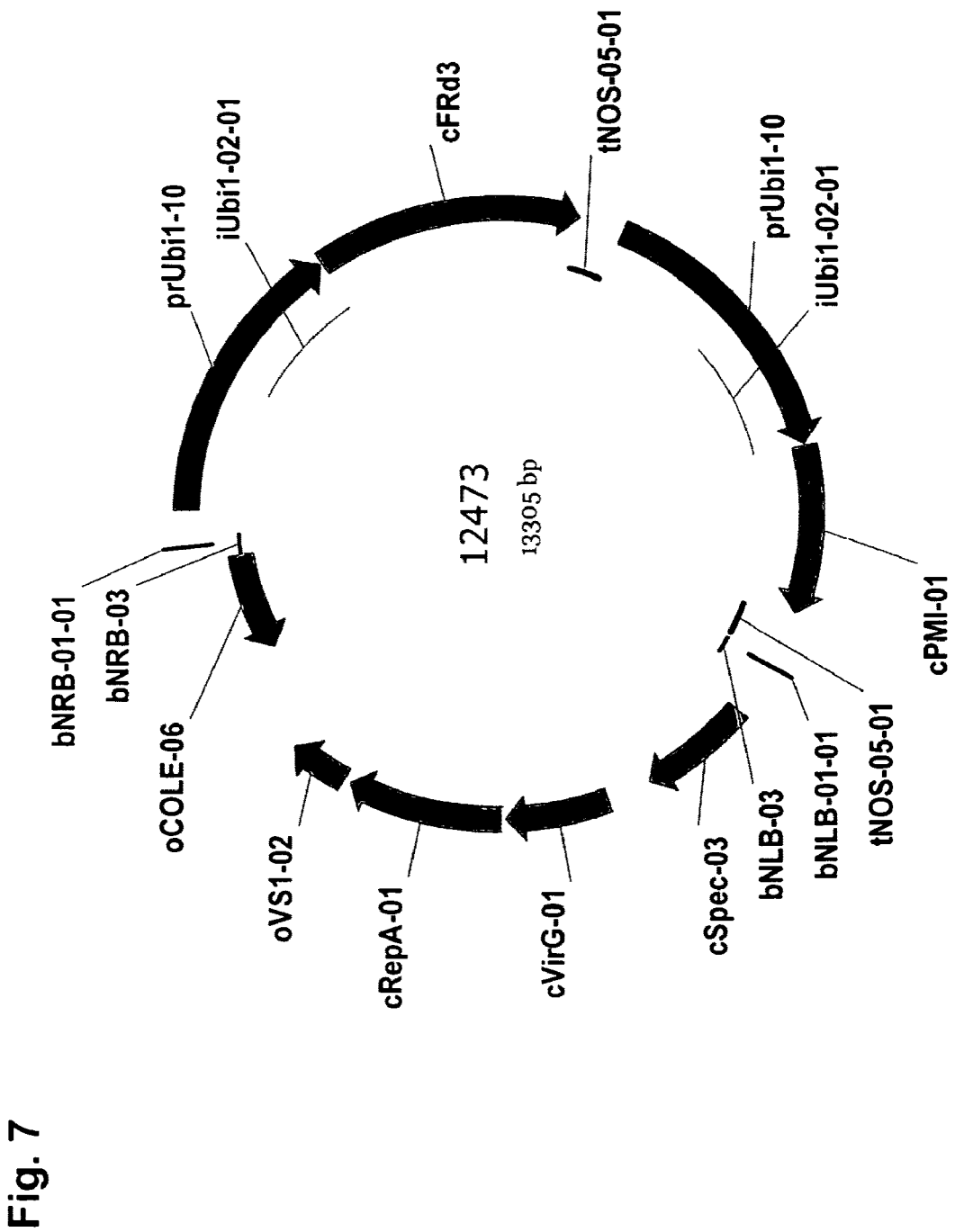
FIG. 7 shows a map of recombinant vector 12473 used to transform corn comprising an expression cassette with a maize ubiquitin promoter (ubi) operably linked to a FRD3 coding sequence operably linked to a NOS terminator.
Figure 8:
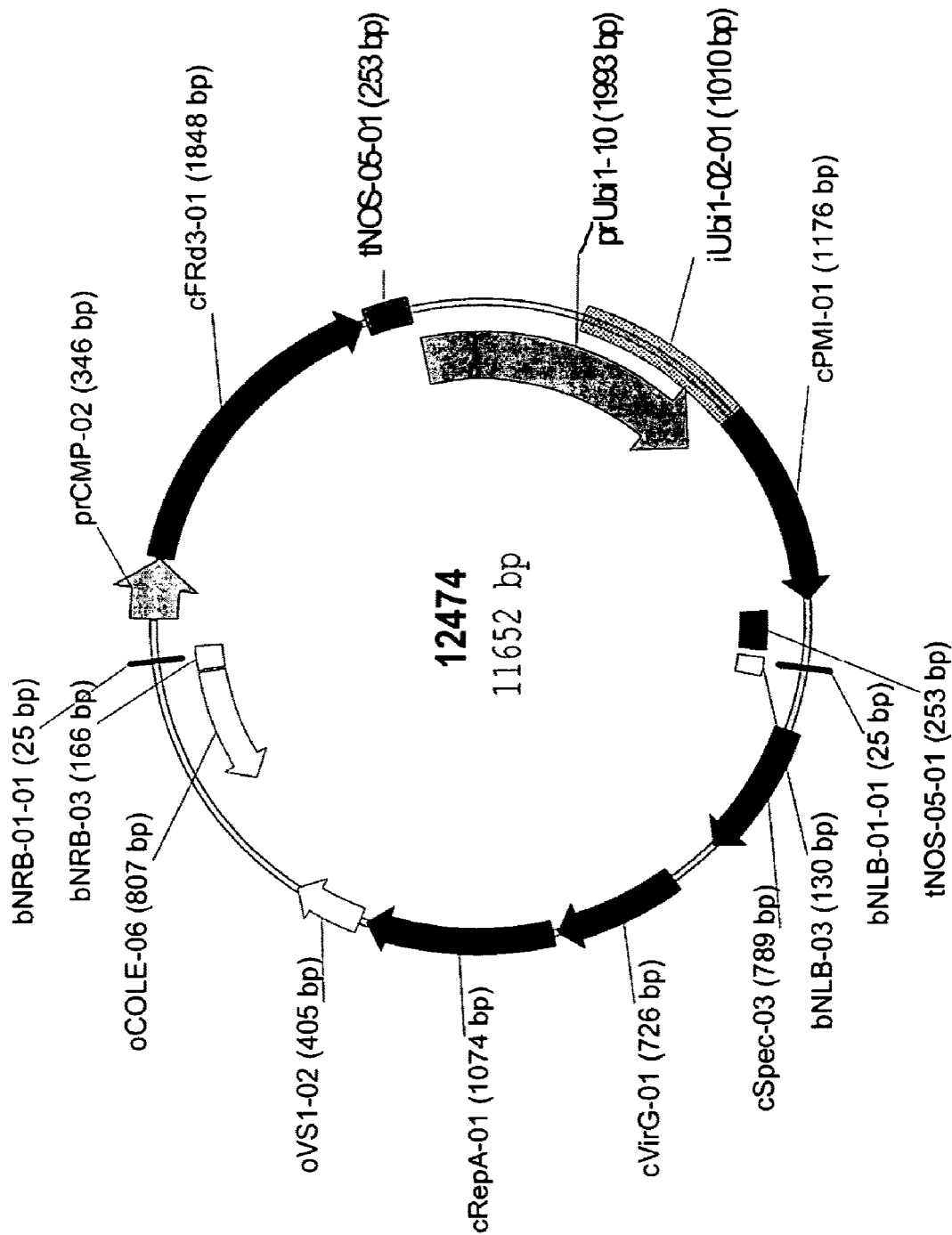
FIG. 8 shows a map of recombinant vector 12474 used to transform corn comprising an expression cassette with a cestrum yellow leaf curling virus promoter (cmp) operably linked to a FRD3 coding sequence operably linked to a NOS terminator.

Three genes encoding the chimeric insecticidal proteins FR8a, FRCG and FRD3 were chosen for transformation into maize plants. An expression cassette comprising the FR8a or FRCG or FRD3 coding sequence was transferred to a suitable vector for *Agrobacterium*-mediated maize transformation. For this example, the following vectors were used in the transformation experiments: 12207 (FIG. 3), 12161 (FIG. 4), 12208 (FIG. 5), 12274 (FIG. 6), 12473 (FIG. 7) and 12474 (FIG. 8).

Transformation of immature maize embryos was performed essentially as described in Negrotto et al., 2000, Plant Cell Reports 19: 798-803. For this example, all media constituents were essentially as described in Negrotto et al., supra. However, various media constituents known in the art may be substituted.

The genes used for transformation were cloned into a vector suitable for maize transformation. Vectors used in this example contain the phosphomannose isomerase (PMS) gene for selection of transgenic lines (Negrotto et al., supra).

Briefly, *Agrobacterium* strain LBA4404 (pSBI) containing a plant transformation plasmid was grown on YEP (yeast extract (5 g/L), peptone (10 g/L), NaCl (5 g/L), 15 g/l agar, pH 6.8) solid medium for 2-4 days at 28° C. Approximately $0.8 \times 10^9$ *Agrobacterium* were suspended in LS-inf media supplemented with 100 µM As (Negrotto et al., supra). Bacteria were pre-induced in this medium for 30-60 minutes.

Immature embryos from A188 or other suitable genotype are excised from 8-12 day old ears into liquid LS-inf+100 µM As. Embryos are rinsed once with, fresh infection medium. *Agrobacterium* solution is then added and embryos are vortexed for 30 seconds and allowed to settle with the bacteria for 5 minutes. The embryos are then transferred scutellum side up to LSAs medium and cultured in the dark for two to three days. Subsequently, between 20 and 25 embryos per petri plate are transferred to LSDc medium supplemented with cefotaxime (250 mg/l) and silver nitrate (1.6 mg/l) and cultured in the dark for 28° C. for 10 days.

immature embryos, producing embryogenic callus were transferred to LSD1 M0.5S medium. The cultures were selected on this medium for about 6 weeks with a subculture step at about 3 weeks. Surviving calli were transferred to Reg1 medium supplemented with mannose. Following culturing in the light (16 hour light/8 hour dark regiment), green tissues were then transferred to Reg2 medium without growth regulators and incubated for about 1-2 weeks. Plant lets were transferred to Magenta GA-7 boxes (Magenta Corp, Chicago Ill.) containing Reg3 medium and grown in the light. After about 2-3 weeks, plants were tested for the presence of the pmi gene and the FR8a or FRCG genes by PCR. Positive plants from the PCR assay were transferred to the greenhouse and tested for resistance to corn rootworm.

Example 45

Analysis of Transgenic Maize Plants for Corn Rootworm Efficacy: Root Excision Bioassay Typically, corn plants are sampled as they are being transplanted from Magenta GA-7 boxes into soil. This allows the roots to be sampled from a reasonably sterile environment relative to soil conditions. Sampling consists of cutting a small piece of root (ca. 2-4 cm long) and placing it onto enriched phytagar (phytagar, 12 g., sucrose, 9 g., MS salts, 3 ml., MS vitamins, 3 ml., Nystatin (25 mg/ml), 3 ml., Cefotaxime (50 mg/ml), 7 ml., Aureomycin (50 mg/ml), 7 ml. Streptomycin (50 mg/ml), 7 ml., dH$_2$O, 600 ml) in a small petri-dish. Negative controls are either transgenic plants that are PCR negative for the FR8a or FRCG gene from the same transformation experiment, or from non-transgenic plants (of a similar size to test plants) that were being grown in the phytotron.

Roots are also sampled after plants have been growing in soil. If sampling roots from soil, the root pieces are washed with wafer to remove soil residue, dipped in Nystatin solution (5 mg/ml), removed from the dip, blotted dry with paper toweling, and placed into a phytagar dish as above.

Root samples are inoculated with western corn rootworms by placing about 10 first instar larvae onto the inside surface of the lid of each phytagar dish and the lids then tightly resealed over the exposed root piece. Larvae are handled using a fine tip paintbrush. After all dishes were inoculated, the tray of dishes was placed in the dark at room temperature until data collection.

At about 2-4 days after root inoculation, data were collected. The percent mortality of the larvae was calculated along with a visual damage rating of the root. Feeding damage was scored by observing the number of feeding holes (FH) in the root piece caused by the rootworm larvae and was rated as high, moderate, low, or absent and given a numerical value of category 3, 2, or 1, respectively (with Category 1 including damage ratings of absent and/or low). Category 1 plants typically have 0-FH to 2-FH; Category 2 plants have 3 to 4-FH; and Category 3 plants have >5-FH, Root samples having a damage rating in Category 1 were considered excellent performers, category 2: average performers and category 3: poor performers. Category 1 plants were selected for further testing in the greenhouse and field.

Results in Table 7 show that plants expressing a the FR8a and FRCG eHIPs protected roots from feeding damage caused by western corn rootworm. A majority of events expressing the chimeric insecticidal protein were considered category 1 plants, whereas control plants not expressing a chimeric insecticidal protein were in category 3. Plants expressing the FRD3 eHIP provided comparable levels of control of western, corn rootworm.

TABLE 7

Efficacy of transgenic plants expressing FR8a and FRCG against WCR.

| Vector | Event | Damage Rating (No. FH) | Category | Vector | Event | Damage Rating (No. FH) | Category |
|---|---|---|---|---|---|---|---|
| 12161 | 1 | 1 | 1 | 12207 | 1 | 0 | 1 |
|  | 2 | 1 | 1 |  | 2 | 2 | 1 |
|  | 3 | 0 | 1 |  | 3 | 1 | 1 |
|  | 4 | 3 | 2 |  | 4 | 2 | 1 |
|  | 5 | 2 | 1 |  | 5 | 1 | 1 |
|  | 6 | 0 | 1 |  | 6 | 2 | 1 |
|  | 7 | 0 | 1 |  | 7 | 4 | 2 |
|  | 8 | 0 | 1 |  | 8 | 3 | 2 |
|  | 9 | 1 | 1 |  | 9 | 4 | 2 |
|  | 10 | 1 | 1 |  |  |  |  |
|  | 11 | 4 | 2 | Control | 1 | 7 | 3 |
|  | 12 | 0 | 1 |  | 2 | 9 | 3 |
|  |  |  |  |  | 3 | 8 | 3 |
| Control | 1 | 6 | 3 |  | 4 | 11 | 3 |
|  | 2 | 6 | 3 |  | 5 | 7 | 3 |
|  | 3 | 6 | 3 |  | 6 | 12 | 3 |
|  | 4 | 18 | 3 |  |  |  |  |
| 12208 | 1 | 0 | 1 | 12274 | 1 | 3 | 2 |
|  | 2 | 0 | 1 |  | 2 | 0 | 1 |
|  | 3 | 3 | 2 |  | 3 | 3 | 2 |
|  | 4 | 4 | 2 |  | 4 | 3 | 2 |
|  | 5 | 1 | 1 |  | 5 | 0 | 1 |
|  | 6 | 4 | 2 |  | 6 | 3 | 2 |
|  | 7 | 0 | 1 |  | 7 | 3 | 2 |
|  | 8 | 4 | 2 |  | 8 | 0 | 1 |
|  | 9 | 4 | 2 |  | 9 | 3 | 2 |
|  | 10 | 1 | 1 |  | 10 | 3 | 2 |
|  | 11 | 1 | 1 |  | 11 | 0 | 1 |
|  | 12 | 1 | 1 |  |  |  |  |
|  | 13 | 0 | 1 | Control | 1 | 10 | 3 |
|  |  |  |  |  | 2 | 10 | 3 |
| Control | 1 | 10 | 3 |  | 3 | 10 | 3 |
|  | 2 | 5 | 3 |  | 4 | 7 | 3 |
|  | 3 | 7 | 3 |  | 5 | 8 | 3 |
|  | 4 | 7 | 3 |  | 6 | 6 | 3 |

TABLE 7-continued

Efficacy of transgenic plants expressing FR8a and FRCG against WCR.

| Vector | Event | Damage Rating (No. FH) | Category | Vector | Event | Damage Rating (No. FH) | Category |
|---|---|---|---|---|---|---|---|
|  | 5 | 8 | 3 |  |  |  |  |
|  | 6 | 8 | 3 |  |  |  |  |

Example 46

Analysis of Transgenic Maize Plants for Corn Rootworm Efficacy in the Field

Some positive plants identified using the root excision bioassay described above were evaluated in the field. Eighteen plants from each event were removed from field plots and evaluated for damage to the roots. Root damage was rated using die Iowa State 0 to 3 linear root damage scale (Oleson, J. D. et al., 2005. J. Econ Entomol. 98(1): 1-8), where 0.00=no feeding damage (lowest rating that can be given); 1.00=one node (circle of roots), or the equivalent of an entire node, eaten back to within approximately 1½ inches of the stalk (soil line on the 7th node); 2.00= two complete nodes eaten; 3.00=three or more nodes eaten (highest rating that can be given); and damage in between complete nodes eaten is noted as the percentage of the node missing, i.e. 1.50=1½ nodes eaten, 0.25=¼ of one node eaten, etc.

Results of the field trials against western and northern corn rootworm are shown in Table 8 and against Mexican corn rootworm in Table 9. All transgenic corn expressing the FR8a chimeric insecticidal protein performed better than a standard commercial chemical insecticide against western, northern and Mexican corn rootworm.

TABLE 8

Results of western and northern corn rootworm field trials.

| Event | Plasmid | Root Rating |
|---|---|---|
| 1 | 12161 (ubi: FR8a) | 0.08 |
| 2 | 12161 | 0.05 |
| 3 | 12161 | 0.09 |
| 4 | 12161 | 0.04 |
| 5 | 12274 (cmp: FR8a) | 0.04 |
| 6 | 12274 | 0.08 |
| 7 | 12274 | 0.05 |
| Chemical |  | 0.15 |
| Neg Check |  | 0.87 |

TABLE 9

Results of Mexican corn rootworm field trials.

| Event | Plasmid | Root Rating |
|---|---|---|
| 1 | 12161 (ubi: FR8a) | 0.04 |
| 5 | 12274 (cmp: FR8a) | 0.22 |
| 6 | 12274 | 0.05 |
| Chemical |  | 0.15 |
| Neg Check |  | 1.04 |

SEQUENCE LISTING

```
<160> NUMBER OF SEQ ID NOS: 160

<210> SEQ ID NO 1
<211> LENGTH: 2001
<212> TYPE: DNA
<213> ORGANISM: Artificial Sequence
<220> FEATURE:
<223> OTHER INFORMATION: 2OL-8a coding sequence

<400> SEQUENCE: 1
atggctagca tgactggtgg acagcaaatg ggtcgcggat ccactagtaa cggccgccag      60
tgtgctggaa ttcgcccetta tgacggccga caacaacacc gaggcctgga cagcagcacc     120
accaaggacg tgatccagaa gggcatcagc gtggtgggcg acctgctggg cgtggtgggc     180 ttcccettcg gcggcgccct ggtgagcttc tacaccaact tcctgaacac catctggccc     240
agcgaggacc cctggaaggc cttcatggag caggtggagg ccctgatgga ccagaagatc     300
gccgactacg ccaagaacaa ggcactggcc gagctacagg gcctccagaa caacgtggag     360
gactatgtga gcgccctgag cagctggcag aagaacccecg ctgcaccgtt ccgcaaccce     420 cacagccagg gccgcatccg cgagctgttc agccaggccg agagccactt ccgcaacagc     480
atgcccagct tcgccatcag cggctacgag gtgctgttcc tgaccaccta cgcccaggcc     540
gccaacaccc acctgttcct gctgaaggac gcccaaatct acggagagga gtggggctac     600
gagaaggagg acatcgccga gttctacaag cgccagctga agctgaccca ggagtacacc     660
gaccactgcg tgaagtggta caacgtgggt ctagacaagc tccgcggcag cagctacgag     720
agctgggtga acttcaaccg ctaccgccgc gagatgaccc tgaccgtgct ggacctgatc     780
```

```
gccctgttcc ccctgtacga cgtgcgcctg taccccaagg aggtgaagac cgagctgacc    840
cgcgacgtgc tgaccgaccc catcgtgggc gtgaacaacc tgcgcggcta cggcaccacc    900
ttcagcaaca tcgagaacta catccgcaag ccccacctgt tcgactacct gcaccgcatc    960
cagttccaca cgcgttttcc agcccggcta tacggcaacg acagcttcaa ctactggagc    1020
ggcaactacg tgagcacccg ccccagcatc ggcagcaacg acatcatcac cagccccttc    1080
tacggcaaca gagcagcga gcccgtgcag aaccttgagt tcaacggcga aaggtgtac     1140 cgcgccgtgg ctaacaccaa cctggccgtg tggccctctg cagtgtacag cggcgtgacc    1200
aaggtggagt tcagccagta caacgaccag accgacgagg ccagcaccca gacctacgac    1260
agcaagcgca acgtgggcgc cgtgagctgg acagcatcg accagctgcc cccgagacc     1320 accgacgagc ccctggagaa gggctacagc accagctga actacgtgat gtgcttcctg    1380
atgcagggca gccgcggcac catccccgtg ctgacctgga cccacaagag cgtcgacttc    1440
ttcaacatga tcgacagcaa gaagatcacc cagctgcccc tgaccaagag caccaacctg    1500
ggcagcggca ccagcgtggt gaagggcccc ggcttcaccg gcggcgacat cctgcgccgc    1560
accagccccg gccagatcag cacccctgcgc gtgaacatca ccgccccct gagccagcgc   1620 taccgcgtcc gcatccgcta cgccagcacc accaacctgc agttccacac cagcatcgac   1680
ggccgcccca tcaaccaggg caacttcagc gccaccatga gcagcggcag caacctgcag   1740
agcggcagct tccgcaccgt gggcttcacc acccccttca acttcagcaa cggcagcagc    1800
gtgttcaccc tgagcgccca cgtgttcaac agcggcaacg aggtgtacat cgaccgcatc    1860
gagttcgtgc ccgccgaggt gaccttcgag gccgagtacg acctggagag ggctcagaag    1920
gccgtgaacg agctgttcac cagcagcaac cagatcggcc tgaagaccga cgtgaccgac    1980
taccacatcg atcaggtgta g                                             2001
```

<210> SEQ ID NO 2
<211> LENGTH: 668
<212> TYPE: PRT
<213> ORGANISM: Artificial Sequence
<220> FEATURE:
<223> OTHER INFORMATION: 2OL-8a protein

<400> SEQUENCE: 2

```
Met Ala Ser Met Thr Gly Gly Gln Gln Met Gly Arg Gly Ser Gly Ser
1               5                   10                  15

Thr Ser Asn Gly Arg Gln Cys Ala Gly Ile Arg Pro Tyr Asp Gly Arg
                20                  25                  30

Gln Gln His Arg Gly Leu Asp Ser Ser Thr Thr Lys Asp Val Ile Gln
            35                  40                  45

Lys Gly Ile Ser Val Val Gly Asp Leu Leu Gly Val Val Gly Phe Pro
        50                  55                  60

Phe Gly Gly Ala Leu Val Ser Phe Tyr Thr Asn Phe Leu Asn Thr Ile
65                  70                  75                  80

Trp Pro Ser Glu Asp Pro Trp Lys Ala Phe Met Glu Gln Val Glu Ala
                85                  90                  95

Leu Met Asp Gln Lys Ile Ala Asp Tyr Ala Lys Asn Lys Ala Leu Ala
            100                 105                 110

Glu Leu Gln Gly Leu Gln Asn Asn Val Glu Asp Tyr Val Ser Ala Leu
        115                 120                 125

Ser Ser Trp Gln Lys Asn Pro Ala Ala Pro Phe Arg Asn Pro His Ser
    130                 135                 140

Gln Gly Arg Ile Arg Glu Leu Phe Ser Gln Ala Glu Ser His Phe Arg
```

-continued

```
            145                 150                 155                 160
        Asn Ser Met Pro Ser Phe Ala Ile Ser Gly Tyr Glu Val Leu Phe Leu
                            165                 170                 175

Thr Thr Tyr Ala Gln Ala Ala Asn Thr His Leu Phe Leu Leu Lys Asp
                        180                 185                 190

Ala Gln Ile Tyr Gly Glu Glu Trp Gly Tyr Glu Lys Glu Asp Ile Ala
                    195                 200                 205

Glu Phe Tyr Lys Arg Gln Leu Lys Leu Thr Gln Glu Tyr Thr Asp His
                210                 215                 220

Cys Val Lys Trp Tyr Asn Val Gly Leu Asp Lys Leu Arg Gly Ser Ser
        225                 230                 235                 240

Tyr Glu Ser Trp Val Asn Phe Asn Arg Tyr Arg Glu Met Thr Leu
                        245                 250                 255

Thr Val Leu Asp Leu Ile Ala Leu Phe Pro Leu Tyr Asp Val Arg Leu
                        260                 265                 270

Tyr Pro Lys Glu Val Lys Thr Glu Leu Thr Arg Asp Val Leu Thr Asp
                    275                 280                 285

Pro Ile Val Gly Val Asn Asn Leu Arg Gly Tyr Gly Thr Thr Phe Ser
        290                 295                 300

Asn Ile Glu Asn Tyr Ile Arg Lys Pro His Leu Phe Asp Tyr Leu His
        305                 310                 315                 320

Arg Ile Gln Phe His Thr Arg Phe Gln Pro Gly Tyr Tyr Gly Asn Asp
                            325                 330                 335

Ser Phe Asn Tyr Trp Ser Gly Asn Tyr Val Ser Thr Arg Pro Ser Ile
                        340                 345                 350

Gly Ser Asn Asp Ile Ile Thr Ser Pro Phe Tyr Gly Asn Lys Ser Ser
                    355                 360                 365

Glu Pro Val Gln Asn Leu Glu Phe Asn Gly Glu Lys Val Tyr Arg Ala
                370                 375                 380

Val Ala Asn Thr Asn Leu Ala Val Trp Pro Ser Ala Val Tyr Ser Gly
        385                 390                 395                 400

Val Thr Lys Val Glu Phe Ser Gln Tyr Asn Asp Gln Thr Asp Glu Ala
                            405                 410                 415

Ser Thr Gln Thr Tyr Asp Ser Lys Arg Asn Val Gly Ala Val Ser Trp
                        420                 425                 430

Asp Ser Ile Asp Gln Leu Pro Pro Glu Thr Thr Asp Glu Pro Leu Glu
                    435                 440                 445

Lys Gly Tyr Ser His Gln Leu Asn Tyr Val Met Cys Phe Leu Met Gln
                450                 455                 460

Gly Ser Arg Gly Thr Ile Pro Val Leu Thr Trp Thr His Lys Ser Val
        465                 470                 475                 480

Asp Phe Phe Asn Met Ile Asp Ser Lys Lys Ile Thr Gln Leu Pro Leu
                            485                 490                 495

Thr Lys Ser Thr Asn Leu Gly Ser Gly Thr Ser Val Val Lys Gly Pro
                        500                 505                 510

Gly Phe Thr Gly Gly Asp Ile Leu Arg Arg Thr Ser Pro Gly Gln Ile
                    515                 520                 525

Ser Thr Leu Arg Val Asn Ile Thr Ala Pro Leu Ser Gln Arg Tyr Arg
                530                 535                 540

Val Arg Ile Arg Tyr Ala Ser Thr Thr Asn Leu Gln Phe His Thr Ser
        545                 550                 555                 560

Ile Asp Gly Arg Pro Ile Asn Gln Gly Asn Phe Ser Ala Thr Met Ser
                            565                 570                 575
```

```
Ser Gly Ser Asn Leu Gln Ser Gly Ser Phe Arg Thr Val Gly Phe Thr
            580                 585                 590

Thr Pro Phe Asn Phe Ser Asn Gly Ser Ser Val Phe Thr Leu Ser Ala
        595                 600                 605

His Val Phe Asn Ser Gly Asn Glu Val Tyr Ile Asp Arg Ile Glu Phe
    610                 615                 620

Val Pro Ala Glu Val Thr Phe Glu Ala Glu Tyr Asp Leu Glu Arg Ala
625                 630                 635                 640

Gln Lys Ala Val Asn Glu Leu Phe Thr Ser Ser Asn Gln Ile Gly Leu
                645                 650                 655

Lys Thr Asp Val Thr Asp Tyr His Ile Asp Gln Val
            660                 665
```

<210> SEQ ID NO 3
<211> LENGTH: 1962
<212> TYPE: DNA
<213> ORGANISM: Artificial Sequence
<220> FEATURE:
<223> OTHER INFORMATION: FR8a coding sequence

<400> SEQUENCE: 3

| | | | | | |
|---|---|---|---|---|---|
| atgactagta | acggccgcca | gtgtgctggt | attcgccctt | atgacggccg | acaacaacac | 60 |
| cgaggcctgg | acagcagcac | caccaaggac | gtgatccaga | agggcatcag | cgtggtgggc | 120 |
| gacctgctgg | gcgtggtggg | cttccccttc | ggcggcgccc | tggtgagctt | ctacaccaac | 180 |
| ttcctgaaca | ccatctggcc | cagcgaggac | ccctggaagg | ccttcatgga | gcaggtggag | 240 |
| gccctgatgg | accagaagat | cgccgactac | gccaagaaca | aggcactggc | cgagctacag | 300 |
| ggcctccaga | caacgtggag | gactatgtg | agcgccctga | gcagctggca | gaagaacccc | 360 |
| gctgcaccgt | tccgcaaccc | ccacagccag | ggccgcatcc | gcgagctgtt | cagccaggcc | 420 |
| gagagccact | tccgcaacag | catgcccagc | ttcgccatca | gcggctacga | ggtgctgttc | 480 |
| ctgaccacct | acgcccaggc | cgccaacacc | cacctgttcc | tgctgaagga | cgcccaaatc | 540 |
| tacggagagg | agtggggcta | cgagaaggag | gacatcgccg | agttctacaa | cgccagctg | 600 |
| aagctgaccc | caggagtacac | cgaccactgc | gtgaagtggt | acaacgtggg | tctagacaag | 660 |
| ctccgcggca | gcagctacga | gagctgggtg | aacttcaacc | gctaccgccg | cgagatgacc | 720 |
| ctgaccgtgc | tggacctgat | cgccctgttc | ccctgtacg | acgtgcgcct | gtaccccaag | 780 |
| gaggtgaaga | ccgagctgac | ccgcgacgtg | ctgaccgacc | ccatcgtggg | cgtgaacaac | 840 |
| ctgcgcggct | acggcaccac | cttcagcaac | atcgagaact | acatccgcaa | gccccacctg | 900 |
| ttcgactacc | tgcaccgcat | ccagttccac | acgcgtttcc | agcccggcta | ctacggcaac | 960 |
| gacagcttca | actactggag | cggcaactac | gtgagcaccc | gccccagcat | cggcagcaac | 1020 |
| gacatcatca | ccagccccctt | ctacggcaac | aagagcagcg | agcccgtgca | gaaccttgag | 1080 |
| ttcaacggcg | agaaggtgta | ccgcgccgtg | gctaacacca | acctggccgt | gtggcccctct | 1140 |
| gcagtgtaca | gcggcgtgac | caaggtggag | ttcagccagt | acaacgacca | gaccgacgag | 1200 |
| gccagcaccc | agacctacga | cagcaagcgc | aacgtgggcg | ccgtgagctg | ggacagcatc | 1260 |
| gaccagctgc | cccccgagac | caccgacgag | cccctggaga | agggctacag | ccaccagctg | 1320 |
| aactacgtga | tgtgcttcct | gatgcagggc | agccgcggca | ccatcccccgt | gctgacctgg | 1380 |
| acccacaaga | gcgtcgactt | cttcaacatg | atcgacagca | agaagatcac | ccagctgccc | 1440 |
| ctgaccaaga | gcaccaacct | gggcagcggc | accagcgtgg | tgaagggccc | cggcttcacc | 1500 |
| ggcggcgaca | tcctgcgccg | caccagcccc | ggccagatca | gcaccctgcg | cgtgaacatc | 1560 |

-continued

```
accgcccccc tgagccagcg ctaccgcgtc cgcatccgct acgccagcac caccaacctg    1620
cagttccaca ccagcatcga cggccgcccc atcaaccagg gcaacttcag cgccaccatg    1680
agcagcggca gcaacctgca gagcggcagc ttccgcaccg tgggcttcac caccccttc     1740 aacttcagca acggcagcag cgtgttcacc ctgagcgccc acgtgttcaa cagcggcaac    1800
gaggtgtaca tcgaccgcat cgagttcgtg cccgccgagg tgaccttcga ggccgagtac    1860
gacctggaga gggctcagaa ggccgtgaac gagctgttca ccagcagcaa ccagatcggc    1920
ctgaagaccg acgtgaccga ctaccacatc gatcaggtgt ag                       1962
```

<210> SEQ ID NO 4
<211> LENGTH: 653
<212> TYPE: PRT
<213> ORGANISM: Artificial Sequence
<220> FEATURE:
<223> OTHER INFORMATION: FR8a protein

<400> SEQUENCE: 4

```
Met Thr Ser Asn Gly Arg Gln Cys Ala Gly Ile Arg Pro Tyr Asp Gly
1               5                   10                  15

Arg Gln Gln His Arg Gly Leu Asp Ser Ser Thr Thr Lys Asp Val Ile
            20                  25                  30

Gln Lys Gly Ile Ser Val Val Gly Asp Leu Leu Gly Val Gly Phe
        35                  40                  45

Pro Phe Gly Gly Ala Leu Val Ser Phe Tyr Thr Asn Phe Leu Asn Thr
    50                  55                  60

Ile Trp Pro Ser Glu Asp Pro Trp Lys Ala Phe Met Glu Gln Val Glu
65                  70                  75                  80

Ala Leu Met Asp Gln Lys Ile Ala Asp Tyr Ala Lys Asn Lys Ala Leu
                85                  90                  95

Ala Glu Leu Gln Gly Leu Gln Asn Asn Val Glu Asp Tyr Val Ser Ala
            100                 105                 110

Leu Ser Ser Trp Gln Lys Asn Pro Ala Ala Pro Phe Arg Asn Pro His
        115                 120                 125

Ser Gln Gly Arg Ile Arg Glu Leu Phe Ser Gln Ala Glu Ser His Phe
    130                 135                 140

Arg Asn Ser Met Pro Ser Phe Ala Ile Ser Gly Tyr Glu Val Leu Phe
145                 150                 155                 160

Leu Thr Thr Tyr Ala Gln Ala Ala Asn Thr His Leu Phe Leu Leu Lys
                165                 170                 175

Asp Ala Gln Ile Tyr Gly Glu Glu Trp Gly Tyr Glu Lys Glu Asp Ile
            180                 185                 190

Ala Glu Phe Tyr Lys Arg Gln Leu Lys Leu Thr Gln Glu Tyr Thr Asp
        195                 200                 205

His Cys Val Lys Trp Tyr Asn Val Gly Leu Asp Lys Leu Arg Gly Ser
    210                 215                 220

Ser Tyr Glu Ser Trp Val Asn Phe Asn Arg Tyr Arg Arg Glu Met Thr
225                 230                 235                 240

Leu Thr Val Leu Asp Leu Ile Ala Leu Phe Pro Leu Tyr Asp Val Arg
                245                 250                 255

Leu Tyr Pro Lys Glu Val Lys Thr Glu Leu Thr Arg Asp Val Leu Thr
            260                 265                 270

Asp Pro Ile Val Gly Val Asn Asn Leu Arg Gly Tyr Gly Thr Thr Phe
        275                 280                 285

Ser Asn Ile Glu Asn Tyr Ile Arg Lys Pro His Leu Phe Asp Tyr Leu
    290                 295                 300
```

His Arg Ile Gln Phe His Thr Arg Phe Gln Pro Gly Tyr Tyr Gly Asn
305                 310                 315                 320

Asp Ser Phe Asn Tyr Trp Ser Gly Asn Tyr Val Ser Thr Arg Pro Ser
            325                 330                 335

Ile Gly Ser Asn Asp Ile Ile Thr Ser Pro Phe Tyr Gly Asn Lys Ser
        340                 345                 350

Ser Glu Pro Val Gln Asn Leu Glu Phe Asn Gly Glu Lys Val Tyr Arg
    355                 360                 365

Ala Val Ala Asn Thr Asn Leu Ala Val Trp Pro Ser Ala Val Tyr Ser
370                 375                 380

Gly Val Thr Lys Val Glu Phe Ser Gln Tyr Asn Asp Gln Thr Asp Glu
385                 390                 395                 400

Ala Ser Thr Gln Thr Tyr Asp Ser Lys Arg Asn Val Gly Ala Val Ser
            405                 410                 415

Trp Asp Ser Ile Asp Gln Leu Pro Pro Glu Thr Thr Asp Glu Pro Leu
        420                 425                 430

Glu Lys Gly Tyr Ser His Gln Leu Asn Tyr Val Met Cys Phe Leu Met
    435                 440                 445

Gln Gly Ser Arg Gly Thr Ile Pro Val Leu Thr Trp Thr His Lys Ser
450                 455                 460

Val Asp Phe Phe Asn Met Ile Asp Ser Lys Lys Ile Thr Gln Leu Pro
465                 470                 475                 480

Leu Thr Lys Ser Thr Asn Leu Gly Ser Gly Thr Ser Val Val Lys Gly
            485                 490                 495

Pro Gly Phe Thr Gly Gly Asp Ile Leu Arg Arg Thr Ser Pro Gly Gln
        500                 505                 510

Ile Ser Thr Leu Arg Val Asn Ile Thr Ala Pro Leu Ser Gln Arg Tyr
    515                 520                 525

Arg Val Arg Ile Arg Tyr Ala Ser Thr Thr Asn Leu Gln Phe His Thr
530                 535                 540

Ser Ile Asp Gly Arg Pro Ile Asn Gln Gly Asn Phe Ser Ala Thr Met
545                 550                 555                 560

Ser Ser Gly Ser Asn Leu Gln Ser Gly Ser Phe Arg Thr Val Gly Phe
            565                 570                 575

Thr Thr Pro Phe Asn Phe Ser Asn Gly Ser Ser Val Phe Thr Leu Ser
        580                 585                 590

Ala His Val Phe Asn Ser Gly Asn Glu Val Tyr Ile Asp Arg Ile Glu
    595                 600                 605

Phe Val Pro Ala Glu Val Thr Phe Glu Ala Glu Tyr Asp Leu Glu Arg
610                 615                 620

Ala Gln Lys Ala Val Asn Glu Leu Phe Thr Ser Ser Asn Gln Ile Gly
625                 630                 635                 640

Leu Lys Thr Asp Val Thr Asp Tyr His Ile Asp Gln Val
            645                 650

<210> SEQ ID NO 5
<211> LENGTH: 1959
<212> TYPE: DNA
<213> ORGANISM: Artificial Sequence
<220> FEATURE:
<223> OTHER INFORMATION: FRCG coding sequence

<400> SEQUENCE: 5
atgactagta acggccgcca gtgtgctggt attcgccctt atgacggccg acaacaacac      60
cgaggcctgg acagcagcac caccaaggac gtgatccaga agggcatcag cgtggtgggc     120

```
gacctgctgg gcgtggtggg cttcccttc ggcggcgccc tggtgagctt ctacaccaac    180
ttcctgaaca ccatctggcc cagcgaggac ccctggaagg ccttcatgga gcaggtggag    240
gccctgatgg accagaagat cgccgactac gccaagaaca aggcactggc cgagctacag    300
ggcctccaga caacgtgga ggactatgtg agcgccctga cagctggca aagaaccccc      360 gtctcgagcc gcaaccccca cagccagggc cgcatccgcg agctgttcag ccaggccgag    420
agccacttcc gcaacagcat gcccagcttc gccatcagcg ctacgaggt gctgttcctg     480 accacctacg cccaggccgc caacacccac ctgttcctgc tgaaggacgc ccaaatctac    540
ggagaggagt ggggctacga aaggaggac atcgccgagt tctacaagcg ccagctgaag    600
ctgacccagg agtacaccga ccactgcgtg aagtggtaca acgtgggtct agacaagctc    660
cgcggcagca gctacgagag ctgggtgaac ttcaaccgct accgccgcga gatgaccctg    720
accgtgctgg acctgatcgc cctgttcccc ctgtacgacg tgcgcctgta ccccaaggag    780
gtgaagaccg agctgacccg cgacgtgctg accgacccca tcgtgggcgt gaacaacctg    840
cgcggctacg gcaccacctt cagcaacatc gagaactaca tccgcaagcc ccacctgttc    900
gactacctgc accgcatcca gttccacacg cgtttccagc ccggctacta cggcaacgac    960
agcttcaact actggagcgg caactacgtg agcacccgcc ccagcatcgg cagcaacgac   1020
atcatccacc gcccttcta cggcaacaag agcagcgagc ccgtgcagaa ccttgagttc    1080
aacggcgaga aggtgtaccg cgccgtggct aacaccaacc tggccgtgtg ccctctgca    1140 gtgtacagcg gcgtgaccaa ggtggagttc agccagtaca cgaccagac cgacgaggcc    1200 agcacccaga cctacgacag caagcgcaac gtgggcgccg tgagctggga cagcatcgac   1260
cagctgcccc ccgagaccac cgacgagccc tggagaagg gctacagcca ccagctgaac    1320
tacgtgatgt gcttcctgat gcagggcagc cgcggcacca tccccgtgct gacctggacc   1380
cacaagagcg tcgacttctt caacatgatc gacagcaaga gatcaccca gctgcccctg    1440 accaagagca ccaacctggg cagcggcacc agcgtggtga agggccccgg cttcaccggc    1500
ggcgacatcc tgcgccgcac cagccccggc cagatcagca ccctgcgcgt gaacatcacc    1560 gccccccctga gccagcgcta ccgcgtccgc atccgctacg ccagcaccac caacctgcag    1620
ttccacacca gcatcgacgg ccgccccatc aaccagggca acttcagcgc caccatgagc    1680
agcggcagca acctgcagag cggcagcttc gcaccgtgg gcttcaccac ccccttcaac    1740
ttcagcaacg gcagcagcgt gttcaccctg agcgcccacg tgttcaacag cggcaacgag    1800
gtgtacatcg accgcatcga gttcgtgccc gccgaggtga ccttcgaggc cgagtacgac    1860
ctggagaggg ctcagaaggc cgtgaacgag ctgttcacca gcagcaacca gatcggcctg    1920
aagaccgacg tgaccgacta ccacatcgat caggtgtag                           1959
```

<210> SEQ ID NO 6
<211> LENGTH: 652
<212> TYPE: PRT
<213> ORGANISM: Artificial Sequence
<220> FEATURE:
<223> OTHER INFORMATION: FRCG protein

<400> SEQUENCE: 6

Met Thr Ser Asn Gly Arg Gln Cys Ala Gly Ile Arg Pro Tyr Asp Gly
1               5                   10                  15

Arg Gln Gln His Arg Gly Leu Asp Ser Ser Thr Thr Lys Asp Val Ile
            20                  25                  30

Gln Lys Gly Ile Ser Val Val Gly Asp Leu Leu Gly Val Val Gly Phe

```
            35                  40                  45
Pro Phe Gly Gly Ala Leu Val Ser Phe Tyr Thr Asn Phe Leu Asn Thr
 50                  55                  60
Ile Trp Pro Ser Glu Asp Pro Trp Lys Ala Phe Met Glu Gln Val Glu
 65                  70                  75                  80
Ala Leu Met Asp Gln Lys Ile Ala Asp Tyr Ala Lys Asn Lys Ala Leu
                 85                  90                  95
Ala Glu Leu Gln Gly Leu Gln Asn Asn Val Glu Asp Tyr Val Ser Ala
                100                 105                 110
Leu Ser Ser Trp Gln Lys Asn Pro Val Ser Ser Arg Asn Pro His Ser
                115                 120                 125
Gln Gly Arg Ile Arg Glu Leu Phe Ser Gln Ala Glu Ser His Phe Arg
                130                 135                 140
Asn Ser Met Pro Ser Phe Ala Ile Ser Gly Tyr Glu Val Leu Phe Leu
145                 150                 155                 160
Thr Thr Tyr Ala Gln Ala Ala Asn Thr His Leu Phe Leu Leu Lys Asp
                165                 170                 175
Ala Gln Ile Tyr Gly Glu Glu Trp Gly Tyr Glu Lys Glu Asp Ile Ala
                180                 185                 190
Glu Phe Tyr Lys Arg Gln Leu Lys Leu Thr Gln Glu Tyr Thr Asp His
                195                 200                 205
Cys Val Lys Trp Tyr Asn Val Gly Leu Asp Lys Leu Arg Gly Ser Ser
                210                 215                 220
Tyr Glu Ser Trp Val Asn Phe Asn Arg Tyr Arg Arg Glu Met Thr Leu
225                 230                 235                 240
Thr Val Leu Asp Leu Ile Ala Leu Phe Pro Leu Tyr Asp Val Arg Leu
                245                 250                 255
Tyr Pro Lys Glu Val Lys Thr Glu Leu Thr Arg Asp Val Leu Thr Asp
                260                 265                 270
Pro Ile Val Gly Val Asn Asn Leu Arg Gly Tyr Gly Thr Thr Phe Ser
                275                 280                 285
Asn Ile Glu Asn Tyr Ile Arg Lys Pro His Leu Phe Asp Tyr Leu His
290                 295                 300
Arg Ile Gln Phe His Thr Arg Phe Gln Pro Gly Tyr Tyr Gly Asn Asp
305                 310                 315                 320
Ser Phe Asn Tyr Trp Ser Gly Asn Tyr Val Ser Thr Arg Pro Ser Ile
                325                 330                 335
Gly Ser Asn Asp Ile Ile Thr Ser Pro Phe Tyr Gly Asn Lys Ser Ser
                340                 345                 350
Glu Pro Val Gln Asn Leu Glu Phe Asn Gly Glu Lys Val Tyr Arg Ala
                355                 360                 365
Val Ala Asn Thr Asn Leu Ala Val Trp Pro Ser Ala Val Tyr Ser Gly
370                 375                 380
Val Thr Lys Val Glu Phe Ser Gln Tyr Asn Asp Gln Thr Asp Glu Ala
385                 390                 395                 400
Ser Thr Gln Thr Tyr Asp Ser Lys Arg Asn Val Gly Ala Val Ser Trp
                405                 410                 415
Asp Ser Ile Asp Gln Leu Pro Pro Glu Thr Thr Asp Glu Pro Leu Glu
                420                 425                 430
Lys Gly Tyr Ser His Gln Leu Asn Tyr Val Met Cys Phe Leu Met Gln
                435                 440                 445
Gly Ser Arg Gly Thr Ile Pro Val Leu Thr Trp Thr His Lys Ser Val
450                 455                 460
```

-continued

```
Asp Phe Phe Asn Met Ile Asp Ser Lys Lys Ile Thr Gln Leu Pro Leu
465                 470                 475                 480

Thr Lys Ser Thr Asn Leu Gly Ser Gly Thr Ser Val Val Lys Gly Pro
            485                 490                 495

Gly Phe Thr Gly Gly Asp Ile Leu Arg Arg Thr Ser Pro Gly Gln Ile
        500                 505                 510

Ser Thr Leu Arg Val Asn Ile Thr Ala Pro Leu Ser Gln Arg Tyr Arg
        515                 520                 525

Val Arg Ile Arg Tyr Ala Ser Thr Thr Asn Leu Gln Phe His Thr Ser
    530                 535                 540

Ile Asp Gly Arg Pro Ile Asn Gln Gly Asn Phe Ser Ala Thr Met Ser
545                 550                 555                 560

Ser Gly Ser Asn Leu Gln Ser Gly Ser Phe Arg Thr Val Gly Phe Thr
                565                 570                 575

Thr Pro Phe Asn Phe Ser Asn Gly Ser Ser Val Phe Thr Leu Ser Ala
            580                 585                 590

His Val Phe Asn Ser Gly Asn Glu Val Tyr Ile Asp Arg Ile Glu Phe
        595                 600                 605

Val Pro Ala Glu Val Thr Phe Glu Ala Glu Tyr Asp Leu Glu Arg Ala
    610                 615                 620

Gln Lys Ala Val Asn Glu Leu Phe Thr Ser Ser Asn Gln Ile Gly Leu
625                 630                 635                 640

Lys Thr Asp Val Thr Asp Tyr His Ile Asp Gln Val
                645                 650
```

<210> SEQ ID NO 7
<211> LENGTH: 1962
<212> TYPE: DNA
<213> ORGANISM: Artificial Sequence
<220> FEATURE:
<223> OTHER INFORMATION: FR8a-9F coding sequence

<400> SEQUENCE: 7

```
atgactagta acggccgcca gtgtgctggt attcgcccta tgacggccga caacaacacc      60
gaggccctgg acagcagcac caccaaggac gtgatccaga agggcatcag cgtggtgggc     120
gacctgctgg gcgtggtggg cttccccttc ggcggcgccc tggtgagctt ctacaccaac     180
ttcctgaaca ccatctggcc cagcgaggac ccctggaagg ccttcatgga gcaggtggag     240
gccctgatgg accagaagat cgccgactac gccaagaaca aggcactggc cgagctacag     300
ggcctccaga caacgtggga ggactatgtg agcgccctga gcagctggca gaagaacccc     360
gctgcaccgt tccgcaaccc ccacagccag ggccgcatcc gcgagctgtt cagccaggcc     420
gagagccact tccgcaacag catgcccagc ttcgccatca gcggctacga ggtgctgttc     480
ctgaccacct acgcccaggc cgccaacacc cacctgttcc tgctgaagga cgcccaaatc     540
tacgagagg agtggggcta cgagaaggag gacatcgccg agttctacaa gcgccagctg     600
aagctgaccc aggagtacac cgaccactgc gtgaagtggt acaacgtggg tctagacaag     660
ctccgcggca gcagctacga gctgggtg aacttcaacc gctaccgccg cgagatgacc     720
ctgaccgtgc tggacctgat cgccctgttc cccctgtacg acgtgcgcct gtaccccaag     780
gaggtgaaga ccgagctgac ccgcgacgtg ctgaccgacc catcgtgggg cgtgaacaac     840
ctgcgcggct acggcaccac cttcagcaac atcgagaact acatccgcaa gccccacctg     900
ttcgactacc tgcaccgcat ccagttccac acgcgtttcc agcccggcta ctacggcaac     960
gacagcttca ctactggag cggcaactac gtgagcaccc gccccagcat cggcagcaac    1020
```

```
gacatcatca ccagcccctt ctacggcaac aagagcagcg agcccgtgca gaaccttgag      1080
ttcaacggcg agaaggtgta ccgcgccgtg gctaacacca acctggccgt gtggccctct      1140
gcagtgtaca gcggcgtgac caaggtggag ttcagccagt acaacgacca gaccgacgag      1200
gccagcaccc agacctacga cagcaagcgc aacgtgggcg ccgtgagctg ggacagcatc      1260
gaccagctgc cccccgagac caccgacgag cccctggaga agggctacag ccaccagctg      1320
aactacgtga tgtgcttcct gatgcagggc agccgcggca ccatccccgt gctgacctgg      1380
acccacaaga gcgtcgactt cttcaacatg atcgacagca agaagatcac ccagctgccc      1440
ctgaccaaga gcaccaacct gggcagcggc accagcgtgg tgaagggccc cggcttcacc      1500
ggcggcgaca tcctgcgccg caccagcccc ggccagatca gcaccctgcg cgtgaacatc      1560
accgcccccc tgagccagcg ctaccgcgtc cgcatccgct acgccagcac caccaacctg      1620
cagttccaca ccagcatcga cggccgcccc atcaaccagg caacttcag cgccaccatg       1680 agcagcggca gcaacctgca gagcggcagc ttccgcaccg tgggcttcac caccccccttc      1740 aacttcagca acggcagcag cgtgttcacc ctgagcgccc acgtgttcaa cagcggcaac      1800
gaggtgtaca tcgaccgcat cgagttcgtg cccgccgagg tgaccttcga ggccgagtac      1860
gacctggaga gggctcagaa ggccgtgaac gagctgttca ccagcagcaa ccagatcggc      1920
ctgaagaccg acgtgaccga ctaccacatc gatcaggtgt ag                        1962
```

<210> SEQ ID NO 8
<211> LENGTH: 653
<212> TYPE: PRT
<213> ORGANISM: Artificial Sequence
<220> FEATURE:
<223> OTHER INFORMATION: FR8a-9F protein

<400> SEQUENCE: 8

```
Met Thr Ser Asn Gly Arg Gln Cys Ala Gly Ile Arg Pro Met Thr Ala
1               5                   10                  15

Asp Asn Asn Thr Glu Ala Leu Asp Ser Ser Thr Thr Lys Asp Val Ile
                20                  25                  30

Gln Lys Gly Ile Ser Val Val Gly Asp Leu Leu Gly Val Val Gly Phe
            35                  40                  45

Pro Phe Gly Gly Ala Leu Val Ser Phe Tyr Thr Asn Phe Leu Asn Thr
        50                  55                  60

Ile Trp Pro Ser Glu Asp Pro Trp Lys Ala Phe Met Glu Gln Val Glu
65                  70                  75                  80

Ala Leu Met Asp Gln Lys Ile Ala Asp Tyr Ala Lys Asn Lys Ala Leu
                85                  90                  95

Ala Glu Leu Gln Gly Leu Gln Asn Asn Val Glu Asp Tyr Val Ser Ala
            100                 105                 110

Leu Ser Ser Trp Gln Lys Asn Pro Ala Ala Pro Phe Arg Asn Pro His
        115                 120                 125

Ser Gln Gly Arg Ile Arg Glu Leu Phe Ser Gln Ala Glu Ser His Phe
    130                 135                 140

Arg Asn Ser Met Pro Ser Phe Ala Ile Ser Gly Tyr Glu Val Leu Phe
145                 150                 155                 160

Leu Thr Thr Tyr Ala Gln Ala Ala Asn Thr His Leu Phe Leu Leu Lys
                165                 170                 175

Asp Ala Gln Ile Tyr Gly Glu Glu Trp Gly Tyr Glu Lys Glu Asp Ile
            180                 185                 190

Ala Glu Phe Tyr Lys Arg Gln Leu Lys Leu Thr Gln Glu Tyr Thr Asp
        195                 200                 205
```

```
His Cys Val Lys Trp Tyr Asn Val Gly Leu Asp Lys Leu Arg Gly Ser
    210                 215                 220
Ser Tyr Glu Ser Trp Val Asn Phe Asn Arg Tyr Arg Arg Glu Met Thr
225                 230                 235                 240
Leu Thr Val Leu Asp Leu Ile Ala Leu Phe Pro Leu Tyr Asp Val Arg
                245                 250                 255
Leu Tyr Pro Lys Glu Val Lys Thr Glu Leu Thr Arg Asp Val Leu Thr
            260                 265                 270
Asp Pro Ile Val Gly Val Asn Leu Arg Gly Tyr Gly Thr Thr Phe
            275                 280                 285
Ser Asn Ile Glu Asn Tyr Ile Arg Lys Pro His Leu Phe Asp Tyr Leu
290                 295                 300
His Arg Ile Gln Phe His Thr Arg Phe Gln Pro Gly Tyr Tyr Gly Asn
305                 310                 315                 320
Asp Ser Phe Asn Tyr Trp Ser Gly Asn Tyr Val Ser Thr Arg Pro Ser
                325                 330                 335
Ile Gly Ser Asn Asp Ile Ile Thr Ser Pro Phe Tyr Gly Asn Lys Ser
                340                 345                 350
Ser Glu Pro Val Gln Asn Leu Glu Phe Asn Gly Glu Lys Val Tyr Arg
            355                 360                 365
Ala Val Ala Asn Thr Asn Leu Ala Val Trp Pro Ser Ala Val Tyr Ser
    370                 375                 380
Gly Val Thr Lys Val Glu Phe Ser Gln Tyr Asn Asp Gln Thr Asp Glu
385                 390                 395                 400
Ala Ser Thr Gln Thr Tyr Asp Ser Lys Arg Asn Val Gly Ala Val Ser
                405                 410                 415
Trp Asp Ser Ile Asp Gln Leu Pro Pro Glu Thr Thr Asp Glu Pro Leu
                420                 425                 430
Glu Lys Gly Tyr Ser His Gln Leu Asn Tyr Val Met Cys Phe Leu Met
            435                 440                 445
Gln Gly Ser Arg Gly Thr Ile Pro Val Leu Thr Trp Thr His Lys Ser
    450                 455                 460
Val Asp Phe Phe Asn Met Ile Asp Ser Lys Lys Ile Thr Gln Leu Pro
465                 470                 475                 480
Leu Thr Lys Ser Thr Asn Leu Gly Ser Gly Thr Ser Val Val Lys Gly
                485                 490                 495
Pro Gly Phe Thr Gly Gly Asp Ile Leu Arg Arg Thr Ser Pro Gly Gln
                500                 505                 510
Ile Ser Thr Leu Arg Val Asn Ile Thr Ala Pro Leu Ser Gln Arg Tyr
    515                 520                 525
Arg Val Arg Ile Arg Tyr Ala Ser Thr Thr Asn Leu Gln Phe His Thr
    530                 535                 540
Ser Ile Asp Gly Arg Pro Ile Asn Gln Gly Asn Phe Ser Ala Thr Met
545                 550                 555                 560
Ser Ser Gly Ser Asn Leu Gln Ser Gly Ser Phe Arg Thr Val Gly Phe
                565                 570                 575
Thr Thr Pro Phe Asn Phe Ser Asn Gly Ser Ser Val Phe Thr Leu Ser
                580                 585                 590
Ala His Val Phe Asn Ser Gly Asn Glu Val Tyr Ile Asp Arg Ile Glu
            595                 600                 605
Phe Val Pro Ala Glu Val Thr Phe Glu Ala Glu Tyr Asp Leu Glu Arg
    610                 615                 620
Ala Gln Lys Ala Val Asn Glu Leu Phe Thr Ser Ser Asn Gln Ile Gly
```

```
625               630              635              640
Leu Lys Thr Asp Val Thr Asp Tyr His Ile Asp Gln Val
                645              650

<210> SEQ ID NO 9
<211> LENGTH: 1959
<212> TYPE: DNA
<213> ORGANISM: Artificial Sequence
<220> FEATURE:
<223> OTHER INFORMATION: FR-9F-catg coding sequence

<400> SEQUENCE: 9
atgactagta acggccgcca gtgtgctggt attcgcccta tgacggccga caacaacacc      60
gaggccctgg acagcagcac caccaaggac gtgatccaga agggcatcag cgtggtgggc     120
gacctgctgg gcgtggtggg cttccccttc ggcggcgccc tggtgagctt ctacaccaac     180
ttcctgaaca ccatctggcc cagcgaggac ccctggaagg ccttcatgga gcaggtggag     240
gccctgatgg accagaagat cgccgactac gccaagaaca aggcactggc cgagctacag     300
ggcctccaga caacgtggag gactatgtg agcgccctga gcagctggca gaagaacccc     360
gtctcgagcc gcaaccccca gccagggc cgcatccgcg agctgttcag ccaggccgag     420
agccacttcc gcaacagcat gcccagcttc gccatcagcg gctacgaggt gctgttcctg     480
accacctacg cccaggccgc caacacccac ctgttcctgc tgaaggacgc ccaaatctac     540
ggagaggagt ggggctacga aggaggac atcgccgagt cctacaagcg ccagctgaag     600
ctgacccagt agtacaccga ccactgcgtg aagtggtaca cgtgggtct agacaagctc     660 cgcggcagca gctacgagag ctgggtgaac ttcaaccgct accgccgcga gatgaccctg     720
accgtgctgg acctgatcgc cctgttcccc ctgtacgacg tgcgcctgta ccccaaggag     780
gtgaagaccg agctgacccg cgacgtgctg accgacccca tcgtgggcgt gaacaacctg     840
cgcggctacg gcaccacctt cagcaacatc gagaactaca tccgcaagcc ccacctgttc     900
gactacctgc accgcatcca gttccacacg cgtttccagc ccggctacta cggcaacgac     960
agcttcaact actggagcgg caactacgtg agcacccgcc ccagcatcgg cagcaacgac    1020
atcatcacca gccccttcta cggcaacaag agcagcgagc ccgtgcagaa ccttgagttc    1080
aacggcgaga aggtgtaccg cgccgtggct aacaccaacc tggccgtgtg gccctctgca    1140
gtgtacagcg gcgtgaccaa ggtggagttc agccagtaca cgaccagac cgacgaggcc    1200 agcacccaga cctacgacag caagcgcaac gtgggcgccg tgagctggga cagcatcgac    1260
cagctgcccc ccgagaccac cgacgagccc ctggagaagg gctacagcca ccagctgaac    1320
tacgtgatgt gcttcctgat gcagggcagc cgcggcacca tccccgtgct gacctggacc    1380
cacaagagcg tcgacttctt caacatgatc gacagcaaga agatcaccca gctgcccctg    1440
accaagagca ccaacctggg cagcggcacc agcgtggtga agggcccggg cttcaccggc    1500
ggcgacatcc tgcgccgcac cagcccggc cagatcagca ccctgcgcgt gaacatcacc    1560 gccccctga ccagcgcta ccgcgtccgc atcgctacg ccagcaccac caacctgcag    1620
ttccacacca gcatcgacgg ccgcccatc aaccagggca acttcagcgc caccatgagc    1680
agcggcagca acctgcagag cggcagcttc cgcaccgtgg gcttccacca cccccttcaac    1740 ttcagcaacg gcagcagcgt gttcaccctg agcgcccacg tgttcaacag cggcaacgag    1800
gtgtacatcg accgcatcga gttcgtgccc gccgaggtga ccttcgaggc cgagtacgac    1860
ctggagaggg ctcagaaggc cgtgaacgag ctgttcacca gcagcaacca gatcggcctg    1920
aagaccgacg tgaccgacta ccacatcgat caggtgtag                          1959
```

<210> SEQ ID NO 10
<211> LENGTH: 652
<212> TYPE: PRT
<213> ORGANISM: Artificial Sequence
<220> FEATURE:
<223> OTHER INFORMATION: FR-9F-catg protein

<400> SEQUENCE: 10

Met Thr Ser Asn Gly Arg Gln Cys Ala Gly Ile Arg Pro Met Thr Ala
1               5                   10                  15

Asp Asn Asn Thr Glu Ala Leu Asp Ser Ser Thr Thr Lys Asp Val Ile
            20                  25                  30

Gln Lys Gly Ile Ser Val Val Gly Asp Leu Leu Gly Val Val Gly Phe
        35                  40                  45

Pro Phe Gly Gly Ala Leu Val Ser Phe Tyr Thr Asn Phe Leu Asn Thr
    50                  55                  60

Ile Trp Pro Ser Glu Asp Pro Trp Lys Ala Phe Met Glu Gln Val Glu
65                  70                  75                  80

Ala Leu Met Asp Gln Lys Ile Ala Asp Tyr Ala Lys Asn Lys Ala Leu
                85                  90                  95

Ala Glu Leu Gln Gly Leu Gln Asn Asn Val Glu Asp Tyr Val Ser Ala
            100                 105                 110

Leu Ser Ser Trp Gln Lys Asn Pro Val Ser Ser Arg Asn Pro His Ser
        115                 120                 125

Gln Gly Arg Ile Arg Glu Leu Phe Ser Gln Ala Glu Ser His Phe Arg
    130                 135                 140

Asn Ser Met Pro Ser Phe Ala Ile Ser Gly Tyr Glu Val Leu Phe Leu
145                 150                 155                 160

Thr Thr Tyr Ala Gln Ala Ala Asn Thr His Leu Phe Leu Leu Lys Asp
                165                 170                 175

Ala Gln Ile Tyr Gly Glu Glu Trp Gly Tyr Glu Lys Glu Asp Ile Ala
            180                 185                 190

Glu Phe Tyr Lys Arg Gln Leu Lys Leu Thr Gln Glu Tyr Thr Asp His
        195                 200                 205

Cys Val Lys Trp Tyr Asn Val Gly Leu Asp Lys Leu Arg Gly Ser Ser
    210                 215                 220

Tyr Glu Ser Trp Val Asn Phe Asn Arg Tyr Arg Arg Glu Met Thr Leu
225                 230                 235                 240

Thr Val Leu Asp Leu Ile Ala Leu Phe Pro Leu Tyr Asp Val Arg Leu
                245                 250                 255

Tyr Pro Lys Glu Val Lys Thr Glu Leu Thr Arg Asp Val Leu Thr Asp
            260                 265                 270

Pro Ile Val Gly Val Asn Asn Leu Arg Gly Tyr Gly Thr Thr Phe Ser
        275                 280                 285

Asn Ile Glu Asn Tyr Ile Arg Lys Pro His Leu Phe Asp Tyr Leu His
    290                 295                 300

Arg Ile Gln Phe His Thr Arg Phe Gln Pro Gly Tyr Tyr Gly Asn Asp
305                 310                 315                 320

Ser Phe Asn Tyr Trp Ser Gly Asn Tyr Val Ser Thr Arg Pro Ser Ile
                325                 330                 335

Gly Ser Asn Asp Ile Ile Thr Ser Pro Phe Tyr Gly Asn Lys Ser Ser
            340                 345                 350

Glu Pro Val Gln Asn Leu Glu Phe Asn Gly Glu Lys Val Tyr Arg Ala
        355                 360                 365

```
Val Ala Asn Thr Asn Leu Ala Val Trp Pro Ser Ala Val Tyr Ser Gly
370                 375                 380
Val Thr Lys Val Glu Phe Ser Gln Tyr Asn Asp Gln Thr Asp Glu Ala
385                 390                 395                 400
Ser Thr Gln Thr Tyr Asp Ser Lys Arg Asn Val Gly Ala Val Ser Trp
                405                 410                 415
Asp Ser Ile Asp Gln Leu Pro Pro Glu Thr Thr Asp Glu Pro Leu Glu
            420                 425                 430
Lys Gly Tyr Ser His Gln Leu Asn Tyr Val Met Cys Phe Leu Met Gln
        435                 440                 445
Gly Ser Arg Gly Thr Ile Pro Val Leu Thr Trp Thr His Lys Ser Val
    450                 455                 460
Asp Phe Phe Asn Met Ile Asp Ser Lys Lys Ile Thr Gln Leu Pro Leu
465                 470                 475                 480
Thr Lys Ser Thr Asn Leu Gly Ser Gly Thr Ser Val Val Lys Gly Pro
                485                 490                 495
Gly Phe Thr Gly Gly Asp Ile Leu Arg Arg Thr Ser Pro Gly Gln Ile
            500                 505                 510
Ser Thr Leu Arg Val Asn Ile Thr Ala Pro Leu Ser Gln Arg Tyr Arg
        515                 520                 525
Val Arg Ile Arg Tyr Ala Ser Thr Thr Asn Leu Gln Phe His Thr Ser
    530                 535                 540
Ile Asp Gly Arg Pro Ile Asn Gln Gly Asn Phe Ser Ala Thr Met Ser
545                 550                 555                 560
Ser Gly Ser Asn Leu Gln Ser Gly Ser Phe Arg Thr Val Gly Phe Thr
                565                 570                 575
Thr Pro Phe Asn Phe Ser Asn Gly Ser Ser Val Phe Thr Leu Ser Ala
            580                 585                 590
His Val Phe Asn Ser Gly Asn Glu Val Tyr Ile Asp Arg Ile Glu Phe
        595                 600                 605
Val Pro Ala Glu Val Thr Phe Glu Ala Glu Tyr Asp Leu Glu Arg Ala
    610                 615                 620
Gln Lys Ala Val Asn Glu Leu Phe Thr Ser Ser Asn Gln Ile Gly Leu
625                 630                 635                 640
Lys Thr Asp Val Thr Asp Tyr His Ile Asp Gln Val
                645                 650

<210> SEQ ID NO 11
<211> LENGTH: 1926
<212> TYPE: DNA
<213> ORGANISM: Artificial Sequence
<220> FEATURE:
<223> OTHER INFORMATION: FR8a-12AA coding sequence

<400> SEQUENCE: 11
atgtatgacg ccgacaaca caccgaggc ctggacagca gcaccaccaa ggacgtgatc        60
cagaagggca tcagcgtggt gggcgacctg ctgggcgtgg tgggcttccc cttcggcggc      120
gccctggtga gcttctacac caacttcctg aacaccatct ggcccagcga ggaccccctgg    180 aaggccttca tggagcaggt ggaggccctg atggaccaga gatcgccga ctacgccaag      240 aacaaggcac tggccgagct acagggcctc cagaacaacg tggaggacta tgtgagcgcc    300
ctgagcagct ggcagaagaa ccccgctgca ccgttccgca accccacag ccagggccgc     360 atccgcgagc tgttcagcca ggccgagagc cacttccgca acagcatgcc cagcttcgcc    420
atcagcggct acgaggtgct gttcctgacc acctacgccc aggccgccaa cacccacctg    480
```

```
ttcctgctga aggacgccca aatctacgga gaggagtggg gctacgagaa ggaggacatc    540
gccgagttct acaagcgcca gctgaagctg acccaggagt acaccgacca ctgcgtgaag    600
tggtacaacg tgggtctaga caagctccgc ggcagcagct acgagagctg ggtgaacttc    660
aaccgctacc gccgcgagat gaccctgacc gtgctggacc tgatcgccct gttccccctg    720
tacgacgtgc gcctgtaccc caaggaggtg aagaccgagc tgacccgcga cgtgctgacc    780
gaccccatcg tgggcgtgaa caacctgcgc ggctacggca ccaccttcag caacatcgag    840
aactacatcc gcaagcccca cctgttcgac tacctgcacc gcatccagtt ccacacgcgt    900
ttccagcccg gctactacgg caacgacagc ttcaactact ggagcggcaa ctacgtgagc    960
acccgcccca gcatcggcag caacgacatc atcaccagcc ccttctacgg caacaagagc   1020
agcgagcccg tgcagaacct tgagttcaac ggcgagaagg tgtaccgcgc cgtggctaac   1080
accaacctgg ccgtgtggcc ctctgcagtg tacagcggcg tgaccaaggt ggagttcagc   1140
cagtacaacg accagaccga cgaggccagc acccagacct acgacagcaa gcgcaacgtg   1200
ggcgccgtga gctgggacag catcgaccag ctgccccccg agaccaccga cgagcccctg   1260
gagaagggct acagccacca gctgaactac gtgatgtgct tcctgatgca gggcagccgc   1320
ggcaccatcc ccgtgctgac ctggacccac aagagcgtcg acttcttcaa catgatcgac   1380
agcaagaaga tcacccagct gcccctgacc aagagcacca acctgggcag cggcaccagc   1440
gtggtgaagg cccccggctt caccggcggc gacatcctgc ccgcaccagc cccggccag   1500 atcagcaccc tgcgcgtgaa catcaccgcc cccctgagcc agcgctaccg cgtccgcatc   1560
cgctacgcca gcaccaccaa cctgcagttc cacaccagca tcgacggccg ccccatcaac   1620
cagggcaact tcagcgccac catgagcagc ggcagcaacc tgcagagcgg cagcttccgc   1680
accgtgggct tcaccacccc cttcaacttc agcaacggca gcagcgtgtt cacccctgagc   1740 gcccacgtgt tcaacagcgg caacgaggtg tacatcgacc gcatcgagtt cgtgcccgcc   1800
gaggtgacct tcgaggccga gtacgacctg gagagggctc agaaggccgt gaacgagctg   1860
ttcaccagca gcaaccagat cggcctgaag accgacgtga ccgactacca catcgatcag   1920
gtgtag                                                              1926
```

<210> SEQ ID NO 12
<211> LENGTH: 641
<212> TYPE: PRT
<213> ORGANISM: Artificial Sequence
<220> FEATURE:
<223> OTHER INFORMATION: FR8a-12AA protein

<400> SEQUENCE: 12

```
Met Tyr Asp Gly Arg Gln Gln His Arg Gly Leu Asp Ser Ser Thr Thr
1               5                   10                  15

Lys Asp Val Ile Gln Lys Gly Ile Ser Val Val Gly Asp Leu Leu Gly
            20                  25                  30

Val Val Gly Phe Pro Phe Gly Gly Ala Leu Val Ser Phe Tyr Thr Asn
        35                  40                  45

Phe Leu Asn Thr Ile Trp Pro Ser Glu Asp Pro Trp Lys Ala Phe Met
    50                  55                  60

Glu Gln Val Glu Ala Leu Met Asp Gln Lys Ile Ala Asp Tyr Ala Lys
65                  70                  75                  80

Asn Lys Ala Leu Ala Glu Leu Gln Gly Leu Gln Asn Asn Val Glu Asp
                85                  90                  95

Tyr Val Ser Ala Leu Ser Ser Trp Gln Lys Asn Pro Ala Ala Pro Phe
            100                 105                 110
```

```
Arg Asn Pro His Ser Gln Gly Arg Ile Arg Glu Leu Phe Ser Gln Ala
            115                 120                 125
Glu Ser His Phe Arg Asn Ser Met Pro Ser Phe Ala Ile Ser Gly Tyr
        130                 135                 140
Glu Val Leu Phe Leu Thr Thr Tyr Ala Gln Ala Asn Thr His Leu
145                 150                 155                 160
Phe Leu Leu Lys Asp Ala Gln Ile Tyr Gly Glu Glu Trp Gly Tyr Glu
                165                 170                 175
Lys Glu Asp Ile Ala Glu Phe Tyr Lys Arg Gln Leu Lys Leu Thr Gln
            180                 185                 190
Glu Tyr Thr Asp His Cys Val Lys Trp Tyr Asn Val Gly Leu Asp Lys
        195                 200                 205
Leu Arg Gly Ser Ser Tyr Glu Ser Trp Val Asn Phe Asn Arg Tyr Arg
    210                 215                 220
Arg Glu Met Thr Leu Thr Val Leu Asp Leu Ile Ala Leu Phe Pro Leu
225                 230                 235                 240
Tyr Asp Val Arg Leu Tyr Pro Lys Glu Val Lys Thr Glu Leu Thr Arg
                245                 250                 255
Asp Val Leu Thr Asp Pro Ile Val Gly Val Asn Asn Leu Arg Gly Tyr
            260                 265                 270
Gly Thr Thr Phe Ser Asn Ile Glu Asn Tyr Ile Arg Lys Pro His Leu
        275                 280                 285
Phe Asp Tyr Leu His Arg Ile Gln Phe His Thr Arg Phe Gln Pro Gly
    290                 295                 300
Tyr Tyr Gly Asn Asp Ser Phe Asn Tyr Trp Ser Gly Asn Tyr Val Ser
305                 310                 315                 320
Thr Arg Pro Ser Ile Gly Ser Asn Asp Ile Ile Thr Ser Pro Phe Tyr
                325                 330                 335
Gly Asn Lys Ser Ser Glu Pro Val Gln Asn Leu Glu Phe Asn Gly Glu
            340                 345                 350
Lys Val Tyr Arg Ala Val Ala Asn Thr Asn Leu Ala Val Trp Pro Ser
        355                 360                 365
Ala Val Tyr Ser Gly Val Thr Lys Val Glu Phe Ser Gln Tyr Asn Asp
    370                 375                 380
Gln Thr Asp Glu Ala Ser Thr Gln Thr Tyr Asp Ser Lys Arg Asn Val
385                 390                 395                 400
Gly Ala Val Ser Trp Asp Ser Ile Asp Gln Leu Pro Pro Glu Thr Thr
                405                 410                 415
Asp Glu Pro Leu Glu Lys Gly Tyr Ser His Gln Leu Asn Tyr Val Met
            420                 425                 430
Cys Phe Leu Met Gln Gly Ser Arg Gly Thr Ile Pro Val Leu Thr Trp
        435                 440                 445
Thr His Lys Ser Val Asp Phe Phe Asn Met Ile Asp Ser Lys Lys Ile
    450                 455                 460
Thr Gln Leu Pro Leu Thr Lys Ser Thr Asn Leu Gly Ser Gly Thr Ser
465                 470                 475                 480
Val Val Lys Gly Pro Gly Phe Thr Gly Gly Asp Ile Leu Arg Arg Thr
                485                 490                 495
Ser Pro Gly Gln Ile Ser Thr Leu Arg Val Asn Ile Thr Ala Pro Leu
            500                 505                 510
Ser Gln Arg Tyr Arg Val Arg Ile Arg Tyr Ala Ser Thr Thr Asn Leu
        515                 520                 525
Gln Phe His Thr Ser Ile Asp Gly Arg Pro Ile Asn Gln Gly Asn Phe
```

```
                530             535             540
Ser Ala Thr Met Ser Ser Gly Ser Asn Leu Gln Ser Gly Ser Phe Arg
545                 550                 555                 560

Thr Val Gly Phe Thr Thr Pro Phe Asn Phe Asn Gly Ser Ser Val
                565                 570                 575

Phe Thr Leu Ser Ala His Val Phe Asn Ser Gly Asn Glu Val Tyr Ile
            580                 585                 590

Asp Arg Ile Glu Phe Val Pro Ala Glu Val Thr Phe Gly Ala Glu Tyr
                595                 600                 605

Asp Leu Glu Arg Ala Gln Lys Ala Val Asn Glu Leu Phe Thr Ser Ser
            610                 615                 620

Asn Gln Ile Gly Leu Lys Thr Asp Val Thr Asp Tyr His Ile Asp Gln
625                 630                 635                 640

Val

<210> SEQ ID NO 13
<211> LENGTH: 1800
<212> TYPE: DNA
<213> ORGANISM: Artificial Sequence
<220> FEATURE:
<223> OTHER INFORMATION: WR-9mut coding sequence

<400> SEQUENCE: 13
atgtatgacg ccgacaaca acaccgaggc ctggacagca gcaccaccaa ggacgtgatc      60
cagaagggca tcagcgtggt gggcgacctg ctgggcgtgg tgggcttccc cttcggcggc    120
gccctggtga gcttctacac caacttcctg aacaccatct ggcccagcga ggaccctgg     180 aaggccttca tggagcaggt ggaggccctg atggaccaga gatcgccga ctacgccaag     240 aacaaggcac tggccgagct acagggcctc agaacaacg tggaggacta tgtgagcgcc     300
ctgagcagct ggcagaagaa ccccgctgca ccgttccgca accccacag ccagggccgc     360 atccgcgagc tgttcagcca ggccgagagc cacttccgca cagcatgcc cagcttcgcc     420 atcagcggct acgaggtgct gttcctgacc acctacgccc aggccgccaa cacccacctg     480
ttcctgctga aggacgccca aatctacgga gaggagtggg gctacgagaa ggaggacatc     540
gccgagttct acaagcgcca gctgaagctg acccaggagt acaccgacca ctgcgtgaag     600
tggtacaacg tgggtctaga caagctccgc ggcagcagct acgagagctg ggtgaacttc     660
aaccgctacc gccgcgagat gaccctgacc gtgctggacc tgatcgccct gttccccctg     720
tacgacgtgc gcctgtaccc caaggaggtg aagaccgagc tgacccgcga cgtgctgacc     780
gaccccatcg tgggcgtgaa caacctgcgc ggctacggca ccaccttcag caacatcgag     840
aactacatcc gcaagcccca cctgttcgac tacctgcacc gcatccagtt ccacacgcgt     900
ttccagcccg gctactacgg caacgacagc ttcaactact ggagcggcaa ctacgtgagc     960
acccgcccca gcatcggcag caacgacatc atcaccagcc ccttctacgg caacaagagc    1020
agcgagcccg tgcagaacct tgagttcaac ggcgagaagg tgtaccgcgc cgtggctaac    1080
accaacctgg ccgtgtggcc ctctgcagtg tacagcggcg tgaccaaggt ggagttcagc    1140
cagtacaacg accagaccga cgaggccagc acccagacct acgacagcaa cgcaacgtg     1200 ggcgccgtga gctgggacag catcgaccag ctgccccccg agaccaccga cgagcccctg    1260
gagaagggct acagccacca gctgaactac gtgatgtgct tcctgatgca gggcagccgc    1320
ggcaccatcc ccgtgctgac ctggacccac aagagcgtcg acttcttcaa catgatcgac    1380
agcaagaaga tcacccagct gccccctggtg aaggcctaca gctccagag cggcgccagc    1440
```

```
gtggtggcag ccccccgctt caccggcggc gacatcatcc agtgcaccga aacggcagc    1500 gccgccacca tctacgtgac ccccgacgtg agctacagcc agaagtaccg cgcccgcatc    1560
cactacgcca gcaccagcca gatcaccttc accctgagcc tggacggggc ccccttcaac    1620
caatactact cgacaagac catcaacaag ggcgacaccc tgacctacaa cagcttcaac     1680
ctggccagct tcagcacccc tttcgagctg agcggcaaca acctccagat cggcgtgacc    1740
ggcctgagcg ccggcgacaa ggtgtacatc gacaagatcg agttcatccc cgtgaactag   1800
```

<210> SEQ ID NO 14
<211> LENGTH: 599
<212> TYPE: PRT
<213> ORGANISM: Artificial Sequence
<220> FEATURE:
<223> OTHER INFORMATION: WR-9mut protein

<400> SEQUENCE: 14

```
Met Tyr Asp Gly Arg Gln Gln His Arg Gly Leu Asp Ser Ser Thr Thr
1               5                   10                  15

Lys Asp Val Ile Gln Lys Gly Ile Ser Val Val Gly Asp Leu Leu Gly
            20                  25                  30

Val Val Gly Phe Pro Phe Gly Ala Leu Val Ser Phe Tyr Thr Asn
        35                  40                  45

Phe Leu Asn Thr Ile Trp Pro Ser Glu Asp Pro Trp Lys Ala Phe Met
50                  55                  60

Glu Gln Val Glu Ala Leu Met Asp Gln Lys Ile Ala Asp Tyr Ala Lys
65                  70                  75                  80

Asn Lys Ala Leu Ala Glu Leu Gln Gly Leu Gln Asn Asn Val Glu Asp
                85                  90                  95

Tyr Val Ser Ala Leu Ser Ser Trp Gln Lys Asn Pro Ala Ala Pro Phe
            100                 105                 110

Arg Asn Pro His Ser Gln Gly Arg Ile Arg Glu Leu Phe Ser Gln Ala
        115                 120                 125

Glu Ser His Phe Arg Asn Ser Met Pro Ser Phe Ala Ile Ser Gly Tyr
130                 135                 140

Glu Val Leu Phe Leu Thr Thr Tyr Ala Gln Ala Ala Asn Thr His Leu
145                 150                 155                 160

Phe Leu Leu Lys Asp Ala Gln Ile Tyr Gly Glu Glu Trp Gly Tyr Glu
                165                 170                 175

Lys Glu Asp Ile Ala Glu Phe Tyr Lys Arg Gln Leu Lys Leu Thr Gln
            180                 185                 190

Glu Tyr Thr Asp His Cys Val Lys Trp Tyr Asn Val Gly Leu Asp Lys
        195                 200                 205

Leu Arg Gly Ser Ser Tyr Glu Ser Trp Val Asn Phe Asn Arg Tyr Arg
210                 215                 220

Arg Glu Met Thr Leu Thr Val Leu Asp Leu Ile Ala Leu Phe Pro Leu
225                 230                 235                 240

Tyr Asp Val Arg Leu Tyr Pro Lys Glu Val Lys Thr Glu Leu Thr Arg
                245                 250                 255

Asp Val Leu Thr Asp Pro Ile Val Gly Val Asn Asn Leu Arg Gly Tyr
            260                 265                 270

Gly Thr Thr Phe Ser Asn Ile Glu Asn Tyr Ile Arg Lys Pro His Leu
        275                 280                 285

Phe Asp Tyr Leu His Arg Ile Gln Phe His Thr Arg Phe Gln Pro Gly
290                 295                 300

Tyr Tyr Gly Asn Asp Ser Phe Asn Tyr Trp Ser Gly Asn Tyr Val Ser
```

```
                305                 310                 315                 320
Thr Arg Pro Ser Ile Gly Ser Asn Asp Ile Ile Thr Ser Pro Phe Tyr
                325                 330                 335

Gly Asn Lys Ser Ser Glu Pro Val Gln Asn Leu Glu Phe Asn Gly Glu
                340                 345                 350

Lys Val Tyr Arg Ala Val Ala Asn Thr Asn Leu Ala Val Trp Pro Ser
                355                 360                 365

Ala Val Tyr Ser Gly Val Thr Lys Val Glu Phe Ser Gln Tyr Asn Asp
                370                 375                 380

Gln Thr Asp Glu Ala Ser Thr Gln Thr Tyr Asp Ser Lys Arg Asn Val
385                 390                 395                 400

Gly Ala Val Ser Trp Asp Ser Ile Asp Gln Leu Pro Pro Glu Thr Thr
                405                 410                 415

Asp Glu Pro Leu Glu Lys Gly Tyr Ser His Gln Leu Asn Tyr Val Met
                420                 425                 430

Cys Phe Leu Met Gln Gly Ser Arg Gly Thr Ile Pro Val Leu Thr Trp
                435                 440                 445

Thr His Lys Ser Val Asp Phe Phe Asn Met Ile Asp Ser Lys Lys Ile
                450                 455                 460

Thr Gln Leu Pro Leu Val Lys Ala Tyr Lys Leu Gln Ser Gly Ala Ser
465                 470                 475                 480

Val Val Ala Gly Pro Arg Phe Thr Gly Gly Asp Ile Ile Gln Cys Thr
                485                 490                 495

Glu Asn Gly Ser Ala Ala Thr Ile Tyr Val Thr Pro Asp Val Ser Tyr
                500                 505                 510

Ser Gln Lys Tyr Arg Ala Arg Ile His Tyr Ala Ser Thr Ser Gln Ile
                515                 520                 525

Thr Phe Thr Leu Ser Leu Asp Gly Ala Pro Phe Asn Gln Tyr Tyr Phe
                530                 535                 540

Asp Lys Thr Ile Asn Lys Gly Asp Thr Leu Thr Tyr Asn Ser Phe Asn
545                 550                 555                 560

Leu Ala Ser Phe Ser Thr Pro Phe Glu Leu Ser Gly Asn Asn Leu Gln
                565                 570                 575

Ile Gly Val Thr Gly Leu Ser Ala Gly Asp Lys Val Tyr Ile Asp Lys
                580                 585                 590

Ile Glu Phe Ile Pro Val Asn
                595

<210> SEQ ID NO 15
<211> LENGTH: 1848
<212> TYPE: DNA
<213> ORGANISM: Artificial Sequence
<220> FEATURE:
<223> OTHER INFORMATION: FRD3 coding sequence

<400> SEQUENCE: 15
atgactagta acggccgcca gtgtgctggt attcgccctt atgacggccg acaacaacac      60
cgaggcctgg acagcagcac caccaaggac gtgatccaga agggcatcag cgtggtgggc     120
gacctgctgg gcgtggtggg cttccccttc ggcggcgccc tggtgagctt ctacaccaac     180
ttcctgaaca ccatctggcc cagcgaggac ccctggaagg ccttcatgga gcaggtggag     240
gccctgatgg accagaagat cgccgactac gccaagaaca aggcactggc cgagctacag     300
ggcctccaga caacgtgga ggactatgtg agcgccctga gcagctggca gaagaacccc     360
gctgcaccgt tccgcaaccc ccacagccag ggccgcatcc gcgagctgtt cagccaggcc     420
```

```
gagagccact tccgcaacag catgcccagc ttcgccatca gcggctacga ggtgctgttc    480
ctgaccacct acgcccaggc cgccaacacc cacctgttcc tgctgaagga cgcccaaatc    540
tacggagagg agtggggcta cgagaaggag gacatcgccg agttctacaa gcgccagctg    600
aagctgaccc aggagtacac cgaccactgc gtgaagtggt acaacgtggg tctagacaag    660
ctccgcggca gcagctacga gagctgggtg aacttcaacc gctaccgccg cgagatgacc    720
ctgaccgtgc tggacctgat cgccctgttc cccctgtacg acgtgcgcct gtaccccaag    780
gaggtgaaga ccgagctgac ccgcgacgtg ctgaccgacc ccatcgtggg cgtgaacaac    840 ctgcgcgggct acggcaccac cttcagcaac atcgagaact acatccgcaa gccccacctg    900
ttcgactacc tgcaccgcat ccagttccac acgcgtttcc agcccggcta ctacggcaac    960
gacagcttca actactggag cggcaactac gtgagcaccc gccccagcat cggcagcaac   1020
gacatcatca ccagccccctt ctacggcaac aagagcagcg agcccgtgca gaaccttgag   1080
ttcaacggcg agaaggtgta ccgcgccgtg gctaacacca acctggccgt gtggccctct   1140
gcagtgtaca gcggcgtgac caaggtggag ttcagccagt acaacgacca gaccgacgag   1200
gccagcaccc agacctacga cagcaagcgc aacgtgggcg ccgtgagctg ggacagcatc   1260
gaccagctgc cccccgagac caccgacgag ccccctggaga agggctacag ccaccagctg   1320
aactacgtga tgtgcttcct gatgcagggc agccgcggca ccatccccgt gctgacctgg   1380
acccacaaga gcgtcgactt cttcaacatg atcgacagca agaagatcac ccagctgccc   1440
ctgaccaaga gcaccaacct gggcagcggc accagcgtgg tgaagggccc cggcttcacc   1500
ggcggcgaca tcctgcgccg caccagcccc ggccagatca gcaccctgcg cgtgaacatc   1560
accgcccccc tgagccagcg ctaccgcgtc cgcatccgct acgccagcac caccaacctg   1620
cagttccaca ccagcatcga cggccgcccc atcaaccagg gcaacttcag cgccaccatg   1680
agcagcggca gcaacctgca gagcggcagc ttcgcaccg tgggcttcac cacccccttc   1740
aacttcagca acggcagcag cgtgttcacc ctgagcgccc acgtgttcaa cagcggcaac   1800
gaggtgtaca tcgaccgcat cgagttcgtg cccgccgagg tgacctag              1848
```

<210> SEQ ID NO 16
<211> LENGTH: 615
<212> TYPE: PRT
<213> ORGANISM: Artificial Sequence
<220> FEATURE:
<223> OTHER INFORMATION: FRD3 protein

<400> SEQUENCE: 16

```
Met Thr Ser Asn Gly Arg Gln Cys Ala Gly Ile Arg Pro Tyr Asp Gly
1               5                   10                  15

Arg Gln Gln His Arg Gly Leu Asp Ser Ser Thr Thr Lys Asp Val Ile
            20                  25                  30

Gln Lys Gly Ile Ser Val Val Gly Asp Leu Leu Gly Val Gly Phe
        35                  40                  45

Pro Phe Gly Gly Ala Leu Val Ser Phe Tyr Thr Asn Phe Leu Asn Thr
    50                  55                  60

Ile Trp Pro Ser Glu Asp Pro Trp Lys Ala Phe Met Glu Gln Val Glu
65                  70                  75                  80

Ala Leu Met Asp Gln Lys Ile Ala Asp Tyr Ala Lys Asn Lys Ala Leu
                85                  90                  95

Ala Glu Leu Gln Gly Leu Gln Asn Asn Val Glu Asp Tyr Val Ser Ala
            100                 105                 110

Leu Ser Ser Trp Gln Lys Asn Pro Ala Ala Pro Phe Arg Asn Pro His
```

```
            115                 120                 125
Ser Gln Gly Arg Ile Arg Glu Leu Phe Ser Gln Ala Glu Ser His Phe
130                 135                 140

Arg Asn Ser Met Pro Ser Phe Ala Ile Ser Gly Tyr Glu Val Leu Phe
145                 150                 155                 160

Leu Thr Thr Tyr Ala Gln Ala Ala Asn Thr His Leu Phe Leu Leu Lys
                165                 170                 175

Asp Ala Gln Ile Tyr Gly Glu Glu Trp Gly Tyr Glu Lys Glu Asp Ile
                180                 185                 190

Ala Glu Phe Tyr Lys Arg Gln Leu Lys Leu Thr Gln Glu Tyr Thr Asp
                195                 200                 205

His Cys Val Lys Trp Tyr Asn Val Gly Leu Asp Lys Leu Arg Gly Ser
            210                 215                 220

Ser Tyr Glu Ser Trp Val Asn Phe Asn Arg Tyr Arg Arg Glu Met Thr
225                 230                 235                 240

Leu Thr Val Leu Asp Leu Ile Ala Leu Phe Pro Leu Tyr Asp Val Arg
                245                 250                 255

Leu Tyr Pro Lys Glu Val Lys Thr Glu Leu Thr Arg Asp Val Leu Thr
                260                 265                 270

Asp Pro Ile Val Gly Val Asn Asn Leu Arg Gly Tyr Gly Thr Thr Phe
            275                 280                 285

Ser Asn Ile Glu Asn Tyr Ile Arg Lys Pro His Leu Phe Asp Tyr Leu
290                 295                 300

His Arg Ile Gln Phe His Thr Arg Phe Gln Pro Gly Tyr Tyr Gly Asn
305                 310                 315                 320

Asp Ser Phe Asn Tyr Trp Ser Gly Asn Tyr Val Ser Thr Arg Pro Ser
                325                 330                 335

Ile Gly Ser Asn Asp Ile Ile Thr Ser Pro Phe Tyr Gly Asn Lys Ser
                340                 345                 350

Ser Glu Pro Val Gln Asn Leu Glu Phe Asn Gly Glu Lys Val Tyr Arg
            355                 360                 365

Ala Val Ala Asn Thr Asn Leu Ala Val Trp Pro Ser Ala Val Tyr Ser
370                 375                 380

Gly Val Thr Lys Val Glu Phe Ser Gln Tyr Asn Asp Gln Thr Asp Glu
385                 390                 395                 400

Ala Ser Thr Gln Thr Tyr Asp Ser Lys Arg Asn Val Gly Ala Val Ser
                405                 410                 415

Trp Asp Ser Ile Asp Gln Leu Pro Pro Glu Thr Thr Asp Glu Pro Leu
                420                 425                 430

Glu Lys Gly Tyr Ser His Gln Leu Asn Tyr Val Met Cys Phe Leu Met
            435                 440                 445

Gln Gly Ser Arg Gly Thr Ile Pro Val Leu Thr Trp Thr His Lys Ser
450                 455                 460

Val Asp Phe Phe Asn Met Ile Asp Ser Lys Lys Ile Thr Gln Leu Pro
465                 470                 475                 480

Leu Thr Lys Ser Thr Asn Leu Gly Ser Gly Thr Ser Val Val Lys Gly
                485                 490                 495

Pro Gly Phe Thr Gly Gly Asp Ile Leu Arg Arg Thr Ser Pro Gly Gln
                500                 505                 510

Ile Ser Thr Leu Arg Val Asn Ile Thr Ala Pro Leu Ser Gln Arg Tyr
            515                 520                 525

Arg Val Arg Ile Arg Tyr Ala Ser Thr Thr Asn Leu Gln Phe His Thr
530                 535                 540
```

```
Ser Ile Asp Gly Arg Pro Ile Asn Gln Gly Asn Phe Ser Ala Thr Met
545                 550                 555                 560

Ser Ser Gly Ser Asn Leu Gln Ser Gly Ser Phe Arg Thr Val Gly Phe
            565                 570                 575

Thr Thr Pro Phe Asn Phe Ser Asn Gly Ser Ser Val Phe Thr Leu Ser
            580                 585                 590

Ala His Val Phe Asn Ser Gly Asn Glu Val Tyr Ile Asp Arg Ile Glu
        595                 600                 605

Phe Val Pro Ala Glu Val Thr
    610                 615

<210> SEQ ID NO 17
<211> LENGTH: 1809
<212> TYPE: DNA
<213> ORGANISM: Artificial Sequence
<220> FEATURE:
<223> OTHER INFORMATION: FR-12-cg-dm3 coding sequence

<400> SEQUENCE: 17
atgtatgacg ccgacaaca acaccgaggc ctggacagca gcaccaccaa ggacgtgatc        60
cagaagggca tcagcgtggt gggcgacctg ctgggcgtgg tgggcttccc cttcggcggc       120
gccctggtga gcttctacac caacttcctg aacaccatct ggcccagcga ggaccctgg        180 aaggccttca tggagcaggt ggaggccctg atggaccaga gatcgccga ctacgccaag        240 aacaaggcac tggccgagct acagggcctc cagaacaacg tggaggacta tgtgagcgcc       300
ctgagcagct ggcagaagaa ccccgtctcg agccgcaacc ccacagcca gggccgcatc        360 cgcgagctgt tcagccaggc cgagagccac ttccgcaaca gcatgcccag cttcgccatc       420
agcggctacg aggtgctgtt cctgaccacc tacgcccagg ccgccaacac ccacctgttc       480
ctgctgaagg acgcccaaat ctacggagag gagtggggct acgagaagga ggacatcgcc       540
gagttctaca gcgccagct gaagctgacc caggagtaca ccgaccactg cgtgaagtgg        600
tacaacgtgg gtctagacaa gctccgcggc agcagctacg agagctgggt gaacttcaac       660
cgctaccgcc gcgagatgac cctgaccgtg ctggacctga tcgccctgtt cccctgtac        720 gacgtgcgcc tgtaccccaa ggaggtgaag accgagctga cccgcgacgt gctgaccgac       780
cccatcgtgg gcgtgaacaa cctgcgcggc tacggcacca ccttcagcaa catcgagaac       840
tacatccgca agccccacct gttcgactac ctgcaccgca tccagttcca cacgcgtttc       900
cagcccggct actacggcaa cgacagcttc aactactgga gcggcaacta cgtgagcacc       960
cgccccagca tcggcagcaa cgacatcatc accagcccct tctacggcaa caagagcagc      1020
gagcccgtgc agaaccttga gttcaacggc gagaaggtgt accgcgccgt ggctaacacc      1080
aacctggccg tgtggcccctc tgcagtgtac agcggcgtga ccaaggtgga gttcagccag     1140
tacaacgacc agaccgacga ggccagcacc cagacctacg acagcaagcg caacgtgggc      1200
gccgtgagct gggacagcat cgaccagctg cccccgaga ccaccgacga gcccctggag       1260
aagggctaca gccaccagct gaactacgtg atgtgcttcc tgatgcaggg cagccgcggc      1320
accatccccg tgctgacctg gacccacaag agcgtcgact tcttcaacat gatcgacagc      1380
aagaagatca cccagctgcc cctgaccaag agcaccaacc tgggcagcgg caccagcgtg      1440
gtgaagggcc ccggcttcac cggcggcgac atcctgcgcc gcaccagccc ggccagatc       1500 agcaccctgc gcgtgaacat caccgccccc ctgagccagc gctacgccgt ccgcatccgc      1560
tacgccagca ccaccaacct gcagttccac accagcatcg acggccgccc catcaaccag     1620
ggcaacttca gcgccaccat gagcagcggc agcaacctgc agagcggcag cttccgcacc      1680
```

-continued

```
gtgggcttca ccaccccctt caacttcagc aacggcagca gcgtgttcac cctgagcgcc    1740
cacgtgttca acagcggcaa cgaggtgtac atcgaccgca tcgagttcgt gcccgccgag    1800
gtgacctag                                                            1809
```

<210> SEQ ID NO 18
<211> LENGTH: 602
<212> TYPE: PRT
<213> ORGANISM: Artificial Sequence
<220> FEATURE:
<223> OTHER INFORMATION: FR-12-cg-dm3 protein

<400> SEQUENCE: 18

```
Met Tyr Asp Gly Arg Gln Gln His Arg Gly Leu Asp Ser Ser Thr Thr
1               5                   10                  15

Lys Asp Val Ile Gln Lys Gly Ile Ser Val Val Gly Asp Leu Leu Gly
            20                  25                  30

Val Val Gly Phe Pro Phe Gly Gly Ala Leu Val Ser Phe Tyr Thr Asn
        35                  40                  45

Phe Leu Asn Thr Ile Trp Pro Ser Glu Asp Pro Trp Lys Ala Phe Met
50                  55                  60

Glu Gln Val Glu Ala Leu Met Asp Gln Lys Ile Ala Asp Tyr Ala Lys
65                  70                  75                  80

Asn Lys Ala Leu Ala Glu Leu Gln Gly Leu Gln Asn Asn Val Glu Asp
                85                  90                  95

Tyr Val Ser Ala Leu Ser Ser Trp Gln Lys Asn Pro Val Ser Ser Arg
            100                 105                 110

Asn Pro His Ser Gln Gly Arg Ile Arg Glu Leu Phe Ser Gln Ala Glu
        115                 120                 125

Ser His Phe Arg Asn Ser Met Pro Ser Phe Ala Ile Ser Gly Tyr Glu
130                 135                 140

Val Leu Phe Leu Thr Thr Tyr Ala Gln Ala Ala Asn Thr His Leu Phe
145                 150                 155                 160

Leu Leu Lys Asp Ala Gln Ile Tyr Gly Glu Glu Trp Gly Tyr Glu Lys
                165                 170                 175

Glu Asp Ile Ala Glu Phe Tyr Lys Arg Gln Leu Lys Leu Thr Gln Glu
            180                 185                 190

Tyr Thr Asp His Cys Val Lys Trp Tyr Asn Val Gly Leu Asp Lys Leu
        195                 200                 205

Arg Gly Ser Ser Tyr Glu Ser Trp Val Asn Phe Asn Arg Tyr Arg Arg
210                 215                 220

Glu Met Thr Leu Thr Val Leu Asp Leu Ile Ala Leu Phe Pro Leu Tyr
225                 230                 235                 240

Asp Val Arg Leu Tyr Pro Lys Glu Val Lys Thr Glu Leu Thr Arg Asp
                245                 250                 255

Val Leu Thr Asp Pro Ile Val Gly Val Asn Asn Leu Arg Gly Tyr Gly
            260                 265                 270

Thr Thr Phe Ser Asn Ile Glu Asn Tyr Ile Arg Lys Pro His Leu Phe
        275                 280                 285

Asp Tyr Leu His Arg Ile Gln Phe His Thr Arg Phe Gln Pro Gly Tyr
290                 295                 300

Tyr Gly Asn Asp Ser Phe Asn Tyr Trp Ser Gly Asn Tyr Val Ser Thr
305                 310                 315                 320

Arg Pro Ser Ile Gly Ser Asn Asp Ile Ile Thr Ser Pro Phe Tyr Gly
                325                 330                 335
```

Asn Lys Ser Ser Glu Pro Val Gln Asn Leu Glu Phe Asn Gly Glu Lys
        340                 345                 350

Val Tyr Arg Ala Val Ala Asn Thr Asn Leu Ala Val Trp Pro Ser Ala
            355                 360                 365

Val Tyr Ser Gly Val Thr Lys Val Glu Phe Ser Gln Tyr Asn Asp Gln
        370                 375                 380

Thr Asp Glu Ala Ser Thr Gln Thr Tyr Asp Ser Lys Arg Asn Val Gly
385                 390                 395                 400

Ala Val Ser Trp Asp Ser Ile Asp Gln Leu Pro Pro Glu Thr Thr Asp
                405                 410                 415

Glu Pro Leu Glu Lys Gly Tyr Ser His Gln Leu Asn Tyr Val Met Cys
            420                 425                 430

Phe Leu Met Gln Gly Ser Arg Gly Thr Ile Pro Val Leu Thr Trp Thr
        435                 440                 445

His Lys Ser Val Asp Phe Phe Asn Met Ile Asp Ser Lys Lys Ile Thr
    450                 455                 460

Gln Leu Pro Leu Thr Lys Ser Thr Asn Leu Gly Ser Gly Thr Ser Val
465                 470                 475                 480

Val Lys Gly Pro Gly Phe Thr Gly Gly Asp Ile Leu Arg Arg Thr Ser
                485                 490                 495

Pro Gly Gln Ile Ser Thr Leu Arg Val Asn Ile Thr Ala Pro Leu Ser
            500                 505                 510

Gln Arg Tyr Arg Val Arg Ile Arg Tyr Ala Ser Thr Thr Asn Leu Gln
        515                 520                 525

Phe His Thr Ser Ile Asp Gly Arg Pro Ile Asn Gln Gly Asn Phe Ser
    530                 535                 540

Ala Thr Met Ser Ser Gly Ser Asn Leu Gln Ser Gly Ser Phe Arg Thr
545                 550                 555                 560

Val Gly Phe Thr Thr Pro Phe Asn Phe Ser Asn Gly Ser Ser Val Phe
                565                 570                 575

Thr Leu Ser Ala His Val Phe Asn Ser Gly Asn Glu Val Tyr Ile Asp
            580                 585                 590

Arg Ile Glu Phe Val Pro Ala Glu Val Thr
        595                 600

<210> SEQ ID NO 19
<211> LENGTH: 1941
<212> TYPE: DNA
<213> ORGANISM: Artificial Sequence
<220> FEATURE:
<223> OTHER INFORMATION: 9F-cg-del6 coding sequence

<400> SEQUENCE: 19
atgtgtgctg gtattcgccc tatgacggcc gacaacaaca ccgaggccct ggacagcagc    60
accaccaagg acgtgatcca agggcatc agcgtggtgg cgacctgct gggcgtggtg    120 ggcttcccct tcggcggcgc cctggtgagc ttctacacca acttcctgaa caccatctgg    180
cccagcgagg acccctggaa ggccttcatg agcaggtgg aggccctgat ggaccagaag    240
atcgccgact acgccaagaa caaggcactg gccgagctac agggcctcca gaacaacgtg    300
gaggactatg tgagcgccct gagcagctgg cagaagaacc ccgtctcgag ccgcaacccc    360
cacagccagg ccgcatccg cgagctgttc agcaggccg agagccactt ccgcaacagc    420
atgcccagct cgccatcag cggctacgag gtgctgttcc tgaccaccta cgcccaggcc    480
gccaacaccc cctgttcct gctgaaggac gcccaaatct acggagagga gtggggctac    540
gagaaggagg acatcgccga gttctacaag cgccagctga agctgaccca ggagtacacc    600

```
gaccactgcg tgaagtggta caacgtgggt ctagacaagc tccgcggcag cagctacgag    660
agctgggtga acttcaaccg ctaccgccgc gagatgaccc tgaccgtgct ggacctgatc    720
gccctgttcc ccctgtacga cgtgcgcctg taccccaagg aggtgaagac cgagctgacc    780
cgcgacgtgc tgaccgaccc catcgtgggc gtgaacaacc tgcgcggcta cggcaccacc    840
ttcagcaaca tcgagaacta catccgcaag ccccacctgt tcgactacct gcaccgcatc    900
cagttccaca cgcgtttcca gcccggctac tacggcaaca cagcttcaa ctactggagc    960 ggcaactacg tgagcacccg ccccagcatc ggcagcaacg acatcatcac cagccccttc   1020
tacggcaaca agagcagcga gcccgtgcag aaccttgagt tcaacggcga aaggtgtac    1080 cgcgccgtgg ctaacaccaa cctggccgtg tggccctctg cagtgtacag cggcgtgacc   1140
aaggtggagt tcagccagta caacgaccag accgacgagg ccagcaccca gacctacgac   1200
agcaagcgca acgtgggcgc cgtgagctgg gacagcatcg accagctgcc ccccgagacc   1260
accgacgagc ccctggagaa gggctacagc caccagctga actacgtgat gtgcttcctg   1320
atgcagggca gccgcggcac catccccgtg ctgacctgga cccacaagag cgtcgacttc   1380
ttcaacatga tcgacagcaa gaagatcacc cagctgcccc tgaccaagag caccaacctg   1440
ggcagcggca ccagcgtggt gaagggcccc ggcttcaccg gcggcgacat cctgcgccgc   1500
accagccccg gccagatcag cacccctgcgc gtgaacatca ccgcccccct gagccagcgc   1560
taccgcgtcc gcatccgcta cgccagcacc accaacctgc agttccacac cagcatcgac   1620
ggccgcccca tcaaccaggg caacttcagc gccaccatga gcagcggcag caacctgcag   1680
agcggcagct tccgcaccgt gggcttcacc accccttca acttcagcaa cggcagcagc   1740
gtgttcaccc tgagcgccca cgtgttcaac agcggcaacg aggtgtacat cgaccgcatc   1800
gagttcgtgc ccgccgaggt gaccttcgag gccgagtacg acctggagag ggctcagaag   1860
gccgtgaacg agctgttcac cagcagcaac cagatcggcc tgaagaccga cgtgaccgac   1920
taccacatcg atcaggtgta g                                             1941
```

<210> SEQ ID NO 20
<211> LENGTH: 646
<212> TYPE: PRT
<213> ORGANISM: Artificial Sequence
<220> FEATURE:
<223> OTHER INFORMATION: 9F-cg-del6 protein

<400> SEQUENCE: 20

```
Met Cys Ala Gly Ile Arg Pro Met Thr Ala Asp Asn Asn Thr Glu Ala
1               5                   10                  15

Leu Asp Ser Ser Thr Thr Lys Asp Val Ile Gln Lys Gly Ile Ser Val
            20                  25                  30

Val Gly Asp Leu Leu Gly Val Val Gly Phe Pro Phe Gly Gly Ala Leu
        35                  40                  45

Val Ser Phe Tyr Thr Asn Phe Leu Asn Thr Ile Trp Pro Ser Glu Asp
    50                  55                  60

Pro Trp Lys Ala Phe Met Glu Gln Val Glu Ala Leu Met Asp Gln Lys
65                  70                  75                  80

Ile Ala Asp Tyr Ala Lys Asn Lys Ala Leu Ala Glu Leu Gln Gly Leu
                85                  90                  95

Gln Asn Asn Val Glu Asp Tyr Val Ser Ala Leu Ser Ser Trp Gln Lys
            100                 105                 110

Asn Pro Val Ser Ser Arg Asn Pro His Ser Gln Gly Arg Ile Arg Glu
        115                 120                 125
```

```
Leu Phe Ser Gln Ala Glu Ser His Phe Arg Asn Ser Met Pro Ser Phe
            130                 135                 140
Ala Ile Ser Gly Tyr Glu Val Leu Phe Leu Thr Thr Tyr Ala Gln Ala
145                 150                 155                 160
Ala Asn Thr His Leu Phe Leu Leu Lys Asp Ala Gln Ile Tyr Gly Glu
                165                 170                 175
Glu Trp Gly Tyr Glu Lys Glu Asp Ile Ala Glu Phe Tyr Lys Arg Gln
                180                 185                 190
Leu Lys Leu Thr Gln Glu Tyr Thr Asp His Cys Val Lys Trp Tyr Asn
            195                 200                 205
Val Gly Leu Asp Lys Leu Arg Gly Ser Ser Tyr Glu Ser Trp Val Asn
            210                 215                 220
Phe Asn Arg Tyr Arg Arg Glu Met Thr Leu Thr Val Leu Asp Leu Ile
225                 230                 235                 240
Ala Leu Phe Pro Leu Tyr Asp Val Arg Leu Tyr Pro Lys Glu Val Lys
                245                 250                 255
Thr Glu Leu Thr Arg Asp Val Leu Thr Asp Pro Ile Val Gly Val Asn
            260                 265                 270
Asn Leu Arg Gly Tyr Gly Thr Thr Phe Ser Asn Ile Glu Asn Tyr Ile
            275                 280                 285
Arg Lys Pro His Leu Phe Asp Tyr Leu His Arg Ile Gln Phe His Thr
            290                 295                 300
Arg Phe Gln Pro Gly Tyr Tyr Gly Asn Asp Ser Phe Asn Tyr Trp Ser
305                 310                 315                 320
Gly Asn Tyr Val Ser Thr Arg Pro Ser Ile Gly Ser Asn Asp Ile Ile
                325                 330                 335
Thr Ser Pro Phe Tyr Gly Asn Lys Ser Ser Glu Pro Val Gln Asn Leu
                340                 345                 350
Glu Phe Asn Gly Glu Lys Val Tyr Arg Ala Val Ala Asn Thr Asn Leu
            355                 360                 365
Ala Val Trp Pro Ser Ala Val Tyr Ser Gly Val Thr Lys Val Glu Phe
            370                 375                 380
Ser Gln Tyr Asn Asp Gln Thr Asp Glu Ala Ser Thr Gln Thr Tyr Asp
385                 390                 395                 400
Ser Lys Arg Asn Val Gly Ala Val Ser Trp Asp Ser Ile Asp Gln Leu
                405                 410                 415
Pro Pro Glu Thr Thr Asp Glu Pro Leu Glu Lys Gly Tyr Ser His Gln
                420                 425                 430
Leu Asn Tyr Val Met Cys Phe Leu Met Gln Gly Ser Arg Gly Thr Ile
            435                 440                 445
Pro Val Leu Thr Trp Thr His Lys Ser Val Asp Phe Phe Asn Met Ile
            450                 455                 460
Asp Ser Lys Lys Ile Thr Gln Leu Pro Leu Thr Lys Ser Thr Asn Leu
465                 470                 475                 480
Gly Ser Gly Thr Ser Val Val Lys Gly Pro Gly Phe Thr Gly Gly Asp
                485                 490                 495
Ile Leu Arg Arg Thr Ser Pro Gly Gln Ile Ser Thr Leu Arg Val Asn
            500                 505                 510
Ile Thr Ala Pro Leu Ser Gln Arg Tyr Arg Val Arg Ile Arg Tyr Ala
            515                 520                 525
Ser Thr Thr Asn Leu Gln Phe His Thr Ser Ile Asp Gly Arg Pro Ile
            530                 535                 540
Asn Gln Gly Asn Phe Ser Ala Thr Met Ser Ser Gly Ser Asn Leu Gln
```

```
                545                 550                 555                 560
Ser Gly Ser Phe Arg Thr Val Gly Phe Thr Thr Pro Phe Asn Phe Ser
                565                 570                 575
Asn Gly Ser Ser Val Phe Thr Leu Ser Ala His Val Phe Asn Ser Gly
                580                 585                 590
Asn Glu Val Tyr Ile Asp Arg Ile Glu Phe Val Pro Ala Glu Val Thr
                595                 600                 605
Phe Glu Ala Glu Tyr Asp Leu Glu Arg Ala Gln Lys Ala Val Asn Glu
            610                 615                 620
Leu Phe Thr Ser Ser Asn Gln Ile Gly Leu Lys Thr Asp Val Thr Asp
625                 630                 635                 640
Tyr His Ile Asp Gln Val
                645

<210> SEQ ID NO 21
<211> LENGTH: 1845
<212> TYPE: DNA
<213> ORGANISM: Artificial Sequence
<220> FEATURE:
<223> OTHER INFORMATION: FR-cg-dm3 coding sequence

<400> SEQUENCE: 21
atgactagta acggccgcca gtgtgctggt attcgccctt atgacggccg acaacaacac       60
cgaggcctgg acagcagcac caccaaggac gtgatccaga agggcatcag cgtggtgggc      120
gacctgctgg gcgtggtggg cttccccttc ggcggcgccc tggtgagctt ctacaccaac      180
ttcctgaaca ccatctggcc cagcgaggac ccctggaagg ccttcatgga gcaggtggag      240
gccctgatgg accagaagat cgccgactac gccaagaaca aggcactggc cgagctacag      300
ggcctccaga caacgtgga ggactatgtg agcgccctga gcagctggca aagaaccc         360
gtctcgagcc gcaacccca cagccaggc cgcatccgcg agctgttcag ccaggccgag        420
agccacttcc gcaacagcat gcccagcttc gccatcagcg gctacgaggt gctgttcctg      480
accacctacg cccaggccgc caacacccac ctgttcctgc tgaaggacgc ccaaatctac      540
ggagaggagt ggggctacga agaggaggac atcgccgagt ctacaagcg ccagctgaag       600
ctgacccagg agtacaccga ccactgcgtg aagtggtaca cgtgggtct agacaagctc       660
cgcggcagca gctacgagag ctgggtgaac ttcaaccgct accgccgcga gatgaccctg      720
accgtgctgg acctgatcgc cctgttcccc ctgtacgacg tgcgcctgta ccccaaggag      780
gtgaagaccg agctgaccg cgacgtgctg accgaccca tcgtgggcgt gaacaacctg        840
cgcggctacg gcaccacctt cagcaacatc gagaactaca tccgcaagcc ccacctgttc      900
gactacctgc accgcatcca gttccacacg cgtttccagc ccggctacta cggcaacgac      960
agcttcaact actggagcgg caactacgtg agcacccgcc ccagcatcgg cagcaacgac     1020
atcatcacca gcccttcta cggcaacaag agcagcgagc ccgtgcagaa ccttgagttc      1080
aacggcgaga aggtgtaccg cgccgtggct aacaccaacc tggccgtgtg ccctctgca     1140
gtgtacagcg gcgtgaccaa ggtggagttc agccagtaca cgaccagac cgacgaggcc     1200
agcacccaga cctacgacag caagcgcaac gtgggcgccg tgagctggga cagcatcgac     1260
cagctgcccc ccgagaccac cgacgagccc ctggagaagg ctacagcca ccagctgaac     1320
tacgtgatgt gcttcctgat gcagggcagc cgcggcacca tccccgtgct gacctggacc     1380
cacaagagcg tcgacttctt caacatgatc gacagcaaga agatcaccca gctgccctg     1440
accaagagca ccaacctggg cagcggcacc agcgtggtga agggcccggg cttcaccggc     1500
```

```
ggcgacatcc tgcgccgcac cagccccggc cagatcagca ccctgcgcgt gaacatcacc    1560 gccccctga gccagcgcta ccgcgtccgc atccgctacg ccagcaccac caacctgcag    1620
ttccacacca gcatcgacgg ccgccccatc aaccagggca acttcagcgc caccatgagc    1680
agcggcagca acctgcagag cggcagcttc cgcaccgtgg gcttcaccac ccccttcaac    1740
ttcagcaacg gcagcagcgt gttcaccctg agcgcccacg tgttcaacag cggcaacgag    1800
gtgtacatcg accgcatcga gttcgtgccc gccgaggtga cctag                  1845

<210> SEQ ID NO 22
<211> LENGTH: 614
<212> TYPE: PRT
<213> ORGANISM: Artificial Sequence
<220> FEATURE:
<223> OTHER INFORMATION: FR-cg-dm3 protein

<400> SEQUENCE: 22

Met Thr Ser Asn Gly Arg Gln Cys Ala Gly Ile Arg Pro Tyr Asp Gly
1               5                   10                  15

Arg Gln Gln His Arg Gly Leu Asp Ser Ser Thr Thr Lys Asp Val Ile
            20                  25                  30

Gln Lys Gly Ile Ser Val Val Gly Asp Leu Leu Gly Val Gly Val Phe
        35                  40                  45

Pro Phe Gly Gly Ala Leu Val Ser Phe Tyr Thr Asn Phe Leu Asn Thr
    50                  55                  60

Ile Trp Pro Ser Glu Asp Pro Trp Lys Ala Phe Met Glu Gln Val Glu
65                  70                  75                  80

Ala Leu Met Asp Gln Lys Ile Ala Asp Tyr Ala Lys Asn Lys Ala Leu
                85                  90                  95

Ala Glu Leu Gln Gly Leu Gln Asn Asn Val Glu Asp Tyr Val Ser Ala
            100                 105                 110

Leu Ser Ser Trp Gln Lys Asn Pro Val Ser Ser Arg Asn Pro His Ser
        115                 120                 125

Gln Gly Arg Ile Arg Glu Leu Phe Ser Gln Ala Glu Ser His Phe Arg
    130                 135                 140

Asn Ser Met Pro Ser Phe Ala Ile Ser Gly Tyr Glu Val Leu Phe Leu
145                 150                 155                 160

Thr Thr Tyr Ala Gln Ala Ala Asn Thr His Leu Phe Leu Leu Lys Asp
                165                 170                 175

Ala Gln Ile Tyr Gly Glu Glu Trp Gly Tyr Glu Lys Glu Asp Ile Ala
            180                 185                 190

Glu Phe Tyr Lys Arg Gln Leu Lys Leu Thr Gln Glu Tyr Thr Asp His
        195                 200                 205

Cys Val Lys Trp Tyr Asn Val Gly Leu Asp Lys Leu Arg Gly Ser Ser
    210                 215                 220

Tyr Glu Ser Trp Val Asn Phe Asn Arg Tyr Arg Arg Glu Met Thr Leu
225                 230                 235                 240

Thr Val Leu Asp Leu Ile Ala Leu Phe Pro Leu Tyr Asp Val Arg Leu
                245                 250                 255

Tyr Pro Lys Glu Val Lys Thr Glu Leu Thr Arg Asp Val Leu Thr Asp
            260                 265                 270

Pro Ile Val Gly Val Asn Asn Leu Arg Gly Tyr Gly Thr Thr Phe Ser
        275                 280                 285

Asn Ile Glu Asn Tyr Ile Arg Lys Pro His Leu Phe Asp Tyr Leu His
    290                 295                 300

Arg Ile Gln Phe His Thr Arg Phe Gln Pro Gly Tyr Tyr Gly Asn Asp
```

```
                                305                 310                 315                 320
Ser Phe Asn Tyr Trp Ser Gly Asn Tyr Val Ser Thr Arg Pro Ser Ile
                325                 330                 335

Gly Ser Asn Asp Ile Ile Thr Ser Pro Phe Tyr Gly Asn Lys Ser Ser
                340                 345                 350

Glu Pro Val Gln Asn Leu Glu Phe Asn Gly Glu Lys Val Tyr Arg Ala
                355                 360                 365

Val Ala Asn Thr Asn Leu Ala Val Trp Pro Ser Ala Val Tyr Ser Gly
        370                 375                 380

Val Thr Lys Val Glu Phe Ser Gln Tyr Asn Asp Gln Thr Asp Glu Ala
385                 390                 395                 400

Ser Thr Gln Thr Tyr Asp Ser Lys Arg Asn Val Gly Ala Val Ser Trp
                405                 410                 415

Asp Ser Ile Asp Gln Leu Pro Pro Glu Thr Thr Asp Glu Pro Leu Glu
                420                 425                 430

Lys Gly Tyr Ser His Gln Leu Asn Tyr Val Met Cys Phe Leu Met Gln
                435                 440                 445

Gly Ser Arg Gly Thr Ile Pro Val Leu Thr Trp Thr His Lys Ser Val
        450                 455                 460

Asp Phe Phe Asn Met Ile Asp Ser Lys Lys Ile Thr Gln Leu Pro Leu
465                 470                 475                 480

Thr Lys Ser Thr Asn Leu Gly Ser Gly Thr Ser Val Val Lys Gly Pro
                485                 490                 495

Gly Phe Thr Gly Gly Asp Ile Leu Arg Arg Thr Ser Pro Gly Gln Ile
                500                 505                 510

Ser Thr Leu Arg Val Asn Ile Thr Ala Pro Leu Ser Gln Arg Tyr Arg
                515                 520                 525

Val Arg Ile Arg Tyr Ala Ser Thr Thr Asn Leu Gln Phe His Thr Ser
        530                 535                 540

Ile Asp Gly Arg Pro Ile Asn Gln Gly Asn Phe Ser Ala Thr Met Ser
545                 550                 555                 560

Ser Gly Ser Asn Leu Gln Ser Gly Ser Phe Arg Thr Val Gly Phe Thr
                565                 570                 575

Thr Pro Phe Asn Phe Ser Asn Gly Ser Ser Val Phe Thr Leu Ser Ala
                580                 585                 590

His Val Phe Asn Ser Gly Asn Glu Val Tyr Ile Asp Arg Ile Glu Phe
                595                 600                 605

Val Pro Ala Glu Val Thr
        610

<210> SEQ ID NO 23
<211> LENGTH: 1845
<212> TYPE: DNA
<213> ORGANISM: Artificial Sequence
<220> FEATURE:
<223> OTHER INFORMATION: 9F-cg-dm3 coding sequence

<400> SEQUENCE: 23
atgactagta acggccgcca gtgtgctggt attcgcccta tgacggccga caacaacacc      60
gaggccctgg acagcagcac caccaaggac gtgatccaga agggcatcag cgtggtgggc     120
gacctgctgg gcgtggtggg cttcccctte ggcggcgccc tggtgagctt ctacaccaac     180
ttcctgaaca ccatctggcc cagcgaggac ccctggaagg ccttcatgga gcaggtggag     240
gccctgatgg accagaagat cgccgactac gccaagaaca ggcactggc cgagctacag      300 ggcctccaga acaacgtgga ggactatgtg agcgccctga gcagctggca aagaaccccc     360
```

```
gtctcgagcc gcaaccccca cagccagggc cgcatccgcg agctgttcag ccaggccgag    420
agccacttcc gcaacagcat gcccagcttc gccatcagcg gctacgaggt gctgttcctg    480
accacctacg cccaggccgc caacacccac ctgttcctgc tgaaggacgc ccaaatctac    540
ggagaggagt ggggctacga gaaggaggac atcgccgagt tctacaagcg ccagctgaag    600
ctgacccagg agtacaccga ccactgcgtg aagtggtaca acgtgggtct agacaagctc    660
cgcggcagca gctacgagag ctgggtgaac ttcaaccgct accgccgcga gatgacccctg   720 accgtgctgg acctgatcgc cctgttcccc ctgtacgacg tgcgcctgta ccccaaggag    780
gtgaagaccg agctgacccg cgacgtgctg accgacccca tcgtgggcgt gaacaacctg    840
cgcggctacg gcaccacctt cagcaacatc gagaactaca tccgcaagcc ccacctgttc    900
gactacctgc accgcatcca gttccacacg cgtttccagc ccggctacta cggcaacgac    960
agcttcaact actggagcgg caactacgtg agcacccgcc ccagcatcgg cagcaacgac   1020
atcatccacc gcccccttcta cggcaacaag agcagcgagc ccgtgcagaa ccttgagttc   1080
aacggcgaga aggtgtaccg cgccgtggct aacaccaacc tggccgtgtg ccctctgca    1140 gtgtacagcg gcgtgaccaa ggtggagttc agccagtaca cgaccagac cgacgaggcc    1200 agcacccaga cctacgacag caagcgcaac gtgggcgccg tgagctggga cagcatcgac   1260
cagctgcccc ccgagaccac cgacgagccc tggagaagg gctacagcca ccagctgaac   1320
tacgtgatgt gcttcctgat gcagggcagc cgcggcacca tccccgtgct gacctggacc   1380
cacaagagcg tcgacttctt caacatgatc gacagcaaga gatcaccca gctgcccctg   1440 accaagagca ccaacctggg cagcggcacc agcgtggtga agggcccgg cttcaccggc    1500 ggcgacatcc tgcgccgcac cagccccggc cagatcagca ccctgcgcgt gaacatcacc   1560
gcccccctga gccagcgcta ccgcgtccgc atccgctacg ccagcaccac caacctgcag   1620
ttccacacca gcatcgacgg ccgccccatc aaccagggca acttcagcgc caccatgagc   1680
agcggcagca acctgcagag cggcagcttc cgcaccgtgg gcttcaccac ccccttcaac   1740
ttcagcaacg gcagcagcgt gttcaccctg agcgcccacg tgttcaacag cggcaacgag   1800
gtgtacatcg accgcatcga gttcgtgccc gccgaggtga cctag                   1845
```

<210> SEQ ID NO 24
<211> LENGTH: 614
<212> TYPE: PRT
<213> ORGANISM: Artificial Sequence
<220> FEATURE:
<223> OTHER INFORMATION: 9F-cg-dm3 protein

<400> SEQUENCE: 24

```
Met Thr Ser Asn Gly Arg Gln Cys Ala Gly Ile Arg Pro Met Thr Ala
1               5                   10                  15

Asp Asn Asn Thr Glu Ala Leu Asp Ser Ser Thr Thr Lys Asp Val Ile
            20                  25                  30

Gln Lys Gly Ile Ser Val Val Gly Asp Leu Leu Gly Val Gly Phe
        35                  40                  45

Pro Phe Gly Gly Ala Leu Val Ser Phe Tyr Thr Asn Phe Leu Asn Thr
    50                  55                  60

Ile Trp Pro Ser Glu Asp Pro Trp Lys Ala Phe Met Glu Gln Val Glu
65                  70                  75                  80

Ala Leu Met Asp Gln Lys Ile Ala Asp Tyr Ala Lys Asn Lys Ala Leu
                85                  90                  95

Ala Glu Leu Gln Gly Leu Gln Asn Asn Val Glu Asp Tyr Val Ser Ala
```

```
                100             105             110
Leu Ser Ser Trp Gln Lys Asn Pro Val Ser Arg Asn Pro His Ser
        115             120             125

Gln Gly Arg Ile Arg Glu Leu Phe Ser Gln Ala Glu Ser His Phe Arg
    130             135             140

Asn Ser Met Pro Ser Phe Ala Ile Ser Gly Tyr Glu Val Leu Phe Leu
145             150             155             160

Thr Thr Tyr Ala Gln Ala Ala Asn Thr His Leu Phe Leu Leu Lys Asp
                165             170             175

Ala Gln Ile Tyr Gly Glu Glu Trp Gly Tyr Glu Lys Glu Asp Ile Ala
                180             185             190

Glu Phe Tyr Lys Arg Gln Leu Lys Leu Thr Gln Glu Tyr Thr Asp His
        195             200             205

Cys Val Lys Trp Tyr Asn Val Gly Leu Asp Lys Leu Arg Gly Ser Ser
        210             215             220

Tyr Glu Ser Trp Val Asn Phe Asn Arg Tyr Arg Arg Glu Met Thr Leu
225             230             235             240

Thr Val Leu Asp Leu Ile Ala Leu Phe Pro Leu Tyr Asp Val Arg Leu
                245             250             255

Tyr Pro Lys Glu Val Lys Thr Glu Leu Thr Arg Asp Val Leu Thr Asp
                260             265             270

Pro Ile Val Gly Val Asn Asn Leu Arg Gly Tyr Gly Thr Thr Phe Ser
        275             280             285

Asn Ile Glu Asn Tyr Ile Arg Lys Pro His Leu Phe Asp Tyr Leu His
        290             295             300

Arg Ile Gln Phe His Thr Arg Phe Gln Pro Gly Tyr Tyr Gly Asn Asp
305             310             315             320

Ser Phe Asn Tyr Trp Ser Gly Asn Tyr Val Ser Thr Arg Pro Ser Ile
                325             330             335

Gly Ser Asn Asp Ile Ile Thr Ser Pro Phe Tyr Gly Asn Lys Ser Ser
                340             345             350

Glu Pro Val Gln Asn Leu Glu Phe Asn Gly Glu Lys Val Tyr Arg Ala
        355             360             365

Val Ala Asn Thr Asn Leu Ala Val Trp Pro Ser Ala Val Tyr Ser Gly
    370             375             380

Val Thr Lys Val Glu Phe Ser Gln Tyr Asn Asp Gln Thr Asp Glu Ala
385             390             395             400

Ser Thr Gln Thr Tyr Asp Ser Lys Arg Asn Val Gly Ala Val Ser Trp
                405             410             415

Asp Ser Ile Asp Gln Leu Pro Pro Glu Thr Thr Asp Glu Pro Leu Glu
                420             425             430

Lys Gly Tyr Ser His Gln Leu Asn Tyr Val Met Cys Phe Leu Met Gln
        435             440             445

Gly Ser Arg Gly Thr Ile Pro Val Leu Thr Trp Thr His Lys Ser Val
    450             455             460

Asp Phe Phe Asn Met Ile Asp Ser Lys Lys Ile Thr Gln Leu Pro Leu
465             470             475             480

Thr Lys Ser Thr Asn Leu Gly Ser Gly Thr Ser Val Val Lys Gly Pro
                485             490             495

Gly Phe Thr Gly Gly Asp Ile Leu Arg Arg Thr Ser Pro Gly Gln Ile
        500             505             510

Ser Thr Leu Arg Val Asn Ile Thr Ala Pro Leu Ser Gln Arg Tyr Arg
    515             520             525
```

-continued

```
Val Arg Ile Arg Tyr Ala Ser Thr Thr Asn Leu Gln Phe His Thr Ser
    530                 535                 540
Ile Asp Gly Arg Pro Ile Asn Gln Gly Asn Phe Ser Ala Thr Met Ser
545                 550                 555                 560
Ser Gly Ser Asn Leu Gln Ser Gly Ser Phe Arg Thr Val Gly Phe Thr
                565                 570                 575
Thr Pro Phe Asn Phe Ser Asn Gly Ser Ser Val Phe Thr Leu Ser Ala
                580                 585                 590
His Val Phe Asn Ser Gly Asn Glu Val Tyr Ile Asp Arg Ile Glu Phe
                595                 600                 605
Val Pro Ala Glu Val Thr
    610
```

<210> SEQ ID NO 25
<211> LENGTH: 1863
<212> TYPE: DNA
<213> ORGANISM: Artificial Sequence
<220> FEATURE:
<223> OTHER INFORMATION: B8a coding sequence

<400> SEQUENCE: 25

| | | |
|---|---|---|
| atgacggccg acaacaacac cgaggccctg acagcagca ccaccaagga cgtgatccag | 60 |
| aagggcatca gcgtggtggg cgacctgctg ggcgtggtgg gcttcccctt cggcggcgcc | 120 |
| ctggtgagct tctacaccaa cttcctgaac accatctggc ccagcgagga ccctggaag | 180 |
| gccttcatgg agcaggtgga ggccctgatg accagaaga tcgccgacta cgccaagaac | 240 |
| aaggcactgg ccgagctaca gggcctccag aacaacgtgg aggactatgt gagcgccctg | 300 |
| agcagctggc agaagaaccc cgctgcaccg ttccgcaacc cccacagcca gggccgcatc | 360 |
| cgcgagctgt tcagccaggc cgagagccac ttccgcaaca gcatgcccag cttcgccatc | 420 |
| agcggctacg aggtgctgtt cctgaccacc tacgcccagg ccgccaacac ccacctgttc | 480 |
| ctgctgaagg acgcccaaat ctacggagag gagtggggct acgagaagga ggacatcgcc | 540 |
| gagttctaca gcgccagct gaagctgacc caggagtaca ccgaccactg cgtgaagtgg | 600 |
| tacaacgtgg gtctagacaa gctccgcggc agcagctacg agagctgggt gaacttcaac | 660 |
| cgctaccgcc gcgagatgac cctgaccgtg ctggacctga tcgccctgtt ccccctgtac | 720 |
| gacgtgcgcc tgtaccccaa ggaggtgaag accgagctga cccgcgacgt gctgaccgac | 780 |
| cccatcgtgg gcgtgaacaa cctgcgcggc tacggcacca ccttcagcaa catcgagaac | 840 |
| tacatccgca agccccacct gttcgactac ctgaccgca tccagttcca cacgcgtttc | 900 |
| cagcccggct actacggcaa cgacagcttc aactactgga gcggcaacta cgtgagcacc | 960 |
| cgccccagca tcggcagcaa cgacatcatc accagcccct tctacggcaa caagagcagc | 1020 |
| gagcccgtgc agaaccttga gttcaacggc gagaaggtgt accgcgccgt ggctaacacc | 1080 |
| aacctggccg tgtggcccte tgcagtgtac agcggcgtga ccaaggtgga gttcagccag | 1140 |
| tacaacgacc agaccgacga ggccagcacc cagacctacg acagcaagcg caacgtgggc | 1200 |
| gccgtgagct gggacagcat cgaccagctg ccccccgaga ccaccgacga gccctggag | 1260 |
| aagggctaca gccaccagct gaactacgtg atgtgcttcc tgatgcaggg cagccgcggc | 1320 |
| accatccccg tgctgaccctg gacccacaag agcgtcgact tcttcaacat gatcgacagc | 1380 |
| aagaagatca cccagctgcc cctggtgaag gccagcgagc tgcccagggg caccaccgtg | 1440 |
| gttcgcggcc ccggcttcac cggaggcgac atcctgcgac gcaccaacac cggcggcttc | 1500 |
| ggccccatcc gcgtgaccgt gaacggcccc ctgacccagc gctaccgcat cggcttccgc | 1560 |

-continued

```
tacgccagca ccgtggactt cgacttcttc gtgagccgcg gcggcaccac cgtgaacaac    1620
ttccgcttcc tgcgcaccat gaacagcggc gacgagctga agtacggcaa cttcgtgcgc    1680
cgcgccttca ccaccccctt caccttcacc cagatccagg acatcatccg caccagcatc    1740
cagggcctga gcggcaacgg cgaggtgtac atcgacaaga tcgagatcat ccccgtgacc    1800
gccaccttcg aggccgagta cgacctagag cgcgcccagg aggccgtgaa cgccctgttc    1860
tag                                                                   1863
```

<210> SEQ ID NO 26
<211> LENGTH: 620
<212> TYPE: PRT
<213> ORGANISM: Artificial Sequence
<220> FEATURE:
<223> OTHER INFORMATION: B8a protein

<400> SEQUENCE: 26

```
Met Thr Ala Asp Asn Asn Thr Glu Ala Leu Asp Ser Ser Thr Thr Lys
1               5                   10                  15

Asp Val Ile Gln Lys Gly Ile Ser Val Val Gly Asp Leu Leu Gly Val
            20                  25                  30

Val Gly Phe Pro Phe Gly Gly Ala Leu Val Ser Phe Tyr Thr Asn Phe
        35                  40                  45

Leu Asn Thr Ile Trp Pro Ser Glu Asp Pro Trp Lys Ala Phe Met Glu
    50                  55                  60

Gln Val Glu Ala Leu Met Asp Gln Lys Ile Ala Asp Tyr Ala Lys Asn
65                  70                  75                  80

Lys Ala Leu Ala Glu Leu Gln Gly Leu Gln Asn Asn Val Glu Asp Tyr
                85                  90                  95

Val Ser Ala Leu Ser Ser Trp Gln Lys Asn Pro Ala Ala Pro Phe Arg
            100                 105                 110

Asn Pro His Ser Gln Gly Arg Ile Arg Glu Leu Phe Ser Gln Ala Glu
        115                 120                 125

Ser His Phe Arg Asn Ser Met Pro Ser Phe Ala Ile Ser Gly Tyr Glu
    130                 135                 140

Val Leu Phe Leu Thr Thr Tyr Ala Gln Ala Ala Asn Thr His Leu Phe
145                 150                 155                 160

Leu Leu Lys Asp Ala Gln Ile Tyr Gly Glu Glu Trp Gly Tyr Glu Lys
                165                 170                 175

Glu Asp Ile Ala Glu Phe Tyr Lys Arg Gln Leu Lys Leu Thr Gln Glu
            180                 185                 190

Tyr Thr Asp His Cys Val Lys Trp Tyr Asn Val Gly Leu Asp Lys Leu
        195                 200                 205

Arg Gly Ser Ser Tyr Glu Ser Trp Val Asn Phe Asn Arg Tyr Arg Arg
    210                 215                 220

Glu Met Thr Leu Thr Val Leu Asp Leu Ile Ala Leu Phe Pro Leu Tyr
225                 230                 235                 240

Asp Val Arg Leu Tyr Pro Lys Glu Val Lys Thr Glu Leu Thr Arg Asp
                245                 250                 255

Val Leu Thr Asp Pro Ile Val Gly Val Asn Asn Leu Arg Gly Tyr Gly
            260                 265                 270

Thr Thr Phe Ser Asn Ile Glu Asn Tyr Ile Arg Lys Pro His Leu Phe
        275                 280                 285

Asp Tyr Leu His Arg Ile Gln Phe His Thr Arg Phe Gln Pro Gly Tyr
    290                 295                 300

Tyr Gly Asn Asp Ser Phe Asn Tyr Trp Ser Gly Asn Tyr Val Ser Thr
```

```
                 305                 310                 315                 320
Arg Pro Ser Ile Gly Ser Asn Asp Ile Ile Thr Ser Pro Phe Tyr Gly
                    325                 330                 335

Asn Lys Ser Ser Glu Pro Val Gln Asn Leu Glu Phe Asn Gly Glu Lys
                340                 345                 350

Val Tyr Arg Ala Val Ala Asn Thr Asn Leu Ala Val Trp Pro Ser Ala
            355                 360                 365

Val Tyr Ser Gly Val Thr Lys Val Glu Phe Ser Gln Tyr Asn Asp Gln
        370                 375                 380

Thr Asp Glu Ala Ser Thr Gln Thr Tyr Asp Ser Lys Arg Asn Val Gly
385                 390                 395                 400

Ala Val Ser Trp Asp Ser Ile Asp Gln Leu Pro Pro Glu Thr Thr Asp
                405                 410                 415

Glu Pro Leu Glu Lys Gly Tyr Ser His Gln Leu Asn Tyr Val Met Cys
            420                 425                 430

Phe Leu Met Gln Gly Ser Arg Gly Thr Ile Pro Val Leu Thr Trp Thr
        435                 440                 445

His Lys Ser Val Asp Phe Phe Asn Met Ile Asp Ser Lys Lys Ile Thr
    450                 455                 460

Gln Leu Pro Leu Val Lys Ala Ser Glu Leu Pro Gln Gly Thr Thr Val
465                 470                 475                 480

Val Arg Gly Pro Gly Phe Thr Gly Gly Asp Ile Leu Arg Arg Thr Asn
                485                 490                 495

Thr Gly Gly Phe Gly Pro Ile Arg Val Thr Val Asn Gly Pro Leu Thr
            500                 505                 510

Gln Arg Tyr Arg Ile Gly Phe Arg Tyr Ala Ser Thr Val Asp Phe Asp
        515                 520                 525

Phe Phe Val Ser Arg Gly Gly Thr Thr Val Asn Asn Phe Arg Phe Leu
    530                 535                 540

Arg Thr Met Asn Ser Gly Asp Glu Leu Lys Tyr Gly Asn Phe Val Arg
545                 550                 555                 560

Arg Ala Phe Thr Thr Pro Phe Thr Phe Thr Gln Ile Gln Asp Ile Ile
                565                 570                 575

Arg Thr Ser Ile Gln Gly Leu Ser Gly Asn Gly Glu Val Tyr Ile Asp
            580                 585                 590

Lys Ile Glu Ile Ile Pro Val Thr Ala Thr Phe Glu Ala Glu Tyr Asp
        595                 600                 605

Leu Glu Arg Ala Gln Glu Ala Val Asn Ala Leu Phe
    610                 615                 620

<210> SEQ ID NO 27
<211> LENGTH: 1902
<212> TYPE: DNA
<213> ORGANISM: Artificial Sequence
<220> FEATURE:
<223> OTHER INFORMATION: 5*B8a coding sequence

<400> SEQUENCE: 27
atgactagta acggccgcca gtgtgctggt attcgccctt atgacggccg acaacaacac      60
cgaggcctgg acagcagcac caccaaggac gtgatccaga agggcatcag cgtggtgggc     120
gacctgctgg gcgtggtggg cttccccttc ggcggcgccc tggtgagctt ctacaccaac     180
ttcctgaaca ccatctggcc cagcgaggac ccctggaagg ccttcatgga gcaggtggag     240
gccctgatgg accagaagat cgccgactac gccaagaaca ggcactggcc gagctacag      300 ggcctccaga acaacgtgga ggactatgtg agcgccctga gcagctggca agaaccccc      360
```

```
gctgcaccgt tccgcaaccc ccacagccag ggccgcatcc gcgagctgtt cagccaggcc    420
gagagccact tccgcaacag catgcccagc ttcgccatca gcggctacga ggtgctgttc    480
ctgaccacct acgcccaggc cgccaacacc cacctgttcc tgctgaagga cgcccaaatc    540
tacggagagg agtggggcta cgagaaggag gacatcgccg agttctacaa gcgccagctg    600
aagctgaccc aggagtacac cgaccactgc gtgaagtggt acaacgtggg tctagacaag    660
ctccgcggca gcagctacga gagctgggtg aacttcaacc gctaccgccg cgagatgacc    720
ctgaccgtgc tggacctgat cgccctgttc cccctgtacg acgtgcgcct gtaccccaag    780
gaggtgaaga ccgagctgac ccgcgacgtg ctgaccgacc ccatcgtggg cgtgaacaac    840
ctgcgcggct acggcaccac cttcagcaac atcgagaact acatccgcaa gccccacctg    900
ttcgactacc tgcaccgcat ccagttccac acgcgtttcc agcccggcta ctacggcaac    960
gacagcttca actactggag cggcaactac gtgagcaccc gccccagcat cggcagcaac    1020
gacatcatca ccagcccctt ctacggcaac aagagcagcg agcccgtgca gaaccttgag    1080
ttcaacggcg agaaggtgta ccgcgccgtg gctaacacca acctggccgt gtggccctct    1140
gcagtgtaca cgcgcgtgac caaggtggag ttcagccagt acaacgacca gaccgacgag    1200
gccagcaccc agacctacga cagcaagcgc aacgtgggcg ccgtgagctg gacagcatc     1260 gaccagctgc cccccgagac caccgacgag ccccctggaga agggctacag ccaccagctg   1320
aactacgtga tgtgcttcct gatgcagggc agccgcggca ccatccccgt gctgacctgg   1380
acccacaaga gcgtcgactt cttcaacatg atcgacagca gaagatcac ccagctgccc     1440 ctggtgaagg ccagcgagct gccccagggc accaccgtgg ttcgcggccc cggcttcacc   1500
ggaggcgaca tcctgcgacg caccaacacc ggcggcttcg gccccatccg cgtgaccgtg   1560
aacggccccc tgacccagcg ctaccgcatc ggcttccgct acgccagcac cgtggacttc   1620
gacttcttcg tgagccgcgg cggcaccacc gtgaacaact tccgcttcct gcgcaccatg   1680
aacagcggcg acgagctgaa gtacggcaac ttcgtgcgcc gcgccttcac cacccccttc   1740
accttcaccc cagatccagga catcatccgc accagcatcc agggcctgag cggcaacggc   1800
gaggtgtaca tcgacaagat cgagatcatc cccgtgaccg ccaccttcga ggccgagtac   1860
gacctagagc gcgcccagga ggccgtgaac gccctgttct ag                       1902
```

<210> SEQ ID NO 28
<211> LENGTH: 633
<212> TYPE: PRT
<213> ORGANISM: Artificial Sequence
<220> FEATURE:
<223> OTHER INFORMATION: 5*B8a Protein

<400> SEQUENCE: 28

```
Met Thr Ser Asn Gly Arg Gln Cys Ala Gly Ile Arg Pro Tyr Asp Gly
1               5                   10                  15

Arg Gln Gln His Arg Gly Leu Asp Ser Ser Thr Thr Lys Asp Val Ile
            20                  25                  30

Gln Lys Gly Ile Ser Val Val Gly Asp Leu Leu Gly Val Gly Phe
        35                  40                  45

Pro Phe Gly Gly Ala Leu Val Ser Phe Tyr Thr Asn Phe Leu Asn Thr
    50                  55                  60

Ile Trp Pro Ser Glu Asp Pro Trp Lys Ala Phe Met Glu Gln Val Glu
65                  70                  75                  80

Ala Leu Met Asp Gln Lys Ile Ala Asp Tyr Ala Lys Asn Lys Ala Leu
                85                  90                  95
```

```
Ala Glu Leu Gln Gly Leu Gln Asn Asn Val Glu Asp Tyr Val Ser Ala
            100                 105                 110
Leu Ser Ser Trp Gln Lys Asn Pro Ala Ala Pro Phe Arg Asn Pro His
            115                 120                 125
Ser Gln Gly Arg Ile Arg Glu Leu Phe Ser Gln Ala Glu Ser His Phe
        130                 135                 140
Arg Asn Ser Met Pro Ser Phe Ala Ile Ser Gly Tyr Glu Val Leu Phe
145                 150                 155                 160
Leu Thr Thr Tyr Ala Gln Ala Ala Asn Thr His Leu Phe Leu Leu Lys
                165                 170                 175
Asp Ala Gln Ile Tyr Gly Glu Glu Trp Gly Tyr Glu Lys Glu Asp Ile
            180                 185                 190
Ala Glu Phe Tyr Lys Arg Gln Leu Lys Leu Thr Gln Glu Tyr Thr Asp
            195                 200                 205
His Cys Val Lys Trp Tyr Asn Val Gly Leu Asp Lys Leu Arg Gly Ser
        210                 215                 220
Ser Tyr Glu Ser Trp Val Asn Phe Asn Arg Tyr Arg Arg Glu Met Thr
225                 230                 235                 240
Leu Thr Val Leu Asp Leu Ile Ala Leu Phe Pro Leu Tyr Asp Val Arg
                245                 250                 255
Leu Tyr Pro Lys Glu Val Lys Thr Glu Leu Thr Arg Asp Val Leu Thr
            260                 265                 270
Asp Pro Ile Val Gly Val Asn Asn Leu Arg Gly Tyr Gly Thr Thr Phe
        275                 280                 285
Ser Asn Ile Glu Asn Tyr Ile Arg Lys Pro His Leu Phe Asp Tyr Leu
290                 295                 300
His Arg Ile Gln Phe His Thr Arg Phe Gln Pro Gly Tyr Tyr Gly Asn
305                 310                 315                 320
Asp Ser Phe Asn Tyr Trp Ser Gly Asn Tyr Val Ser Thr Arg Pro Ser
                325                 330                 335
Ile Gly Ser Asn Asp Ile Ile Thr Ser Pro Phe Tyr Gly Asn Lys Ser
            340                 345                 350
Ser Glu Pro Val Gln Asn Leu Glu Phe Asn Gly Glu Lys Val Tyr Arg
        355                 360                 365
Ala Val Ala Asn Thr Asn Leu Ala Val Trp Pro Ser Ala Val Tyr Ser
370                 375                 380
Gly Val Thr Lys Val Glu Phe Ser Gln Tyr Asn Asp Gln Thr Asp Glu
385                 390                 395                 400
Ala Ser Thr Gln Thr Tyr Asp Ser Lys Arg Asn Val Gly Ala Val Ser
                405                 410                 415
Trp Asp Ser Ile Asp Gln Leu Pro Pro Glu Thr Thr Asp Glu Pro Leu
            420                 425                 430
Glu Lys Gly Tyr Ser His Gln Leu Asn Tyr Val Met Cys Phe Leu Met
        435                 440                 445
Gln Gly Ser Arg Gly Thr Ile Pro Val Leu Thr Trp Thr His Lys Ser
    450                 455                 460
Val Asp Phe Phe Asn Met Ile Asp Ser Lys Lys Ile Thr Gln Leu Pro
465                 470                 475                 480
Leu Val Lys Ala Ser Glu Leu Pro Gln Gly Thr Thr Val Val Arg Gly
                485                 490                 495
Pro Gly Phe Thr Gly Gly Asp Ile Leu Arg Arg Thr Asn Thr Gly Gly
            500                 505                 510
Phe Gly Pro Ile Arg Val Thr Val Asn Gly Pro Leu Thr Gln Arg Tyr
```

```
                515                 520                 525
Arg Ile Gly Phe Arg Tyr Ala Ser Thr Val Asp Phe Asp Phe Phe Val
        530                 535                 540

Ser Arg Gly Gly Thr Thr Val Asn Asn Phe Arg Phe Leu Arg Thr Met
545                 550                 555                 560

Asn Ser Gly Asp Glu Leu Lys Tyr Gly Asn Phe Val Arg Arg Ala Phe
            565                 570                 575

Thr Thr Pro Phe Thr Phe Thr Gln Ile Gln Asp Ile Ile Arg Thr Ser
                580                 585                 590

Ile Gln Gly Leu Ser Gly Asn Gly Glu Val Tyr Ile Asp Lys Ile Glu
            595                 600                 605

Ile Ile Pro Val Thr Ala Thr Phe Glu Ala Glu Tyr Asp Leu Glu Arg
        610                 615                 620

Ala Gln Glu Ala Val Asn Ala Leu Phe
625                 630

<210> SEQ ID NO 29
<211> LENGTH: 1791
<212> TYPE: DNA
<213> ORGANISM: Artificial Sequence
<220> FEATURE:
<223> OTHER INFORMATION: V3A coding sequence

<400> SEQUENCE: 29
atgacggccg acaacaacac cgaggccctg acagcagca ccaccaagga cgtgatccag      60
aagggcatca gcgtggtggg cgacctgctg ggcgtggtgg gcttcccctt cggcggcgcc    120
ctggtgagct tctacaccaa cttcctgaac accatctggc ccagcgagga ccctggaag    180
gccttcatgg agcaggtgga ggccctgatg accagaagaa tcgccgacta cgccaagaac    240
aaggcactgg ccgagctaca gggcctccag aacaacgtgg aggactatgt gagcgccctg    300
agcagctggc agaagaaccc cgctgcaccg ttccgcaacc ccacagcca gggccgcatc    360
cgcgagctgt tcagccaggc cgagagccac ttccgcaaca gcatgcccag cttcgccatc    420
agcggctacg aggtgctgtt cctgaccacc tacgcccagg ccgccaacac ccacctgttc    480
ctgctgaagg acgcccaaat ctacggagag gagtggggct acgagaagga ggacatcgcc    540
gagttctaca gcgccagct gaagctgacc caggagtaca ccgaccactg cgtgaagtgg    600
tacaacgtgg gtctagacaa gctccgcggc agcagctacg agagctgggt gaacttcaac    660
cgctaccgcc gcgagatgac cctgaccgtg ctggacatcg tgagcctgtt ccccaactac    720
gacagccgca cctaccccat ccgcaccgtg agccagctga cccgcgagat ttacaccaac    780
cccgtgctgg agaacttcga cggcagcttc gcgggcagcg cccagggcat cgagggcagc    840
atccgcagcc cccacctgat ggacatcctg aacagcatca ccatctacac cgacgcccac    900
cgcggcgagt actactggag cggccaccag atcatggcca gccccgtcgg cttcagcggc    960
cccgagttca ccttccccct gtacggcacc atgggcaacg ctgcacctca gcagcgcatc   1020
gtggcacagc tgggccaggg agtgtaccgc accctgagca gcaccctgta ccgtcgacct   1080
ttcaacatcg gcatcaacaa ccagcagctg agcgtgctgg acggaccga gttcgcctac   1140
ggcaccagca gcaacctgcc cagcgccgtg taccgcaaga gcggcaccgt ggacagcctg   1200
gacgagatcc cccctcagaa caacaacgtg ccacctcgac agggcttcag ccaccgtctg   1260
agccacgtga gcatgttccg cagtggcttc agcaacagca gcgtgagcat catccgtgca   1320
cctatgttca gctggattca ccgcagtgcc gagttcaaca acatcatccc cagcagccag   1380
atcacccaga tcccctggt gaaggcctac aagctccaga gcggcgccag cgtggtggca   1440
```

```
ggcccccgct tcaccggcgg cgacatcatc cagtgcaccg agaacggcag cgccgccacc    1500
atctacgtga cccccgacgt gagctacagc cagaagtacc gcgcccgcat ccactacgcc    1560
agcaccagcc agatcacctt caccctgagc ctggacgggg ccccttcaa ccaatactac     1620 ttcgacaaga ccatcaacaa gggcgacacc ctgacctaca acagcttcaa cctggccagc    1680
ttcagcaccc ctttcgagct gagcggcaac aacctccaga tcggcgtgac cggcctgagc    1740
gccggcgaca aggtgtacat cgacaagatc gagttcatcc ccgtgaacta g             1791
```

<210> SEQ ID NO 30
<211> LENGTH: 596
<212> TYPE: PRT
<213> ORGANISM: Artificial Sequence
<220> FEATURE:
<223> OTHER INFORMATION: V3A protein

<400> SEQUENCE: 30

```
Met Thr Ala Asp Asn Asn Thr Glu Ala Leu Asp Ser Ser Thr Thr Lys
1               5                   10                  15

Asp Val Ile Gln Lys Gly Ile Ser Val Val Gly Asp Leu Leu Gly Val
            20                  25                  30

Val Gly Phe Pro Phe Gly Gly Ala Leu Val Ser Phe Tyr Thr Asn Phe
        35                  40                  45

Leu Asn Thr Ile Trp Pro Ser Glu Asp Pro Trp Lys Ala Phe Met Glu
    50                  55                  60

Gln Val Glu Ala Leu Met Asp Gln Lys Ile Ala Asp Tyr Ala Lys Asn
65                  70                  75                  80

Lys Ala Leu Ala Glu Leu Gln Gly Leu Gln Asn Asn Val Glu Asp Tyr
                85                  90                  95

Val Ser Ala Leu Ser Ser Trp Gln Lys Asn Pro Ala Ala Pro Phe Arg
            100                 105                 110

Asn Pro His Ser Gln Gly Arg Ile Arg Glu Leu Phe Ser Gln Ala Glu
        115                 120                 125

Ser His Phe Arg Asn Ser Met Pro Ser Phe Ala Ile Ser Gly Tyr Glu
    130                 135                 140

Val Leu Phe Leu Thr Thr Tyr Ala Gln Ala Ala Asn Thr His Leu Phe
145                 150                 155                 160

Leu Leu Lys Asp Ala Gln Ile Tyr Gly Glu Glu Trp Gly Tyr Glu Lys
                165                 170                 175

Glu Asp Ile Ala Glu Phe Tyr Lys Arg Gln Leu Lys Leu Thr Gln Glu
            180                 185                 190

Tyr Thr Asp His Cys Val Lys Trp Tyr Asn Val Gly Leu Asp Lys Leu
        195                 200                 205

Arg Gly Ser Ser Tyr Glu Ser Trp Val Asn Phe Asn Arg Tyr Arg Arg
    210                 215                 220

Glu Met Thr Leu Thr Val Leu Asp Ile Val Ser Leu Phe Pro Asn Tyr
225                 230                 235                 240

Asp Ser Arg Thr Tyr Pro Ile Arg Thr Val Ser Gln Leu Thr Arg Glu
                245                 250                 255

Ile Tyr Thr Asn Pro Val Leu Glu Asn Phe Asp Gly Ser Phe Arg Gly
            260                 265                 270

Ser Ala Gln Gly Ile Glu Gly Ser Ile Arg Ser Pro His Leu Met Asp
        275                 280                 285

Ile Leu Asn Ser Ile Thr Ile Tyr Thr Asp Ala His Arg Gly Glu Tyr
    290                 295                 300
```

```
Tyr Trp Ser Gly His Gln Ile Met Ala Ser Pro Val Gly Phe Ser Gly
305                 310                 315                 320

Pro Glu Phe Thr Phe Pro Leu Tyr Gly Thr Met Gly Asn Ala Ala Pro
            325                 330                 335

Gln Gln Arg Ile Val Ala Gln Leu Gly Gln Gly Val Tyr Arg Thr Leu
        340                 345                 350

Ser Ser Thr Leu Tyr Arg Arg Pro Phe Asn Ile Gly Ile Asn Asn Gln
    355                 360                 365

Gln Leu Ser Val Leu Asp Gly Thr Glu Phe Ala Tyr Gly Thr Ser Ser
370                 375                 380

Asn Leu Pro Ser Ala Val Tyr Arg Lys Ser Gly Thr Val Asp Ser Leu
385                 390                 395                 400

Asp Glu Ile Pro Pro Gln Asn Asn Asn Val Pro Pro Arg Gln Gly Phe
            405                 410                 415

Ser His Arg Leu Ser His Val Ser Met Phe Arg Ser Gly Phe Ser Asn
        420                 425                 430

Ser Ser Val Ser Ile Ile Arg Ala Pro Met Phe Ser Trp Ile His Arg
    435                 440                 445

Ser Ala Glu Phe Asn Asn Ile Ile Pro Ser Ser Gln Ile Thr Gln Ile
450                 455                 460

Pro Leu Val Lys Ala Tyr Lys Leu Gln Ser Gly Ala Ser Val Val Ala
465                 470                 475                 480

Gly Pro Arg Phe Thr Gly Gly Asp Ile Ile Gln Cys Thr Glu Asn Gly
            485                 490                 495

Ser Ala Ala Thr Ile Tyr Val Thr Pro Asp Val Ser Tyr Ser Gln Lys
        500                 505                 510

Tyr Arg Ala Arg Ile His Tyr Ala Ser Thr Ser Gln Ile Thr Phe Thr
    515                 520                 525

Leu Ser Leu Asp Gly Ala Pro Phe Asn Gln Tyr Tyr Phe Asp Lys Thr
530                 535                 540

Ile Asn Lys Gly Asp Thr Leu Thr Tyr Asn Ser Phe Asn Leu Ala Ser
545                 550                 555                 560

Phe Ser Thr Pro Phe Glu Leu Ser Gly Asn Asn Leu Gln Ile Gly Val
            565                 570                 575

Thr Gly Leu Ser Ala Gly Asp Lys Val Tyr Ile Asp Lys Ile Glu Phe
        580                 585                 590

Ile Pro Val Asn
        595

<210> SEQ ID NO 31
<211> LENGTH: 1797
<212> TYPE: DNA
<213> ORGANISM: Artificial Sequence
<220> FEATURE:
<223> OTHER INFORMATION: V4F coding sequence

<400> SEQUENCE: 31
atgacggccg acaacaacac cgaggccctg acagcagca ccaccaagga cgtgatccag      60
aagggcatca gcgtggtggg cgacctgctg ggcgtggtgg gcttcccctt cggcggcgcc    120
ctggtgagct tctacaccaa cttcctgaac accatctggc ccagcgagga ccctggaag     180 gccttcatga gcaggtgga ggccctgatg accagaaga tcgccgacta cgccaagaac      240
aaggcactgg ccgagctaca gggcctccag aacaacgtgg aggactatgt gagcgccctg    300
agcagctggc agaagaaccc cgctgcaccg ttccgcaacc cccacagcca ggccgcatc     360 cgcgagctgt tcagccaggc cgagagccac ttccgcaaca gcatgccag cttcgccatc    420
```

-continued

```
agcggctacg aggtgctgtt cctgaccacc tacgcccagg ccgccaacac ccacctgttc    480
ctgctgaagg acgcccaaat ctacggagag gagtggggct acgagaagga ggacatcgcc    540
gagttctaca agcgccagct gaagctgacc caggagtaca ccgaccactg cgtgaagtgg    600
tacaacgtgg gtctagacaa gctccgcggc agcagctacg agagctgggt gaacttcaac    660
cgctaccgcc gcgagatgac cctgaccgtg ctggacctga tcgccctgtt ccccctgtac    720
gacgtgcgcc tgtaccccaa ggaggtgaag accgagctga cccgcgacgt gctgaccgac    780
cccatcgtgg gcgtgaacaa cctgcgcggc tacggcacca ccttcagcaa catcgagaac    840
tacatccgca agccccacct gttcgactac ctgcaccgca tccagttcca cacgcgtttc    900
cagcccggct actacggcaa cgacagcttc aactactgga gcggcaacta cgtgagcacc    960
cgccccagca tcggcagcaa cgacatcatc accagcccct tctacggcaa caagagcagc   1020
gagcccgtgc agaaccttga gttcaacggc gagaaggtgt accgcgccgt ggctaacacc   1080
aacctggccg tgtggccctc tgcagtgtac agcggcgtga ccaaggtgga gttcagccag   1140
tacaacgacc agaccgacga ggccagcacc cagacctacg acagcaagcg caacgtgggc   1200
gccgtgagct gggacagcat cgaccagctg ccccccgaga ccaccgacga gcccctggag   1260
aagggctaca gccaccagct gaactacgtg atgtgcttcc tgatgcaggg cagccgcggc   1320
accatccccg tgctgacctg gacccacaag agcgtcgact cttcaacat gatcgacagc   1380 aagaagatca cccagctcgc cctgaccaag agcaccaacc tgggcagcgg caccagcgtg   1440
gtgaagggcc ccggcttcac cggcggcgac atcctgcgcc gcaccagccc cggccagatc   1500 agcacccctgc gcgtgaacat caccgccccc ctgagccagc gctaccgcgt ccgcatccac   1560
tacgccagca ccagccagat cacccttacc ctgagcctgg acgggcccc cttcaaccaa   1620 tactacttcg acaagaccat caacaagggc gacacccctga cctacaacag cttcaacctg   1680
gccagcttca gcaccccttt cgagctgagc ggcaacaacc tccagatcgg cgtgaccggc   1740
ctgagcgccg gcgacaaggt gtacatcgac aagatcgagt tcatccccgt gaactag       1797
```

<210> SEQ ID NO 32
<211> LENGTH: 598
<212> TYPE: PRT
<213> ORGANISM: Artificial Sequence
<220> FEATURE:
<223> OTHER INFORMATION: V4F protein

<400> SEQUENCE: 32

```
Met Thr Ala Asp Asn Asn Thr Glu Ala Leu Asp Ser Ser Thr Thr Lys
1               5                   10                  15

Asp Val Ile Gln Lys Gly Ile Ser Val Val Gly Asp Leu Leu Gly Val
            20                  25                  30

Val Gly Phe Pro Phe Gly Gly Ala Leu Val Ser Phe Tyr Thr Asn Phe
        35                  40                  45

Leu Asn Thr Ile Trp Pro Ser Glu Asp Pro Trp Lys Ala Phe Met Glu
    50                  55                  60

Gln Val Glu Ala Leu Met Asp Gln Lys Ile Ala Asp Tyr Ala Lys Asn
65                  70                  75                  80

Lys Ala Leu Ala Glu Leu Gln Gly Leu Gln Asn Asn Val Glu Asp Tyr
                85                  90                  95

Val Ser Ala Leu Ser Ser Trp Gln Lys Asn Pro Ala Ala Pro Phe Arg
            100                 105                 110

Asn Pro His Ser Gln Gly Arg Ile Arg Glu Leu Phe Ser Gln Ala Glu
        115                 120                 125
```

```
Ser His Phe Arg Asn Ser Met Pro Ser Phe Ala Ile Ser Gly Tyr Glu
    130                 135                 140

Val Leu Phe Leu Thr Thr Tyr Ala Gln Ala Ala Asn Thr His Leu Phe
145                 150                 155                 160

Leu Leu Lys Asp Ala Gln Ile Tyr Gly Glu Trp Gly Tyr Glu Lys
                165                 170                 175

Glu Asp Ile Ala Glu Phe Tyr Lys Arg Gln Leu Lys Leu Thr Gln Glu
                180                 185                 190

Tyr Thr Asp His Cys Val Lys Trp Tyr Asn Val Gly Leu Asp Lys Leu
            195                 200                 205

Arg Gly Ser Ser Tyr Glu Ser Trp Val Asn Phe Asn Arg Tyr Arg Arg
        210                 215                 220

Glu Met Thr Leu Thr Val Leu Asp Leu Ile Ala Leu Phe Pro Leu Tyr
225                 230                 235                 240

Asp Val Arg Leu Tyr Pro Lys Glu Val Lys Thr Glu Leu Thr Arg Asp
                245                 250                 255

Val Leu Thr Asp Pro Ile Val Gly Val Asn Asn Leu Arg Gly Tyr Gly
            260                 265                 270

Thr Thr Phe Ser Asn Ile Glu Asn Tyr Ile Arg Lys Pro His Leu Phe
        275                 280                 285

Asp Tyr Leu His Arg Ile Gln Phe His Thr Arg Phe Gln Pro Gly Tyr
290                 295                 300

Tyr Gly Asn Asp Ser Phe Asn Tyr Trp Ser Gly Asn Tyr Val Ser Thr
305                 310                 315                 320

Arg Pro Ser Ile Gly Ser Asn Asp Ile Ile Thr Ser Pro Phe Tyr Gly
                325                 330                 335

Asn Lys Ser Ser Glu Pro Val Gln Asn Leu Glu Phe Asn Gly Glu Lys
            340                 345                 350

Val Tyr Arg Ala Val Ala Asn Thr Asn Leu Ala Val Trp Pro Ser Ala
        355                 360                 365

Val Tyr Ser Gly Val Thr Lys Val Glu Phe Ser Gln Tyr Asn Asp Gln
370                 375                 380

Thr Asp Glu Ala Ser Thr Gln Thr Tyr Asp Ser Lys Arg Asn Val Gly
385                 390                 395                 400

Ala Val Ser Trp Asp Ser Ile Asp Gln Leu Pro Pro Glu Thr Thr Asp
                405                 410                 415

Glu Pro Leu Glu Lys Gly Tyr Ser His Gln Leu Asn Tyr Val Met Cys
            420                 425                 430

Phe Leu Met Gln Gly Ser Arg Gly Thr Ile Pro Val Leu Thr Trp Thr
        435                 440                 445

His Lys Ser Val Asp Phe Phe Asn Met Ile Asp Ser Lys Lys Ile Thr
    450                 455                 460

Gln Leu Ala Leu Thr Lys Ser Thr Asn Leu Gly Ser Gly Thr Ser Val
465                 470                 475                 480

Val Lys Gly Pro Gly Phe Thr Gly Gly Asp Ile Leu Arg Arg Thr Ser
                485                 490                 495

Pro Gly Gln Ile Ser Thr Leu Arg Val Asn Ile Thr Ala Pro Leu Ser
            500                 505                 510

Gln Arg Tyr Arg Val Arg Ile His Tyr Ala Ser Thr Ser Gln Ile Thr
        515                 520                 525

Phe Thr Leu Ser Leu Asp Gly Ala Pro Phe Asn Gln Tyr Tyr Phe Asp
530                 535                 540

Lys Thr Ile Asn Lys Gly Asp Thr Leu Thr Tyr Asn Ser Phe Asn Leu
```

```
           545                 550                 555                 560

Ala Ser Phe Ser Thr Pro Phe Glu Leu Ser Gly Asn Asn Leu Gln Ile
                565                 570                 575

Gly Val Thr Gly Leu Ser Ala Gly Asp Lys Val Tyr Ile Asp Lys Ile
                580                 585                 590

Glu Phe Ile Pro Val Asn
                595

<210> SEQ ID NO 33
<211> LENGTH: 1836
<212> TYPE: DNA
<213> ORGANISM: Artificial Sequence
<220> FEATURE:
<223> OTHER INFORMATION: 5*V4F coding sequence

<400> SEQUENCE: 33
atgactagta acggccgcca gtgtgctggt attcgccctt atgacggccg acaacaacac      60
cgaggcctgg acagcagcac caccaaggac gtgatccaga agggcatcag cgtggtgggc     120
gacctgctgg gcgtggtggg cttccccttc ggcggcgccc tggtgagctt ctacaccaac     180
ttcctgaaca ccatcctggcc cagcgaggac ccctggaagg ccttcatgga gcaggtggag     240
gccctgatgg accagaagat cgccgactac gccaagaaca aggcactggc cgagctacag     300
ggcctccaga caacgtggga ggactatgtg agcgccctga gcagtggca gaagaacccc      360 gctgcaccgt ccgcaacccc cacagccag ggccgcatcc gcgagctgtt cagccaggcc      420
gagagccact ccgcaacag catgcccagc ttcgccatca cggctacga ggtgctgttc       480 ctgaccacct acgcccaggc cgccaacacc cacctgttcc tgctgaagga cgcccaaatc     540
tacggagagg agtggggcta cgagaaggag gacatcgccg agttctacaa cgccagctg      600 aagctgaccc aggagtacac cgaccactgc gtgaagtggt acaacgtggg tctagacaag     660
ctccgcggca gcagctacga gagctgggtg aacttcaacc gctaccgccg cgagatgacc     720
ctgaccgtgc tggacctgat cgccctgttc ccctgtacg acgtgcgcct gtaccccaag     780
gaggtgaaga ccgagctgac ccgcgacgtg ctgaccgacc ccatcgtggg cgtgaacaac     840
ctgcgcggct acggcaccac cttcagcaac atcgagaact acatccgcaa gccccacctg    900
ttcgactacc tgcaccgcat ccagttccac acgcgtttcc agcccggcta ctacggcaac    960
gacagcttca actactggag cggcaactac gtgagcaccc gccccagcat cggcagcaac   1020
gacatcatca ccagcccctt ctacggcaac aagagcagcg agcccgtgca gaaccttgag   1080
ttcaacggcg agaaggtgta ccgcgccgtg gctaacacca acctggccgt gtggccctct   1140
gcagtgtaca cggcgtgac caaggtggag ttcagccagt acaacgacca gaccgacgag   1200
gccagcaccc agacctacga cagcaagcgc aacgtgggcg ccgtgagctg ggacagcatc   1260
gaccagctgc cccccgagac caccgacgag cccctggaga agggctacag ccaccagctg   1320
aactacgtga tgtgcttcct gatgcagggc agccgcggca ccatcccgt gctgacctgg   1380 acccacaaga cgtcgacttt cttcaacatg atcgacagca agaagatcac ccagctcgcc   1440
ctgaccaaga gcaccaacct gggcagcggc accagcgtgg tgaagggccc cggcttcacc   1500
ggcggcgaca tcctgcgccg caccagcccc ggccagatca gcaccctgcg cgtgaacatc   1560
accgcccccc tgagccagcg ctaccgcgtc cgcatccact acgccagcac cagccagatc   1620
accttcaccc tgagcctgga cggggccccc ttcaaccaat actacttcga caagaccatc   1680
aacaagggcg acaccctgac ctacaacagc ttcaacctgg ccagcttcag cacccctttc   1740
gagctgagcg gcaacaacct ccagatcggc gtgaccggcc tgagcgccgg cgacaaggtg   1800
```
tacatcgaca agatcgagtt catccccgtg aactag             1836

<210> SEQ ID NO 34
<211> LENGTH: 611
<212> TYPE: PRT
<213> ORGANISM: Artificial Sequence
<220> FEATURE:
<223> OTHER INFORMATION: 5*V4F Protein

<400> SEQUENCE: 34

| Met | Thr | Ser | Asn | Gly | Arg | Gln | Cys | Ala | Gly | Ile | Arg | Pro | Tyr | Asp | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Arg Gln Gln His Arg Gly Leu Asp Ser Ser Thr Lys Asp Val Ile
            20                  25                  30

Gln Lys Gly Ile Ser Val Val Gly Asp Leu Leu Gly Val Val Gly Phe
        35                  40                  45

Pro Phe Gly Gly Ala Leu Val Ser Phe Tyr Thr Asn Phe Leu Asn Thr
50                  55                  60

Ile Trp Pro Ser Glu Asp Pro Trp Lys Ala Phe Met Glu Gln Val Glu
65                  70                  75                  80

Ala Leu Met Asp Gln Lys Ile Ala Asp Tyr Ala Lys Asn Lys Ala Leu
                85                  90                  95

Ala Glu Leu Gln Gly Leu Gln Asn Asn Val Glu Asp Tyr Val Ser Ala
            100                 105                 110

Leu Ser Ser Trp Gln Lys Asn Pro Ala Ala Pro Phe Arg Asn Pro His
        115                 120                 125

Ser Gln Gly Arg Ile Arg Glu Leu Phe Ser Gln Ala Glu Ser His Phe
130                 135                 140

Arg Asn Ser Met Pro Ser Phe Ala Ile Ser Gly Tyr Glu Val Leu Phe
145                 150                 155                 160

Leu Thr Thr Tyr Ala Gln Ala Ala Asn Thr His Leu Phe Leu Leu Lys
                165                 170                 175

Asp Ala Gln Ile Tyr Gly Glu Glu Trp Gly Tyr Glu Lys Glu Asp Ile
            180                 185                 190

Ala Glu Phe Tyr Lys Arg Gln Leu Lys Leu Thr Gln Glu Tyr Thr Asp
        195                 200                 205

His Cys Val Lys Trp Tyr Asn Val Gly Leu Asp Lys Leu Arg Gly Ser
210                 215                 220

Ser Tyr Glu Ser Trp Val Asn Phe Asn Arg Tyr Arg Arg Glu Met Thr
225                 230                 235                 240

Leu Thr Val Leu Asp Leu Ile Ala Leu Phe Pro Leu Tyr Asp Val Arg
                245                 250                 255

Leu Tyr Pro Lys Glu Val Lys Thr Glu Leu Thr Arg Asp Val Leu Thr
            260                 265                 270

Asp Pro Ile Val Gly Val Asn Asn Leu Arg Gly Tyr Gly Thr Thr Phe
        275                 280                 285

Ser Asn Ile Glu Asn Tyr Ile Arg Lys Pro His Leu Phe Asp Tyr Leu
290                 295                 300

His Arg Ile Gln Phe His Thr Arg Phe Gln Pro Gly Tyr Tyr Gly Asn
305                 310                 315                 320

Asp Ser Phe Asn Tyr Trp Ser Gly Asn Tyr Val Ser Thr Arg Pro Ser
                325                 330                 335

Ile Gly Ser Asn Asp Ile Ile Thr Ser Pro Phe Tyr Gly Asn Lys Ser
            340                 345                 350

Ser Glu Pro Val Gln Asn Leu Glu Phe Asn Gly Glu Lys Val Tyr Arg

| | | | | | | | | | | | |
|---|---|---|---|---|---|---|---|---|---|---|---|
| | | | 355 | | | 360 | | | 365 | | |
| Ala | Val | Ala | Asn | Thr | Asn | Leu | Ala | Val | Trp | Pro | Ser | Ala | Val | Tyr | Ser |
| | 370 | | | | 375 | | | | 380 | | |

Ala Val Ala Asn Thr Asn Leu Ala Val Trp Pro Ser Ala Val Tyr Ser
    370                      375                      380

Gly Val Thr Lys Val Glu Phe Ser Gln Tyr Asn Asp Gln Thr Asp Glu
385                      390                      395                      400

Ala Ser Thr Gln Thr Tyr Asp Ser Lys Arg Asn Val Gly Ala Val Ser
                405                      410                      415

Trp Asp Ser Ile Asp Gln Leu Pro Pro Glu Thr Thr Asp Glu Pro Leu
            420                      425                      430

Glu Lys Gly Tyr Ser His Gln Leu Asn Tyr Val Met Cys Phe Leu Met
      435                      440                      445

Gln Gly Ser Arg Gly Thr Ile Pro Val Leu Thr Trp Thr His Lys Ser
450                      455                      460

Val Asp Phe Phe Asn Met Ile Asp Ser Lys Lys Ile Thr Gln Leu Ala
465                      470                      475                      480

Leu Thr Lys Ser Thr Asn Leu Gly Ser Gly Thr Ser Val Val Lys Gly
                485                      490                      495

Pro Gly Phe Thr Gly Gly Asp Ile Leu Arg Arg Thr Ser Pro Gly Gln
            500                      505                      510

Ile Ser Thr Leu Arg Val Asn Ile Thr Ala Pro Leu Ser Gln Arg Tyr
      515                      520                      525

Arg Val Arg Ile His Tyr Ala Ser Thr Ser Gln Ile Thr Phe Thr Leu
530                      535                      540

Ser Leu Asp Gly Ala Pro Phe Asn Gln Tyr Tyr Phe Asp Lys Thr Ile
545                      550                      555                      560

Asn Lys Gly Asp Thr Leu Thr Tyr Asn Ser Phe Asn Leu Ala Ser Phe
                565                      570                      575

Ser Thr Pro Phe Glu Leu Ser Gly Asn Asn Leu Gln Ile Gly Val Thr
            580                      585                      590

Gly Leu Ser Ala Gly Asp Lys Val Tyr Ile Asp Lys Ile Glu Phe Ile
      595                      600                      605

Pro Val Asn
    610

<210> SEQ ID NO 35
<211> LENGTH: 1901
<212> TYPE: DNA
<213> ORGANISM: Artificial Sequence
<220> FEATURE:
<223> OTHER INFORMATION: 20L-7 coding sequence

<400> SEQUENCE: 35

```
atgacggccg acaacaacac cgaggccctg gacagcagca ccaccaagga cgtgatccag    60
aagggcatca gcgtggtggg cgacctgctg ggcgtggtgg gcttcccctt cggcggcgcc   120
ctggtgagct tctacaccaa cttcctgaac accatctggc cagcgagga ccctggaag    180 gccttcatgg agcaggtgga ggccctgatg accagaaga tcgccgacta cgccaagaac    240
aaggcactgg ccgagctaca gggcctccag aacaacgtgg aggactatgt gagcgccctg    300
agcagctggc agaagaaccc cgctgcaccg ttccgcaacc cccacagcca gggccgcatc    360
cgcgagctgt tcagccaggc cgagagccac ttccgcaaca gcatgcccag cttcgccatc    420
agcggctacg aggtgctgtt cctgaccacc tacgtgcagg ccgccaacct gcacctgagc    480
gtgctgcgcg acgtcagcgt gttcggccag cgctggggct cgacgccgc caccatcaac    540 agccgctaca cgacctgac ccgcctgatc ggcaactaca ccgaccacgc cgtgcgctgg    600
```

-continued

```
tacaacaccg gcctggagcg cgtgtggggt cccgacagcc gcgactggat caggtacaac    660
cagttccgcc gcgagctgac cctgaccgtg ctggacatcg tgagcctgtt ccccaactac    720
gacagccgca cctaccccat ccgcaccgtg agccagctga cccgcgagat ttacaccaac    780
cccgtgctgg agaacttcga cggcagcttc gcggcagcg cccagggcat cgagggcagc     840
atccgcagcc ccacctgat ggacatcctg aacagcatca ccatctacac cgacgcccac     900
cgcggcgagt actactggag cggccaccag atcatggcca gccccgtcgg cttcagcggc    960
cccgagttca ccttcccccct gtacggcacc atgggcaacg ctgcacctca gcagcgcatc   1020
gtggcacagc tgggccaggg agtgtaccgc accctgagca gcaccctgta ccgtcgacct   1080
ttcaacatcg gcatcaacaa ccagcagctg agcgtgctgg acggcaccga gttcgcctac    1140
ggcaccagca gcaacctgcc cagcgccgtg taccgcaaga gcggcaccgt ggacagcctg    1200
gacgagatcc cccctcagaa caacaacgtg ccacctcgac agggcttcag ccaccgtctg    1260
agccacgtga gcatgttccg cagtggcttc agcaacagca gcgtgagcat catccgtgca    1320
cctatgttca gctggattca ccgcagtgcc gagttcaaca acatcatccc cagcagccag    1380
atcacccaga tcccctgac caagagcacc aacctgggca gcggcaccag cgtggtgaag    1440
ggccccggct tcaccggcgg cgacatcctg cgccgcacca gccccggcca gatcagcacc    1500
ctgcgcgtga acatcaccgc ccccctgagc agcgctacc gcgtccgcat ccgctacgcc    1560
agcaccacca acctgcagtt ccacaccagc atcgacggcc gccccatcaa ccagggcaac    1620
ttcagcgcca ccatgagcag cggcagcaac ctgcagagcg cagcttccg caccgtgggc    1680
ttcaccaccc ccttcaactt cagcaacggc agcagcgtgt caccctgag cgcccacgtg    1740
ttcaacagcg gcaacgaggt gtacatcgac cgcatcgagt tcgtgcccgc cgaggtgacc    1800
ttcgaggccg agtacgacct ggagagggct cagaaggccg tgaacgagct gttcaccagc    1860
agcaaccaga tcggcctgaa gaccgacgtg accgactacc a                        1901
```

<210> SEQ ID NO 36
<211> LENGTH: 633
<212> TYPE: PRT
<213> ORGANISM: Artificial Sequence
<220> FEATURE:
<223> OTHER INFORMATION: 2OL-7 protein

<400> SEQUENCE: 36

```
Met Thr Ala Asp Asn Asn Thr Glu Ala Leu Asp Ser Ser Thr Thr Lys
1               5                   10                  15

Asp Val Ile Gln Lys Gly Ile Ser Val Val Gly Asp Leu Leu Gly Val
            20                  25                  30

Val Gly Phe Pro Phe Gly Gly Ala Leu Val Ser Phe Tyr Thr Asn Phe
        35                  40                  45

Leu Asn Thr Ile Trp Pro Ser Glu Asp Pro Trp Lys Ala Phe Met Glu
    50                  55                  60

Gln Val Glu Ala Leu Met Asp Gln Lys Ile Ala Asp Tyr Ala Lys Asn
65                  70                  75                  80

Lys Ala Leu Ala Glu Leu Gln Gly Leu Gln Asn Asn Val Glu Asp Tyr
                85                  90                  95

Val Ser Ala Leu Ser Ser Trp Gln Lys Asn Pro Ala Ala Pro Phe Arg
            100                 105                 110

Asn Pro His Ser Gln Gly Arg Ile Arg Glu Leu Phe Ser Gln Ala Glu
        115                 120                 125

Ser His Phe Arg Asn Ser Met Pro Ser Phe Ala Ile Ser Gly Tyr Glu
    130                 135                 140
```

```
Val Leu Phe Leu Thr Thr Tyr Val Gln Ala Ala Asn Leu His Leu Ser
145                 150                 155                 160

Val Leu Arg Asp Val Ser Val Phe Gly Gln Arg Trp Gly Phe Asp Ala
                165                 170                 175

Ala Thr Ile Asn Ser Arg Tyr Asn Asp Leu Thr Arg Leu Ile Gly Asn
            180                 185                 190

Tyr Thr Asp His Ala Val Arg Trp Tyr Asn Thr Gly Leu Glu Arg Val
        195                 200                 205

Trp Gly Pro Asp Ser Arg Asp Trp Ile Arg Tyr Asn Gln Phe Arg Arg
    210                 215                 220

Glu Leu Thr Leu Thr Val Leu Asp Ile Val Ser Leu Phe Pro Asn Tyr
225                 230                 235                 240

Asp Ser Arg Thr Tyr Pro Ile Arg Thr Val Ser Gln Leu Thr Arg Glu
                245                 250                 255

Ile Tyr Thr Asn Pro Val Leu Glu Asn Phe Asp Gly Ser Phe Arg Gly
            260                 265                 270

Ser Ala Gln Gly Ile Glu Gly Ser Ile Arg Ser Pro His Leu Met Asp
        275                 280                 285

Ile Leu Asn Ser Ile Thr Ile Tyr Thr Asp Ala His Arg Gly Glu Tyr
    290                 295                 300

Tyr Trp Ser Gly His Gln Ile Met Ala Ser Pro Val Gly Phe Ser Gly
305                 310                 315                 320

Pro Glu Phe Thr Phe Pro Leu Tyr Gly Thr Met Gly Asn Ala Ala Pro
                325                 330                 335

Gln Gln Arg Ile Val Ala Gln Leu Gly Gln Gly Val Tyr Arg Thr Leu
            340                 345                 350

Ser Ser Thr Leu Tyr Arg Arg Pro Phe Asn Ile Gly Ile Asn Asn Gln
        355                 360                 365

Gln Leu Ser Val Leu Asp Gly Thr Glu Phe Ala Tyr Gly Thr Ser Ser
    370                 375                 380

Asn Leu Pro Ser Ala Val Tyr Arg Lys Ser Gly Thr Val Asp Ser Leu
385                 390                 395                 400

Asp Glu Ile Pro Pro Gln Asn Asn Asn Val Pro Pro Arg Gln Gly Phe
                405                 410                 415

Ser His Arg Leu Ser His Val Ser Met Phe Arg Ser Gly Phe Ser Asn
            420                 425                 430

Ser Ser Val Ser Ile Ile Arg Ala Pro Met Phe Ser Trp Ile His Arg
        435                 440                 445

Ser Ala Glu Phe Asn Asn Ile Ile Pro Ser Ser Gln Ile Thr Gln Ile
    450                 455                 460

Pro Leu Thr Lys Ser Thr Asn Leu Gly Ser Gly Thr Ser Val Val Lys
465                 470                 475                 480

Gly Pro Gly Phe Thr Gly Gly Asp Ile Leu Arg Arg Thr Ser Pro Gly
                485                 490                 495

Gln Ile Ser Thr Leu Arg Val Asn Ile Thr Ala Pro Leu Ser Gln Arg
            500                 505                 510

Tyr Arg Val Arg Ile Arg Tyr Ala Ser Thr Thr Asn Leu Gln Phe His
        515                 520                 525

Thr Ser Ile Asp Gly Arg Pro Ile Asn Gln Gly Asn Phe Ser Ala Thr
    530                 535                 540

Met Ser Ser Gly Ser Asn Leu Gln Ser Gly Ser Phe Arg Thr Val Gly
545                 550                 555                 560

Phe Thr Thr Pro Phe Asn Phe Ser Asn Gly Ser Ser Val Phe Thr Leu
```

```
                    565                 570                 575
Ser Ala His Val Phe Asn Ser Gly Asn Glu Val Tyr Ile Asp Arg Ile
            580                 585                 590

Glu Phe Val Pro Ala Glu Val Thr Phe Glu Ala Glu Tyr Asp Leu Glu
            595                 600                 605

Arg Ala Gln Lys Ala Val Asn Glu Leu Phe Thr Ser Ser Asn Gln Ile
            610                 615                 620

Gly Leu Lys Thr Asp Val Thr Asp Tyr
625                 630

<210> SEQ ID NO 37
<211> LENGTH: 1943
<212> TYPE: DNA
<213> ORGANISM: Artificial Sequence
<220> FEATURE:
<223> OTHER INFORMATION: T7-2OL-7 coding sequence

<400> SEQUENCE: 37
atggctagca tgactggtgg acagcaaatg ggtcgcggat ccatgacggc cgacaacaac      60
accgaggccc tggacagcag caccaccaag gacgtgatcc agaagggcat cagcgtggtg     120
ggcgacctgc tgggcgtggt gggcttcccc ttcggcggcg ccctggtgag cttctacacc     180
aacttcctga caccatctg gcccagcgag gaccctggaa ggccttcat ggagcaggtg      240 gaggccctga tggaccagaa gatcgccgac tacgccaaga caaggcact ggccgagcta      300 cagggcctcc agaacaacgt ggaggactat gtgagcgccc tgagcagctg gcagaagaac     360
cccgctgcac cgttccgcaa ccccccacagc cagggccgca tccgcgagct gttcagccag    420
gccgagagcc acttccgcaa cagcatgccc agcttcgcca tcagcggcta cgaggtgctg     480
ttcctgacca cctacgtgca ggccgccaac ctgcacctga gcgtgctgcg cgacgtcagc    540
gtgttcggcc agcgctgggg cttcgacgcc gccaccatca cagccgcta caacgacctg      600 acccgcctga tcggcaacta caccgaccac gccgtgcgct ggtacaacac cggcctggag    660
cgcgtgtggg gtcccgacag ccgcgactgg atcaggtaca accagttccg ccgcgagctg    720
accctgaccg tgctggacat cgtgagcctg ttccccaact acgacagccg cacctacccc    780
atccgcaccg tgagccagct gacccgcgag atttacacca ccccgtgct ggagaacttc      840 gacggcagct ccgcggcag cgcccagggc atcgagggca gcatccgcag ccccacctg      900 atggacatcc tgaacagcat caccatctac accgacgccc accgcggcga gtactactgg    960
agcggccacc agatcatggc cagccccgtc ggcttcagcg ccccgagtt cacccttccc     1020 ctgtacggca ccatgggcaa cgctgcacct cagcagcgca tcgtggcaca gctgggccag    1080
ggagtgtacc gcaccctgag cagcaccctg taccgtcgac cttttcaacat cggcatcaac    1140 aaccagcagc tgagcgtgct ggacggcacc gagttcgcct acggcaccag cagcaacctg    1200
cccagcgccg tgtaccgcaa gagcggcacc gtggacagcc tggacgagat ccccccctcag   1260 aacaacaacg tgccacctcg acagggcttc agccaccgtc tgagccacgt gagcatgttc    1320
cgcagtggct tcagcaacag cagcgtgagc atcatccgtg cacctatgtt cagctggatt    1380
caccgcagtg ccgagttcaa caacatcatc cccagcagcc agatcaccca gatcccctg    1440 accaagagca ccaacctggg cagcggcacc agcgtggtga agggcccccgg cttcaccggc   1500 ggcgacatcc tgcgccgcac cagccccggc cagatcagca cctgcgcgt gaacatcacc    1560 gcccccctga ccagcgcta ccgcgtccgc atccgctacg ccagcaccac caacctgcag    1620
ttccacacca gcatcgacgg ccgccccatc aaccagggca acttcagcgc caccatgagc    1680
```

```
agcggcagca acctgcagag cggcagcttc cgcaccgtgg gcttcaccac cccccttcaac   1740 ttcagcaacg gcagcagcgt gttcaccctg agcgcccacg tgttcaacag cggcaacgag   1800
gtgtacatcg accgcatcga gttcgtgccc gccgaggtga ccttcgaggc cgagtacgac   1860
ctggagaggg ctcagaaggc cgtgaacgag ctgttcacca gcagcaacca gatcggcctg   1920
aagaccgacg tgaccgacta cca                                           1943
```

<210> SEQ ID NO 38
<211> LENGTH: 647
<212> TYPE: PRT
<213> ORGANISM: Artificial Sequence
<220> FEATURE:
<223> OTHER INFORMATION: T7-20L-7 protein

<400> SEQUENCE: 38

```
Met Ala Ser Met Thr Gly Gly Gln Gln Met Gly Arg Gly Ser Met Thr
  1               5                  10                  15

Ala Asp Asn Asn Thr Glu Ala Leu Asp Ser Ser Thr Thr Lys Asp Val
             20                  25                  30

Ile Gln Lys Gly Ile Ser Val Val Gly Asp Leu Leu Gly Val Val Gly
         35                  40                  45

Phe Pro Phe Gly Gly Ala Leu Val Ser Phe Tyr Thr Asn Phe Leu Asn
 50                  55                  60

Thr Ile Trp Pro Ser Glu Asp Pro Trp Lys Ala Phe Met Glu Gln Val
 65                  70                  75                  80

Glu Ala Leu Met Asp Gln Lys Ile Ala Asp Tyr Ala Lys Asn Lys Ala
             85                  90                  95

Leu Ala Glu Leu Gln Gly Leu Gln Asn Asn Val Glu Asp Tyr Val Ser
        100                 105                 110

Ala Leu Ser Ser Trp Gln Lys Asn Pro Ala Ala Pro Phe Arg Asn Pro
        115                 120                 125

His Ser Gln Gly Arg Ile Arg Glu Leu Phe Ser Gln Ala Glu Ser His
    130                 135                 140

Phe Arg Asn Ser Met Pro Ser Phe Ala Ile Ser Gly Tyr Glu Val Leu
145                 150                 155                 160

Phe Leu Thr Thr Tyr Val Gln Ala Ala Asn Leu His Leu Ser Val Leu
                165                 170                 175

Arg Asp Val Ser Val Phe Gly Gln Arg Trp Gly Phe Asp Ala Ala Thr
            180                 185                 190

Ile Asn Ser Arg Tyr Asn Asp Leu Thr Arg Leu Ile Gly Asn Tyr Thr
        195                 200                 205

Asp His Ala Val Arg Trp Tyr Asn Thr Gly Leu Glu Arg Val Trp Gly
    210                 215                 220

Pro Asp Ser Arg Asp Trp Ile Arg Tyr Asn Gln Phe Arg Arg Glu Leu
225                 230                 235                 240

Thr Leu Thr Val Leu Asp Ile Val Ser Leu Phe Pro Asn Tyr Asp Ser
                245                 250                 255

Arg Thr Tyr Pro Ile Arg Thr Val Ser Gln Leu Thr Arg Glu Ile Tyr
            260                 265                 270

Thr Asn Pro Val Leu Glu Asn Phe Asp Gly Ser Phe Arg Gly Ser Ala
        275                 280                 285

Gln Gly Ile Glu Gly Ser Ile Arg Ser Pro His Leu Met Asp Ile Leu
    290                 295                 300

Asn Ser Ile Thr Ile Tyr Thr Asp Ala His Arg Gly Glu Tyr Tyr Trp
305                 310                 315                 320
```

Ser Gly His Gln Ile Met Ala Ser Pro Val Gly Phe Ser Gly Pro Glu
            325                 330                 335

Phe Thr Phe Pro Leu Tyr Gly Thr Met Gly Asn Ala Ala Pro Gln Gln
            340                 345                 350

Arg Ile Val Ala Gln Leu Gly Gln Gly Val Tyr Arg Thr Leu Ser Ser
            355                 360                 365

Thr Leu Tyr Arg Arg Pro Phe Asn Ile Gly Ile Asn Asn Gln Gln Leu
        370                 375                 380

Ser Val Leu Asp Gly Thr Glu Phe Ala Tyr Gly Thr Ser Ser Asn Leu
385                 390                 395                 400

Pro Ser Ala Val Tyr Arg Lys Ser Gly Thr Val Asp Ser Leu Asp Glu
                405                 410                 415

Ile Pro Pro Gln Asn Asn Asn Val Pro Pro Arg Gln Gly Phe Ser His
            420                 425                 430

Arg Leu Ser His Val Ser Met Phe Arg Ser Gly Phe Ser Asn Ser Ser
        435                 440                 445

Val Ser Ile Ile Arg Ala Pro Met Phe Ser Trp Ile His Arg Ser Ala
450                 455                 460

Glu Phe Asn Asn Ile Ile Pro Ser Ser Gln Ile Thr Gln Ile Pro Leu
465                 470                 475                 480

Thr Lys Ser Thr Asn Leu Gly Ser Gly Thr Ser Val Val Lys Gly Pro
                485                 490                 495

Gly Phe Thr Gly Gly Asp Ile Leu Arg Arg Thr Ser Pro Gly Gln Ile
            500                 505                 510

Ser Thr Leu Arg Val Asn Ile Thr Ala Pro Leu Ser Gln Arg Tyr Arg
        515                 520                 525

Val Arg Ile Arg Tyr Ala Ser Thr Thr Asn Leu Gln Phe His Thr Ser
530                 535                 540

Ile Asp Gly Arg Pro Ile Asn Gln Gly Asn Phe Ser Ala Thr Met Ser
545                 550                 555                 560

Ser Gly Ser Asn Leu Gln Ser Gly Ser Phe Arg Thr Val Gly Phe Thr
                565                 570                 575

Thr Pro Phe Asn Phe Ser Asn Gly Ser Ser Val Phe Thr Leu Ser Ala
            580                 585                 590

His Val Phe Asn Ser Gly Asn Glu Val Tyr Ile Asp Arg Ile Glu Phe
        595                 600                 605

Val Pro Ala Glu Val Thr Phe Glu Ala Glu Tyr Asp Leu Glu Arg Ala
610                 615                 620

Gln Lys Ala Val Asn Glu Leu Phe Thr Ser Ser Asn Gln Ile Gly Leu
625                 630                 635                 640

Lys Thr Asp Val Thr Asp Tyr
                645

<210> SEQ ID NO 39
<211> LENGTH: 1940
<212> TYPE: DNA
<213> ORGANISM: Artificial Sequence
<220> FEATURE:
<223> OTHER INFORMATION: 5*2OL-7 coding sequence

<400> SEQUENCE: 39
atgactagta acggccgcca gtgtgctggt attcgccctt atgacggccg acaacaacac    60
cgaggcctgg acagcagcac caccaaggac gtgatccaga agggcatcag cgtggtgggc   120
gacctgctgg gcgtggtggg cttccccttc ggcggcgccc tggtgagctt ctacaccaac   180
ttcctgaaca ccatctggcc cagcgaggac ccctggaagg ccttcatgga gcaggtggag   240

-continued

```
gccctgatgg accagaagat cgccgactac gccaagaaca aggcactggc cgagctacag      300
ggcctccaga caacgtgga ggactatgtg agcgccctga gcagctggca gaagaacccc      360
gctgcaccgt tccgcaaccc ccacagccag ggccgcatcc gcgagctgtt cagccaggcc      420
gagagccact tccgcaacag catgcccagc ttcgccatca gcggctacga ggtgctgttc      480
ctgaccacct acgtgcaggc cgccaacctg cacctgagcg tgctgcgcga cgtcagcgtg      540
ttcggccagc gctggggctt cgacgccgcc accatcaaca gccgctacaa cgacctgacc      600
cgcctgatcg gcaactacac cgaccacgcc gtgcgctggt acaacaccgg cctggagcgc      660
gtgtggggtc ccgacagccg cgactggatc aggtacaacc agttccgccg cgagctgacc      720
ctgaccgtgc tggacatcgt gagcctgttc cccaactacg acagccgcac ctacccccatc      780 cgcaccgtga gccagctgac ccgcgagatt tacaccaacc ccgtgctgga aacttcgac      840 ggcagcttcc gcggcagcgc ccagggcatc gagggcagca tccgcagccc ccacctgatg      900
gacatcctga cagcatcac catctacacc gacgcccacc gcggcgagta ctactggagc      960
ggccaccaga tcatggccag ccccgtcggc ttcagcggcc ccgagttcac cttccccctg     1020
tacggcacca tgggcaacgc tgcacctcag cagcgcatcg tggcacagct gggccaggga     1080
gtgtaccgca ccctgagcag caccctgtac cgtcgacctt tcaacatcgg catcaacaac     1140
cagcagctga gcgtgctgga cggcaccgag ttcgcctacg gcaccagcag caacctgccc     1200
agcgccgtgt accgcaagag cggcaccgtg gacagcctgg acgagatccc ccctcagaac     1260
aacaacgtgc cacctcgaca gggcttcagc caccgtctga gccacgtgag catgttccgc     1320
agtggcttca gcaacagcag cgtgagcatc atccgtgcac ctatgttcag ctggattcac     1380
cgcagtgccg agttcaacaa catcatcccc agcagccaga tcacccagat ccccctgacc     1440
aagagcacca acctgggcag cggcaccagc gtggtgaagg gccccggctt caccggcggc     1500
gacatcctgc gccgcaccag ccccggccag atcagcaccc tgcgcgtgaa catcaccgcc     1560
cccctgagcc agcgctaccg cgtccgcatc cgctacgcca gcaccaccaa cctgcagttc     1620
cacaccagca tcgacggccg ccccatcaac cagggcaact tcagcgccac catgagcagc     1680
ggcagcaacc tgcagagcgg cagcttccgc accgtgggct tcaccacccc cttcaacttc     1740
agcaacggca gcagcgtgtt cacccctgagc gcccacgtgt tcaacagcgg caacgaggtg     1800
tacatcgacc gcatcgagtt cgtgcccgcc gaggtgacct tcgaggccga gtacgacctg     1860
gagagggctc agaaggccgt gaacgagctg ttcaccagca gcaaccagat cggcctgaag     1920
accgacgtga ccgactacca                                                 1940
```

<210> SEQ ID NO 40
<211> LENGTH: 646
<212> TYPE: PRT
<213> ORGANISM: Artificial Sequence
<220> FEATURE:
<223> OTHER INFORMATION: 5*2OL-7 protein

<400> SEQUENCE: 40

```
Met Thr Ser Asn Gly Arg Gln Cys Ala Gly Ile Arg Pro Tyr Asp Gly
1               5                   10                  15

Arg Gln Gln His Arg Gly Leu Asp Ser Ser Thr Thr Lys Asp Val Ile
                20                  25                  30

Gln Lys Gly Ile Ser Val Val Gly Asp Leu Leu Gly Val Val Gly Phe
            35                  40                  45

Pro Phe Gly Gly Ala Leu Val Ser Phe Tyr Thr Asn Phe Leu Asn Thr
        50                  55                  60
```

```
Ile Trp Pro Ser Glu Asp Pro Trp Lys Ala Phe Met Glu Gln Val Glu
 65                  70                  75                  80

Ala Leu Met Asp Gln Lys Ile Ala Asp Tyr Ala Lys Asn Lys Ala Leu
                 85                  90                  95

Ala Glu Leu Gln Gly Leu Gln Asn Asn Val Glu Asp Tyr Val Ser Ala
            100                 105                 110

Leu Ser Ser Trp Gln Lys Asn Pro Ala Ala Pro Phe Arg Asn Pro His
        115                 120                 125

Ser Gln Gly Arg Ile Arg Glu Leu Phe Ser Gln Ala Glu Ser His Phe
    130                 135                 140

Arg Asn Ser Met Pro Ser Phe Ala Ile Ser Gly Tyr Glu Val Leu Phe
145                 150                 155                 160

Leu Thr Thr Tyr Val Gln Ala Ala Asn Leu His Leu Ser Val Leu Arg
                165                 170                 175

Asp Val Ser Val Phe Gly Gln Arg Trp Gly Phe Asp Ala Ala Thr Ile
            180                 185                 190

Asn Ser Arg Tyr Asn Asp Leu Thr Arg Leu Ile Gly Asn Tyr Thr Asp
        195                 200                 205

His Ala Val Arg Trp Tyr Asn Thr Gly Leu Glu Arg Val Trp Gly Pro
    210                 215                 220

Asp Ser Arg Asp Trp Ile Arg Tyr Asn Gln Phe Arg Arg Glu Leu Thr
225                 230                 235                 240

Leu Thr Val Leu Asp Ile Val Ser Leu Phe Pro Asn Tyr Asp Ser Arg
                245                 250                 255

Thr Tyr Pro Ile Arg Thr Val Ser Gln Leu Thr Arg Glu Ile Tyr Thr
            260                 265                 270

Asn Pro Val Leu Glu Asn Phe Asp Gly Ser Phe Arg Gly Ser Ala Gln
        275                 280                 285

Gly Ile Glu Gly Ser Ile Arg Ser Pro His Leu Met Asp Ile Leu Asn
    290                 295                 300

Ser Ile Thr Ile Tyr Thr Asp Ala His Arg Gly Glu Tyr Tyr Trp Ser
305                 310                 315                 320

Gly His Gln Ile Met Ala Ser Pro Val Gly Phe Ser Gly Pro Glu Phe
                325                 330                 335

Thr Phe Pro Leu Tyr Gly Thr Met Gly Asn Ala Ala Pro Gln Gln Arg
            340                 345                 350

Ile Val Ala Gln Leu Gly Gln Gly Val Tyr Arg Thr Leu Ser Ser Thr
        355                 360                 365

Leu Tyr Arg Arg Pro Phe Asn Ile Gly Ile Asn Asn Gln Gln Leu Ser
    370                 375                 380

Val Leu Asp Gly Thr Glu Phe Ala Tyr Gly Thr Ser Ser Asn Leu Pro
385                 390                 395                 400

Ser Ala Val Tyr Arg Lys Ser Gly Thr Val Asp Ser Leu Asp Glu Ile
                405                 410                 415

Pro Pro Gln Asn Asn Asn Val Pro Pro Arg Gln Gly Phe Ser His Arg
            420                 425                 430

Leu Ser His Val Ser Met Phe Arg Ser Gly Phe Ser Asn Ser Ser Val
        435                 440                 445

Ser Ile Ile Arg Ala Pro Met Phe Ser Trp Ile His Arg Ser Ala Glu
    450                 455                 460

Phe Asn Asn Ile Ile Pro Ser Ser Gln Ile Thr Gln Ile Pro Leu Thr
465                 470                 475                 480

Lys Ser Thr Asn Leu Gly Ser Gly Thr Ser Val Val Lys Gly Pro Gly
```

```
                      485                 490                 495
Phe Thr Gly Gly Asp Ile Leu Arg Arg Thr Ser Pro Gly Gln Ile Ser
                500                 505                 510
Thr Leu Arg Val Asn Ile Thr Ala Pro Leu Ser Gln Arg Tyr Arg Val
            515                 520                 525
Arg Ile Arg Tyr Ala Ser Thr Thr Asn Leu Gln Phe His Thr Ser Ile
        530                 535                 540
Asp Gly Arg Pro Ile Asn Gln Gly Asn Phe Ser Ala Thr Met Ser Ser
545                 550                 555                 560
Gly Ser Asn Leu Gln Ser Gly Ser Phe Arg Thr Val Gly Phe Thr Thr
                565                 570                 575
Pro Phe Asn Phe Ser Asn Gly Ser Ser Val Phe Thr Leu Ser Ala His
                580                 585                 590
Val Phe Asn Ser Gly Asn Glu Val Tyr Ile Asp Arg Ile Glu Phe Val
                595                 600                 605
Pro Ala Glu Val Thr Phe Glu Ala Glu Tyr Asp Leu Glu Arg Ala Gln
            610                 615                 620
Lys Ala Val Asn Glu Leu Phe Thr Ser Ser Asn Gln Ile Gly Leu Lys
625                 630                 635                 640
Thr Asp Val Thr Asp Tyr
                645

<210> SEQ ID NO 41
<211> LENGTH: 1917
<212> TYPE: DNA
<213> ORGANISM: Artificial Sequence
<220> FEATURE:
<223> OTHER INFORMATION: 2OL-10 coding sequence

<400> SEQUENCE: 41
atgacggccg acaacaacac cgaggccctg acagcagca ccaccaagga cgtgatccag      60
aagggcatca gcgtggtggg cgacctgctg ggcgtggtgg gcttcccctt cggcggcgcc     120
ctggtgagct tctacaccaa cttcctgaac accatctggc ccagcgagga cccctggaag     180
gccttcatgg agcaggtgga ggccctgatg accagaagaa tcgccgacta cgccaagaac     240
aaggcactgg ccgagctaca gggcctccag aacaacgtgg aggactatgt gagcgccctg     300
agcagctggc agaagaaccc cgctgcaccg ttccgcaacc ccacagcca gggccgcatc     360 cgcgagctgt tcagccaggc cgagagccac ttccgcaaca gcatgcccag cttcgccatc     420
agcggctacg aggtgctgtt cctgaccacc tacgcccagg ccgccaacac ccacctgttc     480
ctgctgaagg acgcccaaat ctacggagag gagtggggct acgagaagga ggacatcgcc     540
gagttctaca gcgccagct gaagctgacc caggagtaca ccgaccactg cgtgaagtgg     600
tacaacgtgg gtctagacaa gctccgcggc agcagctacg agagctgggt gaacttcaac     660
cgctaccgcc gcgagatgac cctgaccgtg ctggacatcg tgagcctgtt ccccaactac     720
gacagccgca cctaccccat ccgcaccgtg agccagctga cccgcgagat tacaccaac     780 cccgtgctgg agaacttcga cggcagcttc cgcggcagcg cccagggcat cgagggcagc     840
atccgcagcc cccacctgat ggacatcctg aacagcatca ccatctacac cgacgcccac     900
cgcggcgagt actactggag cggccaccag atcatggcca gccccgtcgg cttcagcggc     960
cccgagttca ccttcccccct gtacggcacc atgggcaacg ctgcacctca gcagcgcatc    1020
gtggcacagc tgggccaggg agtgtaccgc acccctgagca gcaccctgta ccgtcgacct    1080
ttcaacatcg gcatcaacaa ccagcagctg agcgtgctgg acggcaccga gttcgcctac    1140
```

-continued

```
ggcaccagca gcaacctgcc cagcgccgtg taccgcaaga gcggcaccgt ggacagcctg    1200
gacgagatcc ccctcagaa caacaacgtg ccacctcgac agggcttcag ccaccgtctg     1260
agccacgtga gcatgttccg cagtggcttc agcaacagca gcgtgagcat catccgtgca    1320
cctatgttca gctggattca ccgcagtgcc gagttcaaca acatcatccc cagcagccag    1380
atcacccaga tcccctgac aagagcacc aacctgggca gcggcaccag cgtggtgaag      1440
ggccccggct tcaccggcgg cgacatcctg cgccgcacca gccccggcca gatcagcacc    1500
ctgcgcgtga acatcaccgc ccccctgagc cagcgctacc gcgtccgcat ccgctacgcc    1560
agcaccacca acctgcagtt ccacaccagc atcgacggcc gccccatcaa ccagggcaac    1620
ttcagcgcca ccatgagcag cggcagcaac ctgcagagcg gcagcttccg caccgtgggc    1680
ttcaccaccc ccttcaactt cagcaacggc agcagcgtgt tcaccctgag cgcccacgtg    1740
ttcaacagcg gcaacgaggt gtacatcgac cgcatcgagt tcgtgcccgc cgaggtgacc    1800
ttcgaggccg agtacgacct ggagagggct cagaaggccg tgaacgagct gttcaccagc    1860
agcaaccaga tcggcctgaa gaccgacgtg accgactacc acatcgatca ggtgtag       1917
```

<210> SEQ ID NO 42
<211> LENGTH: 638
<212> TYPE: PRT
<213> ORGANISM: Artificial Sequence
<220> FEATURE:
<223> OTHER INFORMATION: 2OL-10 protein

<400> SEQUENCE: 42

```
Met Thr Ala Asp Asn Asn Thr Glu Ala Leu Asp Ser Thr Thr Lys
1               5                   10                  15

Asp Val Ile Gln Lys Gly Ile Ser Val Val Gly Asp Leu Leu Gly Val
                20                  25                  30

Val Gly Phe Pro Phe Gly Gly Ala Leu Val Ser Phe Tyr Thr Asn Phe
            35                  40                  45

Leu Asn Thr Ile Trp Pro Ser Glu Asp Pro Trp Lys Ala Phe Met Glu
        50                  55                  60

Gln Val Glu Ala Leu Met Asp Gln Lys Ile Ala Asp Tyr Ala Lys Asn
65                  70                  75                  80

Lys Ala Leu Ala Glu Leu Gln Gly Leu Gln Asn Asn Val Glu Asp Tyr
                85                  90                  95

Val Ser Ala Leu Ser Ser Trp Gln Lys Asn Pro Ala Ala Pro Phe Arg
            100                 105                 110

Asn Pro His Ser Gln Gly Arg Ile Arg Glu Leu Phe Ser Gln Ala Glu
        115                 120                 125

Ser His Phe Arg Asn Ser Met Pro Ser Phe Ala Ile Ser Gly Tyr Glu
    130                 135                 140

Val Leu Phe Leu Thr Thr Tyr Ala Gln Ala Ala Asn Thr His Leu Phe
145                 150                 155                 160

Leu Leu Lys Asp Ala Gln Ile Tyr Gly Glu Glu Trp Gly Tyr Glu Lys
                165                 170                 175

Glu Asp Ile Ala Glu Phe Tyr Lys Arg Gln Leu Lys Leu Thr Gln Glu
            180                 185                 190

Tyr Thr Asp His Cys Val Lys Trp Tyr Asn Val Gly Leu Asp Lys Leu
        195                 200                 205

Arg Gly Ser Ser Tyr Glu Ser Trp Val Asn Phe Asn Arg Tyr Arg Arg
    210                 215                 220

Glu Met Thr Leu Thr Val Leu Asp Ile Val Ser Leu Phe Pro Asn Tyr
225                 230                 235                 240
```

```
Asp Ser Arg Thr Tyr Pro Ile Arg Thr Val Ser Gln Leu Thr Arg Glu
            245                 250                 255

Ile Tyr Thr Asn Pro Val Leu Glu Asn Phe Asp Gly Ser Phe Arg Gly
        260                 265                 270

Ser Ala Gln Gly Ile Glu Gly Ser Ile Arg Ser Pro His Leu Met Asp
        275                 280                 285

Ile Leu Asn Ser Ile Thr Ile Tyr Thr Asp Ala His Arg Gly Glu Tyr
        290                 295                 300

Tyr Trp Ser Gly His Gln Ile Met Ala Ser Pro Val Gly Phe Ser Gly
305                 310                 315                 320

Pro Glu Phe Thr Phe Pro Leu Tyr Gly Thr Met Gly Asn Ala Ala Pro
                325                 330                 335

Gln Gln Arg Ile Val Ala Gln Leu Gly Gln Gly Val Tyr Arg Thr Leu
            340                 345                 350

Ser Ser Thr Leu Tyr Arg Arg Pro Phe Asn Ile Gly Ile Asn Asn Gln
        355                 360                 365

Gln Leu Ser Val Leu Asp Gly Thr Glu Phe Ala Tyr Gly Thr Ser Ser
    370                 375                 380

Asn Leu Pro Ser Ala Val Tyr Arg Lys Ser Gly Thr Val Asp Ser Leu
385                 390                 395                 400

Asp Glu Ile Pro Pro Gln Asn Asn Val Pro Pro Arg Gln Gly Phe
                405                 410                 415

Ser His Arg Leu Ser His Val Ser Met Phe Arg Ser Gly Phe Ser Asn
            420                 425                 430

Ser Ser Val Ser Ile Ile Arg Ala Pro Met Phe Ser Trp Ile His Arg
        435                 440                 445

Ser Ala Glu Phe Asn Asn Ile Ile Pro Ser Ser Gln Ile Thr Gln Ile
    450                 455                 460

Pro Leu Thr Lys Ser Thr Asn Leu Gly Ser Gly Thr Ser Val Val Lys
465                 470                 475                 480

Gly Pro Gly Phe Thr Gly Gly Asp Ile Leu Arg Arg Thr Ser Pro Gly
                485                 490                 495

Gln Ile Ser Thr Leu Arg Val Asn Ile Thr Ala Pro Leu Ser Gln Arg
            500                 505                 510

Tyr Arg Val Arg Ile Arg Tyr Ala Ser Thr Thr Asn Leu Gln Phe His
        515                 520                 525

Thr Ser Ile Asp Gly Arg Pro Ile Asn Gln Gly Asn Phe Ser Ala Thr
    530                 535                 540

Met Ser Ser Gly Ser Asn Leu Gln Ser Gly Ser Phe Arg Thr Val Gly
545                 550                 555                 560

Phe Thr Thr Pro Phe Asn Phe Ser Asn Gly Ser Ser Val Phe Thr Leu
                565                 570                 575

Ser Ala His Val Phe Asn Ser Gly Asn Glu Val Tyr Ile Asp Arg Ile
            580                 585                 590

Glu Phe Val Pro Ala Glu Val Thr Phe Glu Ala Glu Tyr Asp Leu Glu
        595                 600                 605

Arg Ala Gln Lys Ala Val Asn Glu Leu Phe Thr Ser Ser Asn Gln Ile
    610                 615                 620

Gly Leu Lys Thr Asp Val Thr Asp Tyr His Ile Asp Gln Val
625                 630                 635

<210> SEQ ID NO 43
<211> LENGTH: 1956
<212> TYPE: DNA
```

<213> ORGANISM: Artificial Sequence
<220> FEATURE:
<223> OTHER INFORMATION: 5*2OL-10 coding sequence

<400> SEQUENCE: 43

```
atgactagta acggccgcca gtgtgctggt attcgccctt atgacggccg acaacaacac      60
cgaggcctgg acagcagcac caccaaggac gtgatccaga agggcatcag cgtggtgggc     120
gacctgctgg gcgtggtggg cttccccttc ggcggcgccc tggtgagctt ctacaccaac     180
ttcctgaaca ccatctggcc cagcgaggac ccctggaagg ccttcatgga gcaggtggag     240
gccctgatgg accagaagat cgccgactac gccaagaaca aggcactggc cgagctacag     300
ggcctccaga acaacgtgga ggactatgtg agcgccctga gcagctggca gaagaacccc     360
gctgcaccgt tccgcaaccc ccacagccag ggccgcatcc gcgagctgtt cagccaggcc     420
gagagccact tccgcaacag catgcccagc ttcgccatca gcggctacga ggtgctgttc     480
ctgaccacct acgcccaggc cgccaacacc cacctgttcc tgctgaagga cgcccaaatc     540
tacggagagg agtggggcta cgagaaggag gacatcgccg agttctacaa cgccagctg      600
aagctgaccc aggagtacac cgaccactgc gtgaagtggt acaacgtggg tctagacaag     660
ctccgcggca gcagctacga gagctgggtg aacttcaacc gctaccgccg cgagatgacc     720
ctgaccgtgc tggacatcgt gagcctgttc cccaactacg acagccgcac ctaccccatc     780
cgcaccgtga gccagctgac ccgcgagatt tacaccaacc ccgtgctgga gaacttcgac     840
ggcagcttcc gcggcagcgc ccagggcatc gagggcagca tccgcagccc ccacctgatg     900
gacatcctga acagcatcac catctacacc gacgcccacc gcggcgagta ctactggagc     960
ggccaccaga tcatggccag ccccgtcggc ttcagcggcc ccgagttcac cttcccctg     1020
tacggcacca tgggcaacgc tgcacctcag cagcgcatcg tggcacagct gggccaggga    1080
gtgtaccgca ccctgagcag caccctgtac cgtcgacctt caacatcgg catcaacaac     1140
cagcagctga gcgtgctgga cggcaccgag ttcgcctacg caccagcag caacctgccc     1200
agcgccgtgt accgcaagag cggcaccgtg acagcctgg acgagatccc ccctcagaac     1260
aacaacgtgc cacctcgaca gggcttcagc caccgtctga ccacgtgag catgttccgc     1320
agtggcttca gcaacagcag cgtgagcatc atccgtgcac ctatgttcag ctggattcac     1380
cgcagtgccg agttcaacaa catcatcccc agcagccaga tcacccagat cccctgacc     1440
aagagcacca acctgggcag cggcaccagc gtggtgaagg ccccggctt caccggcggc     1500
gacatcctgc gccgcaccag ccccggccag atcagcaccc tgcgcgtgaa catcaccgcc     1560
ccctgagcc agcgctaccg cgtccgcatc cgctacgcca gcaccaccaa cctgcagttc     1620
cacaccagca tcgacggccg ccccatcaac cagggcaact tcagcgccac catgagcagc     1680
ggcagcaacc tgcagagcgg cagcttccgc accgtgggct tcaccacccc cttcaacttc     1740
agcaacggca gcagcgtgtt cacccctgagc gcccacgtgt tcaacagcgg caacgaggtg     1800
tacatcgacc gcatcgagtt cgtgcccgcc gaggtgacct tcgaggccga gtacgacctg     1860
gagagggctc agaaggccgt gaacgagctg ttcaccagca gcaaccagat cggcctgaag     1920
accgacgtga ccgactacca catcgatcag gtgtag                                1956
```

<210> SEQ ID NO 44
<211> LENGTH: 651
<212> TYPE: PRT
<213> ORGANISM: Artificial Sequnece
<220> FEATURE:
<223> OTHER INFORMATION: 5*2OL-10 protein

<400> SEQUENCE: 44

```
Met Thr Ser Asn Gly Arg Gln Cys Ala Gly Ile Arg Pro Tyr Asp Gly
1               5                   10                  15

Arg Gln Gln His Arg Gly Leu Asp Ser Ser Thr Thr Lys Asp Val Ile
            20                  25                  30

Gln Lys Gly Ile Ser Val Val Gly Asp Leu Leu Gly Val Val Gly Phe
        35                  40                  45

Pro Phe Gly Gly Ala Leu Val Ser Phe Tyr Thr Asn Phe Leu Asn Thr
    50                  55                  60

Ile Trp Pro Ser Glu Asp Pro Trp Lys Ala Phe Met Glu Gln Val Glu
65                  70                  75                  80

Ala Leu Met Asp Gln Lys Ile Ala Asp Tyr Ala Lys Asn Lys Ala Leu
            85                  90                  95

Ala Glu Leu Gln Gly Leu Gln Asn Asn Val Glu Asp Tyr Val Ser Ala
        100                 105                 110

Leu Ser Ser Trp Gln Lys Asn Pro Ala Ala Pro Phe Arg Asn Pro His
    115                 120                 125

Ser Gln Gly Arg Ile Arg Glu Leu Phe Ser Gln Ala Glu Ser His Phe
130                 135                 140

Arg Asn Ser Met Pro Ser Phe Ala Ile Ser Gly Tyr Glu Val Leu Phe
145                 150                 155                 160

Leu Thr Thr Tyr Ala Gln Ala Ala Asn Thr His Leu Phe Leu Leu Lys
                165                 170                 175

Asp Ala Gln Ile Tyr Gly Glu Glu Trp Gly Tyr Glu Lys Glu Asp Ile
            180                 185                 190

Ala Glu Phe Tyr Lys Arg Gln Leu Lys Leu Thr Gln Glu Tyr Thr Asp
        195                 200                 205

His Cys Val Lys Trp Tyr Asn Val Gly Leu Asp Lys Leu Arg Gly Ser
210                 215                 220

Ser Tyr Glu Ser Trp Val Asn Phe Asn Arg Tyr Arg Arg Glu Met Thr
225                 230                 235                 240

Leu Thr Val Leu Asp Ile Val Ser Leu Phe Pro Asn Tyr Asp Ser Arg
                245                 250                 255

Thr Tyr Pro Ile Arg Thr Val Ser Gln Leu Thr Arg Glu Ile Tyr Thr
            260                 265                 270

Asn Pro Val Leu Glu Asn Phe Asp Gly Ser Phe Arg Gly Ser Ala Gln
        275                 280                 285

Gly Ile Glu Gly Ser Ile Arg Ser Pro His Leu Met Asp Ile Leu Asn
290                 295                 300

Ser Ile Thr Ile Tyr Thr Asp Ala His Arg Gly Glu Tyr Tyr Trp Ser
305                 310                 315                 320

Gly His Gln Ile Met Ala Ser Pro Val Gly Phe Ser Gly Pro Glu Phe
                325                 330                 335

Thr Phe Pro Leu Tyr Gly Thr Met Gly Asn Ala Ala Pro Gln Gln Arg
            340                 345                 350

Ile Val Ala Gln Leu Gly Gln Gly Val Tyr Arg Thr Leu Ser Ser Thr
        355                 360                 365

Leu Tyr Arg Arg Pro Phe Asn Ile Gly Ile Asn Asn Gln Gln Leu Ser
    370                 375                 380

Val Leu Asp Gly Thr Glu Phe Ala Tyr Gly Thr Ser Ser Asn Leu Pro
385                 390                 395                 400

Ser Ala Val Tyr Arg Lys Ser Gly Thr Val Asp Ser Leu Asp Glu Ile
                405                 410                 415
```

```
Pro Pro Gln Asn Asn Val Pro Pro Arg Gln Gly Phe Ser His Arg
        420                 425                 430
Leu Ser His Val Ser Met Phe Arg Ser Gly Phe Ser Asn Ser Ser Val
            435                 440                 445
Ser Ile Ile Arg Ala Pro Met Phe Ser Trp Ile His Arg Ser Ala Glu
450                 455                 460
Phe Asn Asn Ile Ile Pro Ser Ser Gln Ile Thr Gln Ile Pro Leu Thr
465                 470                 475                 480
Lys Ser Thr Asn Leu Gly Ser Gly Thr Ser Val Val Lys Gly Pro Gly
                485                 490                 495
Phe Thr Gly Gly Asp Ile Leu Arg Arg Thr Ser Pro Gln Ile Ser
            500                 505                 510
Thr Leu Arg Val Asn Ile Thr Ala Pro Leu Ser Gln Arg Tyr Arg Val
            515                 520                 525
Arg Ile Arg Tyr Ala Ser Thr Thr Asn Leu Gln Phe His Thr Ser Ile
    530                 535                 540
Asp Gly Arg Pro Ile Asn Gln Gly Asn Phe Ser Ala Thr Met Ser Ser
545                 550                 555                 560
Gly Ser Asn Leu Gln Ser Gly Ser Phe Arg Thr Val Gly Phe Thr Thr
                565                 570                 575
Pro Phe Asn Phe Ser Asn Gly Ser Ser Val Phe Thr Leu Ser Ala His
            580                 585                 590
Val Phe Asn Ser Gly Asn Glu Val Tyr Ile Asp Arg Ile Glu Phe Val
            595                 600                 605
Pro Ala Glu Val Thr Phe Glu Ala Glu Tyr Asp Leu Glu Arg Ala Gln
    610                 615                 620
Lys Ala Val Asn Glu Leu Phe Thr Ser Ser Asn Gln Ile Gly Leu Lys
625                 630                 635                 640
Thr Asp Val Thr Asp Tyr His Ile Asp Gln Val
                645                 650

<210> SEQ ID NO 45
<211> LENGTH: 1821
<212> TYPE: DNA
<213> ORGANISM: Artificial Sequence
<220> FEATURE:
<223> OTHER INFORMATION: 2OL-12A coding sequence

<400> SEQUENCE: 45
atggacaaca accccaacat caacgagtgc atcccctaca actgcctgag caaccccgag      60
gtggaggtgc tgggcggcga gcgcatcgag accggctaca cccccatcga catcagcctg     120
agcctgaccc agttcctgct gagcgagttc gtgcccggcg ccggcttcgt gctgggcctg     180
gtggacatca tctgggcat cttcggcccc agccagtggg acgccttcct ggtgcagatc     240
gagcagttga taaccaacg catagaggaa ttcgcccgca accaggccat cagccgcctg     300
gagggcctga gcaacctgta ccaaatctac gccgagagct ccgcgagtg ggaggccgac     360 cccaccaacc ccgccctgcg cgaggagatg cgcatccagt tcaacgacat gaacagcgcc     420
ctgaccaccg ccatcccct gttcgccgtg cagaactacc aggtgcccct gctgagcgtg     480
tacgtgcagg ccgccaacct gcacctgagc gtgctgcgcg acgtcagcgt gttcggccag     540
cgctggggct cgacgccgc caccatcaac agccgctaca cgacctgac ccgcctgatc     600 ggcaactaca ccgaccacgc cgtgcgctgg tacaacaccg gcctggagcg cgtgtggggt     660
cccgacagcc gcgactggat caggtacaac cagttccgcc gcgagctgac cctgaccgtg     720
ctggacatcg tgagcctgtt ccccaactac gacagccgca cctaccccat ccgcaccgtg     780
```

```
agccagctga cccgcgagat ttacaccaac cccgtgctgg agaacttcga cggcagcttc    840
cgcggcagcg cccagggcat cgagggcagc atccgcagcc cccacctgat ggacatcctg    900
aacagcatca ccatctacac cgacgcccac cgcggcgagt actactggag cggccaccag    960
atcatggcca gccccgtcgg cttcagcggc cccgagttca ccttccccct gtacggcacc   1020
atgggcaacg ctgcacctca gcagcgcatc gtggcacagc tgggccaggg agtgtaccgc   1080
accctgagca gcacctgta ccgtcgacct ttcaacatcg catcaacaa ccagcagctg   1140
agcgtgctgg acggcaccga gttcgcctac ggcaccagca gcaacctgcc cagcgccgtg   1200
taccgcaaga gcggcaccgt ggacagcctg gacgagatcc ccctcagaa caacaacgtg   1260
ccacctcgac agggcttcag ccaccgtctg agccacgtga gcatgttccg cagtggcttc   1320
agcaacagca gcgtgagcat catccgtgca cctatgttca gctggattca ccgcagtgcc   1380
gagttcaaca acatcatccc cagcagccag atcacccaga tcccctggt gaaggcctac   1440
aagctccaga gcggcgccag cgtggtggca ggccccgct tcaccggcgg cgacatcatc   1500
cagtgcaccg agaacggcag cgccgccacc atctacgtga ccccgacgt gagctacagc   1560
cagaagtacc gcgcccgcat ccactacgcc agcaccagcc agatcacctt caccctgagc   1620
ctggacgggg ccccttcaa ccaatactac ttcgacaaga ccatcaacaa gggcgacacc   1680
ctgacctaca cagcttcaa cctggccagc ttcagcaccc ctttcgagct gagcggcaac   1740
aacctccaga tcggcgtgac cggcctgagc gccggcgaca aggtgtacat cgacaagatc   1800
gagttcatcc ccgtgaacta g                                             1821
```

<210> SEQ ID NO 46  
<211> LENGTH: 606  
<212> TYPE: PRT  
<213> ORGANISM: Artificial Sequence  
<220> FEATURE:  
<223> OTHER INFORMATION: 20L-12A protein

<400> SEQUENCE: 46

```
Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175
```

```
Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
            195                 200                 205

Arg Trp Tyr Asn Thr Gly Leu Glu Arg Val Trp Gly Pro Asp Ser Arg
            210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
                260                 265                 270

Leu Glu Asn Phe Asp Gly Ser Phe Arg Gly Ser Ala Gln Gly Ile Glu
            275                 280                 285

Gly Ser Ile Arg Ser Pro His Leu Met Asp Ile Leu Asn Ser Ile Thr
            290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
                340                 345                 350

Gln Leu Gly Gln Gly Val Tyr Arg Thr Leu Ser Ser Thr Leu Tyr Arg
            355                 360                 365

Arg Pro Phe Asn Ile Gly Ile Asn Asn Gln Gln Leu Ser Val Leu Asp
            370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
                420                 425                 430

Val Ser Met Phe Arg Ser Gly Phe Ser Asn Ser Ser Val Ser Ile Ile
            435                 440                 445

Arg Ala Pro Met Phe Ser Trp Ile His Arg Ser Ala Glu Phe Asn Asn
450                 455                 460

Ile Ile Pro Ser Ser Gln Ile Thr Gln Ile Pro Leu Val Lys Ala Tyr
465                 470                 475                 480

Lys Leu Gln Ser Gly Ala Ser Val Val Ala Gly Pro Arg Phe Thr Gly
                485                 490                 495

Gly Asp Ile Ile Gln Cys Thr Glu Asn Gly Ser Ala Ala Thr Ile Tyr
                500                 505                 510

Val Thr Pro Asp Val Ser Tyr Ser Gln Lys Tyr Arg Ala Arg Ile His
            515                 520                 525

Tyr Ala Ser Thr Ser Gln Ile Thr Phe Thr Leu Ser Leu Asp Gly Ala
            530                 535                 540

Pro Phe Asn Gln Tyr Tyr Phe Asp Lys Thr Ile Asn Lys Gly Asp Thr
545                 550                 555                 560

Leu Thr Tyr Asn Ser Phe Asn Leu Ala Ser Phe Ser Thr Pro Phe Glu
                565                 570                 575

Leu Ser Gly Asn Asn Leu Gln Ile Gly Val Thr Gly Leu Ser Ala Gly
            580                 585                 590

Asp Lys Val Tyr Ile Asp Lys Ile Glu Phe Ile Pro Val Asn
            595                 600                 605
```

<210> SEQ ID NO 47
<211> LENGTH: 1791
<212> TYPE: DNA
<213> ORGANISM: Artificial Sequence
<220> FEATURE:
<223> OTHER INFORMATION: 2OL-13 coding sequence

<400> SEQUENCE: 47

```
atgacggccg acaacaacac cgaggccctg gacagcagca ccaccaagga cgtgatccag      60
aagggcatca gcgtggtggg cgacctgctg ggcgtggtgg gcttcccctt cggcggcgcc     120
ctggtgagct tctacaccaa cttcctgaac accatctggc ccagcgagga cccctggaag     180
gccttcatgg agcaggtgga ggccctgatg accagaaga tcgccgacta cgccaagaac     240
aaggcactgg ccgagctaca gggcctccag aacaacgtgg aggactatgt gagcgccctg     300
agcagctggc agaagaaccc cgctgcaccg ttccgcaacc cccacagcca gggccgcatc     360
cgcgagctgt tcagccaggc cgagagccac ttccgcaaca gcatgcccag cttcgccatc     420
agcggctacg aggtgctgtt cctgaccacc tacgcccagg ccgccaacac ccacctgagc     480
gtgctgcgcg acgtcagcgt gttcggccag cgctggggct cgacgccgc caccatcaac     540
agccgctaca cgacctgac cgcctgatc ggcaactaca ccgaccacgc cgtgcgctgg     600
tacaacaccg gcctggagcg cgtgtggggt cccgacagcc gcgactggat caggtacaac     660
cagttccgcc gcgagctgac cctgaccgtg ctggacatcg tgagcctgtt ccccaactac     720
gacagccgca cctaccccat ccgcaccgtg agccagctga cccgcgagat ttacaccaac     780
cccgtgctgg agaacttcga cggcagcttc gcggcagcg cccagggcat cgagggcagc     840
atccgcagcc cccacctgat ggacatcctg aacagcatca ccatctacac cgacgcccac     900
cgcggcgagt actactggag cggccaccag atcatggcca gccccgtcgg cttcagcggc     960
cccgagttca ccttcccct gtacggcacc atgggcaacg ctgcacctca gcagcgcatc    1020
gtggcacagc tgggccaggg agtgtaccgc accctgagca gcaccctgta ccgtcgacct    1080
ttcaacatcg gcatcaacaa ccagcagctg agcgtgctgg acggaccga gttcgcctac    1140
ggcaccagca gcaacctgcc cagcgccgtg taccgcaaga gcggcaccgt ggacagcctg    1200
gacgagatcc cccctcagaa caacaacgtg ccacctcgac agggcttcag ccaccgtctg    1260
agccacgtga gcatgttccg cagtggcttc agcaacagca gcgtgagcat catccgtgca    1320
cctatgttca gctggattca ccgcagtgcc gagttcaaca acatcatccc cagcagccag    1380
atcacccaga tccccctgac caagagcacc aacctgggca gcggcaccag cgtggtgaag    1440
ggccccggct tcaccggcgg cgacatcctg cgccgcacca gccccggcca gatcagcacc    1500
ctgcgcgtga acatcaccgc ccccctgagc cagcgctacc gcgcccgcat ccactacgcc    1560
agcaccagcc agatcacctt caccctgagc ctggacgggg ccccttcaa ccaatactac    1620
ttcgacaaga ccatcaacaa gggcgacacc ctgacctaca cagcttcaa cctggccagc    1680
ttcagcaccc ctttcgagct gagcggcaac aacctccaga tcggcgtgac cggcctgagc    1740
gccggcgaca aggtgtacat cgacaagatc gagttcatcc ccgtgaacta g              1791
```

<210> SEQ ID NO 48
<211> LENGTH: 596
<212> TYPE: PRT
<213> ORGANISM: Artificial Sequence
<220> FEATURE:
<223> OTHER INFORMATION: 2OL-13 protein

<400> SEQUENCE: 48

```
Met Thr Ala Asp Asn Asn Thr Glu Ala Leu Asp Ser Ser Thr Thr Lys
1               5                   10                  15

Asp Val Ile Gln Lys Gly Ile Ser Val Val Gly Asp Leu Leu Gly Val
            20                  25                  30

Val Gly Phe Pro Phe Gly Gly Ala Leu Val Ser Phe Tyr Thr Asn Phe
        35                  40                  45

Leu Asn Thr Ile Trp Pro Ser Glu Asp Pro Trp Lys Ala Phe Met Glu
    50                  55                  60

Gln Val Glu Ala Leu Met Asp Gln Lys Ile Ala Asp Tyr Ala Lys Asn
65                  70                  75                  80

Lys Ala Leu Ala Glu Leu Gln Gly Leu Gln Asn Asn Val Glu Asp Tyr
                85                  90                  95

Val Ser Ala Leu Ser Ser Trp Gln Lys Asn Pro Ala Ala Pro Phe Arg
            100                 105                 110

Asn Pro His Ser Gln Gly Arg Ile Arg Glu Leu Phe Ser Gln Ala Glu
        115                 120                 125

Ser His Phe Arg Asn Ser Met Pro Ser Phe Ala Ile Ser Gly Tyr Glu
    130                 135                 140

Val Leu Phe Leu Thr Thr Tyr Ala Gln Ala Ala Asn Thr His Leu Ser
145                 150                 155                 160

Val Leu Arg Asp Val Ser Val Phe Gly Gln Arg Trp Gly Phe Asp Ala
                165                 170                 175

Ala Thr Ile Asn Ser Arg Tyr Asn Asp Leu Thr Arg Leu Ile Gly Asn
            180                 185                 190

Tyr Thr Asp His Ala Val Arg Trp Tyr Asn Thr Gly Leu Glu Arg Val
        195                 200                 205

Trp Gly Pro Asp Ser Arg Asp Trp Ile Arg Tyr Asn Gln Phe Arg Arg
    210                 215                 220

Glu Leu Thr Leu Thr Val Leu Asp Ile Val Ser Leu Phe Pro Asn Tyr
225                 230                 235                 240

Asp Ser Arg Thr Tyr Pro Ile Arg Thr Val Ser Gln Leu Thr Arg Glu
                245                 250                 255

Ile Tyr Thr Asn Pro Val Leu Glu Asn Phe Asp Gly Ser Phe Arg Gly
            260                 265                 270

Ser Ala Gln Gly Ile Glu Gly Ser Ile Arg Ser Pro His Leu Met Asp
        275                 280                 285

Ile Leu Asn Ser Ile Thr Ile Tyr Thr Asp Ala His Arg Gly Glu Tyr
    290                 295                 300

Tyr Trp Ser Gly His Gln Ile Met Ala Ser Pro Val Gly Phe Ser Gly
305                 310                 315                 320

Pro Glu Phe Thr Phe Pro Leu Tyr Gly Thr Met Gly Asn Ala Ala Pro
                325                 330                 335

Gln Gln Arg Ile Val Ala Gln Leu Gly Gln Gly Val Tyr Arg Thr Leu
            340                 345                 350

Ser Ser Thr Leu Tyr Arg Arg Pro Phe Asn Ile Gly Ile Asn Asn Gln
        355                 360                 365

Gln Leu Ser Val Leu Asp Gly Thr Glu Phe Ala Tyr Gly Thr Ser Ser
    370                 375                 380

Asn Leu Pro Ser Ala Val Tyr Arg Lys Ser Gly Thr Val Asp Ser Leu
385                 390                 395                 400

Asp Glu Ile Pro Pro Gln Asn Asn Asn Val Pro Pro Arg Gln Gly Phe
                405                 410                 415

Ser His Arg Leu Ser His Val Ser Met Phe Arg Ser Gly Phe Ser Asn
```

```
                420             425             430
Ser Ser Val Ser Ile Ile Arg Ala Pro Met Phe Ser Trp Ile His Arg
            435                 440                 445
Ser Ala Glu Phe Asn Asn Ile Ile Pro Ser Ser Gln Ile Thr Gln Ile
        450                 455                 460
Pro Leu Thr Lys Ser Thr Asn Leu Gly Ser Gly Thr Ser Val Val Lys
465                 470                 475                 480
Gly Pro Gly Phe Thr Gly Gly Asp Ile Leu Arg Arg Thr Ser Pro Gly
                485                 490                 495
Gln Ile Ser Thr Leu Arg Val Asn Ile Thr Ala Pro Leu Ser Gln Arg
            500                 505                 510
Tyr Arg Ala Arg Ile His Tyr Ala Ser Thr Ser Gln Ile Thr Phe Thr
        515                 520                 525
Leu Ser Leu Asp Gly Ala Pro Phe Asn Gln Tyr Tyr Phe Asp Lys Thr
530                 535                 540
Ile Asn Lys Gly Asp Thr Leu Thr Tyr Asn Ser Phe Asn Leu Ala Ser
545                 550                 555                 560
Phe Ser Thr Pro Phe Glu Leu Ser Gly Asn Asn Leu Gln Ile Gly Val
                565                 570                 575
Thr Gly Leu Ser Ala Gly Asp Lys Val Tyr Ile Asp Lys Ile Glu Phe
            580                 585                 590
Ile Pro Val Asn
        595

<210> SEQ ID NO 49
<211> LENGTH: 1923
<212> TYPE: DNA
<213> ORGANISM: Artificial Sequence
<220> FEATURE:
<223> OTHER INFORMATION: V5&6 coding sequence

<400> SEQUENCE: 49
atgacggccg acaacaacac cgaggccctg acagcagca ccaccaagga cgtgatccag      60
aagggcatca gcgtggtggg cgacctgctg ggcgtggtgg gcttcccctt cggcggcgcc     120
ctggtgagct tctacaccaa cttcctgaac accatctggc cagcgagga ccctggaag      180 gccttcatgg agcaggtgga ggccctgatg accagaaga tcgccgacta cgccaagaac     240
aaggcactgg ccgagctaca gggcctccag aacaacgtgg aggactatgt gagcgccctg     300
agcagctggc agaagaaccc cgctgcaccg ttccgcaacc ccacagcca gggccgcatc     360 cgcgagctgt tcagccaggc cgagagccac ttccgcaaca gcatgcccag cttcgccatc     420
agcggctacg aggtgctgtt cctgaccacc tacgcccagg ccgccaacac ccacctgttc     480
ctgctgaagg acgcccaaat ctacggagag gagtggggct acgagaagga ggacatcgcc     540
gagttctaca gcgccagct gaagctgacc caggagtaca ccgaccactg cgtgaagtgg     600
tacaacgtgg gtctagacaa gctccgcggc agcagctacg agagctgggt gaacttcaac     660
cgctaccgcc gcgagatgac cctgaccgtg ctggacctga tcgccctgtt ccccctgtac     720
gacgtgcgcc tgtaccccaa ggaggtgaag accgagctga cccgcgacgt gctgaccgac     780
cccatcgtgg gcgtgaacaa cctgcgcggc tacggcacca ccttcagcaa catcgagaac     840
tacatccgca gccccacct gttcgactac ctgcaccgca tccagttcca cacgcgtttc     900
cagcccggct actacggcaa cgacagcttc aactactgga gcggcaacta cgtgagcacc     960
cgccccagca tcggcagcaa cgacatcatc accagcccct tctacggcaa caagagcagc    1020
gagcccgtgc agaaccttga gttcaacggc gagaaggtgt accgcgccgt ggctaacacc    1080
```

```
aacctggccg tgtggccctc tgcagtgtac agcggcgtga ccaaggtgga gttcagccag    1140
tacaacgacc agaccgacga ggccagcacc cagacctacg acagcaagcg caacgtgggc    1200
gccgtgagct gggacagcat cgaccagctg ccccccgaga ccaccgacga gccctggag     1260 aagggctaca gccaccagct gaactacgtg atgtgcttcc tgatgcaggg cagccgcggc    1320
accatccccg tgctgacctg gacccacaag agcgtcgact tcttcaacat gatcgacagc    1380
aagaagatca cccagctgcc cctggtgaag gcctacaagc tccagagcgg cgccagcgtg    1440
gtggcaggcc cccgcttcac cggcggcgac atcatccagt gcaccgagaa cggcagcgcc    1500
gccaccatct acgtgacccc cgacgtgagc tacagccaga agtaccgcgc ccgcatccac    1560
tacgccagca ccaccaacct gcagttccac accagcatcg acggccgccc catcaaccag    1620
ggcaacttca gcgccaccat gagcagcggc agcaacctgc agagcggcag cttccgcacc    1680
gtgggcttca ccaccccctt caacttcagc aacggcagca gcgtgttcac cctgagcgcc    1740
cacgtgttca cagcggcaa cgaggtgtac atcgaccgca tcgagttcgt gcccgccgag     1800
gtgaccttcg aggccgagta cgacctggag agggctcaga aggccgtgaa cgagctgttc    1860
accagcagca accagatcgg cctgaagacc gacgtgaccg actaccacat cgatcaggtg    1920
tag                                                                  1923

<210> SEQ ID NO 50
<211> LENGTH: 640
<212> TYPE: PRT
<213> ORGANISM: Artificial Sequence
<220> FEATURE:
<223> OTHER INFORMATION: V5&6 protein

<400> SEQUENCE: 50

Met Thr Ala Asp Asn Asn Thr Glu Ala Leu Asp Ser Ser Thr Thr Lys
1               5                   10                  15

Asp Val Ile Gln Lys Gly Ile Ser Val Val Gly Asp Leu Leu Gly Val
                20                  25                  30

Val Gly Phe Pro Phe Gly Gly Ala Leu Val Ser Phe Tyr Thr Asn Phe
            35                  40                  45

Leu Asn Thr Ile Trp Pro Ser Glu Asp Pro Trp Lys Ala Phe Met Glu
    50                  55                  60

Gln Val Glu Ala Leu Met Asp Gln Lys Ile Ala Asp Tyr Ala Lys Asn
65                  70                  75                  80

Lys Ala Leu Ala Glu Leu Gln Gly Leu Gln Asn Asn Val Glu Asp Tyr
                85                  90                  95

Val Ser Ala Leu Ser Ser Trp Gln Lys Asn Pro Ala Ala Pro Phe Arg
            100                 105                 110

Asn Pro His Ser Gln Gly Arg Ile Arg Glu Leu Phe Ser Gln Ala Glu
        115                 120                 125

Ser His Phe Arg Asn Ser Met Pro Ser Phe Ala Ile Ser Gly Tyr Glu
    130                 135                 140

Val Leu Phe Leu Thr Thr Tyr Ala Gln Ala Ala Asn Thr His Leu Phe
145                 150                 155                 160

Leu Leu Lys Asp Ala Gln Ile Tyr Gly Glu Glu Trp Gly Tyr Glu Lys
                165                 170                 175

Glu Asp Ile Ala Glu Phe Tyr Lys Arg Gln Leu Lys Leu Thr Gln Glu
            180                 185                 190

Tyr Thr Asp His Cys Val Lys Trp Tyr Asn Val Gly Leu Asp Lys Leu
        195                 200                 205
```

-continued

```
Arg Gly Ser Ser Tyr Glu Ser Trp Val Asn Phe Asn Arg Tyr Arg Arg
    210                 215                 220

Glu Met Thr Leu Thr Val Leu Asp Leu Ile Ala Leu Phe Pro Leu Tyr
225                 230                 235                 240

Asp Val Arg Leu Tyr Pro Lys Glu Val Lys Thr Glu Leu Thr Arg Asp
                245                 250                 255

Val Leu Thr Asp Pro Ile Val Gly Val Asn Asn Leu Arg Gly Tyr Gly
            260                 265                 270

Thr Thr Phe Ser Asn Ile Glu Asn Tyr Ile Arg Lys Pro His Leu Phe
        275                 280                 285

Asp Tyr Leu His Arg Ile Gln Phe His Thr Arg Phe Gln Pro Gly Tyr
    290                 295                 300

Tyr Gly Asn Asp Ser Phe Asn Tyr Trp Ser Gly Asn Tyr Val Ser Thr
305                 310                 315                 320

Arg Pro Ser Ile Gly Ser Asn Asp Ile Ile Thr Ser Pro Phe Tyr Gly
                325                 330                 335

Asn Lys Ser Ser Glu Pro Val Gln Asn Leu Glu Phe Asn Gly Glu Lys
            340                 345                 350

Val Tyr Arg Ala Val Ala Asn Thr Asn Leu Ala Val Trp Pro Ser Ala
        355                 360                 365

Val Tyr Ser Gly Val Thr Lys Val Glu Phe Ser Gln Tyr Asn Asp Gln
    370                 375                 380

Thr Asp Glu Ala Ser Thr Gln Thr Tyr Asp Ser Lys Arg Asn Val Gly
385                 390                 395                 400

Ala Val Ser Trp Asp Ser Ile Asp Gln Leu Pro Pro Glu Thr Thr Asp
                405                 410                 415

Glu Pro Leu Glu Lys Gly Tyr Ser His Gln Leu Asn Tyr Val Met Cys
            420                 425                 430

Phe Leu Met Gln Gly Ser Arg Gly Thr Ile Pro Val Leu Thr Trp Thr
        435                 440                 445

His Lys Ser Val Asp Phe Phe Asn Met Ile Asp Ser Lys Lys Ile Thr
    450                 455                 460

Gln Leu Pro Leu Val Lys Ala Tyr Lys Leu Gln Ser Gly Ala Ser Val
465                 470                 475                 480

Val Ala Gly Pro Arg Phe Thr Gly Gly Asp Ile Ile Gln Cys Thr Glu
                485                 490                 495

Asn Gly Ser Ala Ala Thr Ile Tyr Val Thr Pro Asp Val Ser Tyr Ser
            500                 505                 510

Gln Lys Tyr Arg Ala Arg Ile His Tyr Ala Ser Thr Thr Asn Leu Gln
        515                 520                 525

Phe His Thr Ser Ile Asp Gly Arg Pro Ile Asn Gln Gly Asn Phe Ser
    530                 535                 540

Ala Thr Met Ser Ser Gly Ser Asn Leu Gln Ser Gly Ser Phe Arg Thr
545                 550                 555                 560

Val Gly Phe Thr Thr Pro Phe Asn Phe Ser Asn Gly Ser Ser Val Phe
                565                 570                 575

Thr Leu Ser Ala His Val Phe Asn Ser Gly Asn Glu Val Tyr Ile Asp
            580                 585                 590

Arg Ile Glu Phe Val Pro Ala Glu Val Thr Phe Glu Ala Glu Tyr Asp
        595                 600                 605

Leu Glu Arg Ala Gln Lys Ala Val Asn Glu Leu Phe Thr Ser Ser Asn
    610                 615                 620

Gln Ile Gly Leu Lys Thr Asp Val Thr Asp Tyr His Ile Asp Gln Val
625                 630                 635                 640
```

<210> SEQ ID NO 51
<211> LENGTH: 1962
<212> TYPE: DNA
<213> ORGANISM: Artificial Sequence
<220> FEATURE:
<223> OTHER INFORMATION: 5*V5&6 coding sequence

<400> SEQUENCE: 51

| | | | | | |
|---|---|---|---|---|---|
| atgactagta | acggccgcca | gtgtgctggt | attcgccctt | atgacggccg | acaacaacac | 60 |
| cgaggcctgg | acagcagcac | caccaaggac | gtgatccaga | agggcatcag | cgtggtgggc | 120 |
| gacctgctgg | gcgtggtggg | cttccccttc | ggcggcgccc | tggtgagctt | ctacaccaac | 180 |
| ttcctgaaca | ccatctggcc | cagcgaggac | ccctggaagg | ccttcatgga | gcaggtggag | 240 |
| gccctgatgg | accagaagat | cgccgactac | gccaagaaca | aggcactggc | cgagctacag | 300 |
| ggcctccaga | caacgtggag | ggactatgtg | agcgccctga | gcagctggca | gaagaacccc | 360 |
| gctgcaccgt | tccgcaaccc | ccacagccag | ggccgcatcc | gcgagctgtt | cagccaggcc | 420 |
| gagagccact | ccgcaacag | catgcccagc | ttcgccatca | gcggctacga | ggtgctgttc | 480 |
| ctgaccacct | acgccaggc | cgccaacacc | cacctgttcc | tgctgaagga | cgcccaaatc | 540 |
| tacggagagg | agtggggcta | cgagaaggag | gacatcgccg | agttctacaa | gccagctg | 600 |
| aagctgaccc | aggagtacac | cgaccactgc | gtgaagtggt | acaacgtggg | tctagacaag | 660 |
| ctccgcggca | gcagctacga | gagctgggtg | aacttcaacc | gctaccgccg | cgagatgacc | 720 |
| ctgaccgtgc | tggacctgat | cgccctgttc | cccctgtacg | acgtgcgcct | gtaccccaag | 780 |
| gaggtgaaga | ccgagctgac | ccgcgacgtg | ctgaccgacc | ccatcgtggg | cgtgaacaac | 840 |
| ctgcgcggct | acggcaccac | cttcagcaac | atcgagaact | acatccgcaa | gccccacctg | 900 |
| ttcgactacc | tgcaccgcat | ccagttccac | acgcgtttcc | agcccggcta | ctacggcaac | 960 |
| gacagcttca | actactggag | cggcaactac | gtgagcaccc | gccccagcat | cggcagcaac | 1020 |
| gacatcatca | ccagccccct | ctacggcaac | aagagcagcg | agcccgtgca | gaaccttgag | 1080 |
| ttcaacggcg | agaaggtgta | ccgcgccgtg | gctaacacca | acctggccgt | gtggcccctct | 1140 |
| gcagtgtaca | gcggcgtgac | caaggtggag | ttcagccagt | acaacgacca | gaccgacgag | 1200 |
| gccagcaccc | agacctacga | cagcaagcgc | aacgtgggcg | ccgtgagctg | ggacagcatc | 1260 |
| gaccagctgc | cccccgagac | caccgacgag | cccctggaga | agggctacag | ccaccagctg | 1320 |
| aactacgtga | tgtgcttcct | gatgcagggc | agccgcggca | ccatcccgt | gctgacctgg | 1380 |
| acccacaaga | gcgtcgactt | cttcaacatg | atcgacagca | agaagatcac | ccagctgccc | 1440 |
| ctggtgaagg | cctacaagct | ccagagcggc | gccagcgtgg | tggcaggccc | ccgcttcacc | 1500 |
| ggcggcgaca | tcatccagtg | caccgagaac | ggcagcgccg | ccaccatcta | cgtgaccccc | 1560 |
| gacgtgagct | acagccagaa | gtaccgcgcc | cgcatccact | acgccagcac | caccaacctg | 1620 |
| cagttccaca | ccagcatcga | cggccgcccc | atcaaccagg | gcaacttcag | cgccaccatg | 1680 |
| agcagcggca | gcaacctgca | gagcggcagc | ttccgcaccg | tgggcttcac | cacccccttc | 1740 |
| aacttcagca | acggcagcag | cgtgttcacc | ctgagcgccc | acgtgttcaa | cagcggcaac | 1800 |
| gaggtgtaca | tcgaccgcat | cgagttcgtg | cccgccgagg | tgaccttcga | ggccgagtac | 1860 |
| gacctggaga | gggctcagaa | ggccgtgaac | gagctgttca | ccagcagcaa | ccagatcggc | 1920 |
| ctgaagaccg | acgtgaccga | ctaccacatc | gatcaggtgt | ag | | 1962 |

<210> SEQ ID NO 52
<211> LENGTH: 653

```
<212> TYPE: PRT
<213> ORGANISM: Artificial Sequence
<220> FEATURE:
<223> OTHER INFORMATION: 5*V5&6 protein

<400> SEQUENCE: 52

Met Thr Ser Asn Gly Arg Gln Cys Ala Gly Ile Arg Pro Tyr Asp Gly
1               5                   10                  15

Arg Gln Gln His Arg Gly Leu Asp Ser Ser Thr Thr Lys Asp Val Ile
            20                  25                  30

Gln Lys Gly Ile Ser Val Val Gly Asp Leu Leu Gly Val Gly Phe
        35                  40                  45

Pro Phe Gly Gly Ala Leu Val Ser Phe Tyr Thr Asn Phe Leu Asn Thr
    50                  55                  60

Ile Trp Pro Ser Glu Asp Pro Trp Lys Ala Phe Met Glu Gln Val Glu
65                  70                  75                  80

Ala Leu Met Asp Gln Lys Ile Ala Asp Tyr Ala Lys Asn Lys Ala Leu
                85                  90                  95

Ala Glu Leu Gln Gly Leu Gln Asn Asn Val Glu Asp Tyr Val Ser Ala
            100                 105                 110

Leu Ser Ser Trp Gln Lys Asn Pro Ala Ala Pro Phe Arg Asn Pro His
        115                 120                 125

Ser Gln Gly Arg Ile Arg Glu Leu Phe Ser Gln Ala Glu Ser His Phe
    130                 135                 140

Arg Asn Ser Met Pro Ser Phe Ala Ile Ser Gly Tyr Glu Val Leu Phe
145                 150                 155                 160

Leu Thr Thr Tyr Ala Gln Ala Ala Asn Thr His Leu Phe Leu Leu Lys
                165                 170                 175

Asp Ala Gln Ile Tyr Gly Glu Glu Trp Gly Tyr Glu Lys Glu Asp Ile
            180                 185                 190

Ala Glu Phe Tyr Lys Arg Gln Leu Lys Leu Thr Gln Glu Tyr Thr Asp
        195                 200                 205

His Cys Val Lys Trp Tyr Asn Val Gly Leu Asp Lys Leu Arg Gly Ser
    210                 215                 220

Ser Tyr Glu Ser Trp Val Asn Phe Asn Arg Tyr Arg Arg Glu Met Thr
225                 230                 235                 240

Leu Thr Val Leu Asp Leu Ile Ala Leu Phe Pro Leu Tyr Asp Val Arg
                245                 250                 255

Leu Tyr Pro Lys Glu Val Lys Thr Glu Leu Thr Arg Asp Val Leu Thr
            260                 265                 270

Asp Pro Ile Val Gly Val Asn Asn Leu Arg Gly Tyr Gly Thr Thr Phe
        275                 280                 285

Ser Asn Ile Glu Asn Tyr Ile Arg Lys Pro His Leu Phe Asp Tyr Leu
    290                 295                 300

His Arg Ile Gln Phe His Thr Arg Phe Gln Pro Gly Tyr Tyr Gly Asn
305                 310                 315                 320

Asp Ser Phe Asn Tyr Trp Ser Gly Asn Tyr Val Ser Thr Arg Pro Ser
                325                 330                 335

Ile Gly Ser Asn Asp Ile Ile Thr Ser Pro Phe Tyr Gly Asn Lys Ser
            340                 345                 350

Ser Glu Pro Val Gln Asn Leu Glu Phe Asn Gly Glu Lys Val Tyr Arg
        355                 360                 365

Ala Val Ala Asn Thr Asn Leu Ala Val Trp Pro Ser Ala Val Tyr Ser
    370                 375                 380

Gly Val Thr Lys Val Glu Phe Ser Gln Tyr Asn Asp Gln Thr Asp Glu
```

```
                385                 390                 395                 400
Ala Ser Thr Gln Thr Tyr Asp Ser Lys Arg Asn Val Gly Ala Val Ser
                    405                 410                 415
Trp Asp Ser Ile Asp Gln Leu Pro Pro Glu Thr Thr Asp Glu Pro Leu
                    420                 425                 430
Glu Lys Gly Tyr Ser His Gln Leu Asn Tyr Val Met Cys Phe Leu Met
                    435                 440                 445
Gln Gly Ser Arg Gly Thr Ile Pro Val Leu Thr Trp Thr His Lys Ser
                    450                 455                 460
Val Asp Phe Phe Asn Met Ile Asp Ser Lys Lys Ile Thr Gln Leu Pro
465                 470                 475                 480
Leu Val Lys Ala Tyr Lys Leu Gln Ser Gly Ala Ser Val Val Ala Gly
                    485                 490                 495
Pro Arg Phe Thr Gly Gly Asp Ile Ile Gln Cys Thr Glu Asn Gly Ser
                    500                 505                 510
Ala Ala Thr Ile Tyr Val Thr Pro Asp Val Ser Tyr Ser Gln Lys Tyr
                    515                 520                 525
Arg Ala Arg Ile His Tyr Ala Ser Thr Thr Asn Leu Gln Phe His Thr
                    530                 535                 540
Ser Ile Asp Gly Arg Pro Ile Asn Gln Gly Asn Phe Ser Ala Thr Met
545                 550                 555                 560
Ser Ser Gly Ser Asn Leu Gln Ser Gly Ser Phe Arg Thr Val Gly Phe
                    565                 570                 575
Thr Thr Pro Phe Asn Phe Ser Asn Gly Ser Ser Val Phe Thr Leu Ser
                    580                 585                 590
Ala His Val Phe Asn Ser Gly Asn Glu Val Tyr Ile Asp Arg Ile Glu
                    595                 600                 605
Phe Val Pro Ala Glu Val Thr Phe Glu Ala Glu Tyr Asp Leu Glu Arg
                    610                 615                 620
Ala Gln Lys Ala Val Asn Glu Leu Phe Thr Ser Ser Asn Gln Ile Gly
625                 630                 635                 640
Leu Lys Thr Asp Val Thr Asp Tyr His Ile Asp Gln Val
                    645                 650

<210> SEQ ID NO 53
<211> LENGTH: 1845
<212> TYPE: DNA
<213> ORGANISM: Artificial Sequence
<220> FEATURE:
<223> OTHER INFORMATION: 88A-dm3 coding sequence

<400> SEQUENCE: 53
atgactagta acggccgcca gtgtgctggt attcgcccct tatgacggcc gacaacaacac     60 cgaggcctgg acagcagcac caccaaggac gtgatccaga agggcatcag cgtggtgggc    120
gacctgctgg gcgtggtggg cttccccttc ggcggcgccc tggtgagctt ctacaccaac    180
ttcctgaaca ccatctggcc cagcgaggac ccctggaagg ccttcatgga gcaggtggag    240
gccctgatgg accagaagat cgccgactac gccaagaaca aggcactggc cgagctacag    300
ggcctccaga caacgtggga ggactatgtg agcgccctga gcagctggca agaaccccc    360 gctgcaccgt tccgcaaccc ccacagccag ggccgcatcc gcgagctgtt cagccaggcc    420
gagagccact tccgcaacag catgcccagc ttcgccatca gcggctacga ggtgctgttc    480
ctgaccacct acgcccaggc cgccaacacc cacctgttcc tgctgaagga cgcccaaatc    540
tacggagagg agtggggcta cgagaaggag gacatcgccg agttctacaa gcgccagctg    600
```

-continued

```
aagctgaccc aggagtacac cgaccactgc gtgaagtggt acaacgtggg tctagacaag    660
ctccgcggca gcagctacga gagctgggtg aacttcaacc gctaccgccg cgagatgacc    720
ctgaccgtgc tggacctgat cgccctgttc cccctgtacg acgtgcgcct gtaccccaag    780
gaggtgaaga ccgagctgac ccgcgacgtg ctgaccgacc ccatcgtggg cgtgaacaac    840
ctgcgcggct acggcaccac cttcagcaac atcgagaact acatccgcaa gccccacctg    900
ttcgactacc tgcaccgcat ccagttccac acgcgtttcc agcccggcta ctacggcaac    960
gacagcttca actactggag cggcaactac gtgagcaccc gccccagcat cggcagcaac   1020
gacatcatca ccagcccctt ctacggcaac aagagcagcg agcccgtgca gaaccttgag   1080
ttcaacggcg agaaggtgta ccgcgccgtg gctaacacca acctggccgt gtggccctct   1140
gcagtgtaca gcggcgtgac caaggtggag ttcagccagt acaacgacca gaccgacgag   1200
gccagcaccc agacctacga cagcaagcgc aacgtgggcg ccgtgagctg ggacagcatc   1260
gaccagctgc cccccgagac caccgacgag ccccctggaga agggctacag ccaccagctg   1320
aactacgtga tgtgcttcct gatgcagggc agccgcggca ccatccccgt gctgacctgg   1380
acccacaaga gcgtcgactt cttcaacatg atcgacagca gaagatcac ccagctgccc   1440 ctggtaaagg gagacatgtt atatctaggg ggttccgtag tacagggtcc tggatttaca   1500
ggaggagata tattaaaaag aaccaatcct agcatattag ggacctttgc ggttacagta   1560
aatgggtcgt tatcacaaag atatcgtgta agaattcgct atgcctctac aacagatttt   1620
gaatttactc tataccttgg cgacacaata gaaaaaaata gatttaacaa aactatggat   1680
aatggggcat ctttaacgta tgaaacattt aaattcgcaa gtttcattac tgatttccaa   1740
ttcagagaaa cacaagataa aatactccta tccatgggtg attttagctc cggtcaagaa   1800
gtttatatag accgaatcga attcatccca gtagatgaga catag                   1845
```

<210> SEQ ID NO 54
<211> LENGTH: 614
<212> TYPE: PRT
<213> ORGANISM: Artificial Sequence
<220> FEATURE:
<223> OTHER INFORMATION: 88A-dm3 protein

<400> SEQUENCE: 54

```
Met Thr Ser Asn Gly Arg Gln Cys Ala Gly Ile Arg Pro Tyr Asp Gly
1               5                   10                  15

Arg Gln Gln His Arg Gly Leu Asp Ser Ser Thr Thr Lys Asp Val Ile
                20                  25                  30

Gln Lys Gly Ile Ser Val Val Gly Asp Leu Leu Gly Val Val Gly Phe
            35                  40                  45

Pro Phe Gly Gly Ala Leu Val Ser Phe Tyr Thr Asn Phe Leu Asn Thr
        50                  55                  60

Ile Trp Pro Ser Glu Asp Pro Trp Lys Ala Phe Met Glu Gln Val Glu
65                  70                  75                  80

Ala Leu Met Asp Gln Lys Ile Ala Asp Tyr Ala Lys Asn Lys Ala Leu
                85                  90                  95

Ala Glu Leu Gln Gly Leu Gln Asn Asn Val Glu Asp Tyr Val Ser Ala
            100                 105                 110

Leu Ser Ser Trp Gln Lys Asn Pro Ala Ala Pro Phe Arg Asn Pro His
        115                 120                 125

Ser Gln Gly Arg Ile Arg Glu Leu Phe Ser Gln Ala Glu Ser His Phe
    130                 135                 140

Arg Asn Ser Met Pro Ser Phe Ala Ile Ser Gly Tyr Glu Val Leu Phe
```

```
                145                 150                 155                 160
        Leu Thr Thr Tyr Ala Gln Ala Asn Thr His Leu Phe Leu Leu Lys
                        165                 170                 175

Asp Ala Gln Ile Tyr Gly Glu Glu Trp Gly Tyr Glu Lys Glu Asp Ile
                        180                 185                 190

Ala Glu Phe Tyr Lys Arg Gln Leu Lys Leu Thr Gln Glu Tyr Thr Asp
                        195                 200                 205

His Cys Val Lys Trp Tyr Asn Val Gly Leu Asp Lys Leu Arg Gly Ser
                        210                 215                 220

Ser Tyr Glu Ser Trp Val Asn Phe Asn Arg Tyr Arg Arg Glu Met Thr
        225                 230                 235                 240

Leu Thr Val Leu Asp Leu Ile Ala Leu Phe Pro Leu Tyr Asp Val Arg
                        245                 250                 255

Leu Tyr Pro Lys Glu Val Lys Thr Glu Leu Thr Arg Asp Val Leu Thr
                        260                 265                 270

Asp Pro Ile Val Gly Val Asn Asn Leu Arg Gly Tyr Gly Thr Thr Phe
                        275                 280                 285

Ser Asn Ile Glu Asn Tyr Ile Arg Lys Pro His Leu Phe Asp Tyr Leu
                        290                 295                 300

His Arg Ile Gln Phe His Thr Arg Phe Gln Pro Gly Tyr Tyr Gly Asn
        305                 310                 315                 320

Asp Ser Phe Asn Tyr Trp Ser Gly Asn Tyr Val Ser Thr Arg Pro Ser
                        325                 330                 335

Ile Gly Ser Asn Asp Ile Ile Thr Ser Pro Phe Tyr Gly Asn Lys Ser
                        340                 345                 350

Ser Glu Pro Val Gln Asn Leu Glu Phe Asn Gly Glu Lys Val Tyr Arg
                        355                 360                 365

Ala Val Ala Asn Thr Asn Leu Ala Val Trp Pro Ser Ala Val Tyr Ser
                        370                 375                 380

Gly Val Thr Lys Val Glu Phe Ser Gln Tyr Asn Asp Gln Thr Asp Glu
        385                 390                 395                 400

Ala Ser Thr Gln Thr Tyr Asp Ser Lys Arg Asn Val Gly Ala Val Ser
                        405                 410                 415

Trp Asp Ser Ile Asp Gln Leu Pro Pro Glu Thr Thr Asp Glu Pro Leu
                        420                 425                 430

Glu Lys Gly Tyr Ser His Gln Leu Asn Tyr Val Met Cys Phe Leu Met
                        435                 440                 445

Gln Gly Ser Arg Gly Thr Ile Pro Val Leu Thr Trp Thr His Lys Ser
                        450                 455                 460

Val Asp Phe Phe Asn Met Ile Asp Ser Lys Lys Ile Thr Gln Leu Pro
        465                 470                 475                 480

Leu Val Lys Gly Asp Met Leu Tyr Leu Gly Ser Val Val Gln Gly
                        485                 490                 495

Pro Gly Phe Thr Gly Gly Asp Ile Leu Lys Arg Thr Asn Pro Ser Ile
                        500                 505                 510

Leu Gly Thr Phe Ala Val Thr Val Asn Gly Ser Leu Ser Gln Arg Tyr
                        515                 520                 525

Arg Val Arg Ile Arg Tyr Ala Ser Thr Thr Asp Phe Glu Phe Thr Leu
                        530                 535                 540

Tyr Leu Gly Asp Thr Ile Glu Lys Asn Arg Phe Asn Lys Thr Met Asp
        545                 550                 555                 560

Asn Gly Ala Ser Leu Thr Tyr Glu Thr Phe Lys Phe Ala Ser Phe Ile
                        565                 570                 575
```

```
Thr Asp Phe Gln Phe Arg Glu Thr Gln Asp Lys Ile Leu Leu Ser Met
            580                 585                 590

Gly Asp Phe Ser Ser Gly Gln Glu Val Tyr Ile Asp Arg Ile Glu Phe
        595                 600                 605

Ile Pro Val Asp Glu Thr
    610

<210> SEQ ID NO 55
<211> LENGTH: 1986
<212> TYPE: DNA
<213> ORGANISM: Artificial Sequence
<220> FEATURE:
<223> OTHER INFORMATION: FR(1Fa) coding sequence

<400> SEQUENCE: 55
atgactagta acggccgcca gtgtgctggt attcgccctt atgacggccg acaacaacac      60
cgaggcctgg acagcagcac caccaaggac gtgatccaga agggcatcag cgtggtgggc     120
gacctgctgg gcgtggtggg cttccccttc ggcggcgccc tggtgagctt ctacaccaac     180
ttcctgaaca ccatctggcc cagcgaggac ccctggaagg ccttcatgga gcaggtggag     240
gccctgatga ccagaagat cgccgactac gccaagaaca aggcactggc cgagctacag      300
ggcctccaga caacgtgga ggactatgtg agcgccctga gcagctggca gaagaacccc      360
gctgcaccgt ccgcaaccc ccacagccag ggccgcatcc gcgagctgtt cagccaggcc      420
gagagccact tccgcaacag catgcccagc ttcgccatca gcggctacga ggtgctgttc     480
ctgaccacct acgcccaggc cgccaacacc cacctgttcc tgctgaagga cgcccaaatc     540
tacggagagg agtggggcta cgagaaggag gacatcgccg agttctacaa cgccagctg      600 aagctgaccc aggagtacac cgaccactgc gtgaagtggt acaacgtggg tctagacaag     660
ctccgcggca gcagctacga gagctggtg aacttcaacc gctaccgccg cgagatgacc      720
ctgaccgtgc tggacctgat cgccctgttc cccctgtacg acgtgcgcct gtaccccaag     780
gaggtgaaga ccgagctgac ccgcgacgtg ctgaccgacc ccatcgtggg cgtgaacaac     840
ctgcgcggct acggcaccac cttcagcaac atcgagaact acatccgcaa gccccacctg     900
ttcgactacc tgcaccgcat ccagttccac acgcgtttcc agcccggcta ctacggcaac     960
gacagcttca actactggag cggcaactac gtgagcaccc gccccagcat cggcagcaac    1020
gacatcatca ccagcccctt ctacggcaac aagagcagcg agcccgtgca gaaccttgag    1080
ttcaacggcg agaaggtgta ccgcgccgtg gctaacacca acctggccgt gtggccctct    1140
gcagtgtaca gcggcgtgac caaggtggag ttcagccagt acaacgacca gaccgacgag    1200
gccagcaccc agacctacga cagcaagcgc aacgtgggcg ccgtgagctg gacagcatc    1260 gaccagctgc cccccgagac caccgacgag cccctggaga agggctacag ccaccagctg    1320
aactacgtga tgtgcttcct gatgcagggc agccgcggca ccatcccgt gctgacctgg    1380 acccacaaga gcgtcgactt cttcaacatg atcgacagca agaagatcac ccagctgccc    1440
ctggtgaagg cccacaccct ccagtccggc accaccgtgg tgcgcggccc gggcttcacc    1500
ggcggcgaca tcctccgccg cacctccggc ggcccgttcg cctacaccat cgtgaacatc    1560
aacggccagc tccgcagcg ctaccgcgcc cgcatccgct acgcctccac caccaacctc    1620
cgcatctacg tgaccgtggc cggcgagcgc atcttcgccg ccagttcaa caagaccatg    1680 gacaccggcg accgctcac cttcagtcc ttctcctacg ccaccatcaa caccgccttc    1740
accttcccga tgtcccagtc ctccttcacc gtggcgccg acaccttctc ctccggcaac    1800
gaggtgtaca tcgaccgctt cgagctgatc ccggtgaccg ccaccttcga ggccgagtac    1860
```

```
gacctggagc gcgcccagaa ggccgtgaac gccctcttca cctccatcaa ccagatcggc    1920
atcaagaccg acgtgaccga ctaccacatc gaccaggtgt ccaacctcgt ggactgctta    1980
agctag                                                               1986
```

<210> SEQ ID NO 56
<211> LENGTH: 661
<212> TYPE: PRT
<213> ORGANISM: Artificial Sequence
<220> FEATURE:
<223> OTHER INFORMATION: FR(1Fa) protein

<400> SEQUENCE: 56

```
Met Thr Ser Asn Gly Arg Gln Cys Ala Gly Ile Arg Pro Tyr Asp Gly
1               5                   10                  15

Arg Gln Gln His Arg Gly Leu Asp Ser Ser Thr Lys Asp Val Ile
            20                  25                  30

Gln Lys Gly Ile Ser Val Val Gly Asp Leu Leu Gly Val Val Gly Phe
        35                  40                  45

Pro Phe Gly Gly Ala Leu Val Ser Phe Tyr Thr Asn Phe Leu Asn Thr
    50                  55                  60

Ile Trp Pro Ser Glu Asp Pro Trp Lys Ala Phe Met Glu Gln Val Glu
65                  70                  75                  80

Ala Leu Met Asp Gln Lys Ile Ala Asp Tyr Ala Lys Asn Lys Ala Leu
                85                  90                  95

Ala Glu Leu Gln Gly Leu Gln Asn Asn Val Glu Asp Tyr Val Ser Ala
            100                 105                 110

Leu Ser Ser Trp Gln Lys Asn Pro Ala Ala Pro Phe Arg Asn Pro His
        115                 120                 125

Ser Gln Gly Arg Ile Arg Glu Leu Phe Ser Gln Ala Glu Ser His Phe
    130                 135                 140

Arg Asn Ser Met Pro Ser Phe Ala Ile Ser Gly Tyr Glu Val Leu Phe
145                 150                 155                 160

Leu Thr Thr Tyr Ala Gln Ala Ala Asn Thr His Leu Phe Leu Leu Lys
                165                 170                 175

Asp Ala Gln Ile Tyr Gly Glu Glu Trp Gly Tyr Glu Lys Glu Asp Ile
            180                 185                 190

Ala Glu Phe Tyr Lys Arg Gln Leu Lys Leu Thr Gln Glu Tyr Thr Asp
        195                 200                 205

His Cys Val Lys Trp Tyr Asn Val Gly Leu Asp Lys Leu Arg Gly Ser
    210                 215                 220

Ser Tyr Glu Ser Trp Val Asn Phe Asn Arg Tyr Arg Arg Glu Met Thr
225                 230                 235                 240

Leu Thr Val Leu Asp Leu Ile Ala Leu Phe Pro Leu Tyr Asp Val Arg
                245                 250                 255

Leu Tyr Pro Lys Glu Val Lys Thr Glu Leu Thr Arg Asp Val Leu Thr
            260                 265                 270

Asp Pro Ile Val Gly Val Asn Asn Leu Arg Gly Tyr Gly Thr Thr Phe
        275                 280                 285

Ser Asn Ile Glu Asn Tyr Ile Arg Lys Pro His Leu Phe Asp Tyr Leu
    290                 295                 300

His Arg Ile Gln Phe His Thr Arg Phe Gln Pro Gly Tyr Tyr Gly Asn
305                 310                 315                 320

Asp Ser Phe Asn Tyr Trp Ser Gly Asn Tyr Val Ser Thr Arg Pro Ser
                325                 330                 335
```

```
Ile Gly Ser Asn Asp Ile Ile Thr Ser Pro Phe Tyr Gly Asn Lys Ser
            340                 345                 350

Ser Glu Pro Val Gln Asn Leu Glu Phe Asn Gly Glu Lys Val Tyr Arg
        355                 360                 365

Ala Val Ala Asn Thr Asn Leu Ala Val Trp Pro Ser Ala Val Tyr Ser
    370                 375                 380

Gly Val Thr Lys Val Glu Phe Ser Gln Tyr Asn Asp Gln Thr Asp Glu
385                 390                 395                 400

Ala Ser Thr Gln Thr Tyr Asp Ser Lys Arg Asn Val Gly Ala Val Ser
                405                 410                 415

Trp Asp Ser Ile Asp Gln Leu Pro Pro Glu Thr Thr Asp Glu Pro Leu
            420                 425                 430

Glu Lys Gly Tyr Ser His Gln Leu Asn Tyr Val Met Cys Phe Leu Met
        435                 440                 445

Gln Gly Ser Arg Gly Thr Ile Pro Val Leu Thr Trp Thr His Lys Ser
    450                 455                 460

Val Asp Phe Phe Asn Met Ile Asp Ser Lys Lys Ile Thr Gln Leu Pro
465                 470                 475                 480

Leu Val Lys Ala His Thr Leu Gln Ser Gly Thr Thr Val Arg Gly
                485                 490                 495

Pro Gly Phe Thr Gly Gly Asp Ile Leu Arg Arg Thr Ser Gly Gly Pro
            500                 505                 510

Phe Ala Tyr Thr Ile Val Asn Ile Asn Gly Gln Leu Pro Gln Arg Tyr
        515                 520                 525

Arg Ala Arg Ile Arg Tyr Ala Ser Thr Thr Asn Leu Arg Ile Tyr Val
    530                 535                 540

Thr Val Ala Gly Glu Arg Ile Phe Ala Gly Gln Phe Asn Lys Thr Met
545                 550                 555                 560

Asp Thr Gly Asp Pro Leu Thr Phe Gln Ser Phe Ser Tyr Ala Thr Ile
                565                 570                 575

Asn Thr Ala Phe Thr Phe Pro Met Ser Gln Ser Ser Phe Thr Val Gly
            580                 585                 590

Ala Asp Thr Phe Ser Ser Gly Asn Glu Val Tyr Ile Asp Arg Phe Glu
        595                 600                 605

Leu Ile Pro Val Thr Ala Thr Phe Glu Ala Glu Tyr Asp Leu Glu Arg
    610                 615                 620

Ala Gln Lys Ala Val Asn Ala Leu Phe Thr Ser Ile Asn Gln Ile Gly
625                 630                 635                 640

Ile Lys Thr Asp Val Thr Asp Tyr His Ile Asp Gln Val Ser Asn Leu
                645                 650                 655

Val Asp Cys Leu Ser
            660

<210> SEQ ID NO 57
<211> LENGTH: 1842
<212> TYPE: DNA
<213> ORGANISM: Artificial Sequence
<220> FEATURE:
<223> OTHER INFORMATION: FR(1Ac) coding sequence

<400> SEQUENCE: 57
atgactagta acggccgcca gtgtgctggt attcgccctt atgacggccg acaacaacac    60
cgaggcctgg acagcagcac caccaaggac gtgatccaga agggcatcag cgtggtgggc   120
gacctgctgg gcgtggtggg cttcccctct ggcggcgccc tggtgagctt ctacaccaac   180
ttcctgaaca ccatctggcc cagcgaggac ccctggaagg ccttcatgga gcaggtggag   240
```

-continued

```
gccctgatgg accagaagat cgccgactac gccaagaaca aggcactggc cgagctacag    300
ggcctccaga caacgtgga ggactatgtg agcgccctga gcagctggca aagaacccc     360 gctgcaccgt ccgcaaccc ccacagccag ggccgcatcc gcgagctgtt cagccaggcc    420
gagagccact tccgcaacag catgcccagc ttcgccatca gcggctacga ggtgctgttc    480
ctgaccacct acgcccaggc cgccaacacc cacctgttcc tgctgaagga cgcccaaatc    540
tacggagagg agtggggcta cgagaaggag gacatcgccg agttctacaa cgccagctg    600 aagctgaccc aggagtacac cgaccactgc gtgaagtggt acaacgtggg tctagacaag    660
ctccgcggca gcagctacga gagctgggtg aacttcaacc gctaccgccg cgagatgacc    720
ctgaccgtgc tggacctgat cgccctgttc cccctgtacg acgtgcgcct gtaccccaag    780
gaggtgaaga ccgagctgac ccgcgacgtg ctgaccgacc ccatcgtggg cgtgaacaac    840
ctgcgcggct acggcaccac cttcagcaac atcgagaact acatccgcaa gccccacctg    900
ttcgactacc tgcaccgcat ccagttccac acgcgtttcc agcccggcta ctacggcaac    960
gacagcttca actactggag cggcaactac gtgagcaccc gccccagcat cggcagcaac   1020
gacatcatca ccagccccctt ctacggcaac aagagcagcg agcccgtgca gaaccttgag   1080
ttcaacggcg agaaggtgta ccgcgccgtg gctaacacca acctggccgt gtggccctct   1140
gcagtgtaca gcggcgtgac caaggtggag ttcagccagt acaacgacca gaccgacgag   1200
gccagcaccc agacctacga cagcaagcgc aacgtgggcg ccgtgagctg ggacagcatc   1260
gaccagctgc ccccgagac caccgacgag ccctggaga agggctacag ccaccagctg   1320
aactacgtga tgtgcttcct gatgcagggc agccgcggca ccatcccgt gctgacctgg   1380 acccacaaga gcgtcgactt cttcaacatg atcgacagca gaagatcac ccagctgccc   1440 ctggtgaagg gaaactttct ttttaatggt tctgtaattt caggaccagg atttactggt    1500
ggggacttag ttagattaaa tagtagtgga ataacattc agaatagagg gtatattgaa    1560
gttccaattc acttcccatc gacatctacc agatatcgag ttcgtgtacg gtatgcttct    1620
gtaaccccga ttcacctcaa cgttaattgg ggtaattcat ccatttttc caatacagta    1680 ccagctacag ctacgtcatt agataatcta caatcaagtg attttggtta ttttgaaagt    1740
gccaatgctt ttacatcttc attaggtaat atagtaggtg ttagaaattt tagtgggact    1800
gcaggagtga taatagacag atttgaattt attccagttt ag                       1842
```

<210> SEQ ID NO 58
<211> LENGTH: 613
<212> TYPE: PRT
<213> ORGANISM: Artificial Sequence
<220> FEATURE:
<223> OTHER INFORMATION: FR(1Ac) protein

<400> SEQUENCE: 58

```
Met Thr Ser Asn Gly Arg Gln Cys Ala Gly Ile Arg Pro Tyr Asp Gly
1               5                   10                  15

Arg Gln Gln His Arg Gly Leu Asp Ser Ser Thr Thr Lys Asp Val Ile
            20                  25                  30

Gln Lys Gly Ile Ser Val Val Gly Asp Leu Leu Gly Val Val Gly Phe
        35                  40                  45

Pro Phe Gly Gly Ala Leu Val Ser Phe Tyr Thr Asn Phe Leu Asn Thr
    50                  55                  60

Ile Trp Pro Ser Glu Asp Pro Trp Lys Ala Phe Met Glu Gln Val Glu
65                  70                  75                  80
```

-continued

```
Ala Leu Met Asp Gln Lys Ile Ala Asp Tyr Ala Lys Asn Lys Ala Leu
             85                  90                  95

Ala Glu Leu Gln Gly Leu Gln Asn Asn Val Glu Asp Tyr Val Ser Ala
        100                 105                 110

Leu Ser Ser Trp Gln Lys Asn Pro Ala Ala Pro Phe Arg Asn Pro His
        115                 120                 125

Ser Gln Gly Arg Ile Arg Glu Leu Phe Ser Gln Ala Glu Ser His Phe
    130                 135                 140

Arg Asn Ser Met Pro Ser Phe Ala Ile Ser Gly Tyr Glu Val Leu Phe
145                 150                 155                 160

Leu Thr Thr Tyr Ala Gln Ala Ala Asn Thr His Leu Phe Leu Leu Lys
            165                 170                 175

Asp Ala Gln Ile Tyr Gly Glu Glu Trp Gly Tyr Glu Lys Glu Asp Ile
        180                 185                 190

Ala Glu Phe Tyr Lys Arg Gln Leu Lys Leu Thr Gln Glu Tyr Thr Asp
    195                 200                 205

His Cys Val Lys Trp Tyr Asn Val Gly Leu Asp Lys Leu Arg Gly Ser
    210                 215                 220

Ser Tyr Glu Ser Trp Val Asn Phe Asn Arg Tyr Arg Arg Glu Met Thr
225                 230                 235                 240

Leu Thr Val Leu Asp Leu Ile Ala Leu Phe Pro Leu Tyr Asp Val Arg
            245                 250                 255

Leu Tyr Pro Lys Glu Val Lys Thr Glu Leu Thr Arg Asp Val Leu Thr
        260                 265                 270

Asp Pro Ile Val Gly Val Asn Asn Leu Arg Gly Tyr Gly Thr Thr Phe
    275                 280                 285

Ser Asn Ile Glu Asn Tyr Ile Arg Lys Pro His Leu Phe Asp Tyr Leu
    290                 295                 300

His Arg Ile Gln Phe His Thr Arg Phe Gln Pro Gly Tyr Tyr Gly Asn
305                 310                 315                 320

Asp Ser Phe Asn Tyr Trp Ser Gly Asn Tyr Val Ser Thr Arg Pro Ser
            325                 330                 335

Ile Gly Ser Asn Asp Ile Ile Thr Ser Pro Phe Tyr Gly Asn Lys Ser
        340                 345                 350

Ser Glu Pro Val Gln Asn Leu Glu Phe Asn Gly Glu Lys Val Tyr Arg
    355                 360                 365

Ala Val Ala Asn Thr Asn Leu Ala Val Trp Pro Ser Ala Val Tyr Ser
    370                 375                 380

Gly Val Thr Lys Val Glu Phe Ser Gln Tyr Asn Asp Gln Thr Asp Glu
385                 390                 395                 400

Ala Ser Thr Gln Thr Tyr Asp Ser Lys Arg Asn Val Gly Ala Val Ser
            405                 410                 415

Trp Asp Ser Ile Asp Gln Leu Pro Pro Glu Thr Thr Asp Glu Pro Leu
        420                 425                 430

Glu Lys Gly Tyr Ser His Gln Leu Asn Tyr Val Met Cys Phe Leu Met
    435                 440                 445

Gln Gly Ser Arg Gly Thr Ile Pro Val Leu Thr Trp Thr His Lys Ser
    450                 455                 460

Val Asp Phe Phe Asn Met Ile Asp Ser Lys Lys Ile Thr Gln Leu Pro
465                 470                 475                 480

Leu Val Lys Gly Asn Phe Leu Phe Asn Gly Ser Val Ile Ser Gly Pro
            485                 490                 495

Gly Phe Thr Gly Gly Asp Leu Val Arg Leu Asn Ser Ser Gly Asn Asn
        500                 505                 510
```

-continued

```
Ile Gln Asn Arg Gly Tyr Ile Glu Val Pro Ile His Phe Pro Ser Thr
            515                 520                 525
Ser Thr Arg Tyr Arg Val Arg Val Arg Tyr Ala Ser Val Thr Pro Ile
        530                 535                 540
His Leu Asn Val Asn Trp Gly Asn Ser Ser Ile Phe Ser Asn Thr Val
545                 550                 555                 560
Pro Ala Thr Ala Thr Ser Leu Asp Asn Leu Gln Ser Ser Asp Phe Gly
                565                 570                 575
Tyr Phe Glu Ser Ala Asn Ala Phe Thr Ser Ser Leu Gly Asn Ile Val
            580                 585                 590
Gly Val Arg Asn Phe Ser Gly Thr Ala Gly Val Ile Ile Asp Arg Phe
            595                 600                 605
Glu Phe Ile Pro Val
    610

<210> SEQ ID NO 59
<211> LENGTH: 2067
<212> TYPE: DNA
<213> ORGANISM: Artificial Sequence
<220> FEATURE:
<223> OTHER INFORMATION: FR(IIa) coding sequence

<400> SEQUENCE: 59
atgactagta acggccgcca gtgtgctggt attcgccctt atgacggccg acaacaacac      60
cgaggcctgg acagcagcac caccaaggac gtgatccaga agggcatcag cgtggtgggc     120
gacctgctgg gcgtggtggg cttccccttc ggcggcgccc tggtgagctt ctacaccaac     180
ttcctgaaca ccatctggcc cagcgaggac ccctggaagg ccttcatgga gcaggtggag     240
gccctgatgg accagaagat cgccgactac gccaagaaca aggcactggc cgagctacag     300
ggcctccaga caacgtgga ggactatgtg agcgccctga gcagctggca gaagaacccc      360
gctgcaccgt tccgcaaccc ccacagccag ggccgcatcc gcgagctgtt cagccaggcc     420
gagagccact tccgcaacag catgcccagc ttcgccatca gcggctacga ggtgctgttc     480
ctgaccacct acgcccaggc cgccaacacc cacctgttcc tgctgaagga cgcccaaatc     540
tacggagagg agtggggcta cgagaaggag gacatcgccg agttctacaa cgccagctg      600 aagctgaccc aggagtacac cgaccactgc gtgaagtggt acaacgtggg tctagacaag     660
ctccgcggca gcagctacga gagctgggtg aacttcaacc gctaccgccg cgagatgacc     720
ctgaccgtgc tggacctgat cgccctgttc cccctgtacg acgtgcgcct gtaccccaag     780
gaggtgaaga ccgagctgac ccgcgacgtg ctgaccgacc ccatcgtggg cgtgaacaac     840
ctgcgcggct acggcaccac cttcagcaac atcgagaact acatccgcaa gccccacctg     900
ttcgactacc tgcaccgcat ccagttccac acgcgtttcc agcccggcta ctacggcaac     960
gacagcttca actactggag cggcaactac gtgagcaccc gccccagcat cggcagcaac    1020
gacatcatca ccagcccctt ctacggcaac aagagcagcg agcccgtgca gaaccttgag    1080
ttcaacggcg agaaggtgta ccgcgccgtg gctaacacca acctggccgt gtggcccctct   1140 gcagtgtaca gcggcgtgac caaggtggag ttcagccagt acaacgacca gaccgacgag    1200
gccagcaccc agacctacga cagcaagcgc aacgtgggcg ccgtgagctg ggacagcatc    1260
gaccagctgc cccccgagac caccgacgag cccctggaga agggctacag ccaccagctg    1320
aactacgtga tgtgcttcct gatgcagggc agccgcggca ccatccccgt gctgacctgg    1380
acccacaaga gcgtcgactt cttcaacatg atcgacagca gaaagatcac ccagctgccc    1440
```

-continued

```
ctggtaaaag ctttcaatct gtcttcaggt gccgctgtag tgagaggacc aggatttaca    1500
ggtggggata tccttcgaag aacgaatact ggtacatttg gggatatacg agtaaatatt    1560
aatccaccat ttgcacaaag atatcgcgtg aggattcgct atgcttctac cacagattta    1620
caattccata cgtcaattaa cggtaaagct attaatcaag gtaattttc agcaactatg    1680 aatagaggag aggacttaga ctataaaacc tttagaactg taggctttac cactccattt    1740 agcttttag atgtacaaag tacattcaca ataggtgctt ggaacttctc ttcaggtaac    1800
gaagtttata tagatagaat tgaatttgtt ccggtagaag taacatatga ggcagaatat    1860 gatttttgaaa aagcgcaaga gaaggttact gcactgttta catctacgaa tccaagagga    1920
ttaaaaacag atgtaaagga ttatcatatt gaccaggtat caaatttagt agagtctcta    1980
tcagatgaat tctatcttga tgaaaagaga gaattattcg agatagttaa atacgcgaag    2040
caactccata ttgagcgtaa catgtag                                         2067
```

<210> SEQ ID NO 60
<211> LENGTH: 688
<212> TYPE: PRT
<213> ORGANISM: Artificial Sequence
<220> FEATURE:
<223> OTHER INFORMATION: FR(IIa) protein

<400> SEQUENCE: 60

```
Met Thr Ser Asn Gly Arg Gln Cys Ala Gly Ile Arg Pro Tyr Asp Gly
1               5                   10                  15

Arg Gln Gln His Arg Gly Leu Asp Ser Ser Thr Thr Lys Asp Val Ile
            20                  25                  30

Gln Lys Gly Ile Ser Val Val Gly Asp Leu Leu Gly Val Gly Phe
        35                  40                  45

Pro Phe Gly Gly Ala Leu Val Ser Phe Tyr Thr Asn Phe Leu Asn Thr
    50                  55                  60

Ile Trp Pro Ser Glu Asp Pro Trp Lys Ala Phe Met Glu Gln Val Glu
65                  70                  75                  80

Ala Leu Met Asp Gln Lys Ile Ala Asp Tyr Ala Lys Asn Lys Ala Leu
                85                  90                  95

Ala Glu Leu Gln Gly Leu Gln Asn Asn Val Glu Asp Tyr Val Ser Ala
            100                 105                 110

Leu Ser Ser Trp Gln Lys Asn Pro Ala Ala Pro Phe Arg Asn Pro His
        115                 120                 125

Ser Gln Gly Arg Ile Arg Glu Leu Phe Ser Gln Ala Glu Ser His Phe
    130                 135                 140

Arg Asn Ser Met Pro Ser Phe Ala Ile Ser Gly Tyr Glu Val Leu Phe
145                 150                 155                 160

Leu Thr Thr Tyr Ala Gln Ala Ala Asn Thr His Leu Phe Leu Leu Lys
                165                 170                 175

Asp Ala Gln Ile Tyr Gly Glu Glu Trp Gly Tyr Glu Lys Glu Asp Ile
            180                 185                 190

Ala Glu Phe Tyr Lys Arg Gln Leu Lys Leu Thr Gln Glu Tyr Thr Asp
        195                 200                 205

His Cys Val Lys Trp Tyr Asn Val Gly Leu Asp Lys Leu Arg Gly Ser
    210                 215                 220

Ser Tyr Glu Ser Trp Val Asn Phe Asn Arg Tyr Arg Arg Glu Met Thr
225                 230                 235                 240

Leu Thr Val Leu Asp Leu Ile Ala Leu Phe Pro Leu Tyr Asp Val Arg
                245                 250                 255
```

```
Leu Tyr Pro Lys Glu Val Lys Thr Glu Leu Thr Arg Asp Val Leu Thr
            260                 265                 270

Asp Pro Ile Val Gly Val Asn Asn Leu Arg Gly Tyr Gly Thr Thr Phe
            275                 280                 285

Ser Asn Ile Glu Asn Tyr Ile Arg Lys Pro His Leu Phe Asp Tyr Leu
            290                 295                 300

His Arg Ile Gln Phe His Thr Arg Phe Gln Pro Gly Tyr Tyr Gly Asn
305                 310                 315                 320

Asp Ser Phe Asn Tyr Trp Ser Gly Asn Tyr Val Ser Thr Arg Pro Ser
                325                 330                 335

Ile Gly Ser Asn Asp Ile Ile Thr Ser Pro Phe Tyr Gly Asn Lys Ser
                340                 345                 350

Ser Glu Pro Val Gln Asn Leu Glu Phe Asn Gly Glu Lys Val Tyr Arg
            355                 360                 365

Ala Val Ala Asn Thr Asn Leu Ala Val Trp Pro Ser Ala Val Tyr Ser
            370                 375                 380

Gly Val Thr Lys Val Glu Phe Ser Gln Tyr Asn Asp Gln Thr Asp Glu
385                 390                 395                 400

Ala Ser Thr Gln Thr Tyr Asp Ser Lys Arg Asn Val Gly Ala Val Ser
                405                 410                 415

Trp Asp Ser Ile Asp Gln Leu Pro Pro Glu Thr Thr Asp Glu Pro Leu
                420                 425                 430

Glu Lys Gly Tyr Ser His Gln Leu Asn Tyr Val Met Cys Phe Leu Met
            435                 440                 445

Gln Gly Ser Arg Gly Thr Ile Pro Val Leu Thr Trp Thr His Lys Ser
            450                 455                 460

Val Asp Phe Phe Asn Met Ile Asp Ser Lys Lys Ile Thr Gln Leu Pro
465                 470                 475                 480

Leu Val Lys Ala Phe Asn Leu Ser Ser Gly Ala Ala Val Val Arg Gly
                485                 490                 495

Pro Gly Phe Thr Gly Gly Asp Ile Leu Arg Arg Thr Asn Thr Gly Thr
            500                 505                 510

Phe Gly Asp Ile Arg Val Asn Ile Asn Pro Pro Phe Ala Gln Arg Tyr
            515                 520                 525

Arg Val Arg Ile Arg Tyr Ala Ser Thr Thr Asp Leu Gln Phe His Thr
530                 535                 540

Ser Ile Asn Gly Lys Ala Ile Asn Gln Gly Asn Phe Ser Ala Thr Met
545                 550                 555                 560

Asn Arg Gly Glu Asp Leu Asp Tyr Lys Thr Phe Arg Thr Val Gly Phe
                565                 570                 575

Thr Thr Pro Phe Ser Phe Leu Asp Val Gln Ser Thr Phe Thr Ile Gly
            580                 585                 590

Ala Trp Asn Phe Ser Ser Gly Asn Glu Val Tyr Ile Asp Arg Ile Glu
                595                 600                 605

Phe Val Pro Val Glu Val Thr Tyr Glu Ala Glu Tyr Asp Phe Glu Lys
            610                 615                 620

Ala Gln Glu Lys Val Thr Ala Leu Phe Thr Ser Thr Asn Pro Arg Gly
625                 630                 635                 640

Leu Lys Thr Asp Val Lys Asp Tyr His Ile Asp Gln Val Ser Asn Leu
                645                 650                 655

Val Glu Ser Leu Ser Asp Glu Phe Tyr Leu Asp Glu Lys Arg Glu Leu
            660                 665                 670

Phe Glu Ile Val Lys Tyr Ala Lys Gln Leu His Ile Glu Arg Asn Met
            675                 680                 685
```

<210> SEQ ID NO 61
<211> LENGTH: 1962
<212> TYPE: DNA
<213> ORGANISM: Artificial Sequence
<220> FEATURE:
<223> OTHER INFORMATION: DM23A coding sequence

<400> SEQUENCE: 61

| | | | | | |
|---|---|---|---|---|---|
| atgactagta | acggccgcca | gtgtgctggt | attcgccctt | atgacggccg | acaacaacac | 60 |
| cgaggcctgg | acagcagcac | caccaaggac | gtgatccaga | agggcatcag | cgtggtgggc | 120 |
| gacctgctgg | gcgtggtggg | cttccccttc | ggcggcgccc | tggtgagctt | ctacaccaac | 180 |
| ttcctgaaca | ccatctggcc | cagcgaggac | ccctggaagg | ccttcatgga | gcaggtggag | 240 |
| gccctgatgg | accagaagat | cgccgactac | gccaagaaca | aggcactggc | cgagctacag | 300 |
| ggcctccaga | caacgtgga | ggactatgtg | agcgccctga | gcagctggca | gaagaacccc | 360 |
| gctgcaccgt | tccgcaaccc | ccacagccag | ggccgcatcc | gcgagctgtt | cagccaggcc | 420 |
| gagagccact | ccgcaacag | catgcccagc | ttcgccatca | gcggctacga | ggtgctgttc | 480 |
| ctgaccacct | acgcccaggc | cgccaacacc | cacctgttcc | tgctgaagga | cgcccaaatc | 540 |
| tacggagagg | agtggggcta | cgagaaggag | gacatcgccg | agttctacaa | gcgccagctg | 600 |
| aagctgaccc | aggagtacac | cgaccactgc | gtgaagtggt | acaacgtggg | tctagacaag | 660 |
| ctccgcggca | gcagctacga | gagctgggtg | aacttcaacc | gctaccgccg | cgagatgacc | 720 |
| ctgaccgtgc | tggacctgat | cgccctgttc | cccctgtacg | acgtgcgcct | gtaccccaag | 780 |
| gaggtgaaga | ccgagctgac | ccgcgacgtg | ctgaccgacc | ccatcgtggg | cgtgaacaac | 840 |
| ctgcgcggct | acggcaccac | cttcagcaac | atcgagaact | acatccgcaa | gccccacctg | 900 |
| ttcgactacc | tgcaccgcat | ccagttccac | acgcgtttcc | agcccggcta | ctacggcaac | 960 |
| gacagcttca | actactggag | cggcaactac | gtgagcaccc | gccccagcat | cggcagcaac | 1020 |
| gacatcatca | ccagccccctt | ctacggcaac | aagagcagcg | agcccgtgca | gaaccttgag | 1080 |
| ttcaacggcg | agaaggtgta | ccgcgccgtg | gctaacacca | acctggccgt | gtggcccctct | 1140 |
| gcagtgtaca | gcggcgtgac | caaggtggag | ttcagccagt | acaacgacca | gaccgacgag | 1200 |
| gccagcaccc | agacctacga | cagcaagcgc | aacgtgggcg | ccgtgagctg | gacagcatc | 1260 |
| gaccagctgc | ccccgagac | caccgacgag | ccctggaga | agggctacag | ccaccagctg | 1320 |
| aactacgtga | tgtgcttcct | gatgcagggc | agccgcggca | ccatcccgt | gctgacctgg | 1380 |
| acccacaaga | gcgccgagtt | caacaacatc | atccccagca | gccagatcac | ccagatcccc | 1440 |
| ctgaccaaga | gcaccaacct | gggcagcggc | accagcgtgg | tgaagggccc | cggcttcacc | 1500 |
| ggcggcgaca | tcctgcgccg | caccagcccc | ggccagatca | gcaccctgcg | cgtgaacatc | 1560 |
| accgcccccc | tgagccagcg | ctaccgcgtc | cgcatccgct | acgccagcac | caccaacctg | 1620 |
| cagttccaca | ccagcatcga | cggccgcccc | atcaaccagg | gcaacttcag | cgccaccatg | 1680 |
| agcagcggca | gcaacctgca | gagcggcagc | ttccgcaccg | tgggcttcac | cacccccttc | 1740 |
| aacttcagca | acggcagcag | cgtgttcacc | ctgcgcgccc | acgtgttcaa | cagcggcaac | 1800 |
| gaggtgtaca | tcgaccgcat | cgagttcgtg | cccgccgagg | tgaccttcga | ggccgagtac | 1860 |
| gacctggaga | gggctcagaa | ggccgtgaac | gagctgttca | ccagcagcaa | ccagatcggc | 1920 |
| ctgaagaccg | acgtgaccga | ctaccacatc | gatcaggtgt | ag | | 1962 |

<210> SEQ ID NO 62
<211> LENGTH: 653

```
<212> TYPE: PRT
<213> ORGANISM: Artificial Sequence
<220> FEATURE:
<223> OTHER INFORMATION: DM23A protein

<400> SEQUENCE: 62
```

| | | | | | | | | | | | | | | |
|---|---|---|---|---|---|---|---|---|---|---|---|---|---|---|
| Met | Thr | Ser | Asn | Gly | Arg | Gln | Cys | Ala | Gly | Ile | Arg | Pro | Tyr | Asp | Gly |
| 1 | | | | 5 | | | | | 10 | | | | | 15 | |

| | | | | | | | | | | | | |
|---|---|---|---|---|---|---|---|---|---|---|---|---|
| Arg | Gln | Gln | His | Arg | Gly | Leu | Asp | Ser | Ser | Thr | Thr | Lys | Asp | Val | Ile |
| | | | 20 | | | | | 25 | | | | | 30 | | |

| Gln | Lys | Gly | Ile | Ser | Val | Val | Gly | Asp | Leu | Leu | Gly | Val | Val | Gly | Phe |
| | | | 35 | | | | | 40 | | | | | 45 | | |

| Pro | Phe | Gly | Gly | Ala | Leu | Val | Ser | Phe | Tyr | Thr | Asn | Phe | Leu | Asn | Thr |
| 50 | | | | | 55 | | | | | 60 | | | | | |

| Ile | Trp | Pro | Ser | Glu | Asp | Pro | Trp | Lys | Ala | Phe | Met | Glu | Gln | Val | Glu |
| 65 | | | | | 70 | | | | | 75 | | | | | 80 |

| Ala | Leu | Met | Asp | Gln | Lys | Ile | Ala | Asp | Tyr | Ala | Lys | Asn | Lys | Ala | Leu |
| | | | | 85 | | | | | 90 | | | | | 95 | |

| Ala | Glu | Leu | Gln | Gly | Leu | Gln | Asn | Asn | Val | Glu | Asp | Tyr | Val | Ser | Ala |
| | | | 100 | | | | | 105 | | | | | 110 | | |

| Leu | Ser | Ser | Trp | Gln | Lys | Asn | Pro | Ala | Ala | Pro | Phe | Arg | Asn | Pro | His |
| | | | 115 | | | | | 120 | | | | | 125 | | |

| Ser | Gln | Gly | Arg | Ile | Arg | Glu | Leu | Phe | Ser | Gln | Ala | Glu | Ser | His | Phe |
| | 130 | | | | | 135 | | | | | 140 | | | | |

| Arg | Asn | Ser | Met | Pro | Ser | Phe | Ala | Ile | Ser | Gly | Tyr | Glu | Val | Leu | Phe |
| 145 | | | | | 150 | | | | | 155 | | | | | 160 |

| Leu | Thr | Thr | Tyr | Ala | Gln | Ala | Ala | Asn | Thr | His | Leu | Phe | Leu | Leu | Lys |
| | | | | 165 | | | | | 170 | | | | | 175 | |

| Asp | Ala | Gln | Ile | Tyr | Gly | Glu | Glu | Trp | Gly | Tyr | Glu | Lys | Glu | Asp | Ile |
| | | | 180 | | | | | 185 | | | | | 190 | | |

| Ala | Glu | Phe | Tyr | Lys | Arg | Gln | Leu | Lys | Leu | Thr | Gln | Glu | Tyr | Thr | Asp |
| | | | 195 | | | | | 200 | | | | | 205 | | |

| His | Cys | Val | Lys | Trp | Tyr | Asn | Val | Gly | Leu | Asp | Lys | Leu | Arg | Gly | Ser |
| | 210 | | | | | 215 | | | | | 220 | | | | |

| Ser | Tyr | Glu | Ser | Trp | Val | Asn | Phe | Asn | Arg | Tyr | Arg | Arg | Glu | Met | Thr |
| 225 | | | | | 230 | | | | | 235 | | | | | 240 |

| Leu | Thr | Val | Leu | Asp | Leu | Ile | Ala | Leu | Phe | Pro | Leu | Tyr | Asp | Val | Arg |
| | | | | 245 | | | | | 250 | | | | | 255 | |

| Leu | Tyr | Pro | Lys | Glu | Val | Lys | Thr | Glu | Leu | Thr | Arg | Asp | Val | Leu | Thr |
| | | | 260 | | | | | 265 | | | | | 270 | | |

| Asp | Pro | Ile | Val | Gly | Val | Asn | Asn | Leu | Arg | Gly | Tyr | Gly | Thr | Thr | Phe |
| | | | 275 | | | | | 280 | | | | | 285 | | |

| Ser | Asn | Ile | Glu | Asn | Tyr | Ile | Arg | Lys | Pro | His | Leu | Phe | Asp | Tyr | Leu |
| | 290 | | | | | 295 | | | | | 300 | | | | |

| His | Arg | Ile | Gln | Phe | His | Thr | Arg | Phe | Gln | Pro | Gly | Tyr | Tyr | Gly | Asn |
| 305 | | | | | 310 | | | | | 315 | | | | | 320 |

| Asp | Ser | Phe | Asn | Tyr | Trp | Ser | Gly | Asn | Tyr | Val | Ser | Thr | Arg | Pro | Ser |
| | | | | 325 | | | | | 330 | | | | | 335 | |

| Ile | Gly | Ser | Asn | Asp | Ile | Ile | Thr | Ser | Pro | Phe | Tyr | Gly | Asn | Lys | Ser |
| | | | 340 | | | | | 345 | | | | | 350 | | |

| Ser | Glu | Pro | Val | Gln | Asn | Leu | Glu | Phe | Asn | Gly | Glu | Lys | Val | Tyr | Arg |
| | | | 355 | | | | | 360 | | | | | 365 | | |

| Ala | Val | Ala | Asn | Thr | Asn | Leu | Ala | Val | Trp | Pro | Ser | Ala | Val | Tyr | Ser |
| | 370 | | | | | 375 | | | | | 380 | | | | |

| Gly | Val | Thr | Lys | Val | Glu | Phe | Ser | Gln | Tyr | Asn | Asp | Gln | Thr | Asp | Glu |

```
                385                 390                 395                 400
Ala Ser Thr Gln Thr Tyr Asp Ser Lys Arg Asn Val Gly Ala Val Ser
                    405                 410                 415
Trp Asp Ser Ile Asp Gln Leu Pro Pro Glu Thr Thr Asp Glu Pro Leu
                420                 425                 430
Glu Lys Gly Tyr Ser His Gln Leu Asn Tyr Val Met Cys Phe Leu Met
            435                 440                 445
Gln Gly Ser Arg Gly Thr Ile Pro Val Leu Thr Trp Thr His Lys Ser
        450                 455                 460
Ala Glu Phe Asn Asn Ile Ile Pro Ser Ser Gln Ile Thr Gln Ile Pro
465                 470                 475                 480
Leu Thr Lys Ser Thr Asn Leu Gly Ser Gly Thr Ser Val Val Lys Gly
                    485                 490                 495
Pro Gly Phe Thr Gly Gly Asp Ile Leu Arg Arg Thr Ser Pro Gly Gln
                500                 505                 510
Ile Ser Thr Leu Arg Val Asn Ile Thr Ala Pro Leu Ser Gln Arg Tyr
            515                 520                 525
Arg Val Arg Ile Arg Tyr Ala Ser Thr Thr Asn Leu Gln Phe His Thr
        530                 535                 540
Ser Ile Asp Gly Arg Pro Ile Asn Gln Gly Asn Phe Ser Ala Thr Met
545                 550                 555                 560
Ser Ser Gly Ser Asn Leu Gln Ser Gly Ser Phe Arg Thr Val Gly Phe
                    565                 570                 575
Thr Thr Pro Phe Asn Phe Ser Asn Gly Ser Ser Val Phe Thr Leu Ser
                580                 585                 590
Ala His Val Phe Asn Ser Gly Asn Glu Val Tyr Ile Asp Arg Ile Glu
            595                 600                 605
Phe Val Pro Ala Glu Val Thr Phe Glu Ala Glu Tyr Asp Leu Glu Arg
        610                 615                 620
Ala Gln Lys Ala Val Asn Glu Leu Phe Thr Ser Ser Asn Gln Ile Gly
625                 630                 635                 640
Leu Lys Thr Asp Val Thr Asp Tyr His Ile Asp Gln Val
                    645                 650

<210> SEQ ID NO 63
<211> LENGTH: 1923
<212> TYPE: DNA
<213> ORGANISM: Artificial Sequence
<220> FEATURE:
<223> OTHER INFORMATION: 8AF coding sequence

<400> SEQUENCE: 63
atgacggccg acaacaacac cgaggccctg gacagcagca ccaccaagga cgtgatccag     60
aagggcatca gcgtggtggg cgacctgctg ggcgtggtgg gcttcccctt cggcggcgcc    120
ctggtgagct tctacaccaa cttcctgaac accatctggc ccagcgagga ccctggaag    180 gccttcatgg agcaggtgga ggccctgatg accagaaga tcgccgacta cgccaagaac    240
aaggcactgg ccgagctaca gggcctccag aacaacgtgg aggactatgt gagcgccctg    300
agcagctggc agaagaaccc cgctgcaccg ttccgcaacc cccacagcca gggccgcatc    360
cgcgagctgt tcagccaggc cgagagccac ttccgcaaca gcatgcccag cttcgccatc    420
agcggctacg aggtgctgtt cctgaccacc tacgcccagg ccgccaacac ccacctgttc    480
ctgctgaagg acgcccaaat ctacggagag agtggggct acgagaagga ggacatcgcc    540
gagttctaca gcgccagct gaagctgacc caggagtaca ccgaccactg cgtgaagtgg    600
```

```
tacaacgtgg gtctagacaa gctccgcggc agcagctacg agagctgggt gaacttcaac    660
cgctaccgcc gcgagatgac cctgaccgtg ctggacctga tcgccctgtt ccccctgtac    720
gacgtgcgcc tgtaccccaa ggaggtgaag accgagctga cccgcgacgt gctgaccgac    780
cccatcgtgg gcgtgaacaa cctgcgcggc tacggcacca ccttcagcaa catcgagaac    840
tacatccgca agccccacct gttcgactac ctgcaccgca tccagttcca cacgcgtttc    900
cagcccggct actacggcaa cgacagcttc aactactgga gcggcaacta cgtgagcacc    960
cgccccagca tcggcagcaa cgacatcatc accagcccct tctacggcaa caagagcagc   1020
gagcccgtgc agaaccttga gttcaacggc gagaaggtgt accgcgccgt ggctaacacc   1080
aacctggccg tgtggccctc tgcagtgtac agcggcgtga ccaaggtgga gttcagccag   1140
tacaacgacc agaccgacga ggccagcacc cagacctacg acagcaagcg caacgtgggc   1200
gccgtgagct gggacagcat cgaccagctg ccccccgaga ccaccgacga gcccctggag   1260
aagggctaca gccaccagct gaactacgtg atgtgcttcc tgatgcaggg cagccgcggc   1320
accatccccg tgctgacctg gacccacaag agcgtcgact tcttcaacat gatcgacagc   1380
aagaagatca cccagctgcc cctgaccaag agcaccaacc tgggcagcgg caccagcgtg   1440
gtgaagggcc ccggcttcac cggcggcgac atcctgcgcc gcaccagccc cggccagatc   1500
agcaccctgc gcgtgaacat caccgccccc ctgagccagc gctaccgcgt ccgcatccgc   1560
tacgccagca ccaccaacct gcagttccac accagcatcg acgccgcccc catcaaccag   1620
ggcaacttca gcgccaccat gagcagcggc agcaacctgc agagcggcag cttccgcacc   1680
gtgggcttca ccaccccctt caacttcagc aacggcagca gcgtgttcac cctgagcgcc   1740
cacgtgttca cagcggcaa cgaggtgtac atcgaccgca tcgagttcgt gcccgccgag   1800
gtgaccttcg aggccgagta cgacctggag agggctcaga aggccgtgaa cgagctgttc   1860
accagcagca ccagatcgg cctgaagacc gacgtgaccg actaccacat cgatcaggtg   1920
tag                                                                 1923
```

<210> SEQ ID NO 64
<211> LENGTH: 640
<212> TYPE: PRT
<213> ORGANISM: Artificial Sequence
<220> FEATURE:
<223> OTHER INFORMATION: 8AF protein

<400> SEQUENCE: 64

```
Met Thr Ala Asp Asn Asn Thr Glu Ala Leu Asp Ser Ser Thr Thr Lys
1               5                   10                  15

Asp Val Ile Gln Lys Gly Ile Ser Val Val Gly Asp Leu Leu Gly Val
            20                  25                  30

Val Gly Phe Pro Phe Gly Gly Ala Leu Val Ser Phe Tyr Thr Asn Phe
        35                  40                  45

Leu Asn Thr Ile Trp Pro Ser Glu Asp Pro Trp Lys Ala Phe Met Glu
    50                  55                  60

Gln Val Glu Ala Leu Met Asp Gln Lys Ile Ala Asp Tyr Ala Lys Asn
65                  70                  75                  80

Lys Ala Leu Ala Glu Leu Gln Gly Leu Gln Asn Asn Val Glu Asp Tyr
                85                  90                  95

Val Ser Ala Leu Ser Ser Trp Gln Lys Asn Pro Ala Ala Pro Phe Arg
            100                 105                 110

Asn Pro His Ser Gln Gly Arg Ile Arg Glu Leu Phe Ser Gln Ala Glu
        115                 120                 125
```

-continued

```
Ser His Phe Arg Asn Ser Met Pro Ser Phe Ala Ile Ser Gly Tyr Glu
    130                 135                 140

Val Leu Phe Leu Thr Thr Tyr Ala Gln Ala Ala Asn Thr His Leu Phe
145                 150                 155                 160

Leu Leu Lys Asp Ala Gln Ile Tyr Gly Glu Glu Trp Gly Tyr Glu Lys
                165                 170                 175

Glu Asp Ile Ala Glu Phe Tyr Lys Arg Gln Leu Lys Leu Thr Gln Glu
                180                 185                 190

Tyr Thr Asp His Cys Val Lys Trp Tyr Asn Val Gly Leu Asp Lys Leu
            195                 200                 205

Arg Gly Ser Ser Tyr Glu Ser Trp Val Asn Phe Asn Arg Tyr Arg Arg
    210                 215                 220

Glu Met Thr Leu Thr Val Leu Asp Leu Ile Ala Leu Phe Pro Leu Tyr
225                 230                 235                 240

Asp Val Arg Leu Tyr Pro Lys Glu Val Lys Thr Glu Leu Thr Arg Asp
                245                 250                 255

Val Leu Thr Asp Pro Ile Val Gly Val Asn Asn Leu Arg Gly Tyr Gly
                260                 265                 270

Thr Thr Phe Ser Asn Ile Glu Asn Tyr Ile Arg Lys Pro His Leu Phe
            275                 280                 285

Asp Tyr Leu His Arg Ile Gln Phe His Thr Arg Phe Gln Pro Gly Tyr
    290                 295                 300

Tyr Gly Asn Asp Ser Phe Asn Tyr Trp Ser Gly Asn Tyr Val Ser Thr
305                 310                 315                 320

Arg Pro Ser Ile Gly Ser Asn Asp Ile Ile Thr Ser Pro Phe Tyr Gly
                325                 330                 335

Asn Lys Ser Ser Glu Pro Val Gln Asn Leu Glu Phe Asn Gly Glu Lys
                340                 345                 350

Val Tyr Arg Ala Val Ala Asn Thr Asn Leu Ala Val Trp Pro Ser Ala
            355                 360                 365

Val Tyr Ser Gly Val Thr Lys Val Glu Phe Ser Gln Tyr Asn Asp Gln
    370                 375                 380

Thr Asp Glu Ala Ser Thr Gln Thr Tyr Asp Ser Lys Arg Asn Val Gly
385                 390                 395                 400

Ala Val Ser Trp Asp Ser Ile Asp Gln Leu Pro Pro Glu Thr Thr Asp
                405                 410                 415

Glu Pro Leu Glu Lys Gly Tyr Ser His Gln Leu Asn Tyr Val Met Cys
                420                 425                 430

Phe Leu Met Gln Gly Ser Arg Gly Thr Ile Pro Val Leu Thr Trp Thr
            435                 440                 445

His Lys Ser Val Asp Phe Phe Asn Met Ile Asp Ser Lys Lys Ile Thr
    450                 455                 460

Gln Leu Pro Leu Thr Lys Ser Thr Asn Leu Gly Ser Gly Thr Ser Val
465                 470                 475                 480

Val Lys Gly Pro Gly Phe Thr Gly Gly Asp Ile Leu Arg Arg Thr Ser
                485                 490                 495

Pro Gly Gln Ile Ser Thr Leu Arg Val Asn Ile Thr Ala Pro Leu Ser
                500                 505                 510

Gln Arg Tyr Arg Val Arg Ile Arg Tyr Ala Ser Thr Thr Asn Leu Gln
            515                 520                 525

Phe His Thr Ser Ile Asp Gly Arg Pro Ile Asn Gln Gly Asn Phe Ser
    530                 535                 540

Ala Thr Met Ser Ser Gly Ser Asn Leu Gln Ser Gly Ser Phe Arg Thr
545                 550                 555                 560
```

```
Val Gly Phe Thr Thr Pro Phe Asn Phe Ser Asn Gly Ser Val Phe
            565                 570                 575

Thr Leu Ser Ala His Val Phe Asn Ser Gly Asn Glu Val Tyr Ile Asp
            580                 585                 590

Arg Ile Glu Phe Val Pro Ala Glu Val Thr Phe Glu Ala Glu Tyr Asp
        595                 600                 605

Leu Glu Arg Ala Gln Lys Ala Val Asn Glu Leu Phe Thr Ser Ser Asn
    610                 615                 620

Gln Ile Gly Leu Lys Thr Asp Val Thr Asp Tyr His Ile Asp Gln Val
625                 630                 635                 640

<210> SEQ ID NO 65
<211> LENGTH: 1836
<212> TYPE: DNA
<213> ORGANISM: Artificial Sequence
<220> FEATURE:
<223> OTHER INFORMATION: 5*cry3A055 coding sequence

<400> SEQUENCE: 65
atgactagta acggccgcca gtgtgctgga attcgccctt atgacggccg acaacaacac      60
cgaggcctgg acagcagcac caccaaggac gtgatccaga agggcatcag cgtggtgggc     120
gacctgctgg gcgtggtggg cttccccttc ggcggcgccc tggtgagctt ctacaccaac     180
ttcctgaaca ccatctggcc cagcgaggac ccctggaagg ccttcatgga gcaggtggag     240
gccctgatgg accagaagat cgccgactac gccaagaaca aggcactggc cgagctacag     300
ggcctccaga caacgtggag ggactatgtg agcgccctga gcagctggca agagaacccc     360
gctgcaccgt ccgcaaccc ccacagccag ggccgcatcc gcgagctgtt cagccaggcc      420
gagagccact tccgcaacag catgcccagc ttcgccatca gcggctacga ggtgctgttc     480
ctgaccacct acgcccaggc cgccaacacc cacctgttcc tgctgaagga cgcccaaatc     540
tacggagagg agtggggcta cgagaaggag gacatcgccg agttctacaa cgccagctg      600 aagctgaccc caggagtacac cgaccactgc gtgaagtggt acaacgtggg tctagacaag     660
ctccgcggca gcagctacga gagctgggtg aacttcaacc gctaccgccg cgagatgacc     720
ctgaccgtgc tggacctgat cgccctgttc ccctgtacg acgtgcgcct gtaccccaag      780
gaggtgaaga ccgagctgac ccgcgacgtg ctgaccgacc ccatcgtggg cgtgaacaac     840
ctgcgcggct acggcaccac cttcagcaac atcgagaact acatccgcaa gccccacctg     900
ttcgactacc tgcaccgcat ccagttccac acgcgtttcc agcccggcta ctacggcaac     960
gacagcttca actactggag cggcaactac gtgagcaccc gccccagcat cggcagcaac    1020
gacatcatca ccagcccctt ctacggcaac aagagcagcg agcccgtgca gaaccttgag    1080
ttcaacggcg agaaggtgta ccgcgccgtg gctaacacca acctggccgt gtggcctct     1140 gcagtgtaca cgcggcgtgac caaggtggag ttcagccagt acaacgacca gaccgacgag    1200
gccagcaccc agacctacga cagcaagcgc aacgtgggcg ccgtgagctg ggacagcatc    1260
gaccagctgc cccccgagac caccgacgag ccctggaga agggctacag ccaccagctg    1320
aactacgtga tgtgcttcct gatgcagggc agccgcggca ccatcccgt gctgacctgg    1380 acccacaaga gcgtcgactt cttcaacatg atcgacagca agaagatcac ccagctgccc    1440
ctggtgaagg cctacaagct ccagagcggc gccagcgtgg tggcaggccc ccgcttcacc    1500
ggcggcgaca tcatccagtg caccgagaac ggcagcgccg ccaccatcta cgtgacccc     1560 gacgtgagct acagccagaa gtaccgcgcc cgcatccact acgccagcac cagccagatc    1620
```

-continued

```
accttcaccc tgagcctgga cgggccccc ttcaaccaat actacttcga caagaccatc    1680
aacaagggcg acaccctgac ctacaacagc ttcaacctgg ccagcttcag cacccctttc    1740
gagctgagcg gcaacaacct ccagatcggc gtgaccggcc tgagcgccgg cgacaaggtg    1800
tacatcgaca agatcgagtt catccccgtg aactag                              1836
```

<210> SEQ ID NO 66
<211> LENGTH: 611
<212> TYPE: PRT
<213> ORGANISM: Artificial Sequence
<220> FEATURE:
<223> OTHER INFORMATION: 5*Cry3A055 protein

<400> SEQUENCE: 66

| Met | Thr | Ser | Asn | Gly | Arg | Gln | Cys | Ala | Gly | Ile | Arg | Pro | Tyr | Asp | Gly |
|---|---|---|---|---|---|---|---|---|---|---|---|---|---|---|---|
| 1 | | | | 5 | | | | | 10 | | | | | 15 | |

| Arg | Gln | Gln | His | Arg | Gly | Leu | Asp | Ser | Ser | Thr | Thr | Lys | Asp | Val | Ile |
| | | | 20 | | | | | 25 | | | | | 30 | | |

| Gln | Lys | Gly | Ile | Ser | Val | Val | Gly | Asp | Leu | Leu | Gly | Val | Val | Gly | Phe |
| | | | 35 | | | | 40 | | | | | 45 | | | |

| Pro | Phe | Gly | Gly | Ala | Leu | Val | Ser | Phe | Tyr | Thr | Asn | Phe | Leu | Asn | Thr |
| 50 | | | | | 55 | | | | | 60 | | | | | |

| Ile | Trp | Pro | Ser | Glu | Asp | Pro | Trp | Lys | Ala | Phe | Met | Glu | Gln | Val | Glu |
| 65 | | | | 70 | | | | | 75 | | | | | 80 | |

| Ala | Leu | Met | Asp | Gln | Lys | Ile | Ala | Asp | Tyr | Ala | Lys | Asn | Lys | Ala | Leu |
| | | | 85 | | | | | 90 | | | | | 95 | | |

| Ala | Glu | Leu | Gln | Gly | Leu | Gln | Asn | Asn | Val | Glu | Asp | Tyr | Val | Ser | Ala |
| | | | 100 | | | | | 105 | | | | | 110 | | |

| Leu | Ser | Ser | Trp | Gln | Lys | Asn | Pro | Ala | Ala | Pro | Phe | Arg | Asn | Pro | His |
| | | | 115 | | | | | 120 | | | | | 125 | | |

| Ser | Gln | Gly | Arg | Ile | Arg | Glu | Leu | Phe | Ser | Gln | Ala | Glu | Ser | His | Phe |
| | 130 | | | | | 135 | | | | | 140 | | | | |

| Arg | Asn | Ser | Met | Pro | Ser | Phe | Ala | Ile | Ser | Gly | Tyr | Glu | Val | Leu | Phe |
| 145 | | | | | 150 | | | | | 155 | | | | | 160 |

| Leu | Thr | Thr | Tyr | Ala | Gln | Ala | Ala | Asn | Thr | His | Leu | Phe | Leu | Leu | Lys |
| | | | | 165 | | | | | 170 | | | | | 175 | |

| Asp | Ala | Gln | Ile | Tyr | Gly | Glu | Glu | Trp | Gly | Tyr | Glu | Lys | Glu | Asp | Ile |
| | | | 180 | | | | | 185 | | | | | 190 | | |

| Ala | Glu | Phe | Tyr | Lys | Arg | Gln | Leu | Lys | Leu | Thr | Gln | Glu | Tyr | Thr | Asp |
| | | | 195 | | | | | 200 | | | | | 205 | | |

| His | Cys | Val | Lys | Trp | Tyr | Asn | Val | Gly | Leu | Asp | Lys | Leu | Arg | Gly | Ser |
| | 210 | | | | | 215 | | | | | 220 | | | | |

| Ser | Tyr | Glu | Ser | Trp | Val | Asn | Phe | Asn | Arg | Tyr | Arg | Arg | Glu | Met | Thr |
| 225 | | | | | 230 | | | | | 235 | | | | | 240 |

| Leu | Thr | Val | Leu | Asp | Leu | Ile | Ala | Leu | Phe | Pro | Leu | Tyr | Asp | Val | Arg |
| | | | | 245 | | | | | 250 | | | | | 255 | |

| Leu | Tyr | Pro | Lys | Glu | Val | Lys | Thr | Glu | Leu | Thr | Arg | Asp | Val | Leu | Thr |
| | | | 260 | | | | | 265 | | | | | 270 | | |

| Asp | Pro | Ile | Val | Gly | Val | Asn | Asn | Leu | Arg | Gly | Tyr | Gly | Thr | Thr | Phe |
| | | | 275 | | | | | 280 | | | | | 285 | | |

| Ser | Asn | Ile | Glu | Asn | Tyr | Ile | Arg | Lys | Pro | His | Leu | Phe | Asp | Tyr | Leu |
| | 290 | | | | | 295 | | | | | 300 | | | | |

| His | Arg | Ile | Gln | Phe | His | Thr | Arg | Phe | Gln | Pro | Gly | Tyr | Tyr | Gly | Asn |
| 305 | | | | | 310 | | | | | 315 | | | | | 320 |

| Asp | Ser | Phe | Asn | Tyr | Trp | Ser | Gly | Asn | Tyr | Val | Ser | Thr | Arg | Pro | Ser |
| | | | | 325 | | | | | 330 | | | | | 335 | |

```
Ile Gly Ser Asn Asp Ile Ile Thr Ser Pro Phe Tyr Gly Asn Lys Ser
            340                 345                 350

Ser Glu Pro Val Gln Asn Leu Glu Phe Asn Gly Glu Lys Val Tyr Arg
        355                 360                 365

Ala Val Ala Asn Thr Asn Leu Ala Val Trp Pro Ser Ala Val Tyr Ser
370                 375                 380

Gly Val Thr Lys Val Glu Phe Ser Gln Tyr Asn Asp Gln Thr Asp Glu
385                 390                 395                 400

Ala Ser Thr Gln Thr Tyr Asp Ser Lys Arg Asn Val Gly Ala Val Ser
                405                 410                 415

Trp Asp Ser Ile Asp Gln Leu Pro Pro Glu Thr Thr Asp Glu Pro Leu
            420                 425                 430

Glu Lys Gly Tyr Ser His Gln Leu Asn Tyr Val Met Cys Phe Leu Met
        435                 440                 445

Gln Gly Ser Arg Gly Thr Ile Pro Val Leu Thr Trp Thr His Lys Ser
450                 455                 460

Val Asp Phe Phe Asn Met Ile Asp Ser Lys Lys Ile Thr Gln Leu Pro
465                 470                 475                 480

Leu Val Lys Ala Tyr Lys Leu Gln Ser Gly Ala Ser Val Val Ala Gly
                485                 490                 495

Pro Arg Phe Thr Gly Gly Asp Ile Ile Gln Cys Thr Glu Asn Gly Ser
            500                 505                 510

Ala Ala Thr Ile Tyr Val Thr Pro Asp Val Ser Tyr Ser Gln Lys Tyr
        515                 520                 525

Arg Ala Arg Ile His Tyr Ala Ser Thr Ser Gln Ile Thr Phe Thr Leu
530                 535                 540

Ser Leu Asp Gly Ala Pro Phe Asn Gln Tyr Tyr Phe Asp Lys Thr Ile
545                 550                 555                 560

Asn Lys Gly Asp Thr Leu Thr Tyr Asn Ser Phe Asn Leu Ala Ser Phe
                565                 570                 575

Ser Thr Pro Phe Glu Leu Ser Gly Asn Asn Leu Gln Ile Gly Val Thr
            580                 585                 590

Gly Leu Ser Ala Gly Asp Lys Val Tyr Ile Asp Lys Ile Glu Phe Ile
        595                 600                 605

Pro Val Asn
    610

<210> SEQ ID NO 67
<211> LENGTH: 1803
<212> TYPE: DNA
<213> ORGANISM: Artificial Sequence
<220> FEATURE:
<223> OTHER INFORMATION: mocry3A coding sequence

<400> SEQUENCE: 67
atgacggccg acaacaacac cgaggccctg gacagcagca ccaccaagga cgtgatccag      60
aagggcatca gcgtggtggg cgacctgctg ggcgtggtgg gcttcccctt cggcggcgcc     120
ctggtgagct tctacaccaa cttcctgaac accatctggc ccagcgagga cccctggaag     180
gccttcatgg agcaggtgga ggccctgatg gaccagaaga tcgccgacta cgccaagaac     240
aaggcactgg ccgagctaca gggcctccag aacaacgtgg aggactatgt gagcgccctg     300
agcagctggc agaagaaccc cgtctcgagc cgcaaccccc acagccaggg ccgcatccgc     360
gagctgttca gccaggccga gagccacttc cgcaacagca tgcccagctt cgccatcagc     420
ggctacgagg tgctgttcct gaccacctac gcccaggccg ccaacaccca cctgttcctg     480
```

```
ctgaaggacg cccaaatcta cggagaggag tggggctacg agaaggagga catcgccgag    540
ttctacaagc gccagctgaa gctgacccag gagtacaccg accactgcgt gaagtggtac    600
aacgtgggtc tagacaagct ccgcggcagc agctacgaga gctgggtgaa cttcaaccgc    660
taccgccgcg agatgaccct gaccgtgctg gacctgatcg ccctgttccc cctgtacgac    720
gtgcgcctgt accccaagga ggtgaagacc gagctgaccc gcgacgtgct gaccgacccc    780
atcgtgggcg tgaacaacct gcgcggctac ggcaccacct tcagcaacat cgagaactac    840
atccgcaagc ccaccctgtt cgactacctg caccgcatcc agttccacac gcgtttccag    900
cccggctact acggcaacga cagcttcaac tactggagcg gcaactacgt gagcacccgc    960
cccagcatcg gcagcaacga catcatcacc agccccttct acggcaacaa gagcagcgag   1020
cccgtgcaga accttgagtt caacggcgag aaggtgtacc gcgccgtggc taacaccaac   1080
ctggccgtgt ggcccctctgc agtgtacagc ggcgtgacca aggtggagtt cagccagtac   1140
aacgaccaga ccgacgaggc cagcacccag acctacgaca gcaagcgcaa cgtgggcgcc   1200
gtgagctggg acagcatcga ccagctgccc ccgagaccaa ccgacgagcc cctggagaag   1260
ggctacagcc accagctgaa ctacgtgatg tgcttcctga tgcagggcag ccgcggcacc   1320
atccccgtgc tgacctggac ccacaagagc gtcgacttct tcaacatgat cgacagcaag   1380
aagatcaccc agctgcccct ggtgaaggcc tacaagctcc agagcggcgc cagcgtggtg   1440
gcaggccccc gcttcaccgg cggcgacatc atccagtgca ccgagaacgg cagcgccgcc   1500
accatctacg tgacccccga cgtgagctac agccagaagt accgcgcccg catccactac   1560
gccagcacca gccagatcac cttcaccctg agcctggacg ggccccctt caaccaatac   1620
tacttcgaca gaccatcaa caagggcgac ccctgacct acaacagctt caacctggcc   1680
agcttcagca ccccctttcga gctgagcggc aacaacctcc agatcggcgt gaccggcctg   1740
agcgccggcg acaaggtgta catcgacaag atcgagttca tccccgtgaa ctagatctga   1800
gct                                                                 1803

<210> SEQ ID NO 68
<211> LENGTH: 597
<212> TYPE: PRT
<213> ORGANISM: Bacillus thuringiensis
<220> FEATURE:
<223> OTHER INFORMATION: moCry3A

<400> SEQUENCE: 68

Met Thr Ala Asp Asn Asn Thr Glu Ala Leu Asp Ser Ser Thr Thr Lys
1               5                   10                  15

Asp Val Ile Gln Lys Gly Ile Ser Val Val Gly Asp Leu Leu Gly Val
            20                  25                  30

Val Gly Phe Pro Phe Gly Gly Ala Leu Val Ser Phe Tyr Thr Asn Phe
        35                  40                  45

Leu Asn Thr Ile Trp Pro Ser Glu Asp Pro Trp Lys Ala Phe Met Glu
    50                  55                  60

Gln Val Glu Ala Leu Met Asp Gln Lys Ile Ala Asp Tyr Ala Lys Asn
65                  70                  75                  80

Lys Ala Leu Ala Glu Leu Gln Gly Leu Gln Asn Asn Val Glu Asp Tyr
                85                  90                  95

Val Ser Ala Leu Ser Ser Trp Gln Lys Asn Pro Val Ser Ser Arg Asn
            100                 105                 110

Pro His Ser Gln Gly Arg Ile Arg Glu Leu Phe Ser Gln Ala Glu Ser
        115                 120                 125
```

His Phe Arg Asn Ser Met Pro Ser Phe Ala Ile Ser Gly Tyr Glu Val
130                 135                 140

Leu Phe Leu Thr Thr Tyr Ala Gln Ala Ala Asn Thr His Leu Phe Leu
145                 150                 155                 160

Leu Lys Asp Ala Gln Ile Tyr Gly Glu Glu Trp Gly Tyr Glu Lys Glu
                165                 170                 175

Asp Ile Ala Glu Phe Tyr Lys Arg Gln Leu Lys Leu Thr Gln Glu Tyr
                180                 185                 190

Thr Asp His Cys Val Lys Trp Tyr Asn Val Gly Leu Asp Lys Leu Arg
            195                 200                 205

Gly Ser Ser Tyr Glu Ser Trp Val Asn Phe Asn Arg Tyr Arg Arg Glu
                210                 215                 220

Met Thr Leu Thr Val Leu Asp Leu Ile Ala Leu Phe Pro Leu Tyr Asp
225                 230                 235                 240

Val Arg Leu Tyr Pro Lys Glu Val Lys Thr Glu Leu Thr Arg Asp Val
                245                 250                 255

Leu Thr Asp Pro Ile Val Gly Val Asn Asn Leu Arg Gly Tyr Gly Thr
                260                 265                 270

Thr Phe Ser Asn Ile Glu Asn Tyr Ile Arg Lys Pro His Leu Phe Asp
                275                 280                 285

Tyr Leu His Arg Ile Gln Phe His Thr Arg Phe Gln Pro Gly Tyr Tyr
            290                 295                 300

Gly Asn Asp Ser Phe Asn Tyr Trp Ser Gly Asn Tyr Val Ser Thr Arg
305                 310                 315                 320

Pro Ser Ile Gly Ser Asn Asp Ile Ile Thr Ser Pro Phe Tyr Gly Asn
                325                 330                 335

Lys Ser Ser Glu Pro Val Gln Asn Leu Glu Phe Asn Gly Glu Lys Val
                340                 345                 350

Tyr Arg Ala Val Ala Asn Thr Asn Leu Ala Val Trp Pro Ser Ala Val
            355                 360                 365

Tyr Ser Gly Val Thr Lys Val Glu Phe Ser Gln Tyr Asn Asp Gln Thr
            370                 375                 380

Asp Glu Ala Ser Thr Gln Thr Tyr Asp Ser Lys Arg Asn Val Gly Ala
385                 390                 395                 400

Val Ser Trp Asp Ser Ile Asp Gln Leu Pro Pro Glu Thr Thr Asp Glu
                405                 410                 415

Pro Leu Glu Lys Gly Tyr Ser His Gln Leu Asn Tyr Val Met Cys Phe
                420                 425                 430

Leu Met Gln Gly Ser Arg Gly Thr Ile Pro Val Leu Thr Trp Thr His
            435                 440                 445

Lys Ser Val Asp Phe Phe Asn Met Ile Asp Ser Lys Lys Ile Thr Gln
            450                 455                 460

Leu Pro Leu Val Lys Ala Tyr Lys Leu Gln Ser Gly Ala Ser Val Val
465                 470                 475                 480

Ala Gly Pro Arg Phe Thr Gly Gly Asp Ile Ile Gln Cys Thr Glu Asn
                485                 490                 495

Gly Ser Ala Ala Thr Ile Tyr Val Thr Pro Asp Val Ser Tyr Ser Gln
            500                 505                 510

Lys Tyr Arg Ala Arg Ile His Tyr Ala Ser Thr Ser Gln Ile Thr Phe
            515                 520                 525

Thr Leu Ser Leu Asp Gly Ala Pro Phe Asn Gln Tyr Tyr Phe Asp Lys
530                 535                 540

Thr Ile Asn Lys Gly Asp Thr Leu Thr Tyr Asn Ser Phe Asn Leu Ala

```
545              550              555              560
Ser Phe Ser Thr Pro Phe Glu Leu Ser Gly Asn Asn Leu Gln Ile Gly
                565              570              575

Val Thr Gly Leu Ser Ala Gly Asp Lys Val Tyr Ile Asp Lys Ile Glu
            580              585              590

Phe Ile Pro Val Asn
        595

<210> SEQ ID NO 69
<211> LENGTH: 1807
<212> TYPE: DNA
<213> ORGANISM: Artificial Sequence
<220> FEATURE:
<223> OTHER INFORMATION: cry3A055 coding sequence

<400> SEQUENCE: 69
atgacggccg acaacaacac cgaggccctg acagcagca ccaccaagga cgtgatccag      60
aagggcatca gcgtggtggg cgacctgctg ggcgtggtgg gcttcccctt cggcggcgcc     120
ctggtgagct tctacaccaa cttcctgaac accatctggc ccagcgagga cccctggaag     180
gccttcatgg agcaggtgga ggccctgatg accagaaga tcgccgacta cgccaagaac     240
aaggcactgg ccgagctaca gggcctccag aacaacgtgg aggactatgt gagcgccctg     300
agcagctggc agaagaaccc cgctgcaccg ttccgcaacc ccacagcca gggccgcatc     360 cgcgagctgt tcagccaggc cgagagccac ttccgcaaca gcatgcccag cttcgccatc     420
agcggctacg aggtgctgtt cctgaccacc tacgcccagg ccgccaacac ccacctgttc     480
ctgctgaagg acgcccaaat ctacggagag gagtggggct acgagaagga ggacatcgcc     540
gagttctaca gcgccagct gaagctgacc caggagtaca ccgaccactg cgtgaagtgg     600
tacaacgtgg gtctagacaa gctccgcggc agcagctacg agagctgggt gaacttcaac     660
cgctaccgcc gcgagatgac cctgaccgtg ctggacctga tcgccctgtt ccccctgtac     720
gacgtgcgcc tgtaccccaa ggaggtgaag accgagctga cccgcgacgt gctgaccgac     780
cccatcgtgg gcgtgaacaa cctgcgcggc tacggcacca ccttcagcaa catcgagaac     840
tacatccgca agcccaccct gttcgactac ctgcaccgca tccagttcca cacgcgtttc     900
cagcccggct actacggcaa cgacagcttc aactactgga gcggcaacta cgtgagcacc     960
cgccccagca tcggcagcaa cgacatcatc accagcccct tctacggcaa caagagcagc    1020
gagcccgtgc agaaccttga gttcaacggc gagaaggtgt accgcgccgt ggctaacacc    1080
aacctggccg tgtggccctc tgcagtgtac agcggcgtga ccaaggtgga gttcagccag    1140
tacaacgacc agaccgacga ggccagcacc cagacctacg acagcaagcg caacgtgggc    1200
gccgtgagct gggacagcat cgaccagctg ccccccgaga ccaccgacga gcccctggag    1260
aagggctaca gccaccagct gaactacgtg atgtgcttcc tgatgcaggg cagccgcggc    1320
accatccccg tgctgacctg gacccacaag agcgtcgact tcttcaacat gatcgacagc    1380
aagaagatca cccagctgcc cctggtgaag gcctacaagc tccagagcgg cgccagcgtg    1440
gtggcaggcc cccgcttcac cggcggcgac atcatccagt gcaccgagaa cggcagcgcc    1500
gccaccatct acgtgacccc cgacgtgagc tacagccaga gtaccgcgc ccgcatccac    1560 tacgccagca ccagccagat caccttcacc ctgagcctgg acggggcccc cttcaaccaa    1620
tactacttcg acaagaccat caacaagggc gacaccctga cctacaacag cttcaacctg    1680
gccagcttca gcacccttt cgagctgagc ggcaacaacc tccagatcgg cgtgaccggc    1740
ctgagcgccg gcgacaaggt gtacatcgac aagatcgagt tcatccccgt gaactagatc    1800
```

```
                                                                    1807
tgagctc
```

<210> SEQ ID NO 70
<211> LENGTH: 598
<212> TYPE: PRT
<213> ORGANISM: Artificial Sequence
<220> FEATURE:
<223> OTHER INFORMATION: Cry3A055 protein

<400> SEQUENCE: 70

```
Met Thr Ala Asp Asn Asn Thr Glu Ala Leu Asp Ser Ser Thr Thr Lys
1               5                   10                  15

Asp Val Ile Gln Lys Gly Ile Ser Val Val Gly Asp Leu Leu Gly Val
            20                  25                  30

Val Gly Phe Pro Phe Gly Gly Ala Leu Val Ser Phe Tyr Thr Asn Phe
        35                  40                  45

Leu Asn Thr Ile Trp Pro Ser Glu Asp Pro Trp Lys Ala Phe Met Glu
    50                  55                  60

Gln Val Glu Ala Leu Met Asp Gln Lys Ile Ala Asp Tyr Ala Lys Asn
65                  70                  75                  80

Lys Ala Leu Ala Glu Leu Gln Gly Leu Gln Asn Asn Val Glu Asp Tyr
                85                  90                  95

Val Ser Ala Leu Ser Ser Trp Gln Lys Asn Pro Ala Ala Pro Phe Arg
            100                 105                 110

Asn Pro His Ser Gln Gly Arg Ile Arg Glu Leu Phe Ser Gln Ala Glu
        115                 120                 125

Ser His Phe Arg Asn Ser Met Pro Ser Phe Ala Ile Ser Gly Tyr Glu
    130                 135                 140

Val Leu Phe Leu Thr Thr Tyr Ala Gln Ala Ala Asn Thr His Leu Phe
145                 150                 155                 160

Leu Leu Lys Asp Ala Gln Ile Tyr Gly Glu Glu Trp Gly Tyr Glu Lys
                165                 170                 175

Glu Asp Ile Ala Glu Phe Tyr Lys Arg Gln Leu Lys Leu Thr Gln Glu
            180                 185                 190

Tyr Thr Asp His Cys Val Lys Trp Tyr Asn Val Gly Leu Asp Lys Leu
        195                 200                 205

Arg Gly Ser Ser Tyr Glu Ser Trp Val Asn Phe Asn Arg Tyr Arg Arg
    210                 215                 220

Glu Met Thr Leu Thr Val Leu Asp Leu Ile Ala Leu Phe Pro Leu Tyr
225                 230                 235                 240

Asp Val Arg Leu Tyr Pro Lys Glu Val Lys Thr Glu Leu Thr Arg Asp
                245                 250                 255

Val Leu Thr Asp Pro Ile Val Gly Val Asn Asn Leu Arg Gly Tyr Gly
            260                 265                 270

Thr Thr Phe Ser Asn Ile Glu Asn Tyr Ile Arg Lys Pro His Leu Phe
        275                 280                 285

Asp Tyr Leu His Arg Ile Gln Phe His Thr Arg Phe Gln Pro Gly Tyr
    290                 295                 300

Tyr Gly Asn Asp Ser Phe Asn Tyr Trp Ser Gly Asn Tyr Val Ser Thr
305                 310                 315                 320

Arg Pro Ser Ile Gly Ser Asn Asp Ile Ile Thr Ser Pro Phe Tyr Gly
                325                 330                 335

Asn Lys Ser Ser Glu Pro Val Gln Asn Leu Glu Phe Asn Gly Glu Lys
            340                 345                 350

Val Tyr Arg Ala Val Ala Asn Thr Asn Leu Ala Val Trp Pro Ser Ala
```

```
                    355                 360                 365
Val Tyr Ser Gly Val Thr Lys Val Glu Phe Ser Gln Tyr Asn Asp Gln
370                 375                 380

Thr Asp Glu Ala Ser Thr Gln Thr Tyr Asp Ser Lys Arg Asn Val Gly
385                 390                 395                 400

Ala Val Ser Trp Asp Ser Ile Asp Gln Leu Pro Pro Glu Thr Thr Asp
                405                 410                 415

Glu Pro Leu Glu Lys Gly Tyr Ser His Gln Leu Asn Tyr Val Met Cys
            420                 425                 430

Phe Leu Met Gln Gly Ser Arg Gly Thr Ile Pro Val Leu Thr Trp Thr
        435                 440                 445

His Lys Ser Val Asp Phe Phe Asn Met Ile Asp Ser Lys Lys Ile Thr
    450                 455                 460

Gln Leu Pro Leu Val Lys Ala Tyr Lys Leu Gln Ser Gly Ala Ser Val
465                 470                 475                 480

Val Ala Gly Pro Arg Phe Thr Gly Gly Asp Ile Ile Gln Cys Thr Glu
                485                 490                 495

Asn Gly Ser Ala Ala Thr Ile Tyr Val Thr Pro Asp Val Ser Tyr Ser
            500                 505                 510

Gln Lys Tyr Arg Ala Arg Ile His Tyr Ala Ser Thr Ser Gln Ile Thr
        515                 520                 525

Phe Thr Leu Ser Leu Asp Gly Ala Pro Phe Asn Gln Tyr Tyr Phe Asp
    530                 535                 540

Lys Thr Ile Asn Lys Gly Asp Thr Leu Thr Tyr Asn Ser Phe Asn Leu
545                 550                 555                 560

Ala Ser Phe Ser Thr Pro Phe Glu Leu Ser Gly Asn Asn Leu Gln Ile
                565                 570                 575

Gly Val Thr Gly Leu Ser Ala Gly Asp Lys Val Tyr Ile Asp Lys Ile
            580                 585                 590

Glu Phe Ile Pro Val Asn
        595
```

<210> SEQ ID NO 71
<211> LENGTH: 1947
<212> TYPE: DNA
<213> ORGANISM: Artificial Sequence
<220> FEATURE:
<223> OTHER INFORMATION: mocry1Ab coding sequence

<400> SEQUENCE: 71

```
atggacaaca accccaacat caacgagtgc atcccctaca actgcctgag caaccccgag      60
gtggaggtgc tgggcggcga gcgcatcgag accggctaca ccccatcga catcagcctg     120 agcctgaccc agttcctgct gagcgagttc gtgcccggcg ccggcttcgt gctgggcctg     180
gtggacatca tctggggcat cttcggcccc agccagtggg acgccttcct ggtgcagatc     240
gagcagttga taaaccaacg catagaggaa ttcgcccgca accaggccat cagccgcctg     300
gagggcctga gcaacctgta ccaaatctac gccgagagct tccgcgagtg ggaggccgac     360 ccaccaacc ccgccctgcg cgaggagatg cgcatccagt tcaacgacat gaacagcgcc     420
ctgaccaccg ccatccccct gttcgccgtg cagaactacc aggtgcccct gctgagcgtg     480
tacgtgcagg ccgccaacct gcacctgagc gtgctgcgcg acgtcagcgt gttcggccag     540
cgctggggct tcgacgccgc caccatcaac agccgctaca acgacctgac ccgcctgatc     600
ggcaactaca ccgaccacgc cgtgcgctgg tacaacaccg gcctgagcg cgtgtggggt     660 cccgacagcc gcgactggat caggtacaac cagttccgcc gcgagctgac cctgaccgtg     720
```

```
ctggacatcg tgagcctgtt ccccaactac gacagccgca cctaccccat ccgcaccgtg    780
agccagctga cccgcgagat ttacaccaac cccgtgctgg agaacttcga cggcagcttc    840
cgcggcagcg cccagggcat cgagggcagc atccgcagcc ccacctgat ggacatcctg     900 aacagcatca ccatctacac cgacgcccac cgcggcgagt actactggag cggccaccag    960
atcatggcca gccccgtcgg cttcagcggc cccgagttca ccttcccccct gtacggcacc   1020 atgggcaacg ctgcacctca gcagcgcatc gtggcacagc tgggccaggg agtgtaccgc    1080
accctgagca gcaccctgta ccgtcgacct tcaacatcg gcatcaacaa ccagcagctg     1140
agcgtgctgg acggcaccga gttcgcctac ggcaccagca gcaacctgcc cagcgccgtg    1200
taccgcaaga gcggcaccgt ggacagcctg gacgagatcc cccctcagaa caacaacgtg    1260
ccacctcgac agggcttcag ccaccgtctg agccacgtga gcatgttccg cagtggcttc    1320
agcaacagca gcgtgagcat catccgtgca cctatgttca gctggattca ccgcagtgcc    1380
gagttcaaca acatcatccc cagcagccag atcacccaga tcccccctga caagagcacc    1440
aacctgggca gcggcaccag cgtggtgaag ggccccggct tcaccggcgg cgacatcctg    1500
cgccgcacca gccccggcca gatcagcacc ctgcgcgtga acatcaccgc cccccctgagc   1560 cagcgctacc gcgtccgcat ccgctacgcc agcaccacca acctgcagtt ccacaccagc    1620
atcgacggcc gccccatcaa ccagggcaac ttcagcgcca ccatgagcag cggcagcaac    1680
ctgcagagcg gcagcttccg caccgtgggc ttcaccaccc ccttcaactt cagcaacggc    1740
agcagcgtgt tcaccctgag cgcccacgtg ttcaacagcg gcaacgaggt gtacatcgac    1800
cgcatcgagt tcgtgcccgc cgaggtgacc ttcgaggccg agtacgacct ggagagggct    1860
cagaaggccg tgaacgagct gttcaccagc agcaaccaga tcggcctgaa gaccgacgtg    1920
accgactacc acatcgatca ggtgtag                                       1947
```

<210> SEQ ID NO 72
<211> LENGTH: 648
<212> TYPE: PRT
<213> ORGANISM: Bacillus thuringiensis
<220> FEATURE:
<223> OTHER INFORMATION: Cry1Ab protein

<400> SEQUENCE: 72

```
Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140
```

-continued

```
Ile Pro Leu Phe Ala Val Gln Asn Tyr Gln Val Pro Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Gly Ser Ile Arg Ser Pro His Leu Met Asp Ile Leu Asn Ser Ile Thr
    290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
    450                 455                 460

Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
                485                 490                 495

Gly Asp Ile Leu Arg Arg Thr Ser Pro Gly Gln Ile Ser Thr Leu Arg
            500                 505                 510

Val Asn Ile Thr Ala Pro Leu Ser Gln Arg Tyr Arg Val Arg Ile Arg
        515                 520                 525

Tyr Ala Ser Thr Thr Asn Leu Gln Phe His Thr Ser Ile Asp Gly Arg
    530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575
```

```
Phe Ser Asn Gly Ser Ser Val Phe Thr Leu Ser Ala His Val Phe Asn
            580                 585                 590

Ser Gly Asn Glu Val Tyr Ile Asp Arg Ile Glu Phe Val Pro Ala Glu
        595                 600                 605

Val Thr Phe Glu Ala Glu Tyr Asp Leu Glu Arg Ala Gln Lys Ala Val
    610                 615                 620

Asn Glu Leu Phe Thr Ser Ser Asn Gln Ile Gly Leu Lys Thr Asp Val
625                 630                 635                 640

Thr Asp Tyr His Ile Asp Gln Val
            645

<210> SEQ ID NO 73
<211> LENGTH: 1971
<212> TYPE: DNA
<213> ORGANISM: Artificial Sequence
<220> FEATURE:
<223> OTHER INFORMATION: mocry1Ba coding sequence

<400> SEQUENCE: 73
```

| | | |
|---|---|---|
| atgaccagca accgcaagaa cgagaacgag atcatcaacg ccgtgagcaa ccacagcgcc | 60 |
| cagatggacc tgctgcccga cgcccgcatc gaggacagcc tgtgcatcgc cgagggcaac | 120 |
| aacatcgacc ccttcgtgag cgctagcacc gtgcagaccg gtatcaacat cgctggccgc | 180 |
| atcctgggcg tgctgggcgt gcccttcgcc ggccagctgg ctagcttcta cagcttcctg | 240 |
| gtcggtgagc tgtggccacg cggccgcgac cagtgggaaa tcttcctgga gcacgtggag | 300 |
| cagctgatca accagcagat caccgagaac gcccgcaaca ccgctcttgc ccgcctgcag | 360 |
| ggtctgggcg acagcttccg cgcctaccag cagagcctgg aggactggct ggagaaccgc | 420 |
| gacgacgccc gcacccgcag cgtgctgtac cccagtaca tcgccctgga gctggacttc | 480 |
| ctgaacgcca tgccctgtt cgccattcga accaggagg tgcccctgct gatggtgtac | 540 |
| gcccaggccg ccaacctgca cctgctgctg ctgcgcgacg ccagcctgtt cggcagcgag | 600 |
| ttcggcctga ccagcagga gatccagcgg tactacgagc gccaggtgga gcgcaccccgc | 660 |
| gactacagca ctactgcgt ggagtggtac aacaccggcc tgaacagctt aaggggcacc | 720 |
| aacgccgcca gctgggtgcg ctacaaccag ttccgccgcg acctgaccct gggcgtgctg | 780 |
| gacctggtgg ccctgttccc cagctacgac cccgcacct accccatcaa ccaccagcgcc | 840 |
| cagctgaccc gcgaggtgta caccgacgcc atcggcgcca ccggcgtgaa catggccagc | 900 |
| atgaactggt acaacaacaa cgcccccagc ttcagcgcca tcgaggccgc cgccatccgc | 960 |
| agcccccacc tgctggactt cctggagcag ctgaccatct tcagtgccag cagccgctgg | 1020 |
| agcaacaccc gccacatgac ctactggcgc ggccacacca tccagtctag acccatcggc | 1080 |
| ggcggcctga acaccagcac ccacggcgcc accaacacca gcatcaaccc cgtgaccctg | 1140 |
| cgcttcgcct cccgagacgt ctaccgcacc gagagctacg ccggcgtgct gctgtggggc | 1200 |
| atctacctgg agcccatcca tggcgtgccc accgtgcgct tcaacttcac caacccccag | 1260 |
| aacatcagcg accgcggcac cgccaactac agccagccct acgagagccc cgggttgcag | 1320 |
| ctgaaggaca gcgagaccga gctgcccccc gagaccaccg agcgcccaa ctacgagagc | 1380 |
| tacagccacc gcctgagcca catcggcatc atcttgcaga ccgcgtgaa cgtgcccgtg | 1440 |
| tacagctgga cccaccgcag cgccgaccgc accaacacca tcggccccaa ccgcatcacc | 1500 |
| cagatcccca tggtgaaggc cagcgagctg cccagggca ccaccgtggt tcgcggcccc | 1560 |
| ggcttcaccg gaggcgacat cctgcgacgc accaacaccg gcggcttcgg ccccatccgc | 1620 |

```
gtgaccgtga acggcccccct gacccagcgc taccgcatcg gcttccgcta cgccagcacc   1680
gtggacttcg acttcttcgt gagccgcggc ggcaccaccg tgaacaactt ccgcttcctg   1740
cgcaccatga acagcggcga cgagctgaag tacggcaact tcgtgcgccg cgccttcacc   1800 accccccttca ccttcacccca gatccaggac atcatccgca ccagcatcca gggcctgagc   1860
ggcaacggcg aggtgtacat cgacaagatc gagatcatcc ccgtgaccgc caccttcgag   1920
gccgagtacg acctagagcg cgcccaggag gccgtgaacg ccctgttcta g   1971
```

<210> SEQ ID NO 74
<211> LENGTH: 656
<212> TYPE: PRT
<213> ORGANISM: Bacillus thuringiensis
<220> FEATURE:
<223> OTHER INFORMATION: Cry1B protein

<400> SEQUENCE: 74

```
Met Thr Ser Asn Arg Lys Asn Glu Asn Glu Ile Ile Asn Ala Val Ser
1               5                   10                  15

Asn His Ser Ala Gln Met Asp Leu Leu Pro Asp Ala Arg Ile Glu Asp
            20                  25                  30

Ser Leu Cys Ile Ala Glu Gly Asn Asn Ile Asp Pro Phe Val Ser Ala
        35                  40                  45

Ser Thr Val Gln Thr Gly Ile Asn Ile Ala Gly Arg Ile Leu Gly Val
    50                  55                  60

Leu Gly Val Pro Phe Ala Gly Gln Leu Ala Ser Phe Tyr Ser Phe Leu
65                  70                  75                  80

Val Gly Glu Leu Trp Pro Arg Gly Arg Asp Gln Trp Glu Ile Phe Leu
                85                  90                  95

Glu His Val Glu Gln Leu Ile Asn Gln Gln Ile Thr Glu Asn Ala Arg
            100                 105                 110

Asn Thr Ala Leu Ala Arg Leu Gln Gly Leu Gly Asp Ser Phe Arg Ala
        115                 120                 125

Tyr Gln Gln Ser Leu Glu Asp Trp Leu Glu Asn Arg Asp Asp Ala Arg
    130                 135                 140

Thr Arg Ser Val Leu Tyr Thr Gln Tyr Ile Ala Leu Glu Leu Asp Phe
145                 150                 155                 160

Leu Asn Ala Met Pro Leu Phe Ala Ile Arg Asn Gln Glu Val Pro Leu
                165                 170                 175

Leu Met Val Tyr Ala Gln Ala Ala Asn Leu His Leu Leu Leu Leu Arg
            180                 185                 190

Asp Ala Ser Leu Phe Gly Ser Glu Phe Gly Leu Thr Ser Gln Glu Ile
        195                 200                 205

Gln Arg Tyr Tyr Glu Arg Gln Val Glu Arg Thr Arg Asp Tyr Ser Asp
    210                 215                 220

Tyr Cys Val Glu Trp Tyr Asn Thr Gly Leu Asn Ser Leu Arg Gly Thr
225                 230                 235                 240

Asn Ala Ala Ser Trp Val Arg Tyr Asn Gln Phe Arg Arg Asp Leu Thr
                245                 250                 255

Leu Gly Val Leu Asp Leu Val Ala Leu Phe Pro Ser Tyr Asp Thr Arg
            260                 265                 270

Thr Tyr Pro Ile Asn Thr Ser Ala Gln Leu Thr Arg Glu Val Tyr Thr
        275                 280                 285

Asp Ala Ile Gly Ala Thr Gly Val Asn Met Ala Ser Met Asn Trp Tyr
    290                 295                 300

Asn Asn Asn Ala Pro Ser Phe Ser Ala Ile Glu Ala Ala Ala Ile Arg
```

```
                305                 310                 315                 320
Ser Pro His Leu Leu Asp Phe Leu Glu Gln Leu Thr Ile Phe Ser Ala
                325                 330                 335
Ser Ser Arg Trp Ser Asn Thr Arg His Met Thr Tyr Trp Arg Gly His
                340                 345                 350
Thr Ile Gln Ser Arg Pro Ile Gly Gly Leu Asn Thr Ser Thr His
                355                 360                 365
Gly Ala Thr Asn Thr Ser Ile Asn Pro Val Thr Leu Arg Phe Ala Ser
            370                 375                 380
Arg Asp Val Tyr Arg Thr Glu Ser Tyr Ala Gly Val Leu Leu Trp Gly
385                 390                 395                 400
Ile Tyr Leu Glu Pro Ile His Gly Val Pro Thr Val Arg Phe Asn Phe
                405                 410                 415
Thr Asn Pro Gln Asn Ile Ser Asp Arg Gly Thr Ala Asn Tyr Ser Gln
                420                 425                 430
Pro Tyr Glu Ser Pro Gly Leu Gln Leu Lys Asp Ser Glu Thr Glu Leu
                435                 440                 445
Pro Pro Glu Thr Thr Glu Arg Pro Asn Tyr Glu Ser Tyr Ser His Arg
450                 455                 460
Leu Ser His Ile Gly Ile Ile Leu Gln Ser Arg Val Asn Val Pro Val
465                 470                 475                 480
Tyr Ser Trp Thr His Arg Ser Ala Asp Arg Thr Asn Thr Ile Gly Pro
                485                 490                 495
Asn Arg Ile Thr Gln Ile Pro Met Val Lys Ala Ser Glu Leu Pro Gln
                500                 505                 510
Gly Thr Thr Val Val Arg Gly Pro Gly Phe Thr Gly Gly Asp Ile Leu
                515                 520                 525
Arg Arg Thr Asn Thr Gly Gly Phe Gly Pro Ile Arg Val Thr Val Asn
            530                 535                 540
Gly Pro Leu Thr Gln Arg Tyr Arg Ile Gly Phe Arg Tyr Ala Ser Thr
545                 550                 555                 560
Val Asp Phe Asp Phe Phe Val Ser Arg Gly Gly Thr Thr Val Asn Asn
                565                 570                 575
Phe Arg Phe Leu Arg Thr Met Asn Ser Gly Asp Glu Leu Lys Tyr Gly
                580                 585                 590
Asn Phe Val Arg Arg Ala Phe Thr Thr Pro Phe Thr Phe Thr Gln Ile
                595                 600                 605
Gln Asp Ile Ile Arg Thr Ser Ile Gln Gly Leu Ser Gly Asn Gly Glu
            610                 615                 620
Val Tyr Ile Asp Lys Ile Glu Ile Ile Pro Val Thr Ala Thr Phe Glu
625                 630                 635                 640
Ala Glu Tyr Asp Leu Glu Arg Ala Gln Glu Ala Val Asn Ala Leu Phe
                645                 650                 655

<210> SEQ ID NO 75
<211> LENGTH: 1950
<212> TYPE: DNA
<213> ORGANISM: Artificial Sequence
<220> FEATURE:
<223> OTHER INFORMATION: mocry1Fa coding sequence

<400> SEQUENCE: 75
atggagaaca acatccagaa ccagtgcgtg ccgtacaact gcctcaacaa cccggaggtg      60
gagatcctca cgaggagcg ctccaccggc cgctcccgc tcgacatctc cctctccctc      120
acccgcttcc tcctctccga gttcgtgccg ggcgtgggcg tggccttcgg cctcttcgac      180
```

```
ctcatctggg gcttcatcac cccgtccgac tggtccctct tcctcctcca gatcgagcag    240
ctcatcgagc agcgcatcga gaccctggag cgcaaccgcg ccatcaccac cctccgcggc    300
ctcgccgact cctacgaaat ctacatcgag gccctccgcg agtgggaggc caacccgaac    360
aacgcccagc tccgcgagga cgtgcgcatc cgcttcgcca acaccgacga cgccctcatc    420
accgccatca caacttcac cctcacctcc ttcgagatcc cgctcctctc cgtgtacgtg    480
caggccgcca acctccacct ctccctcctc cgcgacgccg tgtccttcgg ccagggctgg    540
ggcctcgaca tcgccaccgt gaacaaccac tacaaccgcc tcatcaacct catccaccgc    600
tacaccaagc actgcctcga cacctacaac cagggcctgg agaacctccg cggcaccaac    660
acccgccagt gggcccgctt caaccagttc cgccgcgacc tcaccctcac cgtgctcgac    720
atcgtggccc tcttcccgaa ctacgacgtg cgcacctacc cgatccagac ctcctcccag    780
ctcacccgcg aaatctacac cctcctccgt gatcgaggact cccggtgtc cgccaacatc    840 ccgaacggct tcaaccgcgc cgagttcggc gtgcgcccgc gcacctcat ggacttcatg    900 aactccctct tcgtgaccgc cgagaccgtg cgctcccaga ccgtgtgggg cggccacctc    960
gtgtcctccc gcaacaccgc cggcaaccgc atcaacttcc cgtcctacgg cgtgttcaac   1020
ccgggcggcg ccatctggat cgccgacgag gacccgcgcc cgttctaccg cacccctctcc   1080 gacccggtgt tcgtgcgcgg cggcttcggc aacccgcact acgtgctcgg cctccgcggc   1140
gtggccttcc agcagaccgg caccaaccac acccgcacct tccgcaactc cggcaccatc   1200
gactccctcg acgagatccc gccgcaggac aactccggcg ccccgtggaa cgactactcc   1260
cacgtgctca ccacgtgac cttcgtgcgc tggccgggcg agatatccgg ctccgactcc   1320
tggcgtgcac cgatgttctc ctggaccac cgctccgcca ccccgaccaa caccatcgac   1380
ccggagcgca tcacccagat cccgctcgtg aaggcccaca ccctccagtc cggcaccacc   1440
gtggtgcgcg gccgggcttt caccggcggc gacatcctcc gccgcacctc cggcggcccg   1500
ttcgcctaca ccatcgtgaa catcaacggc cagctcccgc agcgctaccg cgcccgcatc   1560
cgctacgcct ccaccaccaa cctccgcatc tacgtgaccg tggccggcga gcgcatcttc   1620
gccggccagt tcaacaagac catggacacc ggcgaccgc tcaccttcca gtccttctcc   1680
tacgccacca tcaacaccgc cttcaccttc ccgatgtccc agtcctcctt caccgtgggc   1740
gccgacacct tctcctccgg caacgaggtg tacatcgacc gcttcgagct gatcccggtg   1800
accgccacct tcgaggccga gtacgacctg gagcgcgccc agaaggccgt gaacgccctc   1860
ttcacctcca tcaaccagat cggcatcaag accgacgtga ccgactacca catcgaccag   1920
gtgtccaacc tcgtggactg cttaagctag                                    1950
```

<210> SEQ ID NO 76
<211> LENGTH: 649
<212> TYPE: PRT
<213> ORGANISM: Bacillus thguringiensis
<220> FEATURE:
<223> OTHER INFORMATION: Cry1F protein

<400> SEQUENCE: 76

```
Met Glu Asn Asn Ile Gln Asn Gln Cys Val Pro Tyr Asn Cys Leu Asn
1               5                  10                  15

Asn Pro Glu Val Glu Ile Leu Asn Glu Glu Arg Ser Thr Gly Arg Leu
            20                  25                  30

Pro Leu Asp Ile Ser Leu Ser Leu Thr Arg Phe Leu Leu Ser Glu Phe
        35                  40                  45
```

Val Pro Gly Val Gly Val Ala Phe Gly Leu Phe Asp Leu Ile Trp Gly
 50                  55                  60

Phe Ile Thr Pro Ser Asp Trp Ser Leu Phe Leu Gln Ile Glu Gln
 65                  70                  75                  80

Leu Ile Glu Gln Arg Ile Glu Thr Leu Glu Arg Asn Arg Ala Ile Thr
                 85                  90                  95

Thr Leu Arg Gly Leu Ala Asp Ser Tyr Glu Ile Tyr Ile Glu Ala Leu
            100                 105                 110

Arg Glu Trp Glu Ala Asn Pro Asn Asn Ala Gln Leu Arg Glu Asp Val
        115                 120                 125

Arg Ile Arg Phe Ala Asn Thr Asp Asp Ala Leu Ile Thr Ala Ile Asn
    130                 135                 140

Asn Phe Thr Leu Thr Ser Phe Glu Ile Pro Leu Leu Ser Val Tyr Val
145                 150                 155                 160

Gln Ala Ala Asn Leu His Leu Ser Leu Leu Arg Asp Ala Val Ser Phe
                165                 170                 175

Gly Gln Gly Trp Gly Leu Asp Ile Ala Thr Val Asn Asn His Tyr Asn
            180                 185                 190

Arg Leu Ile Asn Leu Ile His Arg Tyr Thr Lys His Cys Leu Asp Thr
        195                 200                 205

Tyr Asn Gln Gly Leu Glu Asn Leu Arg Gly Thr Asn Thr Arg Gln Trp
    210                 215                 220

Ala Arg Phe Asn Gln Phe Arg Arg Asp Leu Thr Leu Thr Val Leu Asp
225                 230                 235                 240

Ile Val Ala Leu Phe Pro Asn Tyr Asp Val Arg Thr Tyr Pro Ile Gln
                245                 250                 255

Thr Ser Ser Gln Leu Thr Arg Glu Ile Tyr Thr Ser Ser Val Ile Glu
            260                 265                 270

Asp Ser Pro Val Ser Ala Asn Ile Pro Asn Gly Phe Asn Arg Ala Glu
        275                 280                 285

Phe Gly Val Arg Pro Pro His Leu Met Asp Phe Met Asn Ser Leu Phe
    290                 295                 300

Val Thr Ala Glu Thr Val Arg Ser Gln Thr Val Trp Gly Gly His Leu
305                 310                 315                 320

Val Ser Ser Arg Asn Thr Ala Gly Asn Arg Ile Asn Phe Pro Ser Tyr
                325                 330                 335

Gly Val Phe Asn Pro Gly Gly Ala Ile Trp Ile Ala Asp Glu Asp Pro
            340                 345                 350

Arg Pro Phe Tyr Arg Thr Leu Ser Asp Pro Val Phe Arg Gly Gly
        355                 360                 365

Phe Gly Asn Pro His Tyr Val Leu Gly Leu Arg Gly Val Ala Phe Gln
    370                 375                 380

Gln Thr Gly Thr Asn His Thr Arg Thr Phe Arg Asn Ser Gly Thr Ile
385                 390                 395                 400

Asp Ser Leu Asp Glu Ile Pro Pro Gln Asp Asn Ser Gly Ala Pro Trp
                405                 410                 415

Asn Asp Tyr Ser His Val Leu Asn His Val Thr Phe Val Arg Trp Pro
            420                 425                 430

Gly Glu Ile Ser Gly Ser Asp Ser Trp Arg Ala Pro Met Phe Ser Trp
        435                 440                 445

Thr His Arg Ser Ala Thr Pro Thr Asn Thr Ile Asp Pro Glu Arg Ile
    450                 455                 460

Thr Gln Ile Pro Leu Val Lys Ala His Thr Leu Gln Ser Gly Thr Thr
465                 470                 475                 480

```
Val Val Arg Gly Pro Gly Phe Thr Gly Gly Asp Ile Leu Arg Arg Thr
                485                 490                 495

Ser Gly Gly Pro Phe Ala Tyr Thr Ile Val Asn Ile Asn Gly Gln Leu
            500                 505                 510

Pro Gln Arg Tyr Arg Ala Arg Ile Arg Tyr Ala Ser Thr Thr Asn Leu
        515                 520                 525

Arg Ile Tyr Val Thr Val Ala Gly Glu Arg Ile Phe Ala Gly Gln Phe
    530                 535                 540

Asn Lys Thr Met Asp Thr Gly Asp Pro Leu Thr Phe Gln Ser Phe Ser
545                 550                 555                 560

Tyr Ala Thr Ile Asn Thr Ala Phe Thr Phe Pro Met Ser Gln Ser Ser
                565                 570                 575

Phe Thr Val Gly Ala Asp Thr Phe Ser Ser Gly Asn Glu Val Tyr Ile
            580                 585                 590

Asp Arg Phe Glu Leu Ile Pro Val Thr Ala Thr Phe Glu Ala Glu Tyr
        595                 600                 605

Asp Leu Glu Arg Ala Gln Lys Ala Val Asn Ala Leu Phe Thr Ser Ile
    610                 615                 620

Asn Gln Ile Gly Ile Lys Thr Asp Val Thr Asp Tyr His Ile Asp Gln
625                 630                 635                 640

Val Ser Asn Leu Val Asp Cys Leu Ser
                645
```

```
<210> SEQ ID NO 77
<211> LENGTH: 3469
<212> TYPE: DNA
<213> ORGANISM: Bacillus thuringiensis
<220> FEATURE:
<221> NAME/KEY: misc_feature
<222> LOCATION: (1)..(3469)
<223> OTHER INFORMATION: cry8Aa coding sequence

<400> SEQUENCE: 77
atgagtccaa ataatcaaaa tgaatatgaa attatagatg cgacaccttc tacatctgta      60
tccagtgatt ctaacagata cccttttgcg aatgagccaa cagatgcgtt acaaaatatg     120
aattataaag attatctgaa aatgtctggg ggagagaatc ctgaattatt tggaaatccg     180
gagacgttta ttagttcatc cacgattcaa actggaattg gcattgttgg tcgaatacta     240
ggagctttag gggttccatt tgctagtcag atagctagtt tctatagttt cattgttggt     300
caattatggc cgtcaaagag cgtagatata tggggagaaa ttatggaacg agtggaagaa     360
ctcgttgatc aaaaaataga aaaatatgta aaagataagg ctcttgctga attaaaaggg     420
ctaggaaatg ctttggatgt atatcagcag tcacttgaag attggctgga aaatcgcaat     480
gatgcaagaa ctagaagtgt tgtttctaat caatttatag ctttagatct taactttgtt     540
agttcaattc catcttttgc agtatccgga cacgaagtac tattattagc agtatatgca     600
caggctgtga acctacattt attgttatta agagatgctt ctatttttgg agaagagtgg     660
ggatttacac caggtgaaat ttctagattt tataatcgtc aagtgcaact taccgctgaa     720
tattcagact attgtgtaaa gtggtataaa atcggcttag ataaattgaa aggtaccact     780
tctaaaagtt ggctgaatta tcatcagttc cgtagagaga tgacattact ggtattagat     840
ttggtggcgt tatttccaaa ctatgacaca catatgtatc caatcgaaac aacagctcaa     900
cttacacggg atgtgtatac agatccgata gcatttaaca tagtgacaag tactggattc     960
tgcaaccctt ggtcaaccca cagtggtatt ctttttttatg aagttgaaaa caacgtaatt    1020
```

```
cgtccgccac acttgtttga tatactcagc tcagtagaaa ttaatacaag tagaggggt     1080 attacgttaa ataatgatgc atatataaac tactggtcag gacatacct aaaatatcgt     1140 agaacagctg attcgaccgt aacatacaca gctaattacg gtcgaatcac ttcagaaaag    1200
aattcatttg cacttgagga tagggatatt tttgaaatta attcaactgt ggcaaaccta    1260
gctaattact accaaaaggc atatggtgtg ccgggatctt ggttccatat ggtaaaagg     1320 ggaacctcat caacaacagc gtatttatat tcaaaaacac atacagctct ccaagggtgt    1380
acacaggttt atgaatcaag tgatgaaata cctctagata gaactgtacc ggtagctgaa    1440
agctatagtc atagattatc tcatattacc tcccattctt tctctaaaaa tgggagtgca    1500
tactatggga gtttccctgt atttgtttgg acacatacta gtgcggattt aaataataca    1560
atatattcag ataaaatcac tcaaattcca gcggtaaagg gagacatgtt atatctaggg    1620
ggttccgtag tacagggtcc tggatttaca ggaggagata tattaaaaag aaccaatcct    1680
agcatattag ggacctttgc ggttacagta aatgggtcgt tatcacaaag atatcgtgta    1740
agaattcgct atgcctctac aacagatttt gaatttactc tataccttgg cgacacaata    1800 gaaaaaata gatttaacaa aactatggat aatgggcat ctttaacgta tgaaacattt    1860
aaattcgcaa gtttcattac tgatttccaa ttcagagaaa cacaagataa aatactccta    1920
tccatgggtg atttagctc cggtcaagaa gtttatatag accgaatcga attcatccca    1980
gtagatgaga catatgaggc ggaacaagat ttagaagcgg cgaagaaagc agtgaatgcc    2040
ttgtttacga atacaaaaga tggcttacga ccaggtgtaa cggattatga agtaaatcaa    2100
gcggcaaact tagtggaatg cctatcggat gatttatatc caaatgaaaa acgattgtta    2160
tttgatgcgg tgagagaggc aaaacgcctc agtggggcac gtaacttact acaagatcca    2220
gatttccaag agataaacgg agaaaatgga tgggcggcaa gtacgggaat tgagattgta    2280 gaagggatg ctgtatttaa aggacgttat ctacgcctac caggtgcacg agaaattgat    2340
acggaaacgt atccaacgta tctgtatcaa aaagtagagg aaggtgtatt aaaaccatac    2400
acaagatata gactgagagg gtttgtggga agtagtcaag gattagaaat ttatacgata    2460
cgtcaccaaa cgaatcgaat tgtaaagaat gtaccagatg atttattgcc agatgtatct    2520
cctgtaaact ctgatggcag tatcaatcga tgcagcgaac aaaagtatgt gaatagccgt    2580
ttagaaggag aaaaccgttc tggtgatgca catgagttct cgctccctat cgatataggga   2640 gagctggatt acaatgaaaa tgcaggaata tgggttggat ttaagattac ggacccagag    2700
ggatacgcaa cacttggaaa tcttgaatta gtcgaagagg gaccttttgt caggagacgca  2760 ttagagcgct tgcaaagaga agaacaacag tggaagattc aaatgacaag aagacgtgaa    2820
gagacagata aagatacat ggcatcgaaa caagcgtag atcgttata tgccgattat     2880 caggatcaac aactgaatcc tgatgtagag attacagatc ttactgcggc tcaagatctg    2940
atacagtcca ttccttacgt atataacgaa atgttcccag aaataccagg gatgaactat    3000
acgaagttta cagaattaac agatcgactc caacaagcgt ggaatttgta tgatcagcga    3060
aatgccatac caaatggtga ttttcgaaat gggttaagta attggaatgc aacgcctggc    3120
gtagaagtac aacaaatcaa tcatacatct gtccttgtga ttccaaactg ggatgaacaa    3180
gtttcacaac agtttacagt tcaaccgaat caaagatatg tattacgagt tactgcaaga    3240
aaagaagggg taggaaatgg atatgtaagt attcgtgatg gtggaaatca atcagaaacg    3300
cttactttta gtgcaagcga ttatgataca aatggtgtgt ataatgacca aaccggctat    3360
atcacaaaaa cagtgacatt catcccgtat acagatcaaa tgtggattga aataagtgaa    3420
```

```
acagaaggta cgttctatat agaaagtgta gaattgattg tagacgtag          3469
```

<210> SEQ ID NO 78
<211> LENGTH: 1156
<212> TYPE: PRT
<213> ORGANISM: Bacillus thuringiensis
<220> FEATURE:
<221> NAME/KEY: MISC_FEATURE
<222> LOCATION: (1)..(1156)
<223> OTHER INFORMATION: Cry8Aa protein

<400> SEQUENCE: 78

```
Met Ser Pro Asn Asn Gln Asn Glu Tyr Glu Ile Ile Asp Ala Thr Pro
1               5                   10                  15

Ser Thr Ser Val Ser Ser Asp Ser Asn Arg Tyr Pro Phe Ala Asn Glu
            20                  25                  30

Pro Thr Asp Ala Leu Gln Asn Met Asn Tyr Lys Asp Tyr Leu Lys Met
        35                  40                  45

Ser Gly Gly Glu Asn Pro Glu Leu Phe Gly Asn Pro Glu Thr Phe Ile
    50                  55                  60

Ser Ser Ser Thr Ile Gln Thr Gly Ile Gly Ile Val Gly Arg Ile Leu
65                  70                  75                  80

Gly Ala Leu Gly Val Pro Phe Ala Ser Gln Ile Ala Ser Phe Tyr Ser
                85                  90                  95

Phe Ile Val Gly Gln Leu Trp Pro Ser Lys Ser Val Asp Ile Trp Gly
            100                 105                 110

Glu Ile Met Glu Arg Val Glu Glu Leu Val Asp Gln Lys Ile Glu Lys
        115                 120                 125

Tyr Val Lys Asp Lys Ala Leu Ala Glu Leu Lys Gly Leu Gly Asn Ala
    130                 135                 140

Leu Asp Val Tyr Gln Gln Ser Leu Glu Asp Trp Leu Glu Asn Arg Asn
145                 150                 155                 160

Asp Ala Arg Thr Arg Ser Val Val Ser Asn Gln Phe Ile Ala Leu Asp
                165                 170                 175

Leu Asn Phe Val Ser Ser Ile Pro Ser Phe Ala Val Ser Gly His Glu
            180                 185                 190

Val Leu Leu Leu Ala Val Tyr Ala Gln Ala Val Asn Leu His Leu Leu
        195                 200                 205

Leu Leu Arg Asp Ala Ser Ile Phe Gly Glu Glu Trp Gly Phe Thr Pro
    210                 215                 220

Gly Glu Ile Ser Arg Phe Tyr Asn Arg Gln Val Gln Leu Thr Ala Glu
225                 230                 235                 240

Tyr Ser Asp Tyr Cys Val Lys Trp Tyr Lys Ile Gly Leu Asp Lys Leu
                245                 250                 255

Lys Gly Thr Thr Ser Lys Ser Trp Leu Asn Tyr His Gln Phe Arg Arg
            260                 265                 270

Glu Met Thr Leu Leu Val Leu Asp Leu Val Ala Leu Phe Pro Asn Tyr
        275                 280                 285

Asp Thr His Met Tyr Pro Ile Glu Thr Thr Ala Gln Leu Thr Arg Asp
    290                 295                 300

Val Tyr Thr Asp Pro Ile Ala Phe Asn Ile Val Thr Ser Thr Gly Phe
305                 310                 315                 320

Cys Asn Pro Trp Ser Thr His Ser Gly Ile Leu Phe Tyr Glu Val Glu
                325                 330                 335

Asn Asn Val Ile Arg Pro Pro His Leu Phe Asp Ile Leu Ser Ser Val
            340                 345                 350
```

```
Glu Ile Asn Thr Ser Arg Gly Gly Ile Thr Leu Asn Asn Asp Ala Tyr
        355                 360                 365

Ile Asn Tyr Trp Ser Gly His Thr Leu Lys Tyr Arg Arg Thr Ala Asp
    370                 375                 380

Ser Thr Val Thr Tyr Thr Ala Asn Tyr Gly Arg Ile Thr Ser Glu Lys
385                 390                 395                 400

Asn Ser Phe Ala Leu Glu Asp Arg Asp Ile Phe Glu Ile Asn Ser Thr
                405                 410                 415

Val Ala Asn Leu Ala Asn Tyr Tyr Gln Lys Ala Tyr Gly Val Pro Gly
            420                 425                 430

Ser Trp Phe His Met Val Lys Arg Gly Thr Ser Ser Thr Thr Ala Tyr
            435                 440                 445

Leu Tyr Ser Lys Thr His Thr Ala Leu Gln Gly Cys Thr Gln Val Tyr
    450                 455                 460

Glu Ser Ser Asp Glu Ile Pro Leu Asp Arg Thr Val Pro Val Ala Glu
465                 470                 475                 480

Ser Tyr Ser His Arg Leu Ser His Ile Thr Ser His Ser Phe Ser Lys
                485                 490                 495

Asn Gly Ser Ala Tyr Tyr Gly Ser Phe Pro Val Phe Val Trp Thr His
            500                 505                 510

Thr Ser Ala Asp Leu Asn Asn Thr Ile Tyr Ser Asp Lys Ile Thr Gln
            515                 520                 525

Ile Pro Ala Val Lys Gly Asp Met Leu Tyr Leu Gly Gly Ser Val Val
530                 535                 540

Gln Gly Pro Gly Phe Thr Gly Gly Asp Ile Leu Lys Arg Thr Asn Pro
545                 550                 555                 560

Ser Ile Leu Gly Thr Phe Ala Val Thr Val Asn Gly Ser Leu Ser Gln
                565                 570                 575

Arg Tyr Arg Val Arg Ile Arg Tyr Ala Ser Thr Thr Asp Phe Glu Phe
            580                 585                 590

Thr Leu Tyr Leu Gly Asp Thr Ile Glu Lys Asn Arg Phe Asn Lys Thr
            595                 600                 605

Met Asp Asn Gly Ala Ser Leu Thr Tyr Glu Thr Phe Lys Phe Ala Ser
    610                 615                 620

Phe Ile Thr Asp Phe Gln Phe Arg Glu Thr Gln Asp Lys Ile Leu Leu
625                 630                 635                 640

Ser Met Gly Asp Phe Ser Ser Gly Gln Glu Val Tyr Ile Asp Arg Ile
                645                 650                 655

Glu Phe Ile Pro Val Asp Glu Thr Tyr Glu Ala Glu Gln Asp Leu Glu
            660                 665                 670

Ala Ala Lys Lys Ala Val Asn Ala Leu Phe Thr Asn Thr Lys Asp Gly
            675                 680                 685

Leu Arg Pro Gly Val Thr Asp Tyr Glu Val Asn Gln Ala Ala Asn Leu
    690                 695                 700

Val Glu Cys Leu Ser Asp Asp Leu Tyr Pro Asn Glu Lys Arg Leu Leu
705                 710                 715                 720

Phe Asp Ala Val Arg Glu Ala Lys Arg Leu Ser Gly Ala Arg Asn Leu
                725                 730                 735

Leu Gln Asp Pro Asp Phe Gln Glu Ile Asn Gly Glu Asn Gly Trp Ala
            740                 745                 750

Ala Ser Thr Gly Ile Glu Ile Val Glu Gly Asp Ala Val Phe Lys Gly
            755                 760                 765

Arg Tyr Leu Arg Leu Pro Gly Ala Arg Glu Ile Asp Thr Glu Thr Tyr
    770                 775                 780
```

Pro Thr Tyr Leu Tyr Gln Lys Val Glu Glu Gly Val Leu Lys Pro Tyr
785                 790                 795                 800

Thr Arg Tyr Arg Leu Arg Gly Phe Val Gly Ser Ser Gln Gly Leu Glu
            805                 810                 815

Ile Tyr Thr Ile Arg His Gln Thr Asn Arg Ile Val Lys Asn Val Pro
        820                 825                 830

Asp Asp Leu Leu Pro Asp Val Ser Pro Val Asn Ser Asp Gly Ser Ile
    835                 840                 845

Asn Arg Cys Ser Glu Gln Lys Tyr Val Asn Ser Arg Leu Glu Gly Glu
850                 855                 860

Asn Arg Ser Gly Asp Ala His Glu Phe Ser Leu Pro Ile Asp Ile Gly
865                 870                 875                 880

Glu Leu Asp Tyr Asn Glu Asn Ala Gly Ile Trp Val Gly Phe Lys Ile
                885                 890                 895

Thr Asp Pro Glu Gly Tyr Ala Thr Leu Gly Asn Leu Glu Leu Val Glu
            900                 905                 910

Glu Gly Pro Leu Ser Gly Asp Ala Leu Glu Arg Leu Gln Arg Glu Glu
        915                 920                 925

Gln Gln Trp Lys Ile Gln Met Thr Arg Arg Glu Glu Thr Asp Arg
930                 935                 940

Arg Tyr Met Ala Ser Lys Gln Ala Val Asp Arg Leu Tyr Ala Asp Tyr
945                 950                 955                 960

Gln Asp Gln Gln Leu Asn Pro Asp Val Glu Ile Thr Asp Leu Thr Ala
                965                 970                 975

Ala Gln Asp Leu Ile Gln Ser Ile Pro Tyr Val Tyr Asn Glu Met Phe
            980                 985                 990

Pro Glu Ile Pro Gly Met Asn Tyr Thr Lys Phe Thr Glu Leu Thr Asp
        995                 1000                1005

Arg Leu Gln Gln Ala Trp Asn Leu Tyr Asp Gln Arg Asn Ala Ile
    1010                1015                1020

Pro Asn Gly Asp Phe Arg Asn Gly Leu Ser Asn Trp Asn Ala Thr
    1025                1030                1035

Pro Gly Val Glu Val Gln Gln Ile Asn His Thr Ser Val Leu Val
    1040                1045                1050

Ile Pro Asn Trp Asp Glu Val Ser Gln Gln Phe Thr Val Gln
    1055                1060                1065

Pro Asn Gln Arg Tyr Val Leu Arg Val Thr Ala Arg Lys Glu Gly
    1070                1075                1080

Val Gly Asn Gly Tyr Val Ser Ile Arg Asp Gly Gly Asn Gln Ser
    1085                1090                1095

Glu Thr Leu Thr Phe Ser Ala Ser Asp Tyr Asp Thr Asn Gly Val
    1100                1105                1110

Tyr Asn Asp Gln Thr Gly Tyr Ile Thr Lys Thr Val Thr Phe Ile
    1115                1120                1125

Pro Tyr Thr Asp Gln Met Trp Ile Glu Ile Ser Glu Thr Glu Gly
    1130                1135                1140

Thr Phe Tyr Ile Glu Ser Val Glu Leu Ile Val Asp Val
    1145                1150                1155

<210> SEQ ID NO 79
<211> LENGTH: 3537
<212> TYPE: DNA
<213> ORGANISM: Bacillus thuringiensis
<220> FEATURE:
<221> NAME/KEY: misc_feature
<222> LOCATION: (1)..(3537)
<223> OTHER INFORMATION: cry1Ac coding sequence

<400> SEQUENCE: 79

```
atggataaca atccgaacat caatgaatgc attccttata attgtttaag taaccctgaa      60
gtagaagtat taggtggaga agaatagaa actggttaca ccccaatcga tatttccttg      120
tcgctaacgc aatttctttt gagtgaattt gttcccggtg ctggatttgt gttaggacta     180
gttgatataa tatggggaat ttttggtccc tctcaatggg acgcatttct tgtacaaatt     240
gaacagttaa ttaaccaaag aatagaagaa ttcgctagga accaagccat ttctagatta     300
gaaggactaa gcaatctttta tcaaatttac gcagaatctt ttagagagtg gaagcagat      360
cctactaatc cagcattaag agaagagatg cgtattcaat tcaatgacat gaacagtgcc     420
cttacaaccg ctattcctct ttttgcagtt caaaattatc aagttcctct tttatcagta     480
tatgttcaag ctgcaaattt acatttatca gttttgagag atgtttcagt gtttggacaa     540
aggtggggat tgatgccgc gactatcaat agtcgttata atgatttaac taggcttatt      600
ggcaactata cagattatgc tgtacgctgg tacaatacgg gattagaacg tgtatgggga     660
ccggattcta gagattgggt aaggtataat caatttagaa gagaattaac actaactgta     720
ttagatatcg ttgctctgtt cccgaattat gatagtagaa gatatccaat tcgaacagtt     780
tcccaattaa caagagaaat ttatacaaac ccagtattag aaaattttga tggtagtttt     840
cgaggctcgg ctcagggcat agaaagaagt attaggagtc acatttgat ggatatactt      900
aacagtataa ccatctatac ggatgctcat aggggttatt attattggtc agggcatcaa     960
ataatggctt ctcctgtagg gttttcgggg ccagaattca cttttccgct atatggaact    1020
atgggaaatg cagctccaca acaacgtatt gttgctcaac taggtcaggg cgtgtataga    1080
acattatcgt ccactttata tagaagacct tttaatatag gataaataa tcaacaacta    1140
tctgttcttg acgggacaga atttgcttat ggaacctcct caaattttgcc atccgctgta    1200
tacagaaaaa gcggaacggt agattcgctg gatgaaatac cgccacagaa taacaacgtg    1260
ccacctaggc aaggatttag tcatcgatta agccatgttt caatgtttcg ttcaggctt     1320
agtaatagta gtgtaagtat aataagagct cctatgttct cttggataca tcgtagtgct    1380
gaattaatta atataattgc atcggatagt attactcaaa tccctgcagt gaagggaaac    1440
tttcttttta atggttctgt aatttcagga ccaggattta ctggtgggga cttagttaga    1500
ttaaatagta gtggaaataa cattcagaat agagggtata ttgaagttcc aattcacttc    1560
ccatcgacat ctaccagata tcgagttcgt gtacggtatg cttctgtaac cccgattcac    1620
ctcaacgtta ttgggggtaa ttcatccatt ttttccaata cagtaccagc tacagctacg    1680
tcattagata atctacaatc aagtgatttt ggttattttg aaaagtgccaa tgcttttaca    1740
tcttcattag gtaatatagt aggtgttaga aattttagtg ggactgcagg agtgataata    1800
gacagatttg aatttattcc agttactgca acactcgagg ctgaatataa tctggaaaga    1860
gcgcagaagg cggtgaatgc gctgtttacg tctacaaacc aactagggct aaaaacaaat    1920
gtaacggatt atcatattga tcaagtgtcc aattagttaa cgtatttatc ggatgaattt    1980
tgtctggatg aaaagcgaga attgtccgag aaagtcaaac atgcgaagcg actcagtgat    2040
gaacgcaatt tactccaaga ttcaaatttc aaagacatta taggcaacc agaacgtggg    2100
tggggcggaa gtacagggat taccatccaa ggagggatg acgtatttaa agaaaattac    2160
gtcacactat caggtacctt tgatgagtgc tatccaacat atttgtatca aaaaatcgat    2220
gaatcaaaat taaaagcctt tacccgttat caattaagag ggtatatcga agatagtcaa    2280
```

-continued

```
gacttagaaa tctatttaat tcgctacaat gcaaaacatg aaacagtaaa tgtgccaggt    2340
acgggttcct tatggccgct ttcagcccaa agtccaatcg aaagtgtgg agagccgaat     2400 cgatgcgcgc cacaccttga atggaatcct gacttagatt gttcgtgtag ggatggagaa    2460
aagtgtgccc atcattcgca tcatttctcc ttagacattg atgtaggatg tacagactta   2520
aatgaggacc taggtgtatg ggtgatcttt aagattaaga cgcaagatgg gcacgcaaga   2580
ctagggaatc tagagtttct cgaagagaaa ccattagtag gagaagcgct agctcgtgtg   2640
aaaagagcgg agaaaaaatg gagagacaaa cgtgaaaaat tggaatggga aacaaatatc   2700
gtttataaag aggcaaaaga atctgtagat gctttatttg taaactctca atatgatcaa   2760
ttacaagcgg atacgaatat tgccatgatt catgcggcag ataaacgtgt tcatagcatt   2820
cgagaagctt atctgcctga gctgtctgtg attccgggtg tcaatgcggc tatttttgaa   2880
gaattagaag ggcgtatttt cactgcattc tccctatatg atgcgagaaa tgtcattaaa   2940
aatggtgatt ttaataatgg cttatcctgc tggaacgtga aagggcatgt agatgtagaa   3000
gaacaaaaca accaacgttc ggtccttgtt gttccggaat gggaagcaga agtgtcacaa   3060
gaagttcgtg tctgtccggg tcgtggctat atccttcgtg tcacagcgta caaggaggga   3120
tatggagaag gttgcgtaac cattcatgag atcgagaaca atacagacga actgaagttt   3180
agcaactgcg tagaagagga aatctatcca aataacacgg taacgtgtaa tgattatact   3240
gtaaatcaag aagaatacgg aggtgcgtac acttctcgta atcgaggata taacgaagct   3300
ccttccgtac cagctgatta tgcgtcagtc tatgaagaaa aatcgtatac agatggacga   3360
agagagaatc cttgtgaatt aacagagggg tataggggatt acacgccact accagttggt   3420
tatgtgacaa aagaattaga atacttccca gaaaccgata aggtatggat tgagattgga   3480
gaaacggaag gaacatttat cgtggacagc gtggaattac tccttatgga ggaatag       3537
```

<210> SEQ ID NO 80
<211> LENGTH: 1178
<212> TYPE: PRT
<213> ORGANISM: Bacillus thuringiensis
<220> FEATURE:
<221> NAME/KEY: MISC_FEATURE
<222> LOCATION: (1)..(1178)
<223> OTHER INFORMATION: Cry1Ac protein

<400> SEQUENCE: 80

```
Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
```

-continued

```
            130                 135                 140
Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
                180                 185                 190

Tyr Asn Asp Leu Thr Arg Leu Ile Gly Asn Tyr Thr Asp Tyr Ala Val
                195                 200                 205

Arg Trp Tyr Asn Thr Gly Leu Glu Arg Val Trp Gly Pro Asp Ser Arg
210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
                260                 265                 270

Leu Glu Asn Phe Asp Gly Ser Phe Arg Gly Ser Ala Gln Gly Ile Glu
                275                 280                 285

Arg Ser Ile Arg Ser Pro His Leu Met Asp Ile Leu Asn Ser Ile Thr
290                 295                 300

Ile Tyr Thr Asp Ala His Arg Gly Tyr Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
                340                 345                 350

Gln Leu Gly Gln Gly Val Tyr Arg Thr Leu Ser Ser Thr Leu Tyr Arg
                355                 360                 365

Arg Pro Phe Asn Ile Gly Ile Asn Asn Gln Gln Leu Ser Val Leu Asp
370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
                420                 425                 430

Val Ser Met Phe Arg Ser Gly Phe Ser Asn Ser Ser Val Ser Ile Ile
                435                 440                 445

Arg Ala Pro Met Phe Ser Trp Ile His Arg Ser Ala Glu Phe Asn Asn
450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
                500                 505                 510

Tyr Ile Glu Val Pro Ile His Phe Pro Ser Thr Ser Thr Arg Tyr Arg
                515                 520                 525

Val Arg Val Arg Tyr Ala Ser Val Thr Pro Ile His Leu Asn Val Asn
                530                 535                 540

Trp Gly Asn Ser Ser Ile Phe Ser Asn Thr Val Pro Ala Thr Ala Thr
545                 550                 555                 560
```

```
Ser Leu Asp Asn Leu Gln Ser Asp Phe Gly Tyr Phe Glu Ser Ala
            565                 570                 575

Asn Ala Phe Thr Ser Ser Leu Gly Asn Ile Val Gly Val Arg Asn Phe
        580                 585                 590

Ser Gly Thr Ala Gly Val Ile Ile Asp Arg Phe Glu Phe Ile Pro Val
            595                 600                 605

Thr Ala Thr Leu Glu Ala Glu Tyr Asn Leu Glu Arg Ala Gln Lys Ala
    610                 615                 620

Val Asn Ala Leu Phe Thr Ser Thr Asn Gln Leu Gly Leu Lys Thr Asn
625                 630                 635                 640

Val Thr Asp Tyr His Ile Asp Gln Val Ser Asn Leu Val Thr Tyr Leu
                645                 650                 655

Ser Asp Glu Phe Cys Leu Asp Glu Lys Arg Glu Leu Ser Glu Lys Val
            660                 665                 670

Lys His Ala Lys Arg Leu Ser Asp Glu Arg Asn Leu Leu Gln Asp Ser
        675                 680                 685

Asn Phe Lys Asp Ile Asn Arg Gln Pro Glu Arg Gly Trp Gly Gly Ser
    690                 695                 700

Thr Gly Ile Thr Ile Gln Gly Gly Asp Asp Val Phe Lys Glu Asn Tyr
705                 710                 715                 720

Val Thr Leu Ser Gly Thr Phe Asp Glu Cys Tyr Pro Thr Tyr Leu Tyr
                725                 730                 735

Gln Lys Ile Asp Glu Ser Lys Leu Lys Ala Phe Thr Arg Tyr Gln Leu
            740                 745                 750

Arg Gly Tyr Ile Glu Asp Ser Gln Asp Leu Glu Ile Tyr Leu Ile Arg
        755                 760                 765

Tyr Asn Ala Lys His Glu Thr Val Asn Val Pro Gly Thr Gly Ser Leu
    770                 775                 780

Trp Pro Leu Ser Ala Gln Ser Pro Ile Gly Lys Cys Gly Glu Pro Asn
785                 790                 795                 800

Arg Cys Ala Pro His Leu Glu Trp Asn Pro Asp Leu Asp Cys Ser Cys
                805                 810                 815

Arg Asp Gly Glu Lys Cys Ala His His Ser His His Phe Ser Leu Asp
            820                 825                 830

Ile Asp Val Gly Cys Thr Asp Leu Asn Glu Asp Leu Gly Val Trp Val
        835                 840                 845

Ile Phe Lys Ile Lys Thr Gln Asp Gly His Ala Arg Leu Gly Asn Leu
    850                 855                 860

Glu Phe Leu Glu Glu Lys Pro Leu Val Gly Glu Ala Leu Ala Arg Val
865                 870                 875                 880

Lys Arg Ala Glu Lys Lys Trp Arg Asp Lys Arg Glu Lys Leu Glu Trp
                885                 890                 895

Glu Thr Asn Ile Val Tyr Lys Glu Ala Lys Glu Ser Val Asp Ala Leu
            900                 905                 910

Phe Val Asn Ser Gln Tyr Asp Gln Leu Gln Ala Asp Thr Asn Ile Ala
        915                 920                 925

Met Ile His Ala Ala Asp Lys Arg Val His Ser Ile Arg Glu Ala Tyr
    930                 935                 940

Leu Pro Glu Leu Ser Val Ile Pro Gly Val Asn Ala Ala Ile Phe Glu
945                 950                 955                 960

Glu Leu Glu Gly Arg Ile Phe Thr Ala Phe Ser Leu Tyr Asp Ala Arg
                965                 970                 975

Asn Val Ile Lys Asn Gly Asp Phe Asn Asn Gly Leu Ser Cys Trp Asn
            980                 985                 990
```

```
Val Lys Gly His Val Asp Val Glu  Glu Gln Asn Asn Gln  Arg Ser Val
         995                1000                1005

Leu Val  Val Pro Glu Trp Glu  Ala Glu Val Ser Gln  Glu Val Arg
    1010             1015                 1020

Val Cys  Pro Gly Arg Gly Tyr  Ile Leu Arg Val Thr  Ala Tyr Lys
    1025             1030                 1035

Glu Gly  Tyr Gly Glu Gly Cys  Val Thr Ile His Glu  Ile Glu Asn
    1040             1045                 1050

Asn Thr  Asp Glu Leu Lys Phe  Ser Asn Cys Val Glu  Glu Glu Ile
    1055             1060                 1065

Tyr Pro  Asn Asn Thr Val Thr  Cys Asn Asp Tyr Thr  Val Asn Gln
    1070             1075                 1080

Glu Glu  Tyr Gly Gly Ala Tyr  Thr Ser Arg Asn Arg  Gly Tyr Asn
    1085             1090                 1095

Glu Ala  Pro Ser Val Pro Ala  Asp Tyr Ala Ser Val  Tyr Glu Glu
    1100             1105                 1110

Lys Ser  Tyr Thr Asp Gly Arg  Arg Glu Asn Pro Cys  Glu Phe Asn
    1115             1120                 1125

Arg Gly  Tyr Arg Asp Tyr Thr  Pro Leu Pro Val Gly  Tyr Val Thr
    1130             1135                 1140

Lys Glu  Leu Glu Tyr Phe Pro  Glu Thr Asp Lys Val  Trp Ile Glu
    1145             1150                 1155

Ile Gly  Glu Thr Glu Gly Thr  Phe Ile Val Asp Ser  Val Glu Leu
    1160             1165                 1170

Leu Leu  Met Glu Glu
    1175

<210> SEQ ID NO 81
<211> LENGTH: 2160
<212> TYPE: DNA
<213> ORGANISM: Bacillus thuringiensis
<220> FEATURE:
<221> NAME/KEY: misc_feature
<222> LOCATION: (1)..(2160)
<223> OTHER INFORMATION: cry1Ia coding sequence

<400> SEQUENCE: 81
atgaaactaa agaatcaaga taagcatcaa agtttttcta gcaatgcgaa agtagataaa      60
atctctacgg attcactaaa aaatgaaaca gatatagaat tacaaaacat taatcatgaa     120
gattgtttga aaatgtctga gtatgaaaat gtagagccgt tgttagtgc atcaacaatt     180 caaacaggta ttggtattgc gggtaaaata cttggtaccc taggcgttcc ttttgcagga     240
caagtagcta gtctttatag ttttatctta ggtgagctat ggcctaaggg gaaaaatcaa     300
tgggaaatct ttatggaaca tgtagaagag attattaatc aaaaaatatc aacttatgca     360
agaaataaag cacttacaga cttgaaagga ttaggagatg ccttagctgt ctaccatgat     420
tcgcttgaaa gttgggttgg aaatcgtaat aacacaaggg ctaggagtgt tgtcaagagc     480
caatatatcg cattagaatt gatgttcgtt cagaaactac cttctttgc agtgtctgga     540 gaggaggtac cattattacc gatatatgcc caagctgcaa atttacattt gttgctatta     600 agatgcat ctattttgg aaaagagtgg ggattatcat cttcagaaat ttcaacattt     660
tataaccgtc aagtcgaacg agcaggagat tattcctacc attgtgtgaa atggtatagc     720
acaggtctaa ataacttgag gggtacaaat gccgaaagtt gggtacgata taatcaattc     780
cgtagagaca tgactttaat ggtactagat ttagtggcac tatttccaag ctatgataca     840
```

```
caaatgtatc caattaaaac tacagcccaa cttacaagag aagtatatac agacgcaatt    900
gggacagtac atccgcatcc aagttttaca agtacgactt ggtataataa taatgcacct    960
tcgttctctg ccatagaggc tgctgttgtt cgaaacccgc atctactcga ttttctagaa   1020
caagttacaa tttacagctt attaagtcga tggagtaaca ctcagtatat gaatatgtgg   1080
ggaggacata aactagaatt ccgaacaata ggaggaacgt taaatatctc aacacaagga   1140
tctactaata cttctattaa tcctgtaaca ttaccgttca cttctcgaga cgtctatagg   1200
actgaatcat tggcagggct gaatctattt ttaactcaac tgttaatgg agtacctagg    1260 gttgattttc attggaaatt cgtcacacat ccgatcgcat ctgataattt ctattatcca   1320
gggtatgctg gaattgggac gcaattacag gattcagaaa atgaattacc acctgaagca   1380
acaggacagc caaattatga atcttatagt catagattat ctcatatagg actcatttca   1440
gcatcacatg tgaaagcatt ggtatattct tggacgcatc gtagtgcaga tcgtacaaat   1500
acaattgagc caaatagcat tacacaaata ccattagtaa aagctttcaa tctgtcttca   1560
ggtgccgctg tagtgagagg accaggattt acaggtgggg atatccttcg aagaacgaat   1620
actggtacat ttggggatat acgagtaaat attaatccac catttgcaca agatatcgc    1680 gtgaggattc gctatgcttc taccacagat ttacaattcc atacgtcaat taacggtaaa   1740
gctattaatc aaggtaattt ttcagcaact atgaatagag gagaggactt agactataaa   1800
acctttagaa ctgtaggctt taccactcca tttagctttt tagatgtaca agtacattc    1860 acaataggtg cttggaactt ctcttcaggt aacgaagttt atatagatag aattgaattt   1920
gttccggtag aagtaacata tgaggcagaa tatgattttg aaaaagcgca agagaaggtt   1980
actgcactgt ttcatctac gaatccaaga ggattaaaaa cagatgtaaa ggattatcat    2040
attgaccagg tatcaaattt agtagagtct ctatcagatg aattctatct tgatgaaaag   2100
agagaattat tcgagatagt taaatacgcg aagcaactcc atattgagcg taacatgtag   2160
```

<210> SEQ ID NO 82
<211> LENGTH: 719
<212> TYPE: PRT
<213> ORGANISM: Bacillus thuringiensis
<220> FEATURE:
<221> NAME/KEY: MISC_FEATURE
<222> LOCATION: (1)..(719)
<223> OTHER INFORMATION: CryIIa protein

<400> SEQUENCE: 82

```
Met Lys Leu Lys Asn Gln Asp Lys His Gln Ser Phe Ser Ser Asn Ala
1               5                   10                  15

Lys Val Asp Lys Ile Ser Thr Asp Ser Leu Lys Asn Glu Thr Asp Ile
            20                  25                  30

Glu Leu Gln Asn Ile Asn His Glu Asp Cys Leu Lys Met Ser Glu Tyr
        35                  40                  45

Glu Asn Val Glu Pro Phe Val Ser Ala Ser Thr Ile Gln Thr Gly Ile
    50                  55                  60

Gly Ile Ala Gly Lys Ile Leu Gly Thr Leu Gly Val Pro Phe Ala Gly
65                  70                  75                  80

Gln Val Ala Ser Leu Tyr Ser Phe Ile Leu Gly Glu Leu Trp Pro Lys
                85                  90                  95

Gly Lys Asn Gln Trp Glu Ile Phe Met Glu His Val Glu Glu Ile Ile
            100                 105                 110

Asn Gln Lys Ile Ser Thr Tyr Ala Arg Asn Lys Ala Leu Thr Asp Leu
        115                 120                 125
```

```
Lys Gly Leu Gly Asp Ala Leu Ala Val Tyr His Asp Ser Leu Glu Ser
130                 135                 140

Trp Val Gly Asn Arg Asn Asn Thr Arg Ala Arg Ser Val Val Lys Ser
145                 150                 155                 160

Gln Tyr Ile Ala Leu Glu Leu Met Phe Val Gln Lys Leu Pro Ser Phe
                165                 170                 175

Ala Val Ser Gly Glu Glu Val Pro Leu Leu Pro Ile Tyr Ala Gln Ala
            180                 185                 190

Ala Asn Leu His Leu Leu Leu Arg Asp Ala Ser Ile Phe Gly Lys
        195                 200                 205

Glu Trp Gly Leu Ser Ser Glu Ile Ser Thr Phe Tyr Asn Arg Gln
210                 215                 220

Val Glu Arg Ala Gly Asp Tyr Ser Tyr His Cys Val Lys Trp Tyr Ser
225                 230                 235                 240

Thr Gly Leu Asn Asn Leu Arg Gly Thr Asn Ala Glu Ser Trp Val Arg
                245                 250                 255

Tyr Asn Gln Phe Arg Arg Asp Met Thr Leu Met Val Leu Asp Leu Val
                260                 265                 270

Ala Leu Phe Pro Ser Tyr Asp Thr Gln Met Tyr Pro Ile Lys Thr Thr
            275                 280                 285

Ala Gln Leu Thr Arg Glu Val Tyr Thr Asp Ala Ile Gly Thr Val His
        290                 295                 300

Pro His Pro Ser Phe Thr Ser Thr Trp Tyr Asn Asn Asn Ala Pro
305                 310                 315                 320

Ser Phe Ser Ala Ile Glu Ala Ala Val Val Arg Asn Pro His Leu Leu
                325                 330                 335

Asp Phe Leu Glu Gln Val Thr Ile Tyr Ser Leu Leu Ser Arg Trp Ser
                340                 345                 350

Asn Thr Gln Tyr Met Asn Met Trp Gly Gly His Lys Leu Glu Phe Arg
                355                 360                 365

Thr Ile Gly Gly Thr Leu Asn Ile Ser Thr Gln Gly Ser Thr Asn Thr
370                 375                 380

Ser Ile Asn Pro Val Thr Leu Pro Phe Thr Ser Arg Asp Val Tyr Arg
385                 390                 395                 400

Thr Glu Ser Leu Ala Gly Leu Asn Leu Phe Leu Thr Gln Pro Val Asn
                405                 410                 415

Gly Val Pro Arg Val Asp Phe His Trp Lys Phe Val Thr His Pro Ile
                420                 425                 430

Ala Ser Asp Asn Phe Tyr Tyr Pro Gly Tyr Ala Gly Ile Gly Thr Gln
                435                 440                 445

Leu Gln Asp Ser Glu Asn Glu Leu Pro Pro Glu Ala Thr Gly Gln Pro
450                 455                 460

Asn Tyr Glu Ser Tyr Ser His Arg Leu Ser His Ile Gly Leu Ile Ser
465                 470                 475                 480

Ala Ser His Val Lys Ala Leu Val Tyr Ser Trp Thr His Arg Ser Ala
                485                 490                 495

Asp Arg Thr Asn Thr Ile Glu Pro Asn Ser Ile Thr Gln Ile Pro Leu
                500                 505                 510

Val Lys Ala Phe Asn Leu Ser Ser Gly Ala Ala Val Val Arg Gly Pro
                515                 520                 525

Gly Phe Thr Gly Gly Asp Ile Leu Arg Arg Thr Asn Thr Gly Thr Phe
            530                 535                 540

Gly Asp Ile Arg Val Asn Ile Asn Pro Pro Phe Ala Gln Arg Tyr Arg
545                 550                 555                 560
```

-continued

```
Val Arg Ile Arg Tyr Ala Ser Thr Thr Asp Leu Gln Phe His Thr Ser
            565                 570                 575
Ile Asn Gly Lys Ala Ile Asn Gln Gly Asn Phe Ser Ala Thr Met Asn
        580                 585                 590
Arg Gly Glu Asp Leu Asp Tyr Lys Thr Phe Arg Thr Val Gly Phe Thr
    595                 600                 605
Thr Pro Phe Ser Phe Leu Asp Val Gln Ser Thr Phe Thr Ile Gly Ala
610                 615                 620
Trp Asn Phe Ser Ser Gly Asn Glu Val Tyr Ile Asp Arg Ile Glu Phe
625                 630                 635                 640
Val Pro Val Glu Val Thr Tyr Glu Ala Glu Tyr Asp Phe Glu Lys Ala
                645                 650                 655
Gln Glu Lys Val Thr Ala Leu Phe Thr Ser Thr Asn Pro Arg Gly Leu
            660                 665                 670
Lys Thr Asp Val Lys Asp Tyr His Ile Asp Gln Val Ser Asn Leu Val
        675                 680                 685
Glu Ser Leu Ser Asp Glu Phe Tyr Leu Asp Glu Lys Arg Glu Leu Phe
    690                 695                 700
Glu Ile Val Lys Tyr Ala Lys Gln Leu His Ile Glu Arg Asn Met
705                 710                 715
```

<210> SEQ ID NO 83
<211> LENGTH: 34
<212> TYPE: DNA
<213> ORGANISM: Artificial Sequence
<220> FEATURE:
<223> OTHER INFORMATION: 53A-1-bam

<400> SEQUENCE: 83
ccggatccat gacggccgac aacaacaccg aggc                                   34

<210> SEQ ID NO 84
<211> LENGTH: 20
<212> TYPE: DNA
<213> ORGANISM: Artificial Sequence
<220> FEATURE:
<223> OTHER INFORMATION: C3-3a-6 primer

<400> SEQUENCE: 84 cagggggcagc tgggtgatct                                                  20

<210> SEQ ID NO 85
<211> LENGTH: 20
<212> TYPE: DNA
<213> ORGANISM: Artificial Sequence
<220> FEATURE:
<223> OTHER INFORMATION: C3-1Ab-3 primer
<220> FEATURE:
<221> NAME/KEY: misc_feature
<222> LOCATION: (1)..(20)
<223> OTHER INFORMATION: 1ab-3 primer

<400> SEQUENCE: 85
agatcaccca gatcccctg                                                    20

<210> SEQ ID NO 86
<211> LENGTH: 39
<212> TYPE: DNA
<213> ORGANISM: Artificial Sequence
<220> FEATURE:
<223> OTHER INFORMATION: 1Ab-6-sac primer

<400> SEQUENCE: 86

```
ccgagctcag ctcctacacc tgatcgatgt ggtagtcgg                          39

<210> SEQ ID NO 87
<211> LENGTH: 56
<212> TYPE: DNA
<213> ORGANISM: Artificial Sequence
<220> FEATURE:
<223> OTHER INFORMATION: 8a-atg-delri primer

<400> SEQUENCE: 87
ccggatccac catgactagt aacggccgcc agtgtgctgg tattcgccct tatgac       56

<210> SEQ ID NO 88
<211> LENGTH: 20
<212> TYPE: DNA
<213> ORGANISM: Artificial Sequence
<220> FEATURE:
<223> OTHER INFORMATION: C2-3A-4 primer

<400> SEQUENCE: 88
gtccagcacg gtcagggtca                                               20

<210> SEQ ID NO 89
<211> LENGTH: 20
<212> TYPE: DNA
<213> ORGANISM: Artificial Sequence
<220> FEATURE:
<223> OTHER INFORMATION: reverse primer

<400> SEQUENCE: 89
gcgtgcagtc aagtcagatc                                               20

<210> SEQ ID NO 90
<211> LENGTH: 38
<212> TYPE: DNA
<213> ORGANISM: Artificial Sequence
<220> FEATURE:
<223> OTHER INFORMATION: FR8a-OL-1 primer

<400> SEQUENCE: 90
ggtgttgttg tcggccgtca tagggcgaat accagcac                           38

<210> SEQ ID NO 91
<211> LENGTH: 39
<212> TYPE: DNA
<213> ORGANISM: Artificial Sequence
<220> FEATURE:
<223> OTHER INFORMATION: FR8a-OL-2 primer

<400> SEQUENCE: 91
gccgacaaca acaccgaggc cctggacagc agcaccacc                          39

<210> SEQ ID NO 92
<211> LENGTH: 27
<212> TYPE: DNA
<213> ORGANISM: Artificial Sequence
<220> FEATURE:
<223> OTHER INFORMATION: C1-3a-2 primer

<400> SEQUENCE: 92
caggtgggtg ttggcggcct gggcgta                                       27

<210> SEQ ID NO 93
<211> LENGTH: 21
<212> TYPE: DNA
<213> ORGANISM: Artificial Sequence
```

```
<220> FEATURE:
<223> OTHER INFORMATION: 5'FR8a primer

<400> SEQUENCE: 93
ggatccacca tgactagtaa c                                              21

<210> SEQ ID NO 94
<211> LENGTH: 36
<212> TYPE: DNA
<213> ORGANISM: Artificial Sequence
<220> FEATURE:
<223> OTHER INFORMATION: 5'fr8a-12aa primer

<400> SEQUENCE: 94
ccggatccac catgtatgac ggccgacaac aacacc                              36

<210> SEQ ID NO 95
<211> LENGTH: 20
<212> TYPE: DNA
<213> ORGANISM: Artificial Sequence
<220> FEATURE:
<223> OTHER INFORMATION: C2-3A-3 primer

<400> SEQUENCE: 95
tgaccctgac cgtgctggac                                                20

<210> SEQ ID NO 96
<211> LENGTH: 27
<212> TYPE: DNA
<213> ORGANISM: Artificial Sequence
<220> FEATURE:
<223> OTHER INFORMATION: 3'1Ab-dm3 primer

<400> SEQUENCE: 96
gagctcctag gtcacctcgg cgggcac                                        27

<210> SEQ ID NO 97
<211> LENGTH: 32
<212> TYPE: DNA
<213> ORGANISM: Artificial Sequence
<220> FEATURE:
<223> OTHER INFORMATION: 5'FR-del6 primer

<400> SEQUENCE: 97
ggatccacca tgtgtgctgg tattcgccct at                                  32

<210> SEQ ID NO 98
<211> LENGTH: 32
<212> TYPE: DNA
<213> ORGANISM: Artificial Sequence
<220> FEATURE:
<223> OTHER INFORMATION: 5'1Ab-bam primer

<400> SEQUENCE: 98
ccggatccat ggacaacaac cccaacatca ac                                  32

<210> SEQ ID NO 99
<211> LENGTH: 20
<212> TYPE: DNA
<213> ORGANISM: Artificial Sequence
<220> FEATURE:
<223> OTHER INFORMATION: C3-3a-7 primer
<220> FEATURE:
<221> NAME/KEY: misc_feature
<222> LOCATION: (1)..(20)
<223> OTHER INFORMATION: C3-3a-7 primer

<400> SEQUENCE: 99
```
gcttcaccgg cggcgacatc                                                     20

<210> SEQ ID NO 100
<211> LENGTH: 20
<212> TYPE: DNA
<213> ORGANISM: Artificial Sequence
<220> FEATURE:
<223> OTHER INFORMATION: C3-3a-8 primer

<400> SEQUENCE: 100
gatgtcgccg ccggtgaagc                                                     20

<210> SEQ ID NO 101
<211> LENGTH: 23
<212> TYPE: DNA
<213> ORGANISM: Artificial Sequence
<220> FEATURE:
<223> OTHER INFORMATION: C4-3a-9 primer

<400> SEQUENCE: 101
ccgcatccac tacgccagca cca                                                 23

<210> SEQ ID NO 102
<211> LENGTH: 23
<212> TYPE: DNA
<213> ORGANISM: Artificial Sequence
<220> FEATURE:
<223> OTHER INFORMATION: C4-3a-10 primer

<400> SEQUENCE: 102
tggtgctggc gtagtggatg cgg                                                 23

<210> SEQ ID NO 103
<211> LENGTH: 44
<212> TYPE: DNA
<213> ORGANISM: Artificial Sequence
<220> FEATURE:
<223> OTHER INFORMATION: 3a-12-sac primer

<400> SEQUENCE: 103
ccgagctcag ctcagatcta gttcacgggg atgaactcga tctt                          44

<210> SEQ ID NO 104
<211> LENGTH: 27
<212> TYPE: DNA
<213> ORGANISM: Artificial Sequence
<220> FEATURE:
<223> OTHER INFORMATION: 3a-22 primer

<400> SEQUENCE: 104
ggccttcacc aggggcagct gggtgat                                             27

<210> SEQ ID NO 105
<211> LENGTH: 31
<212> TYPE: DNA
<213> ORGANISM: Artificial Sequence
<220> FEATURE:
<223> OTHER INFORMATION: 1B-5 primer

<400> SEQUENCE: 105
ccgccgcgac ctgaccctgg gcgtgctgga c                                        31

<210> SEQ ID NO 106
<211> LENGTH: 27
<212> TYPE: DNA
<213> ORGANISM: Artificial Sequence

```
<220> FEATURE:
<223> OTHER INFORMATION: 1B-7 primer

<400> SEQUENCE: 106
atcacccaga tccccatggt gaaggcc                                          27

<210> SEQ ID NO 107
<211> LENGTH: 26
<212> TYPE: DNA
<213> ORGANISM: Artificial Sequence
<220> FEATURE:
<223> OTHER INFORMATION: 1B-10 primer

<400> SEQUENCE: 107
ccgagctcct agaacagggc gttcac                                           26

<210> SEQ ID NO 108
<211> LENGTH: 20
<212> TYPE: DNA
<213> ORGANISM: Artificial Sequence
<220> FEATURE:
<223> OTHER INFORMATION: C3-1Ab-2 primer

<400> SEQUENCE: 108 caggggatc tgggtgatct                                                   20

<210> SEQ ID NO 109
<211> LENGTH: 20
<212> TYPE: DNA
<213> ORGANISM: Artificial Sequence
<220> FEATURE:
<223> OTHER INFORMATION: C3-3A-5 primer

<400> SEQUENCE: 109
agatcaccca gctgcccctg                                                  20

<210> SEQ ID NO 110
<211> LENGTH: 27
<212> TYPE: DNA
<213> ORGANISM: Artificial Sequence
<220> FEATURE:
<223> OTHER INFORMATION: C1-1Ab-1 primer

<400> SEQUENCE: 110
tacgtgcagg ccgccaacct gcacctg                                          27

<210> SEQ ID NO 111
<211> LENGTH: 42
<212> TYPE: DNA
<213> ORGANISM: Artificial Sequence
<220> FEATURE:
<223> OTHER INFORMATION: 5'8Aa-dm3 primer

<400> SEQUENCE: 111
agatcaccca gctgcccctg gtaaagggag acatgttata tc                         42

<210> SEQ ID NO 112
<211> LENGTH: 30
<212> TYPE: DNA
<213> ORGANISM: Artificial Sequence
<220> FEATURE:
<223> OTHER INFORMATION: 3'8Aa-dm3 primer

<400> SEQUENCE: 112
gagctcctat gtctcatcta ctgggatgaa                                       30
```

```
<210> SEQ ID NO 113
<211> LENGTH: 33
<212> TYPE: DNA
<213> ORGANISM: Artificial Sequence
<220> FEATURE:
<223> OTHER INFORMATION: Tant-OL-1 primer

<400> SEQUENCE: 113
acccagctgc ccctggtgaa ggcccacacc ctc                              33

<210> SEQ ID NO 114
<211> LENGTH: 33
<212> TYPE: DNA
<213> ORGANISM: Artificial Sequence
<220> FEATURE:
<223> OTHER INFORMATION: Tant-OL-2 primer

<400> SEQUENCE: 114
gagggtgtgg gccttcacca ggggcagctg ggt                              33

<210> SEQ ID NO 115
<211> LENGTH: 29
<212> TYPE: DNA
<213> ORGANISM: Artificial Sequence
<220> FEATURE:
<223> OTHER INFORMATION: Tant-3'sac primer

<400> SEQUENCE: 115
gagctctagc ttaagcagtc cacgaggtt                                   29

<210> SEQ ID NO 116
<211> LENGTH: 37
<212> TYPE: DNA
<213> ORGANISM: Artificial Sequence
<220> FEATURE:
<223> OTHER INFORMATION: 1Ac-OL-1 primer

<400> SEQUENCE: 116
acccagctgc ccctggtgaa gggaaacttt cttttta                          37

<210> SEQ ID NO 117
<211> LENGTH: 37
<212> TYPE: DNA
<213> ORGANISM: Artificial Sequence
<220> FEATURE:
<223> OTHER INFORMATION: 1Ac-OL-2 primer

<400> SEQUENCE: 117
taaaaagaaa gtttcccttc accaggggca gctgggt                          37

<210> SEQ ID NO 118
<211> LENGTH: 30
<212> TYPE: DNA
<213> ORGANISM: Artificial Sequnce
<220> FEATURE:
<223> OTHER INFORMATION: 1Ac-3'sac primer

<400> SEQUENCE: 118
gagctcctat gttgcagtaa ctggaataaa                                  30

<210> SEQ ID NO 119
<211> LENGTH: 38
<212> TYPE: DNA
<213> ORGANISM: Artificial Sequence
<220> FEATURE:
<223> OTHER INFORMATION: 1Ia-OL-1 primer

<400> SEQUENCE: 119
```
acccagctgc ccctgagtaa aagctttcaa tctgtctt    38

<210> SEQ ID NO 120
<211> LENGTH: 38
<212> TYPE: DNA
<213> ORGANISM: Artificial Sequence
<220> FEATURE:
<223> OTHER INFORMATION: 1Ia-OL-2 primer

<400> SEQUENCE: 120
aagacagatt gaaagctttt actcaggggc agctgggt    38

<210> SEQ ID NO 121
<211> LENGTH: 31
<212> TYPE: DNA
<213> ORGANISM: Artificial Sequence
<220> FEATURE:
<223> OTHER INFORMATION: 1Ia-3'sac primer

<400> SEQUENCE: 121
gagctcctac atgttacgct caatatggag t    31

<210> SEQ ID NO 122
<211> LENGTH: 33
<212> TYPE: DNA
<213> ORGANISM: Artificial Sequence
<220> FEATURE:
<223> OTHER INFORMATION: FR-1Ab-1 primer

<400> SEQUENCE: 122
tggacccaca agagcgccga gttcaacaac atc    33

<210> SEQ ID NO 123
<211> LENGTH: 33
<212> TYPE: DNA
<213> ORGANISM: Artificial Sequence
<220> FEATURE:
<223> OTHER INFORMATION: FR-1Ab-2 primer

<400> SEQUENCE: 123
gatgttgttg aactcggcgc tcttgtgggt cca    33

<210> SEQ ID NO 124
<211> LENGTH: 40
<212> TYPE: DNA
<213> ORGANISM: Artificial Sequence
<220> FEATURE:
<223> OTHER INFORMATION: FR-1Ab-3 primer

<400> SEQUENCE: 124
ccacaagagc gtcgacttca acacatcatc cccagcagcc    40

<210> SEQ ID NO 125
<211> LENGTH: 41
<212> TYPE: DNA
<213> ORGANISM: Artificial Sequence
<220> FEATURE:
<223> OTHER INFORMATION: FR-1Ab-4 primer

<400> SEQUENCE: 125
ggctcgtggg gatgatgttg ttgaagtcga cgctcttgtg g    41

<210> SEQ ID NO 126
<211> LENGTH: 35
<212> TYPE: PRT
<213> ORGANISM: Artificial Sequence

```
<220> FEATURE:
<223> OTHER INFORMATION: Peptidyl fragment 1
<220> FEATURE:
<221> NAME/KEY: MISC_FEATURE
<222> LOCATION: (1)..(14)
<223> OTHER INFORMATION: Derived from pET21a
<220> FEATURE:
<221> NAME/KEY: MISC_FEATURE
<222> LOCATION: (15)..(26)
<223> OTHER INFORMATION: Derived from pCR2.1-TOPO
<220> FEATURE:
<221> NAME/KEY: MISC_FEATURE
<222> LOCATION: (27)..(35)
<223> OTHER INFORMATION: Derived from cry3A055 frame shift.

<400> SEQUENCE: 126

Met Ala Ser Met Thr Gly Gly Gln Gln Met Gly Arg Gly Ser Thr Ser
1               5                   10                  15

Asn Gly Arg Gln Cys Ala Gly Ile Arg Pro Tyr Asp Gly Arg Gln Gln
            20                  25                  30

His Arg Gly
        35

<210> SEQ ID NO 127
<211> LENGTH: 22
<212> TYPE: PRT
<213> ORGANISM: Artificial Sequence
<220> FEATURE:
<223> OTHER INFORMATION: Peptidyl Fragment 2

<400> SEQUENCE: 127

Met Thr Ser Asn Gly Arg Gln Cys Ala Gly Ile Arg Pro Tyr Asp Gly
1               5                   10                  15

Arg Gln Gln His Arg Gly
            20

<210> SEQ ID NO 128
<211> LENGTH: 10
<212> TYPE: PRT
<213> ORGANISM: Artificial Sequence
<220> FEATURE:
<223> OTHER INFORMATION: Peptidyl Fragment 3

<400> SEQUENCE: 128

Met Tyr Asp Gly Arg Gln Gln His Arg Gly
1               5                   10

<210> SEQ ID NO 129
<211> LENGTH: 13
<212> TYPE: PRT
<213> ORGANISM: Artificial Sequence
<220> FEATURE:
<223> OTHER INFORMATION: Peptidyl Fragment 4

<400> SEQUENCE: 129

Met Thr Ser Asn Gly Arg Gln Cys Ala Gly Ile Arg Pro
1               5                   10

<210> SEQ ID NO 130
<211> LENGTH: 7
<212> TYPE: PRT
<213> ORGANISM: Artificial Sequence
<220> FEATURE:
<223> OTHER INFORMATION: Peptidyl fragment 5

<400> SEQUENCE: 130

Met Cys Ala Gly Ile Arg Pro
1               5
```

<210> SEQ ID NO 131
<211> LENGTH: 55
<212> TYPE: PRT
<213> ORGANISM: Artificial Sequence
<220> FEATURE:
<223> OTHER INFORMATION: Peptidyl fragment 6

<400> SEQUENCE: 131

Met Lys Glu Thr Ala Ala Ala Lys Phe Glu Arg Gln His Met Asp Ser
1               5                   10                  15

Pro Asp Leu Gly Thr Leu Val Pro Arg Gly Ser Met Ala Asp Ile Gly
            20                  25                  30

Ser Thr Thr Ser Asn Gly Arg Gln Cys Ala Gly Ile Arg Pro Tyr Asp
        35                  40                  45

Gly Arg Gln Gln His Arg Gly
    50                  55

<210> SEQ ID NO 132
<211> LENGTH: 14
<212> TYPE: PRT
<213> ORGANISM: Artificial Sequence
<220> FEATURE:
<223> OTHER INFORMATION: Chemically synthesized peptidyl fragment 7

<400> SEQUENCE: 132

Met Ala Ser Met Thr Gly Gly Gln Gln Met Gly Arg Gly Ser
1               5                   10

<210> SEQ ID NO 133
<211> LENGTH: 9
<212> TYPE: PRT
<213> ORGANISM: Artificial Sequence
<220> FEATURE:
<223> OTHER INFORMATION: Peptidyl fragment 8

<400> SEQUENCE: 133

Tyr Asp Gly Arg Gln Gln His Arg Gly
1               5

<210> SEQ ID NO 134
<211> LENGTH: 12
<212> TYPE: PRT
<213> ORGANISM: Artificial Sequence
<220> FEATURE:
<223> OTHER INFORMATION: Peptidyl fragment 9

<400> SEQUENCE: 134

Thr Ser Asn Gly Arg Gln Cys Ala Gly Ile Arg Pro
1               5                   10

<210> SEQ ID NO 135
<211> LENGTH: 644
<212> TYPE: PRT
<213> ORGANISM: Bacillus thuringiensis
<220> FEATURE:
<223> OTHER INFORMATION: Full-length Cry3A protein

<400> SEQUENCE: 135

```
Met Asn Pro Asn Asn Arg Ser Glu His Asp Thr Ile Lys Thr Thr Glu
1               5                   10                  15

Asn Asn Glu Val Pro Thr Asn His Val Gln Tyr Pro Leu Ala Glu Thr
            20                  25                  30

Pro Asn Pro Thr Leu Glu Asp Leu Asn Tyr Lys Glu Phe Leu Arg Met
        35                  40                  45
```

Thr Ala Asp Asn Asn Thr Glu Ala Leu Asp Ser Ser Thr Thr Lys Asp
 50                  55                  60

Val Ile Gln Lys Gly Ile Ser Val Val Gly Asp Leu Leu Gly Val Val
 65                  70                  75                  80

Gly Phe Pro Phe Gly Gly Ala Leu Val Ser Phe Tyr Thr Asn Phe Leu
                     85                  90                  95

Asn Thr Ile Trp Pro Ser Glu Asp Pro Trp Lys Ala Phe Met Glu Gln
                 100                 105                 110

Val Glu Ala Leu Met Asp Gln Lys Ile Ala Asp Tyr Ala Lys Asn Lys
             115                 120                 125

Ala Leu Ala Glu Leu Gln Gly Leu Gln Asn Asn Val Glu Asp Tyr Val
 130                 135                 140

Ser Ala Leu Ser Ser Trp Gln Lys Asn Pro Val Ser Ser Arg Asn Pro
 145                 150                 155                 160

His Ser Gln Gly Arg Ile Arg Glu Leu Phe Ser Gln Ala Glu Ser His
                 165                 170                 175

Phe Arg Asn Ser Met Pro Ser Phe Ala Ile Ser Gly Tyr Glu Val Leu
                 180                 185                 190

Phe Leu Thr Thr Tyr Ala Gln Ala Ala Asn Thr His Leu Phe Leu Leu
             195                 200                 205

Lys Asp Ala Gln Ile Tyr Gly Glu Glu Trp Gly Tyr Glu Lys Glu Asp
 210                 215                 220

Ile Ala Glu Phe Tyr Lys Arg Gln Leu Lys Leu Thr Gln Glu Tyr Thr
 225                 230                 235                 240

Asp His Cys Val Lys Trp Tyr Asn Val Gly Leu Asp Lys Leu Arg Gly
                 245                 250                 255

Ser Ser Tyr Glu Ser Trp Val Asn Phe Asn Arg Tyr Arg Arg Glu Met
                 260                 265                 270

Thr Leu Thr Val Leu Asp Leu Ile Ala Leu Phe Pro Leu Tyr Asp Val
             275                 280                 285

Arg Leu Tyr Pro Lys Glu Val Lys Thr Glu Leu Thr Arg Asp Val Leu
 290                 295                 300

Thr Asp Pro Ile Val Gly Val Asn Asn Leu Arg Gly Tyr Gly Thr Thr
 305                 310                 315                 320

Phe Ser Asn Ile Glu Asn Tyr Ile Arg Lys Pro His Leu Phe Asp Tyr
                 325                 330                 335

Leu His Arg Ile Gln Phe His Thr Arg Phe Gln Pro Gly Tyr Tyr Gly
                 340                 345                 350

Asn Asp Ser Phe Asn Tyr Trp Ser Gly Asn Tyr Val Ser Thr Arg Pro
             355                 360                 365

Ser Ile Gly Ser Asn Asp Ile Ile Thr Ser Pro Phe Tyr Gly Asn Lys
 370                 375                 380

Ser Ser Glu Pro Val Gln Asn Leu Glu Phe Asn Gly Glu Lys Val Tyr
385                 390                 395                 400

Arg Ala Val Ala Asn Thr Asn Leu Ala Val Trp Pro Ser Ala Val Tyr
                 405                 410                 415

Ser Gly Val Thr Lys Val Glu Phe Ser Gln Tyr Asn Asp Gln Thr Asp
             420                 425                 430

Glu Ala Ser Thr Gln Thr Tyr Asp Ser Lys Arg Asn Val Gly Ala Val
             435                 440                 445

Ser Trp Asp Ser Ile Asp Gln Leu Pro Pro Glu Thr Thr Asp Glu Pro
 450                 455                 460

Leu Glu Lys Gly Tyr Ser His Gln Leu Asn Tyr Val Met Cys Phe Leu

```
                465                 470                 475                 480
Met Gln Gly Ser Arg Gly Thr Ile Pro Val Leu Thr Trp Thr His Lys
                    485                 490                 495
Ser Val Asp Phe Phe Asn Met Ile Asp Ser Lys Lys Ile Thr Gln Leu
                500                 505                 510
Pro Leu Val Lys Ala Tyr Lys Leu Gln Ser Gly Ala Ser Val Val Ala
                515                 520                 525
Gly Pro Arg Phe Thr Gly Gly Asp Ile Ile Gln Cys Thr Glu Asn Gly
            530                 535                 540
Ser Ala Ala Thr Ile Tyr Val Thr Pro Asp Val Ser Tyr Ser Gln Lys
545                 550                 555                 560
Tyr Arg Ala Arg Ile His Tyr Ala Ser Thr Ser Gln Ile Thr Phe Thr
                565                 570                 575
Leu Ser Leu Asp Gly Ala Pro Phe Asn Gln Tyr Tyr Phe Asp Lys Thr
                580                 585                 590
Ile Asn Lys Gly Asp Thr Leu Thr Tyr Asn Ser Phe Asn Leu Ala Ser
                595                 600                 605
Phe Ser Thr Pro Phe Glu Leu Ser Gly Asn Asn Leu Gln Ile Gly Val
                610                 615                 620
Thr Gly Leu Ser Ala Gly Asp Lys Val Tyr Ile Asp Lys Ile Glu Phe
625                 630                 635                 640
Ile Pro Val Asn

<210> SEQ ID NO 136
<211> LENGTH: 31
<212> TYPE: DNA
<213> ORGANISM: Artificial Sequence
<220> FEATURE:
<223> OTHER INFORMATION: Chemically synthesized CMS94 primer

<400> SEQUENCE: 136
ggcgcgccac catggctagc atgactggtg g                              31

<210> SEQ ID NO 137
<211> LENGTH: 20
<212> TYPE: DNA
<213> ORGANISM: Artificial Sequence
<220> FEATURE:
<223> OTHER INFORMATION: Chemically synthesized CMS95 primer

<400> SEQUENCE: 137
gcaggaacag gtgggtgttg                                           20

<210> SEQ ID NO 138
<211> LENGTH: 20
<212> TYPE: DNA
<213> ORGANISM: Artificial sequence
<220> FEATURE:
<223> OTHER INFORMATION: Chemically synthesized CMS96 primer

<400> SEQUENCE: 138
cctgaacacc atctggccca                                           20

<210> SEQ ID NO 139
<211> LENGTH: 39
<212> TYPE: DNA
<213> ORGANISM: Artificial Sequence
<220> FEATURE:
<223> OTHER INFORMATION: Chemically synthesized CMS97 primer

<400> SEQUENCE: 139
```

```
ctggctgctg gggatgatgt tgttgaagtc gacgctctt                                    39
```

<210> SEQ ID NO 140
<211> LENGTH: 21
<212> TYPE: DNA
<213> ORGANISM: Artificial Sequence
<220> FEATURE:
<223> OTHER INFORMATION: Chemically synthesized CMS98 primer

<400> SEQUENCE: 140

```
gagctcttag gtcacctcgg c                                                       21
```

<210> SEQ ID NO 141
<211> LENGTH: 39
<212> TYPE: DNA
<213> ORGANISM: Artificial Sequence
<220> FEATURE:
<223> OTHER INFORMATION: Chemically synthesized CMS99 primer

<400> SEQUENCE: 141

```
aagagcgtcg acttcaacaa catcatcccc agcagccag                                    39
```

<210> SEQ ID NO 142
<211> LENGTH: 40
<212> TYPE: DNA
<213> ORGANISM: Artificial Sequence
<220> FEATURE:
<223> OTHER INFORMATION: Chemically synthesized CMS100 primer

<400> SEQUENCE: 142

```
gaagtaccgc gcccgcatcc gctacgccag caccaccaac                                   40
```

<210> SEQ ID NO 143
<211> LENGTH: 40
<212> TYPE: DNA
<213> ORGANISM: Artificial Sequence
<220> FEATURE:
<223> OTHER INFORMATION: Chemically synthesized CMS101 primer

<400> SEQUENCE: 143

```
gttggtggtg ctggcgtagc ggatgcgggc gcggtacttc                                   40
```

<210> SEQ ID NO 144
<211> LENGTH: 1966
<212> TYPE: DNA
<213> ORGANISM: Artificial Sequence
<220> FEATURE:
<223> OTHER INFORMATION: T7-8AF coding sequence

<400> SEQUENCE: 144

```
atggctagca tgactggtgg acagcaaatg ggtcgcggat ccatgacggc cgacaacaac       60
accgaggccc tggacagcag caccaccaag gacgtgatcc agaagggcat cagcgtggtg      120
ggcgacctgc tgggcgtggt gggcttcccc ttcggcggcg ccctggtgag cttctacacc      180
aacttcctga caccatctg gcccagcgag gacccctgga aggccttcat ggagcaggtg      240
gaggccctga tggaccagaa gatcgccgac tacgccaaga caaggcact ggccgagcta      300
cagggcctcc agaacaacgt ggaggactat gtgagcgccc tgagcagctg cagaagaac      360
cccgctgcac cgttccgcaa cccccacagc cagggccgca tccgcgagct gttcagccag      420
gccgagagcc acttccgcaa cagcatgccc agcttcgcca tcagcggcta cgaggtgctg      480
ttcctgacca cctacgccca ggccgccaac acccacctgt cctgctgaa ggacgcccaa      540
atctacggag aggagtgggg ctacgagaag gaggacatcg ccgagttcta caagcgccag     600
```

```
ctgaagctga cccaggagta caccgaccac tgcgtgaagt ggtacaacgt gggtctagac    660
aagctccgcg gcagcagcta cgagagctgg gtgaacttca accgctaccg ccgcgagatg    720
accctgaccg tgctggacct gatcgccctg ttcccctgt acgacgtgcg cctgtacccc     780
aaggaggtga agaccgagct gacccgcgac gtgctgaccg accccatcgt gggcgtgaac    840
aacctgcgcg gctacggcac caccttcagc aacatcgaga actacatccg caagccccac    900
ctgttcgact acctgcaccg catccagttc cacacgcgtt tccagcccgg ctactacggc    960
aacgacagct tcaactactg gagcggcaac tacgtgagca cccgccccag catcggcagc   1020
aacgacatca tcaccagccc cttctacggc aacaagagca gcgagcccgt gcagaacctt   1080
gagttcaacg gcgagaaggt gtaccgcgcc gtggctaaca ccaacctggc cgtgtggccc   1140
tctgcagtgt acagcggcgt gaccaaggtg gagttcagcc agtacaacga ccagaccgac   1200
gaggccagca cccagaccta cgacagcaag cgcaacgtgg gcgccgtgag ctgggacagc   1260
atcgaccagc tgcccccga gaccaccgac gagcccctgg agaagggcta cagccaccag   1320
ctgaactacg tgatgtgctt cctgatgcag ggcagccgcg gcaccatccc cgtgctgacc   1380
tggacccaca gagcgtcga cttcttcaac atgatcgaca gcaagaagat cacccagctg   1440
cccctgacca agagcaccaa cctgggcagc ggcaccagcg tggtgaaggg ccccggcttc   1500
accggcggcg acatcctgcg ccgcaccagc cccggccaga tcagcaccct gcgcgtgaac   1560
atcaccgccc ccctgagcca gcgctaccgc gtccgcatcc gctacgccag caccaccaac   1620
ctgcagttcc acaccagcat cgacggccgc cccatcaacc agggcaactt cagcgccacc   1680
atgagcagcg gcagcaacct gcagagcggc agcttccgca ccgtgggctt caccaccccc   1740
ttcaacttca gcaacggcag cagcgtgttc accctgagcg cccacgtgtt caacagcggc   1800
aacgaggtgt acatcgaccg catcgagttc gtgcccgccg aggtgacctt cgaggccgag   1860
tacgacctgg agagggctca gaaggccgtg aacgagctgt tcaccagcag caaccagatc   1920
ggcctgaaga ccgacgtgac cgactaccac atcgatcagg tgtagg                  1966
```

<210> SEQ ID NO 145
<211> LENGTH: 654
<212> TYPE: PRT
<213> ORGANISM: Artificial Sequence
<220> FEATURE:
<223> OTHER INFORMATION: T7-8AF protein

<400> SEQUENCE: 145

```
Met Ala Ser Met Thr Gly Gly Gln Gln Met Gly Arg Gly Ser Met Thr
1               5                   10                  15

Ala Asp Asn Asn Thr Glu Ala Leu Asp Ser Ser Thr Thr Lys Asp Val
            20                  25                  30

Ile Gln Lys Gly Ile Ser Val Val Gly Asp Leu Leu Gly Val Val Gly
        35                  40                  45

Phe Pro Phe Gly Gly Ala Leu Val Ser Phe Tyr Thr Asn Phe Leu Asn
    50                  55                  60

Thr Ile Trp Pro Ser Glu Asp Pro Trp Lys Ala Phe Met Glu Gln Val
65                  70                  75                  80

Glu Ala Leu Met Asp Gln Lys Ile Ala Asp Tyr Ala Lys Asn Lys Ala
                85                  90                  95

Leu Ala Glu Leu Gln Gly Leu Gln Asn Asn Val Glu Asp Tyr Val Ser
            100                 105                 110

Ala Leu Ser Ser Trp Gln Lys Asn Pro Ala Ala Pro Phe Arg Asn Pro
        115                 120                 125
```

-continued

```
His Ser Gln Gly Arg Ile Arg Glu Leu Phe Ser Gln Ala Glu Ser His
    130                 135                 140

Phe Arg Asn Ser Met Pro Ser Phe Ala Ile Ser Gly Tyr Glu Val Leu
145                 150                 155                 160

Phe Leu Thr Thr Tyr Ala Gln Ala Ala Asn Thr His Leu Phe Leu Leu
                165                 170                 175

Lys Asp Ala Gln Ile Tyr Gly Glu Glu Trp Gly Tyr Glu Lys Glu Asp
                180                 185                 190

Ile Ala Glu Phe Tyr Lys Arg Gln Leu Lys Leu Thr Gln Glu Tyr Thr
            195                 200                 205

Asp His Cys Val Lys Trp Tyr Asn Val Gly Leu Asp Lys Leu Arg Gly
    210                 215                 220

Ser Ser Tyr Glu Ser Trp Val Asn Phe Asn Arg Tyr Arg Arg Glu Met
225                 230                 235                 240

Thr Leu Thr Val Leu Asp Leu Ile Ala Leu Phe Pro Leu Tyr Asp Val
                245                 250                 255

Arg Leu Tyr Pro Lys Glu Val Lys Thr Glu Leu Thr Arg Asp Val Leu
                260                 265                 270

Thr Asp Pro Ile Val Gly Val Asn Asn Leu Arg Gly Tyr Gly Thr Thr
            275                 280                 285

Phe Ser Asn Ile Glu Asn Tyr Ile Arg Lys Pro His Leu Phe Asp Tyr
    290                 295                 300

Leu His Arg Ile Gln Phe His Thr Arg Phe Gln Pro Gly Tyr Tyr Gly
305                 310                 315                 320

Asn Asp Ser Phe Asn Tyr Trp Ser Gly Asn Tyr Val Ser Thr Arg Pro
                325                 330                 335

Ser Ile Gly Ser Asn Asp Ile Ile Thr Ser Pro Phe Tyr Gly Asn Lys
                340                 345                 350

Ser Ser Glu Pro Val Gln Asn Leu Glu Phe Asn Gly Glu Lys Val Tyr
            355                 360                 365

Arg Ala Val Ala Asn Thr Asn Leu Ala Val Trp Pro Ser Ala Val Tyr
    370                 375                 380

Ser Gly Val Thr Lys Val Glu Phe Ser Gln Tyr Asn Asp Gln Thr Asp
385                 390                 395                 400

Glu Ala Ser Thr Gln Thr Tyr Asp Ser Lys Arg Asn Val Gly Ala Val
                405                 410                 415

Ser Trp Asp Ser Ile Asp Gln Leu Pro Pro Glu Thr Thr Asp Glu Pro
                420                 425                 430

Leu Glu Lys Gly Tyr Ser His Gln Leu Asn Tyr Val Met Cys Phe Leu
            435                 440                 445

Met Gln Gly Ser Arg Gly Thr Ile Pro Val Leu Thr Trp Thr His Lys
    450                 455                 460

Ser Val Asp Phe Phe Asn Met Ile Asp Ser Lys Lys Ile Thr Gln Leu
465                 470                 475                 480

Pro Leu Thr Lys Ser Thr Asn Leu Gly Ser Gly Thr Ser Val Val Lys
                485                 490                 495

Gly Pro Gly Phe Thr Gly Gly Asp Ile Leu Arg Arg Thr Ser Pro Gly
                500                 505                 510

Gln Ile Ser Thr Leu Arg Val Asn Ile Thr Ala Pro Leu Ser Gln Arg
            515                 520                 525

Tyr Arg Val Arg Ile Arg Tyr Ala Ser Thr Thr Asn Leu Gln Phe His
    530                 535                 540

Thr Ser Ile Asp Gly Arg Pro Ile Asn Gln Gly Asn Phe Ser Ala Thr
545                 550                 555                 560
```

```
Met Ser Ser Gly Ser Asn Leu Gln Ser Gly Ser Phe Arg Thr Val Gly
            565                 570                 575
Phe Thr Thr Pro Phe Asn Phe Ser Asn Gly Ser Ser Val Phe Thr Leu
        580                 585                 590
Ser Ala His Val Phe Asn Ser Gly Asn Glu Val Tyr Ile Asp Arg Ile
    595                 600                 605
Glu Phe Val Pro Ala Glu Val Thr Phe Glu Ala Glu Tyr Asp Leu Glu
610                 615                 620
Arg Ala Gln Lys Ala Val Asn Glu Leu Phe Thr Ser Ser Asn Gln Ile
625                 630                 635                 640
Gly Leu Lys Thr Asp Val Thr Asp Tyr His Ile Asp Gln Val
                645                 650

<210> SEQ ID NO 146
<211> LENGTH: 1920
<212> TYPE: DNA
<213> ORGANISM: Artificial Sequence
<220> FEATURE:
<223> OTHER INFORMATION: -catG8AF coding sequence

<400> SEQUENCE: 146
atgacggccg acaacaacac cgaggccctg acagcagca ccaccaagga cgtgatccag      60
aagggcatca gcgtggtggg cgacctgctg ggcgtggtgg gcttcccctt cggcggcgcc    120
ctggtgagct tctacaccaa cttcctgaac accatctggc ccagcgagga ccctggaag     180 gccttcatgg agcaggtgga ggccctgatg accagaagga tcgccgacta cgccaagaac    240
aaggcactgg ccgagctaca gggcctccag aacaacgtgg aggactatgt gagcgccctg    300
agcagctggc agaagaaccc cgtctcgagc cgcaacccccc acagccaggg ccgcatccgc    360
gagctgttca gccaggccga gccacttcc gcaacagca tgcccagctt cgccatcagc      420
ggctacgagg tgctgttcct gaccacctac gcccaggccg ccaacaccca cctgttcctg    480
ctgaaggacg cccaaatcta cggagaggag tggggctacg agaaggagga catcgccgag    540
ttctacaagc gccagctgaa gctgacccag gagtacaccg accactgcgt gaagtggtac    600
aacgtgggtc tagacaagct ccgcggcagc agctacgaga gctgggtgaa cttcaaccgc    660
taccgccgcg agatgaccct gaccgtgctg gacctgatcg ccctgttccc cctgtacgac    720
gtgcgcctgt accccaagga ggtgaagacc gagctgaccc gcgacgtgct gaccgacccc    780
atcgtgggcg tgaacaacct cgcggctac ggcaccaccct tcagcaacat cgagaactac    840
atccgcaagc cccaccctgtt cgactacctg caccgcatcc agttccacac gcgtttccag    900
cccggctact acggcaacga cagcttcaac tactggagcg gcaactacgt gagcacccgc    960
cccagcatcg gcagcaacga catcatcacc agccccttct acggcaacaa gagcagcgag   1020
cccgtgcaga accttgagtt caacggcgag aaggtgtacc gcgccgtggc taacaccaac   1080
ctggccgtgt ggcctctgc agtgtacagc ggcgtgacca aggtggagtt cagccagtac   1140
aacgaccaga ccgacgaggc cagcacccag acctacgaca gcaagcgcaa cgtgggcgcc   1200
gtgagctggg acagcatcga ccagctgccc ccgagacca ccgacgagcc cctggagaag   1260
ggctacagcc accagctgaa ctacgtgatg tgcttcctga tgcagggcag ccgcggcacc   1320
atccccgtgc tgacctggac ccacaagagc gtcgacttct tcaacatgat cgacagcaag   1380
aagatcaccc agctgcccct gaccaagagc accaacctgg gcagcggcac cagcgtggtg   1440
aagggccccg gcttcaccgg cggcgacatc ctgcgccgca ccagcccggg ccagatcagc   1500
accctgcgcg tgaacatcac cgcccccctg agccagcgct accgcgtccg catccgctac   1560
```

-continued

```
gccagcacca ccaacctgca gttccacacc agcatcgacg gccgcccat caaccagggc    1620 aacttcagcg ccaccatgag cagcggcagc aacctgcaga gcggcagctt ccgcaccgtg    1680
ggcttcacca ccccccttcaa cttcagcaac ggcagcagcg tgttcaccct gagcgcccac    1740
gtgttcaaca gcggcaacga ggtgtacatc gaccgcatcg agttcgtgcc cgccgaggtg    1800
accttcgagg ccgagtacga cctggagagg gctcagaagg ccgtgaacga gctgttcacc    1860
agcagcaacc agatcggcct gaagaccgac gtgaccgact accacatcga tcaggtgtag    1920
```

<210> SEQ ID NO 147
<211> LENGTH: 639
<212> TYPE: PRT
<213> ORGANISM: Artificial Sequence
<220> FEATURE:
<223> OTHER INFORMATION: -catG8AF protein

<400> SEQUENCE: 147

```
Met Thr Ala Asp Asn Asn Thr Glu Ala Leu Asp Ser Ser Thr Thr Lys
  1               5                  10                  15

Asp Val Ile Gln Lys Gly Ile Ser Val Val Gly Asp Leu Leu Gly Val
             20                  25                  30

Val Gly Phe Pro Phe Gly Gly Ala Leu Val Ser Phe Tyr Thr Asn Phe
         35                  40                  45

Leu Asn Thr Ile Trp Pro Ser Glu Asp Pro Trp Lys Ala Phe Met Glu
 50                  55                  60

Gln Val Glu Ala Leu Met Asp Gln Lys Ile Ala Asp Tyr Ala Lys Asn
 65                  70                  75                  80

Lys Ala Leu Ala Glu Leu Gln Gly Leu Gln Asn Asn Val Glu Asp Tyr
                 85                  90                  95

Val Ser Ala Leu Ser Ser Trp Gln Lys Asn Pro Val Ser Ser Arg Asn
            100                 105                 110

Pro His Ser Gln Gly Arg Ile Arg Glu Leu Phe Ser Gln Ala Glu Ser
        115                 120                 125

His Phe Arg Asn Ser Met Pro Ser Phe Ala Ile Ser Gly Tyr Glu Val
130                 135                 140

Leu Phe Leu Thr Thr Tyr Ala Gln Ala Ala Asn Thr His Leu Phe Leu
145                 150                 155                 160

Leu Lys Asp Ala Gln Ile Tyr Gly Glu Glu Trp Gly Tyr Glu Lys Glu
                165                 170                 175

Asp Ile Ala Glu Phe Tyr Lys Arg Gln Leu Lys Leu Thr Gln Glu Tyr
            180                 185                 190

Thr Asp His Cys Val Lys Trp Tyr Asn Val Gly Leu Asp Lys Leu Arg
        195                 200                 205

Gly Ser Ser Tyr Glu Ser Trp Val Asn Phe Asn Arg Tyr Arg Arg Glu
    210                 215                 220

Met Thr Leu Thr Val Leu Asp Leu Ile Ala Leu Phe Pro Leu Tyr Asp
225                 230                 235                 240

Val Arg Leu Tyr Pro Lys Glu Val Lys Thr Glu Leu Thr Arg Asp Val
                245                 250                 255

Leu Thr Asp Pro Ile Val Gly Val Asn Asn Leu Arg Gly Tyr Gly Thr
            260                 265                 270

Thr Phe Ser Asn Ile Glu Asn Tyr Ile Arg Lys Pro His Leu Phe Asp
        275                 280                 285

Tyr Leu His Arg Ile Gln Phe His Thr Arg Phe Gln Pro Gly Tyr Tyr
    290                 295                 300
```

Gly Asn Asp Ser Phe Asn Tyr Trp Ser Gly Asn Tyr Val Ser Thr Arg
305                 310                 315                 320

Pro Ser Ile Gly Ser Asn Asp Ile Ile Thr Ser Pro Phe Tyr Gly Asn
            325                 330                 335

Lys Ser Ser Glu Pro Val Gln Asn Leu Glu Phe Asn Gly Glu Lys Val
        340                 345                 350

Tyr Arg Ala Val Ala Asn Thr Asn Leu Ala Val Trp Pro Ser Ala Val
    355                 360                 365

Tyr Ser Gly Val Thr Lys Val Glu Phe Ser Gln Tyr Asn Asp Gln Thr
370                 375                 380

Asp Glu Ala Ser Thr Gln Thr Tyr Asp Ser Lys Arg Asn Val Gly Ala
385                 390                 395                 400

Val Ser Trp Asp Ser Ile Asp Gln Leu Pro Pro Glu Thr Thr Asp Glu
            405                 410                 415

Pro Leu Glu Lys Gly Tyr Ser His Gln Leu Asn Tyr Val Met Cys Phe
        420                 425                 430

Leu Met Gln Gly Ser Arg Gly Thr Ile Pro Val Leu Thr Trp Thr His
    435                 440                 445

Lys Ser Val Asp Phe Phe Asn Met Ile Asp Ser Lys Lys Ile Thr Gln
450                 455                 460

Leu Pro Leu Thr Lys Ser Thr Asn Leu Gly Ser Gly Thr Ser Val Val
465                 470                 475                 480

Lys Gly Pro Gly Phe Thr Gly Asp Ile Leu Arg Arg Thr Ser Pro
            485                 490                 495

Gly Gln Ile Ser Thr Leu Arg Val Asn Ile Thr Ala Pro Leu Ser Gln
        500                 505                 510

Arg Tyr Arg Val Arg Ile Arg Tyr Ala Ser Thr Thr Asn Leu Gln Phe
    515                 520                 525

His Thr Ser Ile Asp Gly Arg Pro Ile Asn Gln Gly Asn Phe Ser Ala
530                 535                 540

Thr Met Ser Ser Gly Ser Asn Leu Gln Ser Gly Ser Phe Arg Thr Val
545                 550                 555                 560

Gly Phe Thr Thr Pro Phe Asn Phe Ser Asn Gly Ser Ser Val Phe Thr
            565                 570                 575

Leu Ser Ala His Val Phe Asn Ser Gly Asn Glu Val Tyr Ile Asp Arg
        580                 585                 590

Ile Glu Phe Val Pro Ala Glu Val Thr Phe Glu Ala Glu Tyr Asp Leu
    595                 600                 605

Glu Arg Ala Gln Lys Ala Val Asn Glu Leu Phe Thr Ser Ser Asn Gln
610                 615                 620

Ile Gly Leu Lys Thr Asp Val Thr Asp Tyr His Ile Asp Gln Val
625                 630                 635

<210> SEQ ID NO 148
<211> LENGTH: 1809
<212> TYPE: DNA
<213> ORGANISM: Artificial Sequence
<220> FEATURE:
<223> OTHER INFORMATION: 8AFdm3 coding sequence

<400> SEQUENCE: 148
atgacggccg acaacaacac cgaggccctg acagcagca ccaccaagga cgtgatccag      60
aagggcatca gcgtggtggg cgacctgctg ggcgtggtgg gcttcccctt cggcggcgcc     120
ctggtgagct tctacaccaa cttcctgaac accatctggc ccagcgagga ccctggaag     180 gccttcatgg agcaggtgga ggccctgatg accagaaga tcgccgacta cgccaagaac     240

```
aaggcactgg ccgagctaca gggcctccag aacaacgtgg aggactatgt gagcgccctg   300
agcagctggc agaagaaccc cgctgcaccg ttccgcaacc cccacagcca gggccgcatc   360
cgcgagctgt tcagccaggc cgagagccac ttccgcaaca gcatgcccag cttcgccatc   420
agcggctacg aggtgctgtt cctgaccacc tacgcccagg ccgccaacac ccacctgttc   480
ctgctgaagg acgcccaaat ctacggagag gagtggggct acgagaagga ggacatcgcc   540
gagttctaca agcgccagct gaagctgacc caggagtaca ccgaccactg cgtgaagtgg   600
tacaacgtgg gtctagacaa gctccgcggc agcagctacg agagctgggt gaacttcaac   660
cgctaccgcc gcgagatgac cctgaccgtg ctggacctga tcgccctgtt ccccctgtac   720
gacgtgcgcc tgtaccccaa ggaggtgaag accgagctga cccgcgacgt gctgaccgac   780
cccatcgtgg gcgtgaacaa cctgcgcggc tacggcacca ccttcagcaa catcgagaac   840
tacatccgca agccccacct gttcgactac ctgcaccgca tccagttcca cacgcgtttc   900
cagcccggct actacggcaa cgacagcttc aactactgga cggcaactac cgtgagcacc   960
cgccccagca tcggcagcaa cgacatcatc accagcccct ctacggcaa caagagcagc   1020 gagcccgtgc agaaccttga gttcaacggc gagaaggtgt accgcgccgt ggctaacacc   1080
aacctggccg tgtggccctc tgcagtgtac agcggcgtga ccaaggtgga gttcagccag   1140
tacaacgacc agaccgacga ggccagcacc cagacctacg acagcaagcg caacgtgggc   1200
gccgtgagct gggacagcat cgaccagctg ccccccgaga ccaccgacga gcccctggag   1260
aagggctaca gccaccagct gaactacgtg atgtgcttcc tgatgcaggg cagccgcggc   1320
accatccccg tgctgacctg acccacaag agcgtcgact tcaacaacat catccccagc   1380
agccagatca cccagatccc cctgaccaag agcaccaacc tgggcagcgg caccagcgtg   1440
gtgaagggcc ccggcttcac cggcggcgac atcctgcgcc gcaccagccc cggccagatc   1500
agcaccctgc gcgtgaacat caccgccccc ctgagccagc gctaccgcgt ccgcatccgc   1560
tacgccagca ccaccaacct gcagttccac accagcatcg acggccgccc catcaaccag   1620
ggcaacttca gcgccaccat gagcagcggc agcaacctgc agagcggcag cttccgcacc   1680
gtgggcttca ccaccccctt caacttcagc aacggcagca gcgtgttcac cctgagcgcc   1740
cacgtgttca cagcggcaa cgaggtgtac atcgaccgca tcgagttcgt gcccgccgag   1800
gtgacctaa                                                          1809
```

<210> SEQ ID NO 149
<211> LENGTH: 602
<212> TYPE: PRT
<213> ORGANISM: Artificial Sequence
<220> FEATURE:
<223> OTHER INFORMATION: 8AFdm3 protein

<400> SEQUENCE: 149

```
Met Thr Ala Asp Asn Asn Thr Glu Ala Leu Asp Ser Ser Thr Thr Lys
1               5                   10                  15

Asp Val Ile Gln Lys Gly Ile Ser Val Val Gly Asp Leu Leu Gly Val
            20                  25                  30

Val Gly Phe Pro Phe Gly Gly Ala Leu Val Ser Phe Tyr Thr Asn Phe
        35                  40                  45

Leu Asn Thr Ile Trp Pro Ser Glu Asp Pro Trp Lys Ala Phe Met Glu
    50                  55                  60

Gln Val Glu Ala Leu Met Asp Gln Lys Ile Ala Asp Tyr Ala Lys Asn
65                  70                  75                  80
```

-continued

Lys Ala Leu Ala Glu Leu Gln Gly Leu Gln Asn Asn Val Glu Asp Tyr
            85                  90                  95

Val Ser Ala Leu Ser Ser Trp Gln Lys Asn Pro Ala Ala Pro Phe Arg
            100                 105                 110

Asn Pro His Ser Gln Gly Arg Ile Arg Glu Leu Phe Ser Gln Ala Glu
            115                 120                 125

Ser His Phe Arg Asn Ser Met Pro Ser Phe Ala Ile Ser Gly Tyr Glu
            130                 135                 140

Val Leu Phe Leu Thr Thr Tyr Ala Gln Ala Ala Asn Thr His Leu Phe
145                 150                 155                 160

Leu Leu Lys Asp Ala Gln Ile Tyr Gly Glu Trp Gly Tyr Glu Lys
            165                 170                 175

Glu Asp Ile Ala Glu Phe Tyr Lys Arg Gln Leu Lys Leu Thr Gln Glu
            180                 185                 190

Tyr Thr Asp His Cys Val Lys Trp Tyr Asn Val Gly Leu Asp Lys Leu
            195                 200                 205

Arg Gly Ser Ser Tyr Glu Ser Trp Val Asn Phe Asn Arg Tyr Arg Arg
            210                 215                 220

Glu Met Thr Leu Thr Val Leu Asp Leu Ile Ala Leu Phe Pro Leu Tyr
225                 230                 235                 240

Asp Val Arg Leu Tyr Pro Lys Glu Val Lys Thr Glu Leu Thr Arg Asp
            245                 250                 255

Val Leu Thr Asp Pro Ile Val Gly Val Asn Asn Leu Arg Gly Tyr Gly
            260                 265                 270

Thr Thr Phe Ser Asn Ile Glu Asn Tyr Ile Arg Lys Pro His Leu Phe
            275                 280                 285

Asp Tyr Leu His Arg Ile Gln Phe His Thr Arg Phe Gln Pro Gly Tyr
            290                 295                 300

Tyr Gly Asn Asp Ser Phe Asn Tyr Trp Ser Gly Asn Tyr Val Ser Thr
305                 310                 315                 320

Arg Pro Ser Ile Gly Ser Asn Asp Ile Ile Thr Ser Pro Phe Tyr Gly
            325                 330                 335

Asn Lys Ser Ser Glu Pro Val Gln Asn Leu Glu Phe Asn Gly Glu Lys
            340                 345                 350

Val Tyr Arg Ala Val Ala Asn Thr Asn Leu Ala Val Trp Pro Ser Ala
            355                 360                 365

Val Tyr Ser Gly Val Thr Lys Val Glu Phe Ser Gln Tyr Asn Asp Gln
            370                 375                 380

Thr Asp Glu Ala Ser Thr Gln Thr Tyr Asp Ser Lys Arg Asn Val Gly
385                 390                 395                 400

Ala Val Ser Trp Asp Ser Ile Asp Gln Leu Pro Pro Glu Thr Thr Asp
            405                 410                 415

Glu Pro Leu Glu Lys Gly Tyr Ser His Gln Leu Asn Tyr Val Met Cys
            420                 425                 430

Phe Leu Met Gln Gly Ser Arg Gly Thr Ile Pro Val Leu Thr Trp Thr
            435                 440                 445

His Lys Ser Val Asp Phe Asn Asn Ile Ile Pro Ser Ser Gln Ile Thr
            450                 455                 460

Gln Ile Pro Leu Thr Lys Ser Thr Asn Leu Gly Ser Gly Thr Ser Val
465                 470                 475                 480

Val Lys Gly Pro Gly Phe Thr Gly Gly Asp Ile Leu Arg Arg Thr Ser
            485                 490                 495

Pro Gly Gln Ile Ser Thr Leu Arg Val Asn Ile Thr Ala Pro Leu Ser
            500                 505                 510

```
Gln Arg Tyr Arg Val Arg Ile Arg Tyr Ala Ser Thr Thr Asn Leu Gln
        515                 520                 525

Phe His Thr Ser Ile Asp Gly Arg Pro Ile Asn Gln Gly Asn Phe Ser
    530                 535                 540

Ala Thr Met Ser Ser Gly Ser Asn Leu Gln Ser Gly Ser Phe Arg Thr
545                 550                 555                 560

Val Gly Phe Thr Thr Pro Phe Asn Phe Ser Asn Gly Ser Ser Val Phe
                565                 570                 575

Thr Leu Ser Ala His Val Phe Asn Ser Gly Asn Glu Val Tyr Ile Asp
            580                 585                 590

Arg Ile Glu Phe Val Pro Ala Glu Val Thr
            595                 600

<210> SEQ ID NO 150
<211> LENGTH: 1809
<212> TYPE: DNA
<213> ORGANISM: Artificial Sequence
<220> FEATURE:
<223> OTHER INFORMATION: 8AF1omgdm3 coding sequence

<400> SEQUENCE: 150
atgacggccg acaacaacac cgaggccctg acagcagca ccaccaagga cgtgatccag     60
aagggcatca gcgtggtggg cgacctgctg ggcgtggtgg gcttcccctt cggcggcgcc    120
ctggtgagct tctacaccaa cttcctgaac accatctggc cagcgagga ccctggaag     180 gccttcatgg agcaggtgga ggccctgatg accagaaga tcgccgacta cgccaagaac    240
aaggcactgg ccgagctaca gggcctccag aacaacgtgg aggactatgt gagcgccctg    300
agcagctggc agaagaaccc cgctgcaccg ttccgcaacc cccacagcca gggccgcatc    360
cgcgagctgt tcagccaggc cgagagccac ttccgcaaca gcatgccag cttcgccatc    420 agcggctacg aggtgctgtt cctgaccacc tacgcccagg ccgccaacac ccacctgttc    480
ctgctgaagg acgcccaaat ctacggagag gagtggggct acgagaagga ggacatcgcc    540
gagttctaca gcgccagct gaagctgacc caggagtaca ccgaccactg cgtgaagtgg    600
tacaacgtgg gtctagacaa gctccgcggc agcagctacg agagctgggt gaacttcaac    660
cgctaccgcc gcgagatgac cctgaccgtg ctggacctga tcgccctgtt ccccctgtac    720
gacgtgcgcc tgtacccaa ggaggtgaag accgagctga cccgcgacgt gctgaccgac    780
cccatcgtgg gcgtgaacaa cctgcgcggc tacggcacca ccttcagcaa catcgagaac    840
tacatccgca agcccacct gttcgactac ctgcaccgca tccagttcca cacgcgtttc    900
cagcccggct actacggcaa cgacagcttc aactactgga gcggcaacta cgtgagcacc    960
cgccccagca tcggcagcaa cgacatcatc accagcccct tctacggcaa caagagcagc   1020
gagcccgtgc agaaccttga gttcaacggc gagaaggtgt accgcgccgt ggctaacacc   1080
aacctggccg tgtggccctc tgcagtgtac agcggcgtga ccaaggtgga gttcagccag   1140
tacaacgacc agaccgacga ggccagcacc cagacctacg acagcaagcg caacgtgggc   1200
gccgtgagct gggacagcat cgaccagctg ccccccgaga ccaccgacga gcccctggag   1260
aagggctaca gccaccagct gaactacgtg atgtgcttcc tgatgcaggg cagccgcggc   1320
accatccccg tgctgacctg gacccacaag agcgtcgact tcttcaacat gatcgacagc   1380
aagaagatca cccagctgcc cctggtgaag gcctacaagc tccagagcgg cgccagcgtg   1440
gtggcaggcc ccgcttcac cggcggcgac atcatccagt gcaccgagaa cggcagcgcc   1500
gccaccatct acgtgacccc cgacgtgagc tacagccaga agtaccgcgc ccgcatccgc   1560
```

-continued

```
tacgccagca ccaccaacct gcagttccac accagcatcg acggccgccc catcaaccag    1620
ggcaacttca gcgccaccat gagcagcggc agcaacctgc agagcggcag cttccgcacc    1680
gtgggcttca ccaccccctt caacttcagc aacggcagca gcgtgttcac cctgagcgcc    1740
cacgtgttca acagcggcaa cgaggtgtac atcgaccgca tcgagttcgt gcccgccgag    1800
gtgacctaa                                                            1809
```

<210> SEQ ID NO 151
<211> LENGTH: 602
<212> TYPE: PRT
<213> ORGANISM: Artificial Sequence
<220> FEATURE:
<223> OTHER INFORMATION: 8AFlongdm3 protein

<400> SEQUENCE: 151

```
Met Thr Ala Asp Asn Asn Thr Glu Ala Leu Asp Ser Ser Thr Thr Lys
1               5                   10                  15

Asp Val Ile Gln Lys Gly Ile Ser Val Val Gly Asp Leu Leu Gly Val
            20                  25                  30

Val Gly Phe Pro Phe Gly Gly Ala Leu Val Ser Phe Tyr Thr Asn Phe
        35                  40                  45

Leu Asn Thr Ile Trp Pro Ser Glu Asp Pro Trp Lys Ala Phe Met Glu
    50                  55                  60

Gln Val Glu Ala Leu Met Asp Gln Lys Ile Ala Asp Tyr Ala Lys Asn
65                  70                  75                  80

Lys Ala Leu Ala Glu Leu Gln Gly Leu Gln Asn Asn Val Glu Asp Tyr
                85                  90                  95

Val Ser Ala Leu Ser Ser Trp Gln Lys Asn Pro Ala Ala Pro Phe Arg
            100                 105                 110

Asn Pro His Ser Gln Gly Arg Ile Arg Glu Leu Phe Ser Gln Ala Glu
        115                 120                 125

Ser His Phe Arg Asn Ser Met Pro Ser Phe Ala Ile Ser Gly Tyr Glu
    130                 135                 140

Val Leu Phe Leu Thr Thr Tyr Ala Gln Ala Ala Asn Thr His Leu Phe
145                 150                 155                 160

Leu Leu Lys Asp Ala Gln Ile Tyr Gly Glu Glu Trp Gly Tyr Glu Lys
                165                 170                 175

Glu Asp Ile Ala Glu Phe Tyr Lys Arg Gln Leu Lys Leu Thr Gln Glu
            180                 185                 190

Tyr Thr Asp His Cys Val Lys Trp Tyr Asn Val Gly Leu Asp Lys Leu
        195                 200                 205

Arg Gly Ser Ser Tyr Glu Ser Trp Val Asn Phe Asn Arg Tyr Arg Arg
    210                 215                 220

Glu Met Thr Leu Thr Val Leu Asp Leu Ile Ala Leu Phe Pro Leu Tyr
225                 230                 235                 240

Asp Val Arg Leu Tyr Pro Lys Glu Val Lys Thr Glu Leu Thr Arg Asp
                245                 250                 255

Val Leu Thr Asp Pro Ile Val Gly Val Asn Asn Leu Arg Gly Tyr Gly
            260                 265                 270

Thr Thr Phe Ser Asn Ile Glu Asn Tyr Ile Arg Lys Pro His Leu Phe
        275                 280                 285

Asp Tyr Leu His Arg Ile Gln Phe His Thr Arg Phe Gln Pro Gly Tyr
    290                 295                 300

Tyr Gly Asn Asp Ser Phe Asn Tyr Trp Ser Gly Asn Tyr Val Ser Thr
305                 310                 315                 320
```

Arg Pro Ser Ile Gly Ser Asn Asp Ile Ile Thr Ser Pro Phe Tyr Gly
                325                 330                 335

Asn Lys Ser Ser Glu Pro Val Gln Asn Leu Glu Phe Asn Gly Glu Lys
            340                 345                 350

Val Tyr Arg Ala Val Ala Asn Thr Asn Leu Ala Val Trp Pro Ser Ala
        355                 360                 365

Val Tyr Ser Gly Val Thr Lys Val Glu Phe Ser Gln Tyr Asn Asp Gln
    370                 375                 380

Thr Asp Glu Ala Ser Thr Gln Thr Tyr Asp Ser Lys Arg Asn Val Gly
385                 390                 395                 400

Ala Val Ser Trp Asp Ser Ile Asp Gln Leu Pro Pro Glu Thr Thr Asp
                405                 410                 415

Glu Pro Leu Glu Lys Gly Tyr Ser His Gln Leu Asn Tyr Val Met Cys
            420                 425                 430

Phe Leu Met Gln Gly Ser Arg Gly Thr Ile Pro Val Leu Thr Trp Thr
        435                 440                 445

His Lys Ser Val Asp Phe Phe Asn Met Ile Asp Ser Lys Lys Ile Thr
    450                 455                 460

Gln Leu Pro Leu Val Lys Ala Tyr Lys Leu Gln Ser Gly Ala Ser Val
465                 470                 475                 480

Val Ala Gly Pro Arg Phe Thr Gly Gly Asp Ile Ile Gln Cys Thr Glu
                485                 490                 495

Asn Gly Ser Ala Ala Thr Ile Tyr Val Thr Pro Asp Val Ser Tyr Ser
            500                 505                 510

Gln Lys Tyr Arg Ala Arg Ile Arg Tyr Ala Ser Thr Thr Asn Leu Gln
        515                 520                 525

Phe His Thr Ser Ile Asp Gly Arg Pro Ile Asn Gln Gly Asn Phe Ser
    530                 535                 540

Ala Thr Met Ser Ser Gly Ser Asn Leu Gln Ser Gly Ser Phe Arg Thr
545                 550                 555                 560

Val Gly Phe Thr Thr Pro Phe Asn Phe Ser Asn Gly Ser Ser Val Phe
                565                 570                 575

Thr Leu Ser Ala His Val Phe Asn Ser Gly Asn Glu Val Tyr Ile Asp
            580                 585                 590

Arg Ile Glu Phe Val Pro Ala Glu Val Thr
        595                 600

<210> SEQ ID NO 152
<211> LENGTH: 1848
<212> TYPE: DNA
<213> ORGANISM: Artificial Sequence
<220> FEATURE:
<223> OTHER INFORMATION: cap8AFdm3 coding sequence

<400> SEQUENCE: 152
atgactagta acggccgcca gtgtgctggt attcgccctt atgacggccg acaacaacac    60
cgaggcctgg acagcagcac caccaaggac gtgatccaga agggcatcag cgtggtgggc   120
gacctgctgg gcgtggtggg cttccccttc ggcggcgccc tggtgagctt ctacaccaac   180
ttcctgaaca ccatctggcc cagcgaggac ccctggaagg ccttcatgga gcaggtggag   240
gccctgatga ccagaagat cgccgactac gccaagaaca aggcactggc cgagctacag   300
ggcctccaga caacgtgga ggactatgtg agcgccctga gcagctggca gaagaacccc   360
gctgcaccgt tccgcaaccc ccacagccag ggccgcatcc gcgagctgtt cagccaggcc   420
gagagccact tccgcaacag catgcccagc ttcgccatca gcggctacga ggtgctgttc   480

```
ctgaccacct acgcccaggc cgccaacacc cacctgttcc tgctgaagga cgcccaaatc    540
tacggagagg agtggggcta cgagaaggag gacatcgccg agttctacaa gcgccagctg    600
aagctgaccc aggagtacac cgaccactgc gtgaagtggt acaacgtggg tctagacaag    660
ctccgcggca gcagctacga gagctgggtg aacttcaacc gctaccgccg cgagatgacc    720
ctgaccgtgc tggacctgat cgccctgttc cccctgtacg acgtgcgcct gtaccccaag    780
gaggtgaaga ccgagctgac ccgcgacgtg ctgaccgacc ccatcgtggg cgtgaacaac    840
ctgcgcggct acggcaccac cttcagcaac atcgagaact acatccgcaa gccccacctg    900
ttcgactacc tgcaccgcat ccagttccac acgcgtttcc agcccggcta ctacggcaac    960
gacagcttca actactggag cggcaactac gtgagcaccc gccccagcat cggcagcaac   1020
gacatcatca ccagccccct tctacggcaac aagagcagcg agcccgtgca gaaccttgag   1080
ttcaacggcg agaaggtgta ccgcgccgtg gctaacacca acctggccgt gtggccctct   1140
gcagtgtaca gcggcgtgac caaggtggag ttcagccagt acaacgacca gaccgacgag   1200
gccagcaccc agacctacga cagcaagcgc aacgtgggcg ccgtgagctg ggacagcatc   1260
gaccagctgc cccccgagac caccgacgag cccctggaga agggctacag ccaccagctg   1320
aactacgtga tgtgcttcct gatgcagggc agccgcggca ccatccccgt gctgacctgg   1380
acccacaaga gcgtcgactt caacaacatc atccccagca gccagatcac ccagatcccc   1440
ctgaccaaga gcaccaacct gggcagcggc accagcgtgg tgaagggccc cggcttcacc   1500
ggcggcgaca tcctgcgccg caccagcccc ggccagatca gcaccctgcg cgtgaacatc   1560
accgcccccc tgagccagcg ctaccgcgtc cgcatccgct acgccagcac caccaacctg   1620
cagttccaca ccagcatcga cggccgcccc atcaaccagg gcaacttcag cgccaccatg   1680
agcagcggca gcaacctgca gagcggcagc ttccgcaccg tgggcttcac cacccccttc   1740
aacttcagca acggcagcag cgtgttcacc ctgagcgccc acgtgttcaa cagcggcaac   1800
gaggtgtaca tcgaccgcat cgagttcgtg cccgccgagg tgacctag              1848
```

<210> SEQ ID NO 153  
<211> LENGTH: 615  
<212> TYPE: PRT  
<213> ORGANISM: Artificial Sequence  
<220> FEATURE:  
<223> OTHER INFORMATION: cap8AFdm3 protein

<400> SEQUENCE: 153

```
Met Thr Ser Asn Gly Arg Gln Cys Ala Gly Ile Arg Pro Tyr Asp Gly
1               5                   10                  15

Arg Gln Gln His Arg Gly Leu Asp Ser Ser Thr Thr Lys Asp Val Ile
            20                  25                  30

Gln Lys Gly Ile Ser Val Val Gly Asp Leu Leu Gly Val Gly Phe
        35                  40                  45

Pro Phe Gly Gly Ala Leu Val Ser Phe Tyr Thr Asn Phe Leu Asn Thr
    50                  55                  60

Ile Trp Pro Ser Glu Asp Pro Trp Lys Ala Phe Met Glu Gln Val Glu
65                  70                  75                  80

Ala Leu Met Asp Gln Lys Ile Ala Asp Tyr Ala Lys Asn Lys Ala Leu
                85                  90                  95

Ala Glu Leu Gln Gly Leu Gln Asn Asn Val Glu Asp Tyr Val Ser Ala
            100                 105                 110

Leu Ser Ser Trp Gln Lys Asn Pro Ala Ala Pro Phe Arg Asn Pro His
        115                 120                 125
```

```
Ser Gln Gly Arg Ile Arg Glu Leu Phe Ser Gln Ala Glu Ser His Phe
    130                 135                 140

Arg Asn Ser Met Pro Ser Phe Ala Ile Ser Gly Tyr Glu Val Leu Phe
145                 150                 155                 160

Leu Thr Thr Tyr Ala Gln Ala Asn Thr His Leu Phe Leu Leu Lys
                165                 170                 175

Asp Ala Gln Ile Tyr Gly Glu Glu Trp Gly Tyr Glu Lys Glu Asp Ile
            180                 185                 190

Ala Glu Phe Tyr Lys Arg Gln Leu Lys Leu Thr Gln Glu Tyr Thr Asp
        195                 200                 205

His Cys Val Lys Trp Tyr Asn Val Gly Leu Asp Lys Leu Arg Gly Ser
    210                 215                 220

Ser Tyr Glu Ser Trp Val Asn Phe Asn Arg Tyr Arg Arg Glu Met Thr
225                 230                 235                 240

Leu Thr Val Leu Asp Leu Ile Ala Leu Phe Pro Leu Tyr Asp Val Arg
                245                 250                 255

Leu Tyr Pro Lys Glu Val Lys Thr Glu Leu Thr Arg Asp Val Leu Thr
            260                 265                 270

Asp Pro Ile Val Gly Val Asn Leu Arg Gly Tyr Gly Thr Thr Phe
        275                 280                 285

Ser Asn Ile Glu Asn Tyr Ile Arg Lys Pro His Leu Phe Asp Tyr Leu
    290                 295                 300

His Arg Ile Gln Phe His Thr Arg Phe Gln Pro Gly Tyr Tyr Gly Asn
305                 310                 315                 320

Asp Ser Phe Asn Tyr Trp Ser Gly Asn Tyr Val Ser Thr Arg Pro Ser
                325                 330                 335

Ile Gly Ser Asn Asp Ile Ile Thr Ser Pro Phe Tyr Gly Asn Lys Ser
            340                 345                 350

Ser Glu Pro Val Gln Asn Leu Glu Phe Asn Gly Glu Lys Val Tyr Arg
        355                 360                 365

Ala Val Ala Asn Thr Asn Leu Ala Val Trp Pro Ser Ala Val Tyr Ser
    370                 375                 380

Gly Val Thr Lys Val Glu Phe Ser Gln Tyr Asn Asp Gln Thr Asp Glu
385                 390                 395                 400

Ala Ser Thr Gln Thr Tyr Asp Ser Lys Arg Asn Val Gly Ala Val Ser
                405                 410                 415

Trp Asp Ser Ile Asp Gln Leu Pro Pro Glu Thr Thr Asp Glu Pro Leu
            420                 425                 430

Glu Lys Gly Tyr Ser His Gln Leu Asn Tyr Val Met Cys Phe Leu Met
        435                 440                 445

Gln Gly Ser Arg Gly Thr Ile Pro Val Leu Thr Trp Thr His Lys Ser
    450                 455                 460

Val Asp Phe Asn Asn Ile Ile Pro Ser Ser Gln Ile Thr Gln Ile Pro
465                 470                 475                 480

Leu Thr Lys Ser Thr Asn Leu Gly Ser Gly Thr Ser Val Val Lys Gly
                485                 490                 495

Pro Gly Phe Thr Gly Gly Asp Ile Leu Arg Arg Thr Ser Pro Gly Gln
            500                 505                 510

Ile Ser Thr Leu Arg Val Asn Ile Thr Ala Pro Leu Ser Gln Arg Tyr
        515                 520                 525

Arg Val Arg Ile Arg Tyr Ala Ser Thr Thr Asn Leu Gln Phe His Thr
    530                 535                 540

Ser Ile Asp Gly Arg Pro Ile Asn Gln Gly Asn Phe Ser Ala Thr Met
```

```
              545                 550                 555                 560
Ser Ser Gly Ser Asn Leu Gln Ser Gly Ser Phe Arg Thr Val Gly Phe
                565                 570                 575

Thr Thr Pro Phe Asn Phe Ser Asn Gly Ser Ser Val Phe Thr Leu Ser
            580                 585                 590

Ala His Val Phe Asn Ser Gly Asn Glu Val Tyr Ile Asp Arg Ile Glu
        595                 600                 605

Phe Val Pro Ala Glu Val Thr
        610                 615

<210> SEQ ID NO 154
<211> LENGTH: 1923
<212> TYPE: DNA
<213> ORGANISM: Artificial Sequence
<220> FEATURE:
<223> OTHER INFORMATION: 8AFdm3 T coding sequence

<400> SEQUENCE: 154
atgacggccg acaacaacac cgaggccctg acagcagca ccaccaagga cgtgatccag      60
aagggcatca gcgtggtggg cgacctgctg ggcgtggtgg gcttcccctt cggcggcgcc     120
ctggtgagct tctacaccaa cttcctgaac accatctggc ccagcgagga ccctggaag     180 gccttcatgg agcaggtgga ggccctgatg accagaaga tcgccgacta cgccaagaac     240
aaggcactgg ccgagctaca gggcctccag aacaacgtgg aggactatgt gagcgccctg     300
agcagctggc agaagaaccc cgctgcaccg ttccgcaacc cccacagcca gggccgcatc     360
cgcgagctgt tcagccaggc cgagagccac ttccgcaaca gcatgcccag cttcgccatc     420
agcggctacg aggtgctgtt cctgaccacc tacgcccagg ccgccaacac ccacctgttc     480
ctgctgaagg acgcccaaat ctacggagag agtgggggct acgagaagga ggacatcgcc     540
gagttctaca gcgccagct gaagctgacc caggagtaca ccgaccactg cgtgaagtgg     600
tacaacgtgg gtctagacaa gctccgcggc agcagctacg agagctgggt gaacttcaac     660
cgctaccgcc gcgagatgac cctgaccgtg ctggacctga tcgccctgtt ccccctgtac     720
gacgtgcgcc tgtaccccaa ggaggtgaag accgagctga cccgcgacgt gctgaccgac     780
cccatcgtgg gcgtgaacaa cctgcgcggc tacggcacca ccttcagcaa catcgagaac     840
tacatccgca agccccacct gttcgactac ctgcaccgca tccagttcca cacgcgtttc     900
cagcccggct actacggcaa cgacagcttc aactactgga gcggcaacta cgtgagcacc     960
cgccccagca tcggcagcaa cgacatcatc accagcccct tctacggcaa caagagcagc    1020
gagcccgtgc agaaccttga gttcaacggc gagaaggtgt accgcgccgt ggctaacacc    1080
aacctggccc tgtggccctc tgcagtgtac agcggcgtga ccaaggtgga gttcagccag    1140
tacaacgacc agaccgacga ggccagcacc cagacctacg acagcaagcg caacgtgggc    1200
gccgtgagct gggacagcat cgaccagctg ccccccgaga ccaccgacga gcccctggag    1260
aagggctaca gccaccagct gaactacgtg atgtgcttcc tgatgcaggg cagccgcggc    1320
accatccccg tgctgacctg acccacaag agcgtcgact tcaacaacat catccccagc    1380
agccagatca cccagatccc cctgaccaag agcaccaacc tgggcagcgg caccagcgtg    1440
gtgaagggcc ccggcttcac cggcggcgac atcctgcgcc gcaccagccc cggccagatc    1500
agcaccctgc gcgtgaacat caccgccccc ctgagccagc gctaccgcgt ccgcatccgc    1560
tacgccagca ccaccaacct gcagttccac accagcatcg acggccgccc catcaaccag    1620
ggcaacttca gcgccaccat gagcagcggc agcaacctgc agagcggcag cttccgcacc    1680
```

-continued

```
gtgggcttca ccaccccctt caacttcagc aacggcagca gcgtgttcac cctgagcgcc    1740
cacgtgttca acagcggcaa cgaggtgtac atcgaccgca tcgagttcgt gcccgccgag    1800
gtgaccttcg aggccgagta cgacctggag agggctcaga aggccgtgaa cgagctgttc    1860
accagcagca accagatcgg cctgaagacc gacgtgaccg actaccacat cgatcaggtg    1920
tag                                                                  1923
```

<210> SEQ ID NO 155
<211> LENGTH: 640
<212> TYPE: PRT
<213> ORGANISM: Artificial Sequence
<220> FEATURE:
<223> OTHER INFORMATION: 8AFdm3 T protein

<400> SEQUENCE: 155

```
Met Thr Ala Asp Asn Asn Thr Glu Ala Leu Asp Ser Ser Thr Thr Lys
1               5                   10                  15

Asp Val Ile Gln Lys Gly Ile Ser Val Val Gly Asp Leu Leu Gly Val
            20                  25                  30

Val Gly Phe Pro Phe Gly Gly Ala Leu Val Ser Phe Tyr Thr Asn Phe
        35                  40                  45

Leu Asn Thr Ile Trp Pro Ser Glu Asp Pro Trp Lys Ala Phe Met Glu
    50                  55                  60

Gln Val Glu Ala Leu Met Asp Gln Lys Ile Ala Asp Tyr Ala Lys Asn
65                  70                  75                  80

Lys Ala Leu Ala Glu Leu Gln Gly Leu Gln Asn Asn Val Glu Asp Tyr
                85                  90                  95

Val Ser Ala Leu Ser Ser Trp Gln Lys Asn Pro Ala Ala Pro Phe Arg
            100                 105                 110

Asn Pro His Ser Gln Gly Arg Ile Arg Glu Leu Phe Ser Gln Ala Glu
        115                 120                 125

Ser His Phe Arg Asn Ser Met Pro Ser Phe Ala Ile Ser Gly Tyr Glu
    130                 135                 140

Val Leu Phe Leu Thr Thr Tyr Ala Gln Ala Ala Asn Thr His Leu Phe
145                 150                 155                 160

Leu Leu Lys Asp Ala Gln Ile Tyr Gly Glu Glu Trp Gly Tyr Glu Lys
                165                 170                 175

Glu Asp Ile Ala Glu Phe Tyr Lys Arg Gln Leu Lys Leu Thr Gln Glu
            180                 185                 190

Tyr Thr Asp His Cys Val Lys Trp Tyr Asn Val Gly Leu Asp Lys Leu
        195                 200                 205

Arg Gly Ser Ser Tyr Glu Ser Trp Val Asn Phe Asn Arg Tyr Arg Arg
    210                 215                 220

Glu Met Thr Leu Thr Val Leu Asp Leu Ile Ala Leu Phe Pro Leu Tyr
225                 230                 235                 240

Asp Val Arg Leu Tyr Pro Lys Glu Val Lys Thr Glu Leu Thr Arg Asp
                245                 250                 255

Val Leu Thr Asp Pro Ile Val Gly Val Asn Asn Leu Arg Gly Tyr Gly
            260                 265                 270

Thr Thr Phe Ser Asn Ile Glu Asn Tyr Ile Arg Lys Pro His Leu Phe
        275                 280                 285

Asp Tyr Leu His Arg Ile Gln Phe His Thr Arg Phe Gln Pro Gly Tyr
    290                 295                 300

Tyr Gly Asn Asp Ser Phe Asn Tyr Trp Ser Gly Asn Tyr Val Ser Thr
305                 310                 315                 320
```

Arg Pro Ser Ile Gly Ser Asn Asp Ile Ile Thr Ser Pro Phe Tyr Gly
            325                 330                 335

Asn Lys Ser Ser Glu Pro Val Gln Asn Leu Glu Phe Asn Gly Glu Lys
            340                 345                 350

Val Tyr Arg Ala Val Ala Asn Thr Asn Leu Ala Val Trp Pro Ser Ala
            355                 360                 365

Val Tyr Ser Gly Val Thr Lys Val Glu Phe Ser Gln Tyr Asn Asp Gln
            370                 375                 380

Thr Asp Glu Ala Ser Thr Gln Thr Tyr Asp Ser Lys Arg Asn Val Gly
385                 390                 395                 400

Ala Val Ser Trp Asp Ser Ile Asp Gln Leu Pro Pro Glu Thr Thr Asp
            405                 410                 415

Glu Pro Leu Glu Lys Gly Tyr Ser His Gln Leu Asn Tyr Val Met Cys
            420                 425                 430

Phe Leu Met Gln Gly Ser Arg Gly Thr Ile Pro Val Leu Thr Trp Thr
            435                 440                 445

His Lys Ser Val Asp Phe Asn Asn Ile Ile Pro Ser Ser Gln Ile Thr
            450                 455                 460

Gln Ile Pro Leu Thr Lys Ser Thr Asn Leu Gly Ser Gly Thr Ser Val
465                 470                 475                 480

Val Lys Gly Pro Gly Phe Thr Gly Gly Asp Ile Leu Arg Arg Thr Ser
            485                 490                 495

Pro Gly Gln Ile Ser Thr Leu Arg Val Asn Ile Thr Ala Pro Leu Ser
            500                 505                 510

Gln Arg Tyr Arg Val Arg Ile Arg Tyr Ala Ser Thr Thr Asn Leu Gln
            515                 520                 525

Phe His Thr Ser Ile Asp Gly Arg Pro Ile Asn Gln Gly Asn Phe Ser
            530                 535                 540

Ala Thr Met Ser Ser Gly Ser Asn Leu Gln Ser Gly Ser Phe Arg Thr
545                 550                 555                 560

Val Gly Phe Thr Thr Pro Phe Asn Phe Ser Asn Gly Ser Ser Val Phe
            565                 570                 575

Thr Leu Ser Ala His Val Phe Asn Ser Gly Asn Glu Val Tyr Ile Asp
            580                 585                 590

Arg Ile Glu Phe Val Pro Ala Glu Val Thr Phe Glu Ala Glu Tyr Asp
            595                 600                 605

Leu Glu Arg Ala Gln Lys Ala Val Asn Glu Leu Phe Thr Ser Ser Asn
            610                 615                 620

Gln Ile Gly Leu Lys Thr Asp Val Thr Asp Tyr His Ile Asp Gln Val
625                 630                 635                 640

<210> SEQ ID NO 156
<211> LENGTH: 1923
<212> TYPE: DNA
<213> ORGANISM: Artificial Sequence
<220> FEATURE:
<223> OTHER INFORMATION: 8AFlongdm3T coding sequence

<400> SEQUENCE: 156
atgacggccg acaacaacac cgaggccctg acagcagca ccaccaagga cgtgatccag      60
aagggcatca gcgtggtggg cgacctgctg ggcgtggtgg gcttcccctt cggcggcgcc     120
ctggtgagct tctacaccaa cttcctgaac accatctggc ccagcgagga ccctggaag     180 gccttcatgg agcaggtgga ggccctgatg accagaaga tcgccgacta cgccaagaac     240
aaggcactgg ccgagctaca gggcctccag aacaacgtgg aggactatgt gagcgccctg     300

-continued

| | |
|---|---|
| agcagctggc agaagaaccc cgctgcaccg ttccgcaacc cccacagcca gggccgcatc | 360 |
| cgcgagctgt tcagccaggc cgagagccac ttccgcaaca gcatgcccag cttcgccatc | 420 |
| agcggctacg aggtgctgtt cctgaccacc tacgcccagg ccgccaacac ccacctgttc | 480 |
| ctgctgaagg acgccaaaat ctacggagag gagtggggct acgagaagga ggacatcgcc | 540 |
| gagttctaca gcgccagct gaagctgacc caggagtaca ccgaccactg cgtgaagtgg | 600 |
| tacaacgtgg gtctagacaa gctccgcggc agcagctacg agagctgggt gaacttcaac | 660 |
| cgctaccgcc gcgagatgac cctgaccgtg ctggacctga tcgccctgtt cccctgtac | 720 |
| gacgtgcgcc tgtaccccaa ggaggtgaag accgagctga cccgcgacgt gctgaccgac | 780 |
| cccatcgtgg gcgtgaacaa cctgcgcggc tacggcacca ccttcagcaa catcgagaac | 840 |
| tacatccgca agccccacct gttcgactac ctgcaccgca tccagttcca cacgcgtttc | 900 |
| cagcccggct actacggcaa cgacagcttc aactactgga gcggcaacta cgtgagcacc | 960 |
| cgccccagca tcggcagcaa cgacatcatc accagcccct tctacggcaa caagagcagc | 1020 |
| gagcccgtgc agaaccttga gttcaacggc gagaaggtgt accgcgccgt ggctaacacc | 1080 |
| aacctggccg tgtggccctc tgcagtgtac agcggcgtga ccaaggtgga gttcagccag | 1140 |
| tacaacgacc agaccgacga ggccagcacc cagacctacg acagcaagcg caacgtgggc | 1200 |
| gccgtgagct gggacagcat cgaccagctg cccccccgaga ccaccgacga gcccctggag | 1260 |
| aagggctaca gccaccagct gaactacgtg atgtgcttcc tgatgcaggg cagccgcggc | 1320 |
| accatccccg tgctgacctg gacccacaag agcgtcgact tcttcaacat gatcgacagc | 1380 |
| aagaagatca cccagctgcc cctggtgaag gcctacaagc tccagagcgg cgccagcgtg | 1440 |
| gtggcaggcc cccgcttcac cggcggcgac atcatccagt gcaccgagaa cggcagcgcc | 1500 |
| gccaccatct acgtgacccc cgacgtgagc tacagccaga agtaccgcgc ccgcatccgc | 1560 |
| tacgccagca ccaccaacct gcagttccac accagcatcg acggccgccc catcaaccag | 1620 |
| ggcaacttca gcgccaccat gagcagcggc agcaacctgc agagcggcag cttccgcacc | 1680 |
| gtgggcttca ccacccccttt caacttcagc aacggcagca gcgtgttcac cctgagcgcc | 1740 |
| cacgtgttca cagcggcaa cgaggtgtac atcgaccgca tcgagttcgt gcccgccgag | 1800 |
| gtgaccttcg aggccgagta cgacctggag agggctcaga aggccgtgaa cgagctgttc | 1860 |
| accagcagca accagatcgg cctgaagacc gacgtgaccg actaccacat cgatcaggtg | 1920 |
| tag | 1923 |

<210> SEQ ID NO 157
<211> LENGTH: 640
<212> TYPE: PRT
<213> ORGANISM: Artificial Sequence
<220> FEATURE:
<223> OTHER INFORMATION: 8AFlongdm3T protein

<400> SEQUENCE: 157

```
Met Thr Ala Asp Asn Asn Thr Glu Ala Leu Asp Ser Ser Thr Thr Lys
1               5                   10                  15

Asp Val Ile Gln Lys Gly Ile Ser Val Val Gly Asp Leu Leu Gly Val
            20                  25                  30

Val Gly Phe Pro Phe Gly Gly Ala Leu Val Ser Phe Tyr Thr Asn Phe
        35                  40                  45

Leu Asn Thr Ile Trp Pro Ser Glu Asp Pro Trp Lys Ala Phe Met Glu
    50                  55                  60

Gln Val Glu Ala Leu Met Asp Gln Lys Ile Ala Asp Tyr Ala Lys Asn
65                  70                  75                  80
```

```
Lys Ala Leu Ala Glu Leu Gln Gly Leu Gln Asn Asn Val Glu Asp Tyr
                 85                  90                  95

Val Ser Ala Leu Ser Ser Trp Gln Lys Asn Pro Ala Ala Pro Phe Arg
                100                 105                 110

Asn Pro His Ser Gln Gly Arg Ile Arg Glu Leu Phe Ser Gln Ala Glu
                115                 120                 125

Ser His Phe Arg Asn Ser Met Pro Ser Phe Ala Ile Ser Gly Tyr Glu
            130                 135                 140

Val Leu Phe Leu Thr Thr Tyr Ala Gln Ala Ala Asn Thr His Leu Phe
145                 150                 155                 160

Leu Leu Lys Asp Ala Gln Ile Tyr Gly Glu Glu Trp Gly Tyr Glu Lys
                165                 170                 175

Glu Asp Ile Ala Glu Phe Tyr Lys Arg Gln Leu Lys Leu Thr Gln Glu
                180                 185                 190

Tyr Thr Asp His Cys Val Lys Trp Tyr Asn Val Gly Leu Asp Lys Leu
            195                 200                 205

Arg Gly Ser Ser Tyr Glu Ser Trp Val Asn Phe Asn Arg Tyr Arg Arg
                210                 215                 220

Glu Met Thr Leu Thr Val Leu Asp Leu Ile Ala Leu Phe Pro Leu Tyr
225                 230                 235                 240

Asp Val Arg Leu Tyr Pro Lys Glu Val Lys Thr Glu Leu Thr Arg Asp
                245                 250                 255

Val Leu Thr Asp Pro Ile Val Gly Val Asn Asn Leu Arg Gly Tyr Gly
                260                 265                 270

Thr Thr Phe Ser Asn Ile Glu Asn Tyr Ile Arg Lys Pro His Leu Phe
            275                 280                 285

Asp Tyr Leu His Arg Ile Gln Phe His Thr Arg Phe Gln Pro Gly Tyr
            290                 295                 300

Tyr Gly Asn Asp Ser Phe Asn Tyr Trp Ser Gly Asn Tyr Val Ser Thr
305                 310                 315                 320

Arg Pro Ser Ile Gly Ser Asn Asp Ile Ile Thr Ser Pro Phe Tyr Gly
                325                 330                 335

Asn Lys Ser Ser Glu Pro Val Gln Asn Leu Glu Phe Asn Gly Glu Lys
                340                 345                 350

Val Tyr Arg Ala Val Ala Asn Thr Asn Leu Ala Val Trp Pro Ser Ala
                355                 360                 365

Val Tyr Ser Gly Val Thr Lys Val Glu Phe Ser Gln Tyr Asn Asp Gln
                370                 375                 380

Thr Asp Glu Ala Ser Thr Gln Thr Tyr Asp Ser Lys Arg Asn Val Gly
385                 390                 395                 400

Ala Val Ser Trp Asp Ser Ile Asp Gln Leu Pro Pro Glu Thr Thr Asp
                405                 410                 415

Glu Pro Leu Glu Lys Gly Tyr Ser His Gln Leu Asn Tyr Val Met Cys
                420                 425                 430

Phe Leu Met Gln Gly Ser Arg Gly Thr Ile Pro Val Leu Thr Trp Thr
            435                 440                 445

His Lys Ser Val Asp Phe Phe Asn Met Ile Asp Ser Lys Lys Ile Thr
            450                 455                 460

Gln Leu Pro Leu Val Lys Ala Tyr Lys Leu Gln Ser Gly Ala Ser Val
465                 470                 475                 480

Val Ala Gly Pro Arg Phe Thr Gly Gly Asp Ile Ile Gln Cys Thr Glu
                485                 490                 495

Asn Gly Ser Ala Ala Thr Ile Tyr Val Thr Pro Asp Val Ser Tyr Ser
```

```
                    500                 505                 510
Gln Lys Tyr Arg Ala Arg Ile Arg Tyr Ala Ser Thr Thr Asn Leu Gln
            515                 520                 525

Phe His Thr Ser Ile Asp Gly Arg Pro Ile Asn Gln Gly Asn Phe Ser
    530                 535                 540

Ala Thr Met Ser Ser Gly Ser Asn Leu Gln Ser Gly Ser Phe Arg Thr
545                 550                 555                 560

Val Gly Phe Thr Thr Pro Phe Asn Phe Ser Asn Gly Ser Val Phe
                565                 570                 575

Thr Leu Ser Ala His Val Phe Asn Ser Gly Asn Glu Val Tyr Ile Asp
            580                 585                 590

Arg Ile Glu Phe Val Pro Ala Glu Val Thr Phe Glu Ala Glu Tyr Asp
        595                 600                 605

Leu Glu Arg Ala Gln Lys Ala Val Asn Glu Leu Phe Thr Ser Ser Asn
    610                 615                 620

Gln Ile Gly Leu Lys Thr Asp Val Thr Asp Tyr His Ile Asp Gln Val
625                 630                 635                 640

<210> SEQ ID NO 158
<211> LENGTH: 1962
<212> TYPE: DNA
<213> ORGANISM: Artificial Sequence
<220> FEATURE:
<223> OTHER INFORMATION: cap8AFdm3T coding serquence

<400> SEQUENCE: 158
atgactagta acggccgcca gtgtgctggt attcgccctt atgacggccg acaacaacac      60
cgaggcctgg acagcagcac caccaaggac gtgatccaga agggcatcag cgtggtgggc     120
gacctgctgg gcgtggtggg cttcccccttc ggcggcgccc tggtgagctt ctacaccaac    180
ttcctgaaca ccatctggcc cagcgaggac ccctggaagg ccttcatgga gcaggtggag     240
gccctgatgg accagaagat cgccgactac gccaagaaca aggcactggc cgagctacag     300
ggcctccaga caacgtgga ggactatgtg agcgccctga gcagctggca gaagaacccc      360
gctgcaccgt tccgcaaccc ccacagccag ggccgcatcc gcgagctgtt cagccaggcc     420
gagagccact tccgcaacag catgccagc ttcgccatca gcggctacga ggtgctgttc      480
ctgaccacct acgcccaggc cgccaacacc cacctgttcc tgctgaagga cgcccaaatc     540
tacggagagg agtggggcta cgagaaggag gacatcgccg agttctacaa cgccagctg     600 aagctgaccc aggagtacac cgaccactgc gtgaagtggt acaacgtggg tctagacaag    660
ctccgcggca gcagctacga gagctgggtg aacttcaacc gctaccgccg cgagatgacc     720
ctgaccgtgc tggacctgat cgccctgttc cccctgtacg acgtgcgcct gtaccccaag     780
gaggtgaaga ccgagctgac ccgcgacgtg ctgaccgacc ccatcgtggg cgtgaacaac     840
ctgcgcggct acggcaccac cttcagcaac atcgagaact catccgcaa gccccacctg     900 ttcgactacc tgcaccgcat ccagttccac acgcgtttcc agcccggcta ctacggcaac     960
gacagcttca actactggag cggcaactac gtgagcaccc gccccagcat cggcagcaac    1020
gacatcatca ccagcccctt ctacggcaac aagagcagcg agcccgtgca gaaccttgag    1080
ttcaacggcg agaaggtgta ccgcgccgtg gctaacacca acctggccgt gtggcccctct  1140 gcagtgtaca gcggcgtgac caaggtggag ttcagccagt acaacgacca gaccgacgag    1200
gccagcaccc agacctacga cagcaagcgc aacgtgggcg ccgtgagctg ggacagcatc    1260
gaccagctgc cccccgagac caccgacgag cccctggaga agggctacag ccaccagctg    1320
```

```
aactacgtga tgtgcttcct gatgcagggc agccgcggca ccatcccccgt gctgacctgg    1380 acccacaaga gcgtcgactt caacaacatc atccccagca gccagatcac ccagatcccc    1440
ctgaccaaga gcaccaacct gggcagcggc accagcgtgg tgaagggccc cggcttcacc    1500
ggcggcgaca tcctgcgccg caccagcccc ggccagatca gcaccctgcg cgtgaacatc    1560
accgcccccc tgagccagcg ctaccgcgtc cgcatccgct acgccagcac caccaacctg    1620
cagttccaca ccagcatcga cggccgcccc atcaaccagg gcaacttcag cgccaccatg    1680
agcagcggca gcaacctgca gagcggcagc ttccgcaccg tgggcttcac cacccccttc    1740
aacttcagca acggcagcag cgtgttcacc ctgagcgccc acgtgttcaa cagcggcaac    1800
gaggtgtaca tcgaccgcat cgagttcgtg cccgccgagg tgaccttcga ggccgagtac    1860
gacctggaga gggctcagaa ggccgtgaac gagctgttca ccagcagcaa ccagatcggc    1920
ctgaagaccg acgtgaccga ctaccacatc gatcaggtgt ag                       1962
```

<210> SEQ ID NO 159
<211> LENGTH: 653
<212> TYPE: PRT
<213> ORGANISM: Artificial Sequence
<220> FEATURE:
<223> OTHER INFORMATION: cap8AFdm3T protein

<400> SEQUENCE: 159

```
Met Thr Ser Asn Gly Arg Gln Cys Ala Gly Ile Arg Pro Tyr Asp Gly
 1               5                  10                  15

Arg Gln Gln His Arg Gly Leu Asp Ser Ser Thr Thr Lys Asp Val Ile
            20                  25                  30

Gln Lys Gly Ile Ser Val Val Gly Asp Leu Leu Gly Val Gly Phe
        35                  40                  45

Pro Phe Gly Gly Ala Leu Val Ser Phe Tyr Thr Asn Phe Leu Asn Thr
    50                  55                  60

Ile Trp Pro Ser Glu Asp Pro Trp Lys Ala Phe Met Glu Gln Val Glu
65                  70                  75                  80

Ala Leu Met Asp Gln Lys Ile Ala Asp Tyr Ala Lys Asn Lys Ala Leu
                85                  90                  95

Ala Glu Leu Gln Gly Leu Gln Asn Asn Val Glu Asp Tyr Val Ser Ala
            100                 105                 110

Leu Ser Ser Trp Gln Lys Asn Pro Ala Ala Pro Phe Arg Asn Pro His
        115                 120                 125

Ser Gln Gly Arg Ile Arg Glu Leu Phe Ser Gln Ala Glu Ser His Phe
    130                 135                 140

Arg Asn Ser Met Pro Ser Phe Ala Ile Ser Gly Tyr Glu Val Leu Phe
145                 150                 155                 160

Leu Thr Thr Tyr Ala Gln Ala Ala Asn Thr His Leu Phe Leu Leu Lys
                165                 170                 175

Asp Ala Gln Ile Tyr Gly Glu Glu Trp Gly Tyr Glu Lys Glu Asp Ile
            180                 185                 190

Ala Glu Phe Tyr Lys Arg Gln Leu Lys Leu Thr Gln Glu Tyr Thr Asp
        195                 200                 205

His Cys Val Lys Trp Tyr Asn Val Gly Leu Asp Lys Leu Arg Gly Ser
    210                 215                 220

Ser Tyr Glu Ser Trp Val Asn Phe Asn Arg Tyr Arg Arg Glu Met Thr
225                 230                 235                 240

Leu Thr Val Leu Asp Leu Ile Ala Leu Phe Pro Leu Tyr Asp Val Arg
                245                 250                 255
```

```
Leu Tyr Pro Lys Glu Val Lys Thr Glu Leu Thr Arg Asp Val Leu Thr
            260                 265                 270

Asp Pro Ile Val Gly Val Asn Asn Leu Arg Gly Tyr Gly Thr Thr Phe
            275                 280                 285

Ser Asn Ile Glu Asn Tyr Ile Arg Lys Pro His Leu Phe Asp Tyr Leu
            290                 295                 300

His Arg Ile Gln Phe His Thr Arg Phe Gln Pro Gly Tyr Tyr Gly Asn
305                 310                 315                 320

Asp Ser Phe Asn Tyr Trp Ser Gly Asn Tyr Val Ser Thr Arg Pro Ser
                325                 330                 335

Ile Gly Ser Asn Asp Ile Ile Thr Ser Pro Phe Tyr Gly Asn Lys Ser
            340                 345                 350

Ser Glu Pro Val Gln Asn Leu Glu Phe Asn Gly Glu Lys Val Tyr Arg
            355                 360                 365

Ala Val Ala Asn Thr Asn Leu Ala Val Trp Pro Ser Ala Val Tyr Ser
            370                 375                 380

Gly Val Thr Lys Val Glu Phe Ser Gln Tyr Asn Asp Gln Thr Asp Glu
385                 390                 395                 400

Ala Ser Thr Gln Thr Tyr Asp Ser Lys Arg Asn Val Gly Ala Val Ser
                405                 410                 415

Trp Asp Ser Ile Asp Gln Leu Pro Pro Glu Thr Thr Asp Glu Pro Leu
            420                 425                 430

Glu Lys Gly Tyr Ser His Gln Leu Asn Tyr Val Met Cys Phe Leu Met
            435                 440                 445

Gln Gly Ser Arg Gly Thr Ile Pro Val Leu Thr Trp Thr His Lys Ser
            450                 455                 460

Val Asp Phe Asn Asn Ile Ile Pro Ser Ser Gln Ile Thr Gln Ile Pro
465                 470                 475                 480

Leu Thr Lys Ser Thr Asn Leu Gly Ser Gly Thr Ser Val Val Lys Gly
                485                 490                 495

Pro Gly Phe Thr Gly Gly Asp Ile Leu Arg Arg Thr Ser Pro Gly Gln
            500                 505                 510

Ile Ser Thr Leu Arg Val Asn Ile Thr Ala Pro Leu Ser Gln Arg Tyr
            515                 520                 525

Arg Val Arg Ile Arg Tyr Ala Ser Thr Thr Asn Leu Gln Phe His Thr
530                 535                 540

Ser Ile Asp Gly Arg Pro Ile Asn Gln Gly Asn Phe Ser Ala Thr Met
545                 550                 555                 560

Ser Ser Gly Ser Asn Leu Gln Ser Gly Ser Phe Arg Thr Val Gly Phe
                565                 570                 575

Thr Thr Pro Phe Asn Phe Ser Asn Gly Ser Ser Val Phe Thr Leu Ser
            580                 585                 590

Ala His Val Phe Asn Ser Gly Asn Glu Val Tyr Ile Asp Arg Ile Glu
            595                 600                 605

Phe Val Pro Ala Glu Val Thr Phe Glu Ala Glu Tyr Asp Leu Glu Arg
            610                 615                 620

Ala Gln Lys Ala Val Asn Glu Leu Phe Thr Ser Ser Asn Gln Ile Gly
625                 630                 635                 640

Leu Lys Thr Asp Val Thr Asp Tyr His Ile Asp Gln Val
                645                 650

<210> SEQ ID NO 160
<211> LENGTH: 687
<212> TYPE: PRT
<213> ORGANISM: Artificial Sequence
```

<220> FEATURE:
<223> OTHER INFORMATION: FR8a+34 protein

<400> SEQUENCE: 160

```
Met Lys Glu Thr Ala Ala Lys Phe Glu Arg Gln His Met Asp Ser
1               5                   10                  15

Pro Asp Leu Gly Thr Leu Val Pro Arg Gly Ser Met Ala Asp Ile Gly
                20                  25                  30

Ser Thr Met Thr Ser Asn Gly Arg Gln Cys Ala Gly Ile Arg Pro Tyr
            35                  40                  45

Asp Gly Arg Gln Gln His Arg Gly Leu Asp Ser Thr Thr Lys Asp
        50                  55                  60

Val Ile Gln Lys Gly Ile Ser Val Val Gly Asp Leu Leu Gly Val Val
65                  70                  75                  80

Gly Phe Pro Phe Gly Ala Leu Val Ser Phe Tyr Thr Asn Phe Leu
                85                  90                  95

Asn Thr Ile Trp Pro Ser Glu Asp Pro Trp Lys Ala Phe Met Glu Gln
                100                 105                 110

Val Glu Ala Leu Met Asp Gln Lys Ile Ala Asp Tyr Ala Lys Asn Lys
            115                 120                 125

Ala Leu Ala Glu Leu Gln Gly Leu Gln Asn Asn Val Glu Asp Tyr Val
        130                 135                 140

Ser Ala Leu Ser Ser Trp Gln Lys Asn Pro Ala Ala Pro Phe Arg Asn
145                 150                 155                 160

Pro His Ser Gln Gly Arg Ile Arg Glu Leu Phe Ser Gln Ala Glu Ser
                165                 170                 175

His Phe Arg Asn Ser Met Pro Ser Phe Ala Ile Ser Gly Tyr Glu Val
            180                 185                 190

Leu Phe Leu Thr Thr Tyr Ala Gln Ala Ala Asn Thr His Leu Phe Leu
        195                 200                 205

Leu Lys Asp Ala Gln Ile Tyr Gly Glu Glu Trp Gly Tyr Glu Lys Glu
        210                 215                 220

Asp Ile Ala Glu Phe Tyr Lys Arg Gln Leu Lys Leu Thr Gln Glu Tyr
225                 230                 235                 240

Thr Asp His Cys Val Lys Trp Tyr Asn Val Gly Leu Asp Lys Leu Arg
                245                 250                 255

Gly Ser Ser Tyr Glu Ser Trp Val Asn Phe Asn Arg Tyr Arg Arg Glu
            260                 265                 270

Met Thr Leu Thr Val Leu Asp Leu Ile Ala Leu Phe Pro Leu Tyr Asp
        275                 280                 285

Val Arg Leu Tyr Pro Lys Glu Val Lys Thr Glu Leu Thr Arg Asp Val
        290                 295                 300

Leu Thr Asp Pro Ile Val Gly Val Asn Asn Leu Arg Gly Tyr Gly Thr
305                 310                 315                 320

Thr Phe Ser Asn Ile Glu Asn Tyr Ile Arg Lys Pro His Leu Phe Asp
                325                 330                 335

Tyr Leu His Arg Ile Gln Phe His Thr Arg Phe Gln Pro Gly Tyr Tyr
            340                 345                 350

Gly Asn Asp Ser Phe Asn Tyr Trp Ser Gly Asn Tyr Val Ser Thr Arg
        355                 360                 365

Pro Ser Ile Gly Ser Asn Asp Ile Ile Thr Ser Pro Phe Tyr Gly Asn
        370                 375                 380

Lys Ser Ser Glu Pro Val Gln Asn Leu Glu Phe Asn Gly Glu Lys Val
385                 390                 395                 400
```

```
Tyr Arg Ala Val Ala Asn Thr Asn Leu Ala Val Trp Pro Ser Ala Val
            405                 410                 415
Tyr Ser Gly Val Thr Lys Val Glu Phe Ser Gln Tyr Asn Asp Gln Thr
            420                 425                 430
Asp Glu Ala Ser Thr Gln Thr Tyr Asp Ser Lys Arg Asn Val Gly Ala
            435                 440                 445
Val Ser Trp Asp Ser Ile Asp Gln Leu Pro Pro Glu Thr Thr Asp Glu
            450                 455                 460
Pro Leu Glu Lys Gly Tyr Ser His Gln Leu Asn Tyr Val Met Cys Phe
465                 470                 475                 480
Leu Met Gln Gly Ser Arg Gly Thr Ile Pro Val Leu Thr Trp Thr His
            485                 490                 495
Lys Ser Val Asp Phe Phe Asn Met Ile Asp Ser Lys Lys Ile Thr Gln
            500                 505                 510
Leu Pro Leu Thr Lys Ser Thr Asn Leu Gly Ser Gly Thr Ser Val Val
            515                 520                 525
Lys Gly Pro Gly Phe Thr Gly Gly Asp Ile Leu Arg Arg Thr Ser Pro
            530                 535                 540
Gly Gln Ile Ser Thr Leu Arg Val Asn Ile Thr Ala Pro Leu Ser Gln
545                 550                 555                 560
Arg Tyr Arg Val Arg Ile Arg Tyr Ala Ser Thr Thr Asn Leu Gln Phe
                565                 570                 575
His Thr Ser Ile Asp Gly Arg Pro Ile Asn Gln Gly Asn Phe Ser Ala
            580                 585                 590
Thr Met Ser Ser Gly Ser Asn Leu Gln Ser Gly Ser Phe Arg Thr Val
            595                 600                 605
Gly Phe Thr Thr Pro Phe Asn Phe Ser Asn Gly Ser Ser Val Phe Thr
    610                 615                 620
Leu Ser Ala His Val Phe Asn Ser Gly Asn Glu Val Tyr Ile Asp Arg
625                 630                 635                 640
Ile Glu Phe Val Pro Ala Glu Val Thr Phe Glu Ala Glu Tyr Asp Leu
                645                 650                 655
Glu Arg Ala Gln Lys Ala Val Asn Glu Leu Phe Thr Ser Ser Asn Gln
            660                 665                 670
Ile Gly Leu Lys Thr Asp Val Thr Asp Tyr His Ile Asp Gln Val
    675                 680                 685
```

What is claimed is:

1. An engineered hybrid insecticidal protein comprising in an N-terminus to C-terminus direction an N-terminal region of a Cry3A protein fused to a C-terminal region of a Cry1Aa or Cry1Ab protein, wherein at least one crossover position between the Cry3A protein and the Cry 1Aa or Cry 1Ab protein is located in conserved block 2, conserved block 3 or variable region 4, and optionally comprising:

(a) at the C-terminus a protoxin tail region of a Bt Cry protein; or (b) at the N-terminus a peptidyl fragment; or (c) both (a) and (b), wherein the engineered hybrid insecticidal protein has at least 80% identity to SEQ ID NO: 64 and has insecticidal activity against western corn rootworm.

2. The engineered hybrid insecticidal protein according to claim 1, wherein the Cry3A is a Cry3Aa or a modified Cry3Aa.

3. The engineered hybrid insecticidal protein according to claim 2, wherein (a) the Cry3Aa comprises SEQ ID NO: 68 or SEQ ID NO: 135, or (b) the modified Cry3Aa comprises SEQ ID NO: 70, and wherein the Cry1Ab comprises SEQ ID NO: 72.

4. The engineered hybrid insecticidal protein according to claim 1 comprising at the C-terminus a protoxin tail region of a Bt Cry protein.

5. The engineered hybrid insecticidal protein according to claim 4, wherein the protoxin tail region is from a Bt Cry protein that is active against a lepidopteran insect.

6. The engineered hybrid insecticidal protein according to claim 5, wherein the Bt Cry protein is a Cry1A.

7. The engineered hybrid insecticidal protein according to claim 6, wherein the Cry1A is a Cry1Aa or a Cry1Ab.

8. The engineered hybrid insecticidal protein according to claim 7, wherein the Cry1Ab protoxin tail region comprises at least 38 amino acids.

9. The engineered hybrid insecticidal protein according to claim 8, wherein the Cry1Ab protoxin tail region comprises an amino acid sequence that corresponds to amino acids 611-648 of SEQ ID NO: 72.

10. The engineered hybrid insecticidal protein according to claim 9, wherein the Cry1Ab protoxin tail region comprises amino acids 611-648 of SEQ ID NO: 72.

11. The engineered hybrid insecticidal protein according to claim 1 comprising at the N-terminus a peptidyl fragment, wherein the peptidyl fragment comprises at least 9 amino acids.

12. The engineered hybrid insecticidal protein according to claim 11, wherein the peptidyl fragment comprises the amino acid sequence YDGRQQHRG (SEQ ID NO:
133) or the amino acid sequence TSNGRQCAGIRP (SEQ ID NO: 134).

13. The engineered hybrid insecticidal protein according to claim 12, wherein the peptidyl fragment is selected from the group consisting of SEQ ID NO: 126, SEQ ID NO: 127, SEQ ID NO: 128, SEQ ID NO: 129, SEQ ID NO: 130, SEQ ID NO: 131 and SEQ ID NO: 132.

14. The engineered hybrid insecticidal protein according to claim 1, wherein the crossover position between Cry3A and Cry1Aa or Cry1Ab is located in a region between amino acids corresponding to amino acid 6 of conserved block 3 to amino acid 7 of conserved block 4.

15. The engineered hybrid insecticidal protein according to claim 14, wherein the crossover position is located in conserved block 3 immediately following an amino acid corresponding to Ser450, Phe454, or Leu468 of SEQ ID NO: 70.

16. The engineered hybrid insecticidal protein according to claim 15, wherein the crossover position is located in conserved block 3 immediately following Ser450, Phe454, or Leu468 of SEQ ID NO: 70.

17. An engineered hybrid insecticidal protein comprising at least two crossover positions between an amino acid sequence from a Cry3A protein and an amino acid sequence from a Cry1Aa or Cry1Ab protein, wherein
  (a) the first crossover position between Cry3A and Cry1Aa or Cry1is located in conserved block 2 immediately following an amino acid corresponding to Asp232 of SEQ ID NO: 70 and a second crossover position between Cry1Aa or Cry1Ab and Cry3A is located in conserved block 3 immediately following an amino acid corresponding to Leu476 of SEQ ID NO: 72; or
  (b) the first crossover position between Cry31A and Cry11Aa or Cry1Ab is located in conserved block 3 immediately following an amino acid corresponding to Leu468 of SEQ ID NO: 70 and the second crossover position between Cry1Aa or Cry1Ab and Cry3A is located in conserved block 4 immediately following an amino acid corresponding to Ile527 of SEQ ID NO: 72.

18. The engineered hybrid insecticidal protein according to claim 17, wherein the Cry3A is Cry3Aa or modified Cry3Aa and the Cry1A is Cry1Ab, and wherein
  (a) the first crossover position between Cry3Aa and Cry1Ab or modified Cry3Aa and Cry 1Ab is located in conserved block 2 immediately following Asp232 of SEQ ID NO: 70 and the second crossover position between Cry1Ab and Cry3Aa or modified Cry3Aa is located in conserved block 3 immediately following Leu476 of SEQ ID NO: 72; or
  (b) the first crossover position between Cry3Aa and Cry1Ab or modified Cry3Aa and Cry 1Ab is located in conserved block 3 immediately following Leu468 of SEQ ID NO: 70 and the second crossover position between Cry1Ab and Cry3Aa or Cry 1Ab and modified Cry3Aa is located in conserved block 4 immediately following Ile527 of SEQ ID NO: 72.

19. The engineered hybrid insecticidal protein according to claim 1, wherein the insecticidal protein is additionally active against northern corn rootworm or Mexican corn rootworm.

20. The engineered hybrid insecticidal protein according to claim 1, comprising an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 16, SEQ ID NO: 18, SEQ ID NO: 22, SEQ ID NO: 24, SEQ ID NO: 44, SEQ ID NO: 62; SEQ ID NO: 64, SEQ ID NO: 147, SEQ ID NO: 153, SEQ ID NO: 155, SEQ ID NO: 159 and SEQ ID NO: 160.

21. An insecticidal composition comprising the engineered hybrid insecticidal protein according to claim 1.

22. A method of controlling insects, comprising delivering to the insects an effective amount of the engineered hybrid insecticidal protein according to claim 1.

23. The engineered hybrid insecticidal protein according to claim 17 comprising at the N-terminus a peptidyl fragment, wherein the peptidyl fragment comprises at least 9 amino acids.

24. The engineered hybrid insecticidal protein according to claim 17, comprising the amino acid sequence of SEQ ID NO: 30 or SEQ ID NO: 34.

* * * * *